United States Patent
Venkatesan et al.

(10) Patent No.: US 6,441,023 B1
(45) Date of Patent: Aug. 27, 2002

(54) N-HYDROXY-2-(ALKYL, ARYL, OR HETEROARYL SULFANYL, SULFINYL OR SULFONYL)-3-SUBSTITUTED ALKYL, ARYL OR HETEROARYLAMIDES AS MATRIX METALLOPROTEINASE INHIBITORS

(75) Inventors: Aranapakam Mudumbai Venkatesan, Rego Park; Jannie Lea Baker, White Plains; Jeremy Ian Levin, New City, all of NY (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/898,604

(22) Filed: Jul. 3, 2001

Related U.S. Application Data

(60) Division of application No. 09/587,560, filed on Jun. 5, 2000, now Pat. No. 6,331,563, which is a division of application No. 09/140,504, filed on Aug. 26, 1998, now Pat. No. 6,197,791, which is a continuation-in-part of application No. 09/026,372, filed on Feb. 19, 1998, now abandoned.
(60) Provisional application No. 60/038,899, filed on Feb. 27, 1997.

(51) Int. Cl.$^7$ ..................... A61K 31/382; C07D 335/02
(52) U.S. Cl. ..................... 514/432; 549/28; 549/9; 549/13; 549/29; 549/64; 549/72; 514/431; 514/438; 514/445; 514/448
(58) Field of Search ................. 514/432, 431, 514/438, 448; 549/13, 9, 28, 29, 72

(56) References Cited

U.S. PATENT DOCUMENTS

| 4,933,367 A | 6/1990 | Wolff et al. |
| 5,455,258 A | 10/1995 | MacPherson et al. |
| 5,672,615 A | 9/1997 | MacPherson et al. |
| 5,747,514 A | 5/1998 | Beckett et al. |

FOREIGN PATENT DOCUMENTS

| EP | 0606046 | 10/1997 | |
| HU | P9601991 | 9/1996 | |
| WO | 9005719 | 5/1990 | |
| WO | 9519961 | 7/1995 | |
| WO | 9535275 | 12/1995 | |
| WO | 9600214 | 1/1996 | |
| WO | 99/25687 | * 5/1999 | ............. 546/184 |

OTHER PUBLICATIONS

R. P. Becker et al. Research Focus, vol. 1, 16–26 (1996).
Nigel Beeley et al., Curr. Opin. Ther. Patents 4(1), 7–16 (1994).
J. R. Morphy et al., Curr. Medicinal Chem. 2:743–762 (1995).
Steven K. Davidson et al., Exp. Opin. Ther. Patents 5(2), 1087–1110 (1995).
John R. Porter et al., Exp. Opin. Ther. Patents 5(12), 1287–1296 (1995).
Salah Zayed et al., Liebigs Ann. Chem. 195–200 (1973).

* cited by examiner

*Primary Examiner*—Charanjit S. Aulakh
(74) *Attorney, Agent, or Firm*—Joy S. Goudie

(57) ABSTRACT

Matrix metalloproteinases (MMPs) are a group of enzymes that have been implicated in the pathological destruction of connective tissue and basement membranes. These zinc containing endopeptidases consist of several subsets of enzymes including collagenases, stromelysins and gelatinases. TNF-α converting enzyme (TACE), a pro-inflmatory cytokine, catalyzes the formation of TNF-α from membrane bound TNF-α precursor protein. It is expected that small molecule inhibitors of MMPs and TACE therefore have the potential for treating a variety of disease states. The present invention provides low molecular weight, non-peptide inhibitors of matrix metalloproteinases (MMPs) and TNF-α converting enzyme (TACE) for the treatment of arthritis, tumor metastasis, tissue ulceration, abnormal wound healing, periodontal disease, bone disease, diabetes (insulin resistance) and HIV infection having the formula

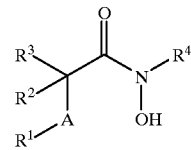

wherein $R^2$ and $R^3$ form a heterocyclic ring and A is S, S(O), or S(O)$_2$, and $R^1$ and $R^4$ are defined herein.

9 Claims, No Drawings

N-HYDROXY-2-(ALKYL, ARYL, OR HETEROARYL SULFANYL, SULFINYL OR SULFONYL)-3-SUBSTITUTED ALKYL, ARYL OR HETEROARYLAMIDES AS MATRIX METALLOPROTEINASE INHIBITORS

This is a divisional of copending application(s) Ser. No. 09/587560 filed on Jun. 5, 2000 (now Pat. No. 6,331,563), which is a divisional of Ser. No. 09/140,504 filed Aug. 26, 1998 (now U.S. Pat. No. 6,197,791), which is a continuation-in-part of U.S. Ser. No. 09/026,372 filed Feb. 19, 1998, which claims the benefit of U.S. Ser. No. 60/038,899 filed Feb. 27, 1997; the entire disclosure of each prior application is hereby incorporated by reference.

BACKGROUND OF THE INVENTION

Matrix metalloproteinases (MMPs) are a group of enzymes that have been implicated in the pathological destruction of connective tissue and basement membranes. These zinc containing endopeptidases consist of several subsets of enzymes including collagenases, stromelysins and gelatinases. Of these classes, the gelatinases have been shown to be the MMPs most intimately involved with the growth and spread of tumors. It is known that the level of expression of gelatinase is elevated in malignancies, and that gelatinase can degrade the basement membrane which leads to tumor metastasis. Angiogenesis, required for the growth of solid tumors, has also recently been shown to have a gelatinase component to its pathology. Furthermore, there is evidence to suggest that gelatinase is involved in plaque rupture associated with atherosclerosis. Other conditions mediated by MMPs are restenosis, MMP-mediated osteopenias, inflammatory diseases of the central nervous system, skin aging, tumor growth, osteoarthritis, rheumatoid arthritis, septic arthritis, corneal ulceration, abnormal wound healing, bone disease, proteinuria, aneurysmal aortic disease, degenerative cartilage loss following traumatic joint injury, demyelinating diseases of the nervous system, cirrhosis of the liver, glomerular disease of the kidney, premature rupture of fetal membranes, inflammatory bowel disease, periodontal disease, age related macular degeneration, diabetic retinopathy, proliferative vitreoretinopathy, retinopathy of prematurity, ocular inflammation, keratoconus, Sjogren's syndrome, myopia, ocular tumors, ocular angiogenesis/neo-vascularization and corneal graft rejection. For recent reviews, see: (1) Recent Advances in Matrix Metalloproteinase Inhibitor Research, R. P. Beckett, A. H. Davidson, A. H. Drummond, P. Huxley and M. Whittaker, Research Focus, Vol. 1, 16–26, (1996), (2) Curr. Opin. Ther. Patents (1994) 4(1): 7–16, (3) Curr. Medicinal Chem. (1995) 2: 743–762, (4) Exp. Opin. Ther. Patents (1995) 5(2): 1087–110, (5) Exp. Opin. Ther. Patents (1995) 5(12): 1287–1196.

TNF-α converting enzyme (TACE) catalyzes the formation of TNF-α from membrane bound TNF-α precursor protein. TNF-α is a pro-inflammatory cytokine that is now thought to have a role in rheumatoid arthritis, septic shock, graft rejection, cachexia, anorexia, inflammation, congestive heart failure, inflammatory disease of the central nervous system, inflammatory bowel disease, insulin resistance and HIV infection in addition to its well. documented antitumor properties. For example, research with anti- TNF-α antibodies and transgenic animals has demonstrated that blocking the formation of TNF-α inhibits the progression of arthritis. This observation has recently been extended to humans as well.

It is expected that small molecule inhibitors of MMPs and TACE therefore have the potential for treating a variety of disease states. While a variety of MMP and TACE inhibitors have been identified and disclosed in the literature, the vast majority of these molecules are peptidic and peptide-like compounds that one would expect to have bioavailability and pharmacokinetic problems common to such compounds that would limit their clinical effectiveness. Low molecular weight, potent, long acting, orally bioavailable inhibitors of MMPs and/or TACE are therefore highly desirable for the potential chronic treatment of the above mentioned disease states.

Recently, two references have appeared (U.S. Pat. No. 5,455,258 and European Patent Appl. 606,046) that disclose arylsulfonamido-substituted hydroxyamic acids. These documents cover compounds exemplified by CGS 27023A. These are the only non-peptide matrix metalloproteinase inhibitors disclosed to date.

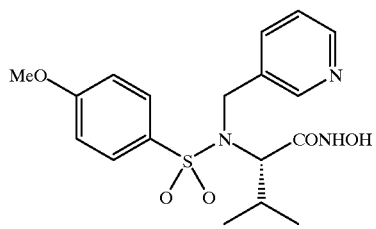

CGS 27023A

Salah et al., Liebigs Ann. Chem. 195, (1973) discloses some aryl substituted thio and aryl substituted sulfonyl acetohydroxamic acid derivatives of general formula 1. These compounds were prepared to study the Mannich reaction. Subsequently, they were tested for their fungicidal activity.

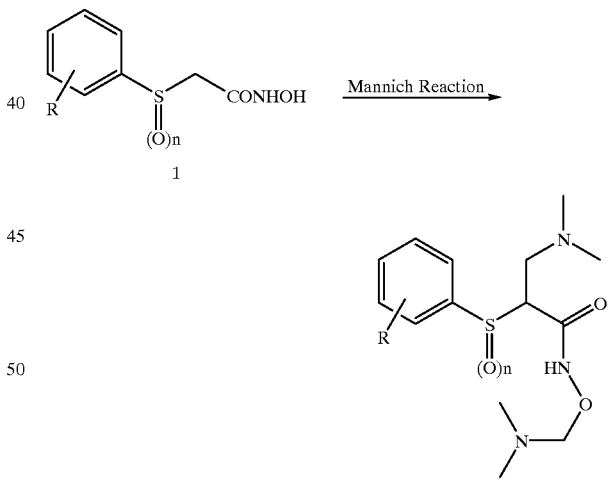

Some sulfone carboxylic acids are disclosed in U.S. Pat. No. 4,933,367. Those compounds were shown to exhibit hypoglycemic activity.

SUMMARY OF THE INVENTION

The present invention relates to novel, low molecular weight, non-peptide inhibitors of matrix metalloproteinases (MMPs) and TNF-α converting enzyme (TACE) for the treatment of arthritis, tumor metastasis, tissue ulceration, abnormal wound healing, periodontal disease, bone disease, diabetes (insulin resistance) and HTV infection.

In accordance with this invention there is provided a group of compounds of general formula I

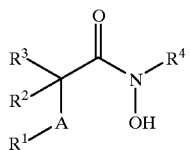

wherein:
 $R^1$ is alkyl of I to 18 carbon atoms, optionally substituted with one or two groups selected independently from $R^5$;
  alkenyl of 3 to 18 carbon atoms having 1 to 3 double bonds, optionally substituted with one or two groups selected independently from $R^5$;
  alkynyl of 3 to 18 carbon atoms having 1 to 3 triple bonds, optionally substituted with one or two groups selected independently from $R^5$;
  aryl of 6 to 10 carbon atoms, optionally substituted with one or two groups selected independently from $R^5$;
  cycloalkyl of 3 to 8 carbon atoms, optionally substituted with one or two groups selected independently from $R^5$;
  saturated or unsaturated 5 to 10 membered mono or bicyclic heterocycle containing one heteroatom selected from O, S or $NR^7$, optionally substituted with one or two groups independently from $R^5$;
  or heteroaryl-$(CH_2)_{0-6}$— wherein the heitroayl group is 5 to 6 membered with one or two heteroatoms selected independently from O, S, and N and may be optionally substituted with one or two groups selected independently from $R^5$;
 A is —S—, —SO— or $SO_2$—;
 $R^2$ and $R^3$, taken with the carbon atom to which they are attached, form a 5 to 7 membered heterocyclic ring contaning O, S or N—$R^7$ optionally having one or two double bonds;
 $R^4$ is hydrogen,
  alkyl of 1 to 6 carbon atoms, optionally substituted with one or two groups selected independently from $R^5$;
  alkenyl of 3 to 18 carbon atoms having 1 to 3 double bonds, optionally substituted with one or two groups selected independently from $R^5$;
  alkynyl of 3 to 18 carbon atoms having 1 to 3 triple bonds, optionally substituted with one or two groups selected independently from $R^5$;
  phenyl or naphthyl optionally substituted with one or two groups selected independently from $R^5$;
  $C_3$ to $C_8$ cycloalkyl or bicycloalkyl optionally substituted with one or two groups selected independently from $R^5$;
  saturated or unsaturated 5 to 10 membered mono or bicyclic heterocycle containing one heteroatom selected from O, S or $NR^7$, optionally substituted with one or two groups selected independently from $R^5$;
 $R^5$ is H, $C_7$–$C_{11}$ aroyl, $C_2$–$C_6$ alkanoyl, $C_1$ to $C_{12}$ alkyl, $C_2$ to $C_{12}$ alkenyl, $C_2$–$C_{12}$ alkynyl, F, Cl, Br, I, CN, CHO, $C_1$–$C_6$ alkoxy, aryloxy, heteroaryloxy, $C_3$–$C_6$ alkenyloxy, $C_3$–$C_6$ allyloxy, $C_1$–$C_6$ alkoxyaryl, $C_1$–$C_6$ alkoxyheteroaryl, $C_1$–$C_6$ alkylamino-$C_1$–$C_6$ alkoxy, $C_1$–$C_2$ alkylene dioxy, aryloxy-$C_1$–$C_6$ alkyl amine, $C_1$–$C_{12}$ perfluoro alkyl, $S(O)_n$—$C_1$–$C_6$ alkyl, $S(O)_n$-aryl where n is 0, 1 or 2; OCOO $C_1$–$C_6$ ayl, OCOOaryl, $OCONR^6$, COOH, COO $C_1$–$C_6$ alkyl, COOaryl, $CONR^6R^6$, CONHOH, $NR^6R^6$, $SO_2NR^6R^6$, $NR^6SO_2$aryl, —$NR^6CONR^6R^6$, $NHSO_2CF_3$, $SO_2$NHheteroaryl,$SO_2$NHCOaryl, $CONHSO_2$-$C_1$–$C_6$ alkyl, $CONHSO_2$aryl, $SO_2$NHCOaryl, $CONHSO_2$-$C_1$–$C_6$ alkyl, $CONHSO_2$aryl, $NH_2$, OH, aryl, heteroaryl, $C_3$ to $C_8$ cycloalkyl; or saturated or unsaturated 5 to 10 membered mono or bicyclic heterocycle containing one heteroatom selected from O, S or $NR^7$, wherein $C_1$–$C_6$
  alkyl is straight or branched, heteroaryl is a 5–10 membered mono or bicyclic heteroaryl group having 1 to 3 heteroatoms selected independently from O, S or $NR^7$ and aryl is phenyl or naphthyl, optionally substituted by 1 or 2 groups selected from halogen, cyano, amino, nitro, $C_1$–$C_6$ alyl, $C_1$–$C_6$ alkoxy, or hydroxy;
 $R^6$ is H, $C_1$ to $C_8$ alkyl optionally substituted with OH; $C_3$ to $C_6$ alkenyl, $C_3$ to $C_6$ alkyl, $C_1$ to $C_6$ perfluoro alkyl, $S(O)_n$-$C_1$–$C_6$ alkyl $S(O)_n$ aryl where n is 0, 1 or 2;, or COheteroaryl, wherein heteroaryl is a 5–10 membered mono or bicyclic heteroaryl group having 1 to 3 heteroatoms selected independently from O, S or $NR^7$ and aryl is phenyl or naphthyl, optionally substituted by 1 or 2 groups selected from halogen, cyano, amino, nitro, $C_1$–$C_6$ alkyl, $C_1$–$C_6$ alkoxy, or hydroxy;
 and $R^7$ is $C_7$–$C_{11}$ aroyl, $C_2$–$C_6$ alkanoyl, $C_1$–$C_{12}$ perfluoro alkyl, $S(O)_n$—$C_1$–$C_6$-alkyl, $S(O)_n$-aryl where n is 0, 1 or 2; COO-$C_1$–$C_6$-alkyl, COOaryl, CONR6, $CONR^6R^6$, CONHOH, $SO_2NR^6R^6$, $SO_2CF_3$, $SO_2$NHheteroaryl, $SO_2$NHCOaryl, $CONHSO$-$C_1$–$C_6$-alkyl, $CONHSO_2$aryl, aryl, or heteroaryl, where aryl is phenyl or naphthyl, optionally substituted by 1 or 2 groups selected independently from halogen, cyano, amino, nitro, $C_1$–$C_6$ alkyI, $C_1$–$C_6$ alkoxy, or hydroxy; and heteroaryl is a 5–10 membered mono or bicyclic heteroaryl group having 1 to 3 heteroatoms selected independently from O, S or N—$C_1$–$C_6$ alkyl;
  alkyl of 1 to 18 carbon atoms, optionally substituted with one or two groups selected independently from $R^5$;
  alkenyl of 3 to 18 carbon atoms having from 1 to 3 double bonds, optionally substituted with one or two groups selected independently from $R^5$;
  alkynyl 3 to 8 carbon atoms having from 1 to 3 triple bonds, optionally substituted with one or two groups selected independently from $R^5$;
  arylalkyl of 7 to 16 carbon atoms, wherein aryl is optionally substituted with one or two groups selected independently from $R^5$;
  heteroarylalkyl wherein alkyl is from 1 to 6 carbon atoms and heteroaryl contains 1 or 2 heteroatoms selected from O, S or N and is optionally substituted with one or two groups selected independently from $R^5$;
  biphenylalkyl of 13 to 18 carbon atoms, wherein biphenyl is optionally substituted with one or two groups selected independently from $R^5$;
  arylalkenyl of 8 to 16 carbon atoms, wherein aryl is optionally substituted with one or two groups selected independently from $R^5$;
  cycloalkylalyl or bicycloalylakyl of 4 to 12 carbon atoms, wherein the cycloalkyI or bicycloalkyl group is optionally substituted with one or two groups selected independently from $R^5$;

saturated or unsaturated mono or bicyclic heterocycle containilg one heteroatom selected from O, S or N—$C_1$–$C_6$ alky, optionally substituted with one or two groups selected independently from $R^5$; or $R^8R^9N$–$C_1$–$C_6$-alkoxyaryl-$C_1$–$C_6$-alkyl where $R^8$ and $R^9$ are independently selected from $C_1$–$C_6$ alkl or $R^8$ and $R^9$ together with the interposed nitrogen forms a 5–7 membered saturated heterocyclic ring optionally containing an oxygen atom, wherein the aryl group is phenyl or naphthyl;

and the pharmaceutically acceptable salts thereof.

A more preferred aspect of the present invention is the group of compounds of general formula (Ia):

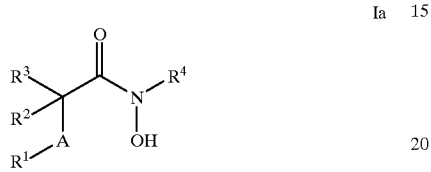

wherein:
$R^1$ is alkl of 1 to 18 carbon atoms, optionally substituted with one or two groups selected independently from $R^5$;
  alkenyl of 3 to 18 carbon atoms having 1 to 3 double bonds, optionally substituted with one or two groups selected independently from $R^5$;
  alkynyl of 3 to 18 carbon atoms having 1 to 3 triple bonds, optionally substituted with one or two groups selected independently from $R^5$;
  aryl of 6 to 10 carbon atoms, optionally substituted with one to two groups selected independently from $R^5$;
  cycloalkyl of 3 to 8 carbon atoms, optionally substituted with one to two groups selected independently from $R^5$;
  saturated or unsaturated mono or bicyclic heterocycle of from 5 to 10 members containing one heteroatom selected from O, S or $NR^7$, optionally substituted with one to two groups selected independently from $R^5$;
  or heteroaryl-$(CH_2)_{0-6}$- wherein the heteroaryl group is 5 to 6 membered with one or two heteroatoms selected independently from O, S, and N and may be optionally substituted with one or two groups selected independently from $R^5$;
A is —S—, —SO— or $SO_2$—;
$R^2$ and $R^3$, taken with the carbon atom to which they are attached, form a 5 to 7 membered heterocyclic ring containing O, S or N—$R^7$ optionally having one or two double bonds;
$R^4$ is hydrogen,
  alkyl of 1 to 6 carbon atoms, optionally substituted with one or two groups selected independently from $R^5$;
  alkenyl of 3 to 18 carbon atoms having 1 to 3 double bonds, optionally substituted with one or two groups selected independently fronm $R^5$;
  alkynyl of 3 to 18 carbon atoms having 1 to 3 triple bonds, optionally substituted with one or two groups selected independently from $R^5$;
  phenyl or naphthyl optionally substituted with one or two groups selected independently from $R^5$;
  $C_3$ to $C_8$ cycloalkyl or bicycloalkyl optionally substituted with one or two groups selected independently from $R^5$;

$R^5$ is H, F, Cl, Br, I, CN, CHO, $C_7$–$C_{11}$ aroyl, $C_2$–$C_6$ alkanoyl, $C_1$ to $C_{12}$ alkyl, $C_2$ to $C_{12}$ alkenyl, $C_2$–$C_{12}$ alkynyl, $C_1$–$C_6$ alkoxy, aryloxy, heteroaryloxy, $C_3$–$C_6$ alkenyloxy, $C_3$–$C_6$ alknyloxy, $C_1$–$C_6$ alkoxyaryl, $C_1$–$C_6$ alkoxyheteroaryl, $C_1$–$C_6$-alkylamino-$C_1$–$C_6$ alkoxy, $C_1$–$C_2$-alkylene dioxy, aryloxy-$C_1$–$C_6$ alkyl amine, $C_1$–$C_{12}$perfluoro alkyl, $S(O)_n$–$C_1$–$C_6$ alkyl, $S(O)_n$-aryl where n is 0, 1 or 2; $OCOO$-$C_1$–$C_6$ alkyl, OCOaryl, $OCONR^6$, COOH, COO-$C_1$–$C_6$ alyl, COOaryl, $CONR^6R^6$, CONHOH, $NR^6R^6$, $SO_2NR^6R^6$, $NR^6SO_2$aryl, $NR^6CONR^6R^6$, $NHSO_2CF_3$, $SO_2$NHheteroaryl, $SO_2$NHCOaryl, $CONHSO_2$–$C_1$–$C_6$ alkyl, $CONHSO_2$aryl, $SO_2NHCO$aryl, $CONHSO_2$–$C_1$–$C_6$ alkyl, $CONHSO_2$aryl, $NH_2$, OH, aryl, heteroaryl, $C_3$ to $C_8$ cycloalkyl; or saturated or unsaturated 5 to 10 membered mono or bicyclic heterocycle containing one heteroatom selected from O, S or $NR^7$;
  wherein heteroaryl is a 5–10 membered mono or bicyclic heteroaryl group having 1 to 3 heteroatoms selected independently from O, S or $NR^7$ and aryl is phenyl or naphthyl, optionally substituted by 1 or 2 groups selected independently from halogen, cyano, amino, nitro, $C_1$–$C_6$ alkyl, $C_1$–$C_6$ alkoxy, or hydroxy;
$R^6$ is H, $C_1$ to $C_{18}$ alkyl optionally substituted with OH; $C_3$ to $C_6$ alkenyl, $C_3$ to $C_6$ alkynyl, $C_1$ to $C_6$ perfluoro alkyl, $S(O)_n$ alkyl or aryl where n is 0, 1, or 2; or COheteroaryl;
  wherein heteroaryl is a 5–10 membered mono or bicyclic heteroaryl group having 1 to 3 heteroatoms selected independently from 0, S or $NR^7$ and aryl is phenyl or naphthyl, optionally substituted by 1 or 2 groups selected from halogen, cyano, amino, nitro, $C_1$–$C_6$ alkyl, $C_1$–$C_6$ alkoxy, or hydroxy;
and $R^7$ is $C_7$–$C_{11}$ aroyl, $C_2$–$C_6$ alkanoyl, $C_1$–$C_{12}$ perfluoro alkyl, $S(O)_n$-alkyl, $S(O)_n$-aryl where n is 0, 1 or 2; COalkyl, COOaryl, $CONHR^6$, $CONR^6R^6$, CONHOH, $SO_2NR^6R^6$,$SO_2CF_3$, $SO_2$NHheteroaryl, $SO_2$NHCOaryl, $CONHSO_2$alkyl, $CONHSO_2$aryl, aryl, heteroaryl; wherein $C_1$–$C_6$ alkyl is straight or branched, heteroaryl is a 5–10 membered mono or bicyclic heteroaryl group having 1 to 3 heteroatoms selected independently from O, S or $NR^7$ and aryl is phenyl or naphthyl, optionally substituted by 1 or 2 groups selected from halogen, cyano, amino, nitro, $C_1$–$C_6$ alkyl, $C_1$–$C_6$ alkoxy, or hydroxy;
  alkyl of 1 to 18 carbon atoms, optionally substituted with one or two groups selected independently from $R^5$;
  alkenyl of 3 to 18 carbon atoms having from 1 to 3 double bonds, optionally substituted with one or two groups selected independently from $R^5$;
  alkynyl of 3 to 18 carbon atoms having from 1 to 3 triple bonds, optionally substituted with one or two groups selected independently from $R^5$;
  arylalkyl of 7 to 16 carbon atoms, wherein aryl is optionally substituted with one or two groups selected independently from $R^5$;
  heteroarylalkyl wherein alkyl is from 1 to 6 carbon atoms and heteroaryl contains 1 or 2 heteroatoms selected from O, S or N and is optionally substituted with one or two groups selected independently from $R^5$;
  biphenylalkyl of 13 to 18 carbon atoms, wherein biphenyl is optionally substituted with one or two groups selected independently from $R^5$;

arylalkenyl of 8 to 16 carbon atoms, wherein aryl is optionally substituted with one or two groups selected independently from $R^5$;

cycloalkylalkyl or bicycloalrlalkyl of 4 to 12 carbon atoms, wherein cycloalkyl or bicycloalkyl is optionally substituted with one or two groups selected independently from $R^5$;

saturated or unsaturated mono or bicyclic heterocycle containing one heteroatom selected from O, S or N–$C_1$–$C_6$ alkyl, optionally substituted with one or two groups selected independently from $R^5$;

$R^8R^9N$–$C_1$–$C_6$-alkoxyaryl-$C_1$–$C_6$-alkyl where $R^8$ and $R^9$ are independently selected from $C_1$–$C_6$ alkyl or $R^8$ and $R^9$ together with the interposed nitrogen forms a 5–7 membered saturated heterocyclic ring optionally containing an oxygen atom, wherein the aryl group is phenyl or naphthyl;

and the pharmaceutically acceptable salts thereof.

The most preferred group of compounds are those of the following formula (Ib):

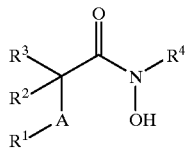

Ib in which $R^1$ is phenyl, naphthyl, alkyl of 1–18 carbon atoms or heteroaryl such as pyridyl, dienyl, imidazolyl or furanyl, optionally substituted with $C_1$–$C_6$ alkyl, $C_1$–$C_6$ alkoxy, $C_6$–$C_{10}$ aryloxy, heteroaryloxy, $C_3$–$C_6$ alkenyloxy, $C_3$–$C_6$ alkyloxy, halogen; or $S(O)_n$–$C_1$–$C_6$alkyl $C_1$–$C_6$ alkoxyaryl or $C_1$–$C_6$ alkoxyheteroaryl;

A is —S—, —SO or —$SO_2$—;

$R^2$ and $R^3$, taken with the carbon atom to which they are attached, form a 5 to 7 membered heterocyclic ring containing O, S or N—$R^7$ optionally having one or two double bonds;

$R^4$ is hydrogen, alkyl of 1 to 6 carbon atoms, optionally substituted with one or two groups selected independently from $R^5$;

alkenyl of 3 to 18 carbon atoms having 1 to 3 double bonds, optionally substituted with one or two groups selected independently from $R^5$;

alkynyl of 3 to 18 carbon atoms having 1 to 3 triple bonds, optionally substituted with one or two groups selected independently from $R^5$;

phenyl or naphthyl optionally substituted with one or two groups selected independently from $R^5$;

$C_3$ to $C_8$ cycloalkyl or bicycloallyl optionally substituted with one or two groups selected independently from $R^5$;

$R^5$ is H, $C_7$–$C_{11}$ aroyl, $C_2$–$C_6$ alkanoyl, $C_1$ to $C_{12}$ alkyl, $C_2$ to $C_{12}$ alkenyl, $C_2$–$C_{12}$ allynyl, F, Cl, Br, I, CN, CHO, $C_1$–$C_6$ alkoxy, aryloxy, heteroaryloxy, $C_3$–$C_6$ alkenyloxy, $C_3$–$C_6$ alkynyloxy, $C_1$–$C_6$ alkylamino-$C_1$–$C_6$ alkoxy, $C_1$–$C_2$ alkylene dioxy, aryloxy-$C_1$–$C_6$ alkyl amine, $C_1$–$C_{12}$ perfluoro alkyl, $S(O)_n$–$C_1$–$C_6$ alkyl, $S(O)_n$-aryl where n is 0, 1 or 2; OCOO $C_1$–$C_6$ aLkyl, OCOOayl, OCONR$^6$, COOH, COO $C_1$–$C_6$ alkyl, COaryl, CONR$^6$R$^6$, CONHOH, NR$^6$R$^6$, $SO_2N$ $^6R^6$, NR$^6SO_2$aryl —NR$^6$CONR$^6R^6$, NHSO$_2$CF$_3$, SO$_2$NHheteroaryl,SO$_2$NHCOaryl, CONHSO$_2$-$C_1$-$C_6$ alkyl, CONHSO$_2$aryl, SO$_2$NHCOaryl, CONHSO$_2$-$C_1$-$C_6$ alkyl, CONHSO$_2$aryl, NH$_2$, OH, aryl, heteroaryl, $C_3$ to $C_8$ cycloalkyl; saturated or unsaturated 5 to 10 membered mono or bicyclic heterocycle containing one heteroatom selected from O, S or NR$^7$, wherein $C_1$–$C_6$ aLkyl is straight or branched, heteroaryl is a 5–10 membered mono or bicyclic heteroaryl group having 1 to 3 heteroatoms selected independently from O, S or NR$^7$ and aryl is phenyl or naphthyl, optionally substituted by 1 or 2 groups selected from halogen, cyano, amino, nitro, $C_1$–$C_6$ alkyl, $C_1$–$C_6$ alkoxy, or hydroxy;

$R^6$ is H, $C_1$ to $C_{18}$ alkyl optionally substituted with OH; $C_3$ to $C_6$ alkenyl, $C_3$ to $C_6$ alkynyl, $C_1$ to $C_6$ perfluoro alkyl, $S(O)_n$ alkyl or aryl where n is 0, 1 or 2; or COheteroaryl; wherein heteroaryl is a 5–10 membered mono or bicyclic heteroaryl group having 1 to 3 heteroatoms selected independently from O, S or NR$^7$ and aryl is phenyl or naphthyl, optionally substituted by 1 or 2 groups selected from halogen, cyano, amino, nitro, $C_1$–$C_6$ alkyl, $C_1$–$C_6$ alkoxy, or hydroxy;

and $R^7$ is $C_7$-$C_{11}$ aroyl, $C_2$–$C_6$ alkanoyl, $C_1$–$C_{12}$ perfluoro alkyl, $S(O)_n$-alkyl, $S(O)_n$-aryl where n is 0, 1 or 2; COOalkl, COOaryl CONHR$^6$, CONR$^6R^6$, CONHOH, SO$_2$NR$^6R^6$,SO$_2$CF$_3$, SO$_2$NHheteroaryl, SO$_2$NHCOaryl, CONHSO$_2$alkyI, CONHSO$_2$aryl aryl, or heteroaryl; where aryl is phenyl or naphthyl, optionally substituted by 1 or 2 groups selected independently from halogen, cyano, amino, nitro, $C_1$–$C_6$ alkyl, $C_1$–$C_6$ alkoxy, or hydroxy; and heteroaryl is a 5–10 membered mono or bicyclic heteroaryl group having 1 to 3 heteroatoms selected independently from O, S or N—$C_1$–$C_6$ alkyl;

alkyl of 1 to 18 carbon atoms, optionally substituted with one or two groups selected independently from $R^5$;

alkenyl of 3 to 18 carbon atoms having from 1 to 3 double bonds, optionally substituted with one or two groups selected independently from $R^5$;

alkynyl of 3 to 18 carbon atoms having from 1 to 3 triple bonds, optionally substituted with one or two groups selected independently from $R^5$;

arylalkyl of 7 to 16 carbon atoms, optionally substituted with one or two groups selected independently from $R^5$;

heteroarylalkyl wherein alkyl is from 1 to 6 carbon atoms and heteroaryl contains 1 or 2 heteroatoms selected from O, S or N and is optionally substituted with one or two groups selected independently from $R^5$;

biphenylalkyl of 13 to 18 carbon atoms, optionally substituted with one or two groups selected independently from $R^5$;

arylalkenyl of 8 to 16 carbon atoms, optionally substituted with one or two groups selected independently from $R^5$;

cycloalkylalkyl or bicycloalkylalkyl of 4 to 12 carbon atoms, optionally substituted with one or two groups selected independently from $R^5$;

saturated or unsaturated mono or bicyclic heterocycle containing one heteroatom selected from O, S or NR–$C_1$–$C_6$ alkyl, optionally substituted with one or two groups selected independently from $R^5$;

$R^8R^9N$–$C_1$–$C_6$-alkoxyaryl-$C_1$–$C_6$-alkyl where $R^8$ and $R^9$ are independently selected from $C_1$–$C_6$ alkyl or $R^8$ and $R^9$ together with the interposed nitrogen forms a 5–7 membered saturated heterocyclic ring optionally containing an oxygen atom, wherein the aryl group is phenyl or naphthyl;

and the pharmaceutically acceptable salts thereof.

The most preferred matrix metalloproteinase and TACE inhibiting compounds of this invention are:

1-benzyl-4-(4-methoxy-benzenesulfonyl)-piperidine-4-carboxylic acid hydroxyamide, 4-(4-methoxy-benzenesulfonyl)-1-(3-methoxy-benzyl)-piperidine-4-carboxylic acid hydroxyamide, 1-(3,4-dichlorobenzyl)-4-(4-methoxy-benzenesulfonyl)-piperidine-4-carboxylic acid hydroxamide, 4-(4methoxy-benzenesulfonyl)-1-(4-methylbenzyl)-piperidine-4-carboxylic acid hydroxamide, 4-(4-methoxy-benzene-sulfonyl)-1-napthalene-2-yl-methylpiperidine-4-carboxylic acid hydroxamide, 1-biphenyl-4-ylmethyl-4-(4-methoxy-benzenesulfonyl) piperidine-4-carboxylic acid hydroxamnide, 4-(4-methoxy-benzene-sulfonyl)-1-(3-methyl-but-2-enyl) piperidine-4-carboxylic acid hydroxamide, 1-(4-bromo-benzyl)4-(4-methoxy-benzenesulfonyl)-piperidine-4-carboxylic acid hydroxamide, 4-(4-methoxy-benzenesulfonyl)-1-(3-phenyl-propyl)-piperidine-4-carboxylic acid hydroxyamide, 1-tert-butyl-4-(4methoxy-benzenesulfonyl)-piperidine-4-carboxylic acid hydroxamide, 1-butyl-4-(4-methoxy-benzenesulfonyl)-piperidine-4-carboxylic acid hydroxyamide, 1-cyclooctyl-4-(4methoxy-benzenesulfonyl)-piperidine-4-carboxylic acid hydroxyamide, 1-ethyl-4-(4-(methoxy-benzenesulfonyl)-piperidine-4-carboxylic acid hydroxyamide, 1-isopropyl-4-(4-methoxy-benzenesulfonyl)-piperidine-4-carboxylic acid hydroxyarnide, 1-methyl-4-(4-methoxy-benzenesulfonyl)-piperidine4-carboxylic acid hydroxyamide, 1-benzyl-4-(4-butoxy-benzenesulfonyl)-piperidine-4-carboxylic acid hydroxyamide, 1-(4-fluoro-benzyl)-4-(4-methoxy-benzenesulfonyl)-piperidine-4-carboxylic acid hydroxyamide, 1-(4-fluoro-benzyl)-4-(4-butoxy-benzenesulfonyl)-piperidine-4-carboxylic acid hydroxyamide, 4-(4-methoxy-benzenesulfonyl)-1-(4-methoxy-benzyl)-piperidine-4-carboxylic acid hydroxyamide, 4-(4-methoxy-benzenesulfonyl)-1-[2-(4-methoxyphenyl) ethyl]-piperidine-4-carboxylic acid hydroxyamide, 4-(4-methoxy-benzenesulfonyl)-1-(2-phenyl-ethyl)-piperidine-4-carboxylic acid hydroxyamide, 4-(4-n-butoxy-benzenesulfonyl)-1-(4-methoxy-benzyl)-piperidine-4-carboxylic acid hydroxyamide, 4-(4-methoxy-benzenesulfonyl)-1-(3-phenoxy-propyl)-piperidine-4-carboxylic acid hydroxyamide, 4-(4-n-butoxy-benzenesulfonyl)-1-(3-phenoxy-propyl)-piperidine-4-carboxylic acid hydroxyamide, 4-(4-methoxy-benzenesulfonyl)-1-(2-phenoxy-ethyl)-piperidine-4-carboxylic acid hydroxyamide, 4-(4-n-butoxy-benzenesulfonyl)-1-(2phenoxyethyl)-piperidine-4-carboxylic acid hydroxyamide, 4-(4-methoxy-benzenesulfonyl)-1-[4-(2-piperidin-1-yl-ethoxy)-benzyl]-piperidine-4-carboxylic acid hydroxyamide, 1-Benzyl-4-(4-benzyloxy-benzenesulfonyl)-piperidine-4-carboxylic acid hydroxyamide, 4-(4-Butoxy-benzenesulfonyl)-1-[4-(2-piperidin-1-yl-ethoxy)-benzyl]-piperidine-4-carboxylic acid hydroxyamide, 4-(4-Butoxy-benzenesulfonyl)-1-[3-(2-morpholinyl-1-yl-ethoxy)-benzyl]-piperidine-4-carboxylic acid hydroxyamide, 1-Methyl-4-(4-butoxy-benzenesulfonyl)-piperidine-4-carboxylic acid hydroxyamide, 1-Ethyl-4-(4-butoxy-benzenesulfonyl)-piperidine-4-carboxylic acid hydroxyamide, 1-n-Butyl-4-(4-butoxy-benzenesulfonyl)-piperidine-4-carboxylic acid hydroxyamide, 4-[4-(4-chloro-phenoxy)-benzenesulfonyl]1-methyl-piperidine-4-carboxylic acid hydroxyamide, 4-[4-(4-chlorophenoxy)-benzenesulfonyl]1-ethyl-piperidine-4-carboxylic acid hydroxyamide, 1-Butyl-4-[4-(4-chloro-phenoxy)-benzenesulfonyl]-piperidine-4-carboxylic acid hydroxyamide, 1-Benzyl-4-[4-(4-chorophenoxy)-benzenesulfonyl]-piperidine-4-carboxylic acid hydroxyamide, 1-Benzyl-4-[4-(3-methyl-butoxy)-benzenesulfonyl]-piperidine-4-carboxylic acid hydroxyamide, 1-Butyl-4-[4-(3-methyl-butoxy)-benzenesulfonyl]-piperidine-4-carboxylic acid hydroxyamide, 1-Benzyl-4-[4-(2-ethyl-butoxy)-benzenesulfonyl]-piperidine-4-carboxylic acid hydroxyamide, 4-(4-butoxy-benzenesulfonyl)-1-(3-methoxy-benzyl)-piperidine-4-carboxylic acid hydroxyamide, 4-(4-Methoxy-benzenesulfonyl)-1-(4-thiophen-2-yl-benzyl)-piperdine-4-carboxylic acid hydroxyamide, 4-(4-methoxy-benzenesulfonyl)-1-(4-pyridin-2-yl-benzyl)-piperidine-4-carboxylic acid hydroxyamide, 1-(3,4-Dichlorobenzyl)-4-(4-butoxy-benzenesulfonyl)-piperidine-4-carboxylic acid hydroxyamide,

[4-(4-Chloro-benzyloxy)-benzenesulfonyl]-1-methylpiperidine-4-carboxylic acid hydroxamide, 4-(4-Butoxy-benzenesulfonyl)-1-(3-phenoxy-benzyl)-piperidine-4-carboxylic acid hydroxamide,

[4-(4-Chloro-benzyloxy)-benzenesulfonyl]-1-(4-methylbenzyl)-piperidine-4-carboxylic acid hydroxamide, 4-(4-Butoxy-benzenesulfonyl)-1-(4methylbenzyl)-piperidine-4-carboxylic acid hydroxyamide, 4-(4-Butoxy-benzenesulfonyl)-1-(4-cyano-benzyl)-piperidine-4-carboxylic acid hydroxyamide, and 4-(4-Butoxy-benzenesulfonyl)-1-pyridin-4-ylmethyl-piperidine-4-carboxylic acid hydroxyamide, and pharmaceutical salts thereof.

It is understood that the definition of the compounds of formulas I, Ia and Ib, when $R^1$, $R^2$, $R^3$ and $R^4$ contains asymmetric carbons, encompass all possible stereoisomers and mixtures thereof which posses the activity discussed below. In particular, it encompasses racemic modifications and any optical isomers which possesses the indicated activity. Optical isomers may be obtained in pure form by standard separation techniques. Where not stated otherwise, the term "alkyl" refers to a straight or branched $C_1$–$C_6$ alkyl group and aryl is phenyl or naphthyl. The ph&mceutically acceptable salts are those derived from pharmaceutically acceptable organic and inorganic acids such as lactic, citric, acetic, tartaric, succinic, maleic, malonic, hydrochloric, hydrobromic, phosphoric, nitric, sulfiric, methanesulfonic, and similarly known acceptable acids.

The present invention accordingly provides a pharmaceutical composition which comprises a compound of this invention in combination or association with a pharmaceutically acceptable carrier. In particular, the present invention provides a pharmaceutical composition which comprises an effective amount of compound of this invention and a pharmaceutically acceptable carrier.

The compositions are preferably adapted for oral administration. However, they may be adapted for other modes of administration, for example, parenteral administration for patients.

In order to obtain consistency of administration, it is preferred that a composition of the invention is in the form of a unit dose. Suitable unit dose forms include tablets, capsules, and powders in sachets or vials. Such unit dose forms may contain from 0.1 to 100 mg of a compound of the invention. The compounds of the present invention can be administered orally at a dose range of about 0.01 to 100 mg per kg. Such composition may be administered from 1 to 6 times a day, more usually from 1 to 4 times a day.

The compositions of the invention may be formulated with conventional excipients, such as fillers, a disintegrating agent, a binder, a lubricant, a flavoring agent, and the like. They are formulated in conventional manner.

Also according to the present invention, there are provided processes for producing the compounds of the present invention.

PROCESS OF THE INVENTION

The compounds of the present invention may be prepared according to one of the general processes out lined below.

The appropriately substituted mercaptan derivative was allated using either substituted (Scheme I) or unsubstituted (Scheme 2) α-bromo acetic acid ester derivative in refluxin acetone using $K_2CO_3$ as base. The sulphide derivative thus obtained was oxidized using m-chloroperbenzoic acid in $CH_2Cl_2$ or by using Oxone in methanol/water. The sulfone obtained from the above mentioned process can be either filrter alkylated using variety of alkyl halides to obtain the disubstituted derivative or it can be hydrolyzed using NaOH/MeOH at room temp. However instead of using the ethyl ester, if the tertiary butyl ester is present, the hydrolysis can be carried out with $TFA/CH_2Cl_2$ at room temperature. Subsiquently, the carboxylic acid obtained was converted to the hydroxamic acid derivative by reaction with oxalyl chloride/DMX (catalytic) and hydroxyl amine/triethyl amine.

SCHEME 1

SYNTHESIS:

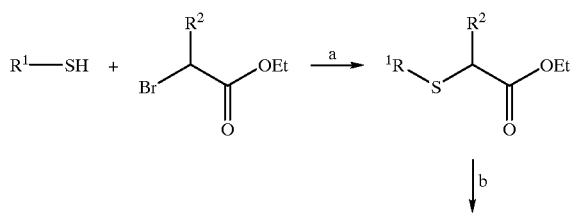

-continued

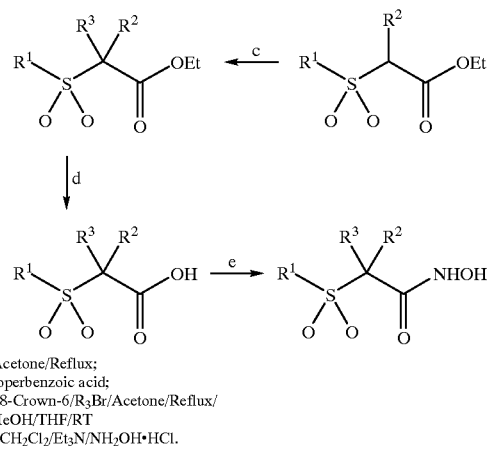

a. $K_2CO_3$/Acetone/Reflux;
b. m-Chloroperbenzoic acid;
c. $K_2CO_3$/18-Crown-6/$R_3$Br/Acetone/Reflux/
d. NaOH/MeOH/THF/RT
e. $(COCl)_2/CH_2Cl_2/Et_3N/NH_2OH \cdot HCl$.

SCHEME 2

SYNTHESIS:

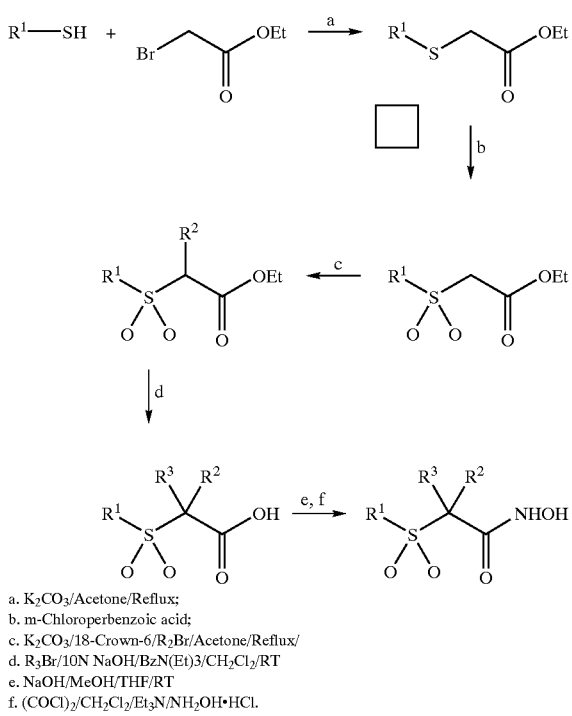

a. $K_2CO_3$/Acetone/Reflux;
b. m-Chloroperbenzoic acid;
c. $K_2CO_3$/18-Crown-6/$R_2$Br/Acetone/Reflux/
d. $R_3$Br/10N NaOH/BzN(Et)3/$CH_2Cl_2$/RT
e. NaOH/MeOH/THF/RT
f. $(COCl)_2/CH_2Cl_2/Et_3N/NH_2OH \cdot HCl$.

As outlined in Scheme 3, the sulfide derivative can be flirter allylated using lithium bis(trimethyl silyl)amide in THF at 0° C. The alkylated or mono substituted compound was hydrolyzed and converted to the hydroxamic acid derivative. The sulfinyl derivatives were prepared by oxidizing the sulfide hydroxamic acid derivatives with $H_2O_2$ in MeOH solution.

SCHEME-3

SYNTHESIS:

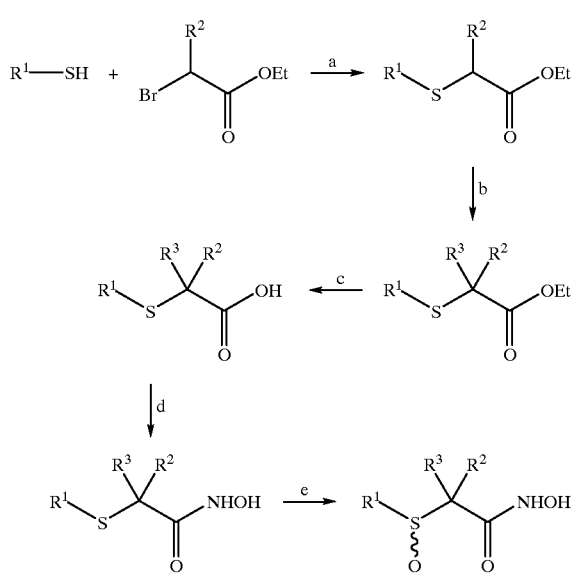

a. K$_2$CO$_3$/Acetone/Reflux;
b. R$_3$Br/HMDS/THF;
c. NaOH/MeOH/THF/RT
d. (COCl)$_2$/CH$_2$Cl$_2$/Et$_3$N/NH$_2$OH•HCl.
e. MeOH/H$_2$O$_2$/RT The corresponding 1-substituted-4-(4methoxy-benzenesulfonyl)-piperidine-4-carboxylic acid hydroxyamides were prepared startng from diethanolamine and appropriately substituted alkyl or aryl halides (Scheme 4). The N-substituted diethanol amine derivatives were converted to the dichioro compounds using thionyl chloride. The corresponding dichlorides were reacted with substituted sulfonyl acetic acid ethyl ester derivatives in the presence of K$_2$CO$_3$/18-Crown-6 in boiling acetone. 1-substituted-4-(methoxy-benzenesulfonyl)-piperidine-4-carboxylic acid ethyl esters thus obtained were converted to the hydroxy amide as outlined in Scheme 4. Alternatively these classes of compounds and other hetrocycles can be prepared as indicated in Scheme 5 and 6.

SCHEME 4

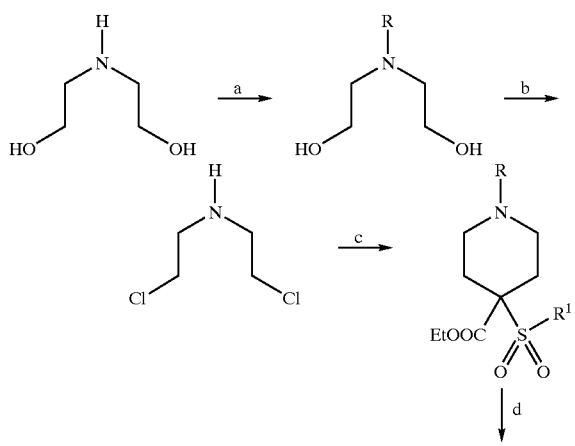

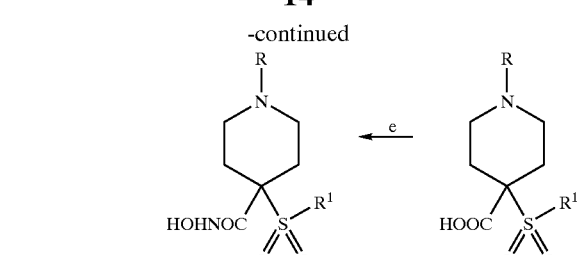

a. K$_2$CO$_3$/RBr/Acetone/Reflux
b. SOCl$_2$/CH$_2$Cl$_2$
c. R$^1$SO$_2$CH$_2$COOEt/K$_2$CO$_3$/18-Crown-6/Acetone/Reflux
d. NaOH/THF/MeOH/RT
e. (COCl)$_2$/NH$_2$OH•HCl/Et$_3$N

SCHEME 5

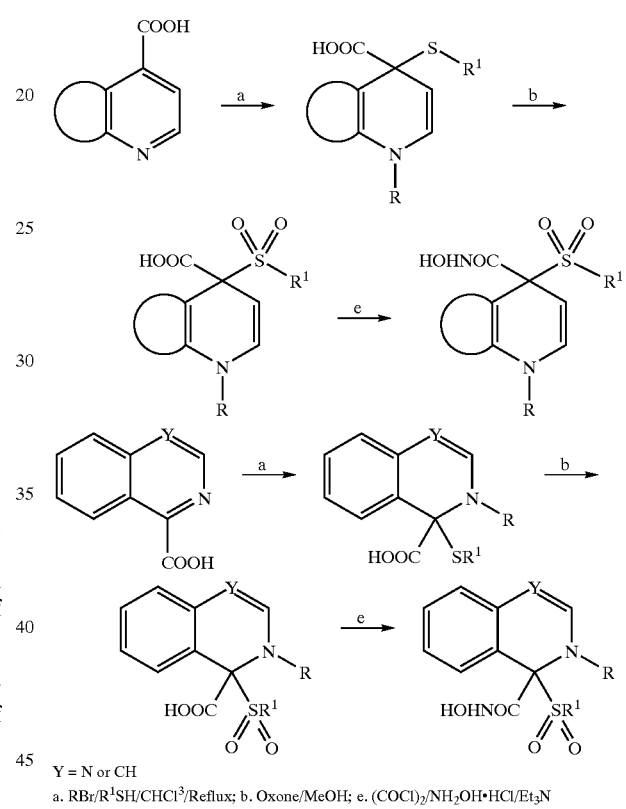

Y = N or CH
a. RBr/R$^1$SH/CHCl$^3$/Reflux; b. Oxone/MeOH; e. (COCl)$_2$/NH$_2$OH•HCl/Et$_3$N

SCHEME 6

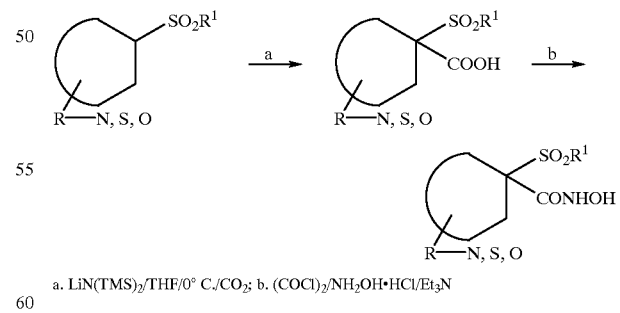

a. LiN(TMS)$_2$/THF/0° C./CO$_2$; b. (COCl)$_2$/NH$_2$OH•HCl/Et$_3$N

Alternatively, Schemes 7 to 11 show methods for the preparation of hydroxamic acid compounds using a solid phase support (P).

Scheme 7

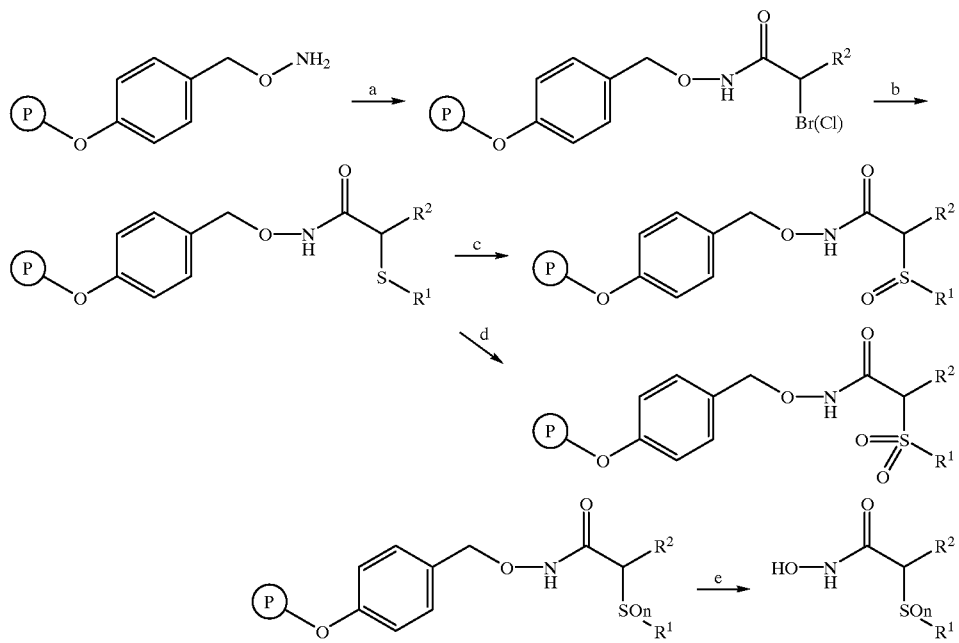

Reagents and Conditions: a) 2-Halo acid (3.0 eq.); 1-hydroxybenzotriazole hydrate (HOBt, 6.0 eq.); 1,3-diisopropylcarbodiimide (DIC, 4.0 eq.); DMF, 25° C.; 2–16 hours. b) Thiol (5.0 eq.); sodium iodide (5.0 eq.); 1,8-diazabicyclo[5.4.0]undec-7-ene (DBU, 3.0 eq.); THF; 25° C.; 12–16 hours. c) 70% tert-butylhydroperoxide (40 eq.); benzenesulfonic acid (2.0 eq.); DCM; 25° C.; 12–24 hours. d) mCPBA (5.0 eq.); DCM; 25° C.; 12–24 hours. e) TFA: DCM (1:1); 25° C.; 1 hour.

The 4-O-methylhydroxylamine-phenoxymethylopoly (styrene-1%-divinylbenzene)-resin (hydroxylamine resin) may be coupled with a 2-halo acid to give the hydroxamate ester resin. The coupling reaction may be carried out in the presence of carbodiimide, such as DIC, in an inert solvent such as DMF at room temperature. The halogen group may be displaced with a thiol in the presence of a base, such as DBU, in an inert solvent such as THF at room temperature. The sulfide may be oxidized to the sulfoxide by reaction with an oxifig agent such as tert-butylhydroperoxide in the presence of an acid catalyst such as benzenesulfonic acid, in an inert solvent such as DCM at room temperature. Alternatively, the sulfide may be oxidized to the sulfone by reaction with an oxidizing agent such as meta-chloroperoxybenzoic acid, in an inert solvent such as DCM at room temperature. The sulfide, sulfoxide, or sulfone may be treated with and acid, such as trifluoroacetic acid, in and inert solvent such as DCM to hlberate the fee hydroxamic acid.

Scheme 8 shows a method of preparing hydroxamic acids having alkoxy groups attached to the aromatic ring.

Scheme 8

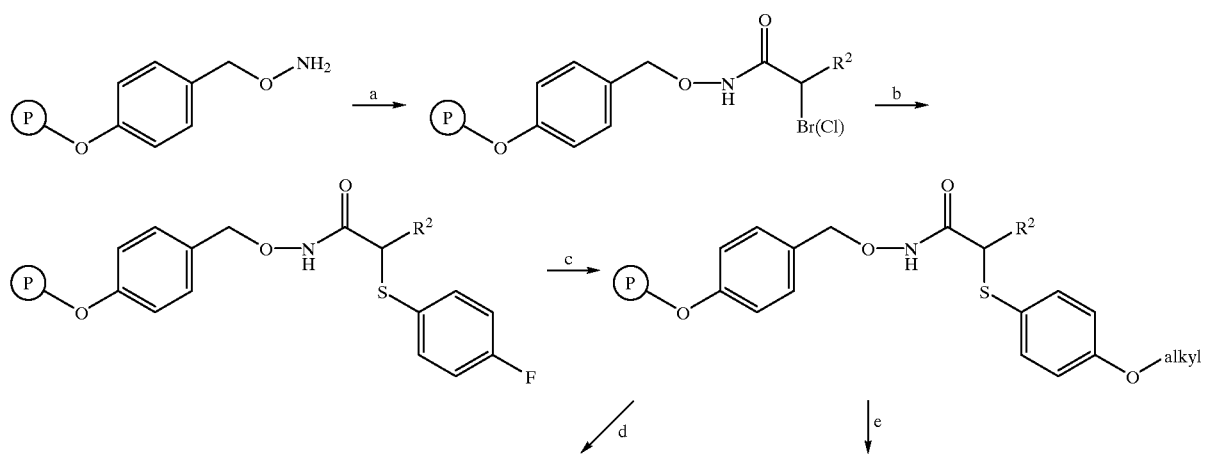

-continued

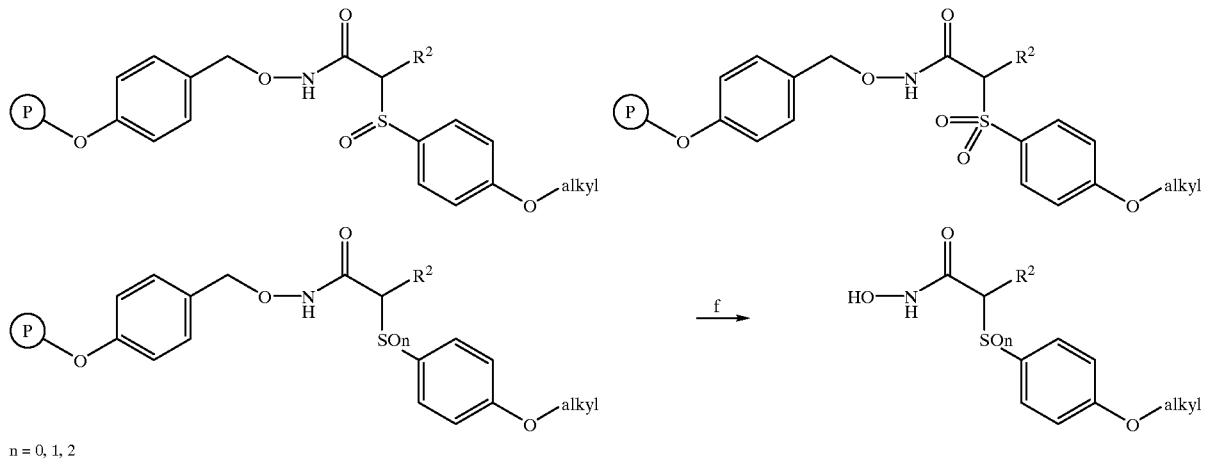

n = 0, 1, 2

Reagents and Conditions: a) 2-Halo acid (3.0 eq.); 1-hydroxybenzotriazole hydrate (HOBt, 6,0 eq.) 1,3-diisopropylcarbodiimide (DIC, 4.0 eq.); DMF, 25° C.; 2–16 hours. b) 4-Fluorobenzenethiol (5.0 eq.;) sodium iodide (5.0 eq.); 1,8-diazabicycle[5.4.0]undec-7-ene (DBU, 3.0 eq.); THF; 25° C.; 12–16 hours. c) Alcohol (15.0 eq.); sodium hydride (15.0 eq.); DMF; 80° C.; 15 hours. d) 70% tert-butylhydroperoxide (40 eq.); benzenesulfonic acid (2.0 eq.); DCM; 25° C.; 12–24 hours. e) mCPBA (5.0 eq.); DCM; 25° C.; 12–24 hours. f) TFA: DCM (1:1); 25° C.; 1 hour.

The hydroxylainie resin may be coupled with the 2-halo acid and the halo group may be displaced by fluorobenzenethiol as previously described. The fluoro group may then be displaced with an alcohol in the presence of a base such as sodium hydride, in an inert solvent such as DMF at about 80° C. The alkoxybenzenesulfanyl hydroxamate ester may then be oxidized either to the corresponding sulfinyl or sulfonyl hydroxamate ester as previously described. The free hydroxamic acids may be liberated as previously descnied Scheme 9 shows a method of preparing 2-bisarylsulfanyl-, sulfinyl-, and sulfonylhydroxamic acids.

Scheme 9

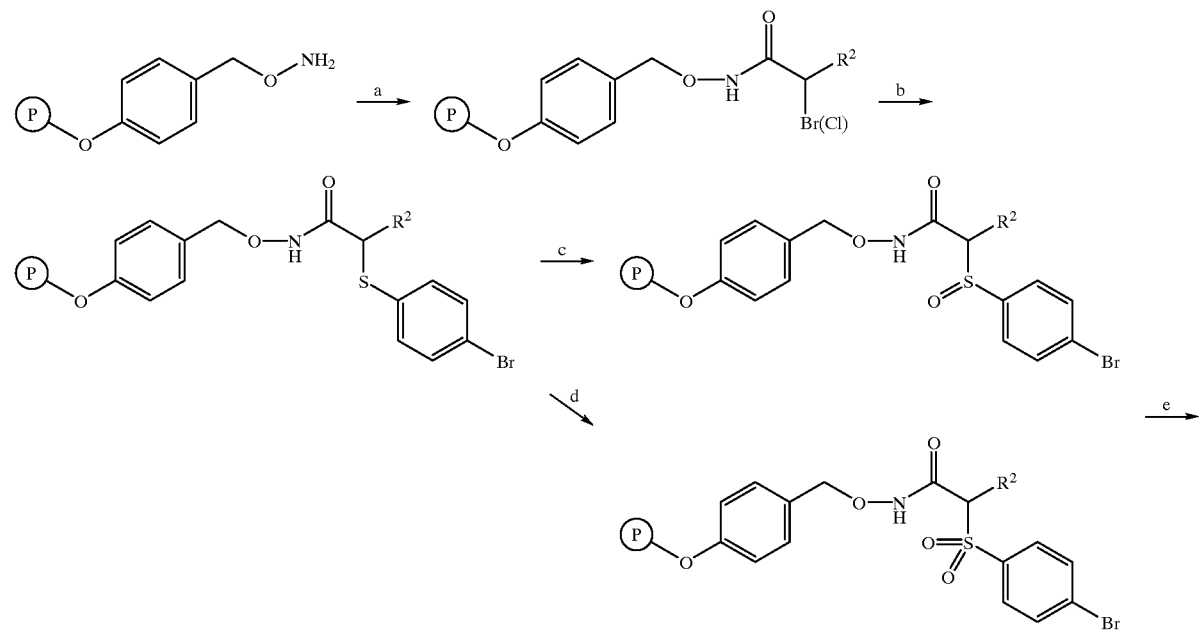

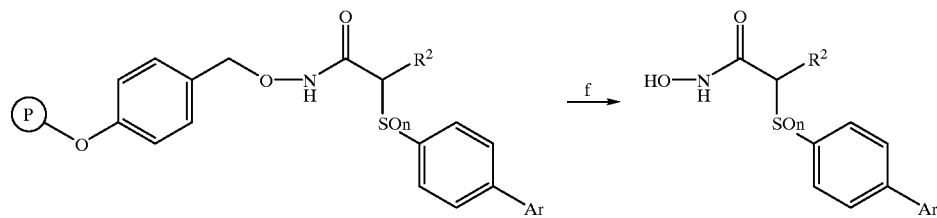

Reagents and conditions: a) 2-Halo acid (3.0 eq.); 1-hydroxybenzotriazole hydrate (HOBt, 6.0 eq.); 1,3-diisopropylcarbodiiliimde (DIC, 4.0 eq.); DMF, 25° C.; 2–16 hours. b) 4-Bromobenzenethiol (5.0 eq.); sodium iodide (5.0 eq.); 1,8diazabicyclo[5.4.0]undec-7ene (DBU, 3.0 eq.); THF; 25° C.; 12–16 hours. c) 70% tert-butylhydroperoxide (40 eq.); benzenesulfonic acid (2.0 eq.); DCM; 25° C.; 12–24 hours. d) mCPBA (5.0 eq.); DCM; 25° C.; 12–24 hours. e) Arylboronic acid (2.0 eq.); tetrakis (triphenylphospliine) palladium(0) (0.1 eq.); 10% aqueous sodium carbonate (10.0 eq.); DME; 80° C.; 8 hours. f) TFA: DCM (1:1); 25° C.; 1 hour.

The hydroxylamine resin may be coupled with the 2-halo acid and the halo group may be displaced by bromobenzenethiol as previously described. The bromobenzenesulfanyl hydroxamate ester may then be oxidized either to the corresponding sulfinyl or sulfonyl hydroxamate ester as previously described. The bromo group may then be replaced with an aryl group by reaction with the arylboronic acid in the presence of a catalyst such as tetrakis (triphenylphosphine) palladium(0), and a base such as sodium carbonate, in anl inert solvent such as DME at about 80° C. The free hydroxamic acids may be liberated as previously described.

Scheme 10 shows a method of preparing hydroxamic acids having amine groups attached to the aromatic ring.

Scheme 10

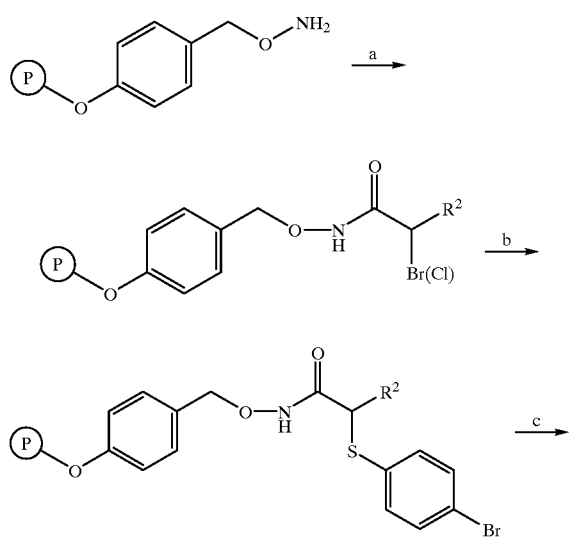

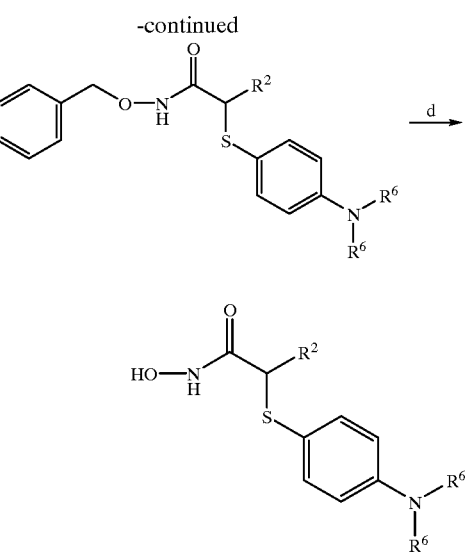

Reagents and Conditions: a) 2-Halo acid (3.0 eq.); 1-hydroxybenzotiiazole hydrate (HOBt, 6.0 eq.); 1,3-diisopropylcarbodiimide (DIC, 4.0 eq.); DMF, 25° C.; 2–16 hours. b) 4-Bromobenzenethiol (5.0 eq.); sodium iodide (5.0 eq.); 1,8-diazabicyclo[5.4.0]undec-7ene (DBU, 3.0 eq.); TBF; 25° C.; 12–16 hours. c) Amine (20.0 eq.); tris (dibenzylideneacetone)-dipalladium(0) (0.2 eq.); (S)-(–)-2, 2'-bis(diphenylphosphimo)-1,1'-binaphthyl ((S)-BINAP, 0.8 eq.); sodium tert-butoxide (18.0 eq.); dioxane; 80° C., 8 hours; d) TFA: DCM (1:1); 25° C.; 1 hour.

The hydroxylamine resin may be coupled with the 2-halo acid and the halo group may be displaced by bromobenzenethiol as previously described. The bromo group may then be displaced with an amine in the presence of a catalyst such as tds(dibenzylideneacetone)-dipalladium(0) and a ligand such as (S)-BINAP and a base such as sodium tert-butoxide, in an inert solvent such as dioxane at about 80° C. The free hydroxarnic acids may be hberated as previously described.

Scheme 11 shows a method of preparing hydroxamic acids having sulfonate groups attached to the aromatic ring.

Scheme 11

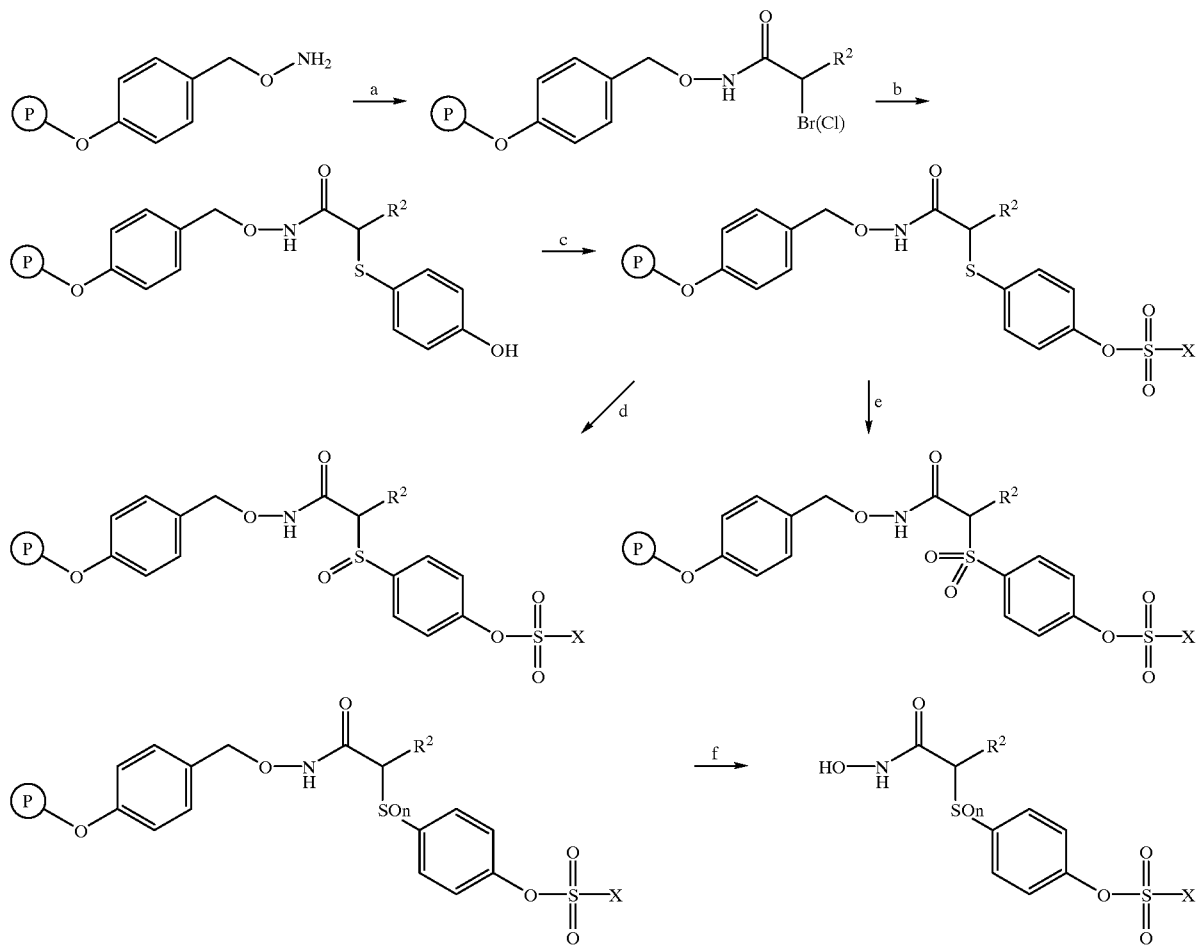

n = 0, 1, 2

X = C₂–C₆ alkyl, aryl

Reagents and Conditions: a) 2-Halo acid (3.0 eq.); 1-hydroxybenzotriazole hydrate (HOBt, 6.0 eq.); 1,3-diisopropylcarbodiimide (DIC, 4.0 eq.); DMF, 25° C.; 2–16 hours. b) 4-Hydroxybenzenethiol (5.0 eq.); sodium iodide (5.0 eq.); 1,8-diazabicyclo[5.4.0]undec-7-ene (DBU, 3.0 eq.); THF; 25° C.; 12–16 hours. c) Sulfonyl chloride (5.0 eq.); triethylamine (2.0 eq.); DCM; 25° C.; 8 hours. d) 70% tert-butylhydroperoxide (40 eq.); benzenesulfonic acid (2.0 eq.); DCM; 25° C.; 12–24 hours. e) mCPBA (5.0 eq.); DCM; 25° C.; 12–24 hours. f) TFA: DCM (1:1); 25° C.; 1 hour.

The hydroxylanmine resin may be coupled with the 2-halo acid and the halo group may be displaced by hydroxybenzenethiol as previously described. The hydroxybenzenesulfanyl hydroxamate ester may then be oxidized either to the corresponding sulfinyl or sulfonyl hydroxamate ester as previously described. The hydroxy group may then be sulfonylated by reaction with a sulfonyl chloride in the presence of a base such as triethylamine, in an inert solvent such as DCM at about room temperature. The free hydroxamic acids may be liberated as previously described.

The following examples are presented to illustrate rather than limit the scope of the invention. HPLC purity of compounds prepared by combinatorial procedures is presented as area percentage at a prescribed wavelength (% @ nm).

EXAMPLE 1

N-Hydroxy-2-(4-methoxy-phenylsulfanyl)-2-methyl-3-phenyl-propionamnide

To stirred solution of 4-methoxybenzenethiol (2.8 gm, 20 mmol) and anhydrous $K_2CO_3$ (10 gm, excess) in dry acetone (100 ml), ethyl 2-bromo-propionate (3.6 gm, 20 mmol) was added in a round bottom flask and the reaction mixture was heated at reflux for 8 hours with good stirring. At the end, reaction was allowed to cool and the potassium salts were filtered off and the reaction mixture was concentrated The residue was extracted with chloroform and washed with $H_2O$ and 0.5 N NaOH solution. The organic layer was further washed well with water, dried over $MgSO_4$, filtered and concentrated to afford 2-(4-methoxy-phenylsulfanyl)-propionic acid ethyl ester as a light yellow oil. Yield 4.5gms (94%); MS; 241 (M+H)⁺.

To a stirred solution of 2-(4-methoxy-phenylsulfanyl)-propionic acid ethyl ester (2.44 g, 10 mmol), in THF (100 ml) at −4° C., lithium bis(trimethylsilyl)amide (1 M solution, −15 ml, 15 mmol) was added slowly. The orange colored reaction mixture was stirred at room temperature for 15 minutes and then it was cooled to 0° C. at which time it was stirred for an additional hour.

The temperature of the mixture was again brought to −40° C. and benzylbromide (1.72 gm, 10 mmol) was added dropwise in THF. The reaction was warmed to room temperature and stirred overnight before it was quenched with ice water, extracted with chloroform and washed with water. The organic layer was dried over $MgSO_4$, filtered and concentrated and chromatographed on a silica-gel column with 10% ethyl acetate:hexane to afford 2-(4-methoxy-phenylsulfanyl)-2-methyl-3-phenyl-propionic acid ethyl ester as a colorless oil. Yield: 860 mg, (26%); MS: 331 $(M+H)^+$.

2-(4-methoxy-phenylsulfanyl)-2-methyl-3-phenyl-propionic acid ethyl ester (4.12 g, 12 mmol) dissolved in methanol (50 ml) and 10 N NaOH (20 ml) was added. The reaction was allowed to stir overnight at room temperature. The reaction mixture was concentrated, diluted with 1:1 hexane:diethyl ether and extracted with $H_2O$. The water layer was cooled with ice and acidified to pH 3. The acid was then extracted with chloroform and the organic layer was dried over $MgSO_4$, filtered and concentrated to afford of 2-(4-methoxy-phenylsulfanyl)-2-methyl-3-phenyl-propionic acid as a low melting solid. Yield 580 mg, 16%; MS: 303.2 $(M+H)^+$.

To a stirred solution of 2-(4methoxy-phenylsulfanyl)-2-methyl-3-phenyl-propionic acid (0.5 g, 1.65 mmol) and DEF (2 drops) in $CH_2Cl_2$ (100 ml) at 0° C., oxalyl chloride (1.0 gm, 8 mmol) was added in a drop-wise manner. After the addition, the reaction mixture was stirred at room temperature for 1 hour. Simultaneously, in a separate flask a mixture of hydroxylamine hydrochloride (2.0 gm, 29 mmol) and triethylamine (5 ml, excess) was stirred in THF:water (5:1, 30 ml) at 0° C. for 1 hour. At the end of 1 hour, the oxalyl chloride reaction mixture was concentrated and the pale yellow residue was dissolved in 10 ml of $CH_2Cl_2$ and added slowly to the hydroxylamine at 0° C. The reaction mixture was stirred at room temperature for 24 hours and concentrated. The residue obtained was extracted with chloroform and washed well with water. The product obtained was purified by silica gel column chromatography and eluted with ethyl acetate. The N-hydroxy-2-(4-methoxyphenylsulfanyl)-2-methyl-3-phenyl-propionamide was isolated as a colorless solid. mp 88° C.; Yield, 300 mg, 57%; MS: 318 $(M+H)^+$; 1H NMR (300 MHz, $CDCl_3$): δ 1.32 (s, 3H), 3.07 (d, J =11 Hz, 1H), 3.23 (d, J=11 Hz, 1H), 3.79 (s, 3H), 6.83–7.36 (m, 9H).

EXAMPLE 2
N-Hydroxy-2-(4-methoxy-phenylsulfanyl)-2-phenyl-acetamide 2-(4-Methoxyphenylsulfanyl)-phenylacetic acid ethyl ester was prepared according to the general method as outlined in Example 1. Staring from ethyl a-bromophenyl acetate (7.18 g, 31.4 mmol) and 4-methoxythiophenol (4.4 g, 31.4 mmol), 8.5 g of the product was isolated as a light yellow oil. Yield 90%; MS: 303.1 $(M+H)^+$.

2-(4-Methoxy-phenylsulfanyl)-2-phenyl acetic acid was prepared starting from 2-(4-methoxy-phenylsulfanyl)-phenyl-acetic acid ethyl ester (3.0 g, 10 mmol) dissolved in methanol (50 ml) and 10 N NaOH (20 ml). The resulting reaction mixture was worked up as in Example 1. Yield 1.9 g, 70%. Low melting solid. MS: 273 $(M+H)^+$.

Starting from 2-(4-methoxy-phenylsulfanyl)-phenyl acetic acid (1.05 g, 3.83 mmol) and following the procedure as outlined in Example 1, 154 mg of N-hydroxy-2-(4-methoxy-phenylsulfanyl)-2-phenyl-acetnmide was isolated as a colorless solid. mp 155° C.; Yield 14%; MS: 290 $(M+H)^+$; 1H NMR (300 MHz, DMSO-$d_6$): δ 3.72 (s, 3H), 4.68 (s, 1H), 6.86–7.44 (m, 9H).

EXAMPLE 3
2-(4-Methoxy-phenylsulfanyl)-2,5 -dimethyl-hex-4-enoic acid hydroxyamide 2-(4-Methoxy-phenylsulfanyl)-2,5-dimethyl-hexenoic acid ethyl ester was prepared following the procedure of Example 1, second paragraph. Starting from (4-methoxy-phenylsulfanyl)-propionic acid ethyl ester (3.5 g, 14.3 mmol), and isoprenyl bromide (2.25 g, 15 mmol), 2.2 g of the product was isolated as an oil. Yield 50%; MS: 310 $(M+H)^+$.

2-(4-Methoxy-phenylsulfanyl)-2,5-dimethyl-hexenoic acid was prepared starting from 2-(4-methoxy-phenylsulfanyl)-2,5-dimethyl-hex-4-enoic acid ethyl ester (2.0 g, 6.4 mmol) dissolved in methanol (50 ml) and 10 N NaOH (20 ml). The resulting reaction mixture was worked up as outlined in Example 1. Yield is 1.9 g, 99% of low melting solid. MS: 280 $(M+H)^+$.

Starting from 2-(4-methoxy-phenylsulfanyl)-2,5-dimethyl-hex4enoic acid (1;67 g, 5.8 mmol) and following the procedure as outlined in Example 1, 1.5 g of 2-(4methoxy-phenylsulfanyl)-2,5 -dimethyl-hex-4-enoic acid hydroxyamide was isolated as a colorless solid. mp 89° C.; Yield 94%; MS: 296 $(M+H)^+$; 1H NMR (300 MHz, $CDCl_3$): δ 1.34 (s, 3H), 1.61 (s, 3H), 1.74 (s, 3H), 2.41–2.58 (m, 2H), 3.80 (s, 3H), 5.17 (t, J=7.5 Hz, IH), 6.86 (d, J=12.4 Hz, 2H), 7.35 (d, J=12.4 Hz, 2H).

EXAMPLE 4
N-Hydroxy-2-(4-methoxy-phenylsulfanyl)-3-methyl-butyramide 2-(4-Methoxy-phenylsulfanyl)-3-methyl-butyric acid ethyl ester was prepared according to the general method of Example 1. Starting from ethyl 2-bromo-3-methyl-butanoate (20.9 g, 100 mmol) and 4-methoxybenzenethiol (14.0 g, 100 mmol), 30 g of the product was isolated. Yield 99%; Light yellow oil; MS: 271 $(M+H)^+$.

2-(4-Methoxy-phenylsulfanyl)-3-methyl-butyric acid was prepared starting from 2-(4-methoxy-phenylsulfanyl)-3-methyl-butyric acid ethyl ester (5.8 g, 21.6 mmol) dissolved in methanol (50 ml) and 10 N NaOH (30 ml). The resulting reaction mixture was worked up as outlined in Example 1. Yield 5.0 g, 99%. Low melting solid. MS: 242 $(M+H)^+$.

Starting from 2-(4-methoxy-phenylsulfanyl)-3-methyl-butyric acid (4.39 g, 18.3 mmol) and following the procedure as outlined in Example 1, 1.5 g of N-hydroxy-2-(4methoxy-phenylsulfanyl)-3-methyl-butyramide was isolated as a colorless solid. mp 119° C.; Yield 33%; MS: 256 $(M+H)^+$; 1H NMR (300 MHz, DMSO-$d_6$): δ 0.90–1.07 (m, 6H), 1.84–1.96 (m, 1H), 3.07 (d, J=8.8 Hz, 1H), 3.75 (s, 3H), 6.88 (d, J=15 Hz, 2H), 7.35 (d, J=15 Hz, 2H).

EXAMPLE 5
N-Hydroxy-2-(4-methoxy-benzenesulfmyl)-2-methyl-3-phenyl-propionamide N-hydroxy-2-(4-methoxy-phenylsulfanyl)-2-methyl-3-phenyl-propionamide (400 mg, 1.26 mmol) (prepared in Example 1) was dissolved in methanol (100 ml) and 30% $H_2O_2$ (10 ml) was added. The reaction mixture was stirred for 48 hours at room temperature at which time it was cooled to 0° C. and quenched with saturated $Na_2SO_3$ (20 ml) solution. The reaction mixture became cloudy. It was stirred for 4 hours before it was concentrated in a room temperature water bath, diluted with water, extracted with $CHCl_3$ and washed with $H_2O$. The organic layer was dried over $MgSO_4$, filtered and concentted. The title compound was isolated by silica gel column chromatography, eluting with 75% ethylacetate:hexane. Low melting solid. Yield: 220 mg (52%); MS: 334.1 $(M+H)^+$; 1H NMR (300 Mz, $CDCl_3$): d 1.11 (s, 2H), 1.22 (s, 3H), 3.84 (s, 3H), 7.00–7.61 (m, 9H).

EXAMPLE 6
2-(4-Methoxy-benzenesulfanyl)-2,5 dimethyl-hex-4-enoic acid hydroxyamide Starting from 2-(4-methoxy-benzenesulfanyl)-2,5-dimethyl-hex-4-enoic hydroxamide (900 mg, 3.0 mmol) (prepared in Example 3) and following the procedure outlined in Example 5, 2-(4-methoxy-benzenesulfmyl)-2,5dimethyl-hex-4-enoic acid hydroxyamide was isolated as a colorless solid. Yield: 104 mg (10%); mp 108° C.; MS: 312 (M+H)$^+$; $^1$H NMR (300 Mz, DMSO-d$_6$): δ 0.88 (s, 3H), 1.59 (s, 3H), 1.68 (s, 3H), 2.27–2.80 (m, 2H), 5.02 (t, J=7.5 Hz, 1H), 7.09 (d, J=9 Hz, 2H), 7.39 (d, J=9 Hz, 2H).

EXAMPLE 7
N-Hydroxy-2-(4-methoxy-benzenesulfinyl)-3-methyl-butyramide

Starting from N-hydroxy-2-(4methoxy-phenylsulfanyl)-3-niethyl-butyramide (1 g, 3.9 mmol) as prepared in Example 4, and following the procedure of Example 5, N-hydroxy-2-(4-methoxy-benzenesulfinyl)-3-methyl-butyramide was isolated as a colorless solid. Yield: 420mg (40%); mp 163° C.; MS: 272 (M+H)$^+$; $^1$H NMR (300 MHz, DMSO-d$_6$): δ 0.89–1.12 (m, 6H), 1.63–1.74 (m, 1H), 3.13 (d, J=7 Hz, 1H), 3.83 (s, 3H), 6.947.65 (m, 4H).

EXAMPLE 8
N-Hydroxy-2-(4-methoxy-benzenesulfinyl)-2-phenyl-acetamide

Starting from N-hydroxy-2-(4-methoxy-phenylsulfanyl)-2-phenyl-acetamide (240 mg, 0.83 mmol) as prepared in Example 2, and following the procedure outlined in Example 5, N-hydroxy-2-(4-methoxy-benzenesulfinyl)-2-phenyl-acetamide was isolated as colorless solid. Yield: 100 mg (40%); mp 135° C.; MS 304 (M+H)$^+$; $^1$H NMR (300 MHz, DMSO-d$_6$): δ 3.75 (s, 3H), 4.38 (s, 1H), 6.92–7.69 (m, 9H)

EXAMPLE 9
N-Hydroxy-2-(4-methoxy-benzenesulfonyl)-3-phenyl-propionarmide.

To a stirred solution of 4-methoxybenzenethiol (2.8 gm, 20 mmol) and anhydrous K$_2$CO$_3$ (10 gm, excess) in dry acetone (100 ml), α-bromo ethyl acetate (3.3 gm, 20 mmol) was added in a round bottom flask and the reaction mixture was heated at reflux for 8 hours with good string. At the end, the reaction mixture was allowed to cool and the potassium salts were filtered off and the reaction mixture was concentrated. The residue was extracted with chloroform and washed with H$_2$O and 0.5 N NaOH solution. The organic layer was further washed well with water, dried over MgSO$_4$, filtered and concentrated. (4methoxy-phenylsulfanyl)-acetic acid ethyl ester was isolated as pale yellow oil. Yield: 4.4 g (100%); MS; 227 (M+H)$^+$.

To a stirred solution of 60% 3-chloroperoxybenzoic acid (14.0 gm, 40 mmol) in methylene chloride (100 ml) at 0° C., (4methoxy-phenylsulfanyl)-acetic acid ethyl ester (4.4 g, 20 mmol) in CH$_2$Cl$_2$ (15 ml) was added slowly. The reaction mixture turned cloudy and was stirred at room temperature for 6 hours. The reaction mixture was then diluted with hexanes (300 ml) and stirred for 15 minutes. The solids were fjitered off and Na$_2$SO$_3$ solution was added to the organic layer which was stirred for at least 3 hours before the mixture was extracted with CHCl$_3$ and washed with H$_2$O. The organic layer was dried over MgSO$_4$, filtered and concentrated and the colorless (4-methoxy-phenylsulfonyl)-acetic acid ethyl ester was isolated as an oil. Yield: 100%; MS: 259.1 (M+H)$^+$.

To stirred solution of the (4-methoxy-benzenesulfonyl)-acetic acid ethyl ester (2.5 g, 10 mmol), benzyl bromide (1.8 gm, 10 mmol) and 18-Crown-6 (500 mg) in acetone (250 ml) was added K$_2$CO$_3$ (10 gms, excess) and the mixture was refluxed for 24 hours. At the end, the reaction mixture was filtered and the acetone layer was concentrated. The residue obtained was extracted with chloroform, washed well with water, dried over anhydrous MgSO$_4$, filtered and concentrated. The product obtained was purified by silica-gel column chromatography, eluting with 30% ethyl acetate: hexane. The product, 2-(4-methoxy-benzenesulfonyl)-3-phenyl-propionic acid ethyl ester was isolated as a low melting solid. Yield: 3.0 gm 86%; Low melting solid; MS: 349 (M+H)$^+$.

To a stirred solution of 2-(4-methoxy-benzenesulfonyl)-3-phenyl-propionic acid ethyl ester (348 mg, 1 mmol) in methanol (25 ml), 10 N NaOH (10 ml) was added. The reaction mixture was stirred at room temperature for 48 hours. At the end, the reaction mixture was concentrated and carefully neutralized with dilute HCl. The residue obtained was extracted with chloroform, washed well with water, dried and concentrated The product obtained was purified by silica-gel column chromatography by eluting with ethyl acetate: methanol (95:5) to afford 24-(methoxy-benzenesulfonyl)-3-phenyl-propionic acid as a colorless oil. Yield: 250 mg, 89%; MS: 321 (M+H)$^+$.

Starting from 2-(4-methoxy-benzenesulfonyl)-3-phenyl-propionic acid (200 mg, 0.625 mmol) and following the procedure as outlined in Example 1, 150 mg of N-hydroxy-2-(4methoxy-benzenesulfonyl)-3-phenyl-propionamide was isolated as a brown solid. Yield: 71 %; mp 180° C.; MS: 336 (M+H)$^+$; $^1$H NMR (300 MHz, CDCl$_3$): δ 3.2 (m, 1H), 3.8 (s, 3H), 4.04.2 (m, 2H), 7.0–8.0 (m, 9H).

EXAMPLE 10
2-(4-Methoxy-benzenesulfonyl)-hexanoic acid hydroxyamide 2-(4-Methoxy-phenylsulfanyl)-hexanoic acid ethyl ester was prepared according to the general method as outlined in Example 1. Starting from ethyl 2-bromo,hexanoate (7 g, 32 mmol) and 4-methoxybenzenethiol (4.2 g, 30 mmol), 8.3 g of the product was isolated. Yield 98%; Light yellow oil; MS: 283 (M+H)$^+$.

Starting from 2-(4-methoxy-phenylsulfanyl)-hexanoic acid ethyl ester. (2.8 g 10 mmol) and following the procedure as outlined in Example 9, 3 g of 2-(4methoxy-benzenesulfonyl)-hexanoic acid ethyl ester was isolated as a colorless solid. Yield: 95%; mp 62° C.; MS: 314 (M+H)$^+$.

Starting from 2-(4-methoxy-benzenesulfonyl)-hexanoic acid ethyl ester (2 g, 6.3 mmol) 1.5 g (83%) of 2-(4-methoxy-benzenesulfonyl)-hexanoic acid was isolated as a colorless solid by following the procedure as outlined in Example 9. Mp 116° C.; MS: 287 (M+H)$^+$.

Starting from 2-(4-methoxy-benzenesulfonyl)-hexanoic acid (1.0 g, 3.1 mmol) and following the procedure as outlined in Example 1, 700 mg of 2-(4medioxy-benzenesulfonyl)-hexanoic acid hydroxyamide was isolated as a colorless solid. Yield: 60%; mp 130° C.; MS: 302 (M+H)$^+$; $^1$H NMR (300 MHz, CDCl$_3$): δ 0.786 (t, J=7.2 Hz, 3H), 1.1–1.3 (m, 411), 1.6–1.8 (m, 2H), 3.7 (m, 1H), 3.9 (s, 3H),7.2 (d, J=11 Hz, 2H), 7.8 (d, J=11 Hz, 2H), 9.3 (s, 1H), 10.9 (s, 1H).

EXAMPLE 11
2-(4-Methoxy-benzene sulfonyl)-tetradecanoic hydroxyamide 2-(4-Methoxy-phenylsulfanyl)-tetradecanoic acid ethyl ester was prepared according to the general method as outlined in Example 1. Starting from the corresponding ethyl -2-bromomyristate (5.0 g, 14.9 mmol) and 4-methoxythiophenol (1.9 g, 13.4 mmol), 5.0 g of the product was isolated. Yield 98%; Light yellow oil; MS: 393 (M+H)+.

Starting from 2-(4-methoxy-phenylsulfanyl)-tetradecanoic acid ethyl ester. (3.9 g 10 mmol) and following the procedure as outlined in Example 9, 3.2 g of 2-(4methoxy-benzenesulfonyl)-tetradecanoic acid ethyl ester was isolated as a colorless solid. yield: 76%; Oil; MS: 425 (M+H)+.

Starting from 2-(4-methoxy-benzenesulfonyl)-tetradecanoic acid ethyl ester (2.5 g, 5.9 mmol), 2.0 g (85%) of 2-(4-methoxy-benzenesulfonyl)-tetradecanoic acid was isolated as a colorless solid by following the procedure as outlined in Example 9. mp 82 ° C; MS: 397 (M+H)+.

Starting from 2-(4-methoxy-benzene sulfonyl)-tetradecanoic acid (1.14 g, 2.9 mmol) and following the procedure as outlined in Example 1, 670 mg of 2-(4-methoxy-benzenesulfonyl)-tetradecanoic hydroxyamide was isolated as an off-white solid Yiefld: 57%; mp 114° C.; MS: 414 (M+H)+; $^1$H NMR (300 MHz, DMSO-$d_6$): δ 0.85 (t, J=7 Hz, 3H), 1.16–1.27 (m, 20 H), 1.66 (m, 2H), 3.62–3.70 (m, 1H), 3.87 (s, 3H), 7.12 (d, J=15 Hz, 2H), 7.73 (d, J=15 Hz, 2H).

EXAMPLE 12
N-Hydroxy-2-(4-methoxy-benzenesulfonyl)-2-methyl-3-phenyl-propionamide To a stirred solution of 2-(4methoxy-benzenesulfonyl)-3-phenyl-propionic acid ethyl ester (1.0 gm, 3mmol) (example 9), methyl iodide (1 ml, excess) and 18-Crown-6 (500 mg) in acetone (250 ml), $K_2CO_3$ (10 gm, excess) was added and the reaction mixture was refluxed for 24 hours. At the end, the reaction mixture was filtered and the acetone layer was concentrated The residue obtained was extracted with chloroform, washed well with water, dried over anhydrous $MgSO_4$, filtered and concentrated The product obtained was purified by silica-gel column chromatography by eluting it with 30% ethyl acetate:hexanes to afford 2-(4-methoxy-benzenesulfonyl)-2-methyl-3-phenyl-propionic acid ethyl ester as a colorless oil. Yield 1.0 g, 98%; MS: 349 (M+H)+.

Starting from 2-(4-methoxy-benzenesulfonyl)-2-methyl-3-phenyl-propionic acid ethyl ester (900 mg, 2.7 mmol), 850 mg (quantitative) of 2-(4-methoxy-benzenesulfonyl)-2-methyl-3-phenyl-propionic acid was isolated by following the procedure as outlined in Example 9. Colorless oil, MS 335 (M+H)+.

Staring from 2-(4-methoxy-benzenesulfonyl)-2-methyl-3-phenyl-propionic acid (900 mg, 2.7 mmol) and following the procedure as outlined in Example 1, 450 mg of N-hydroxy-2-(4-methoxy-benzenesulfonyl)-2-methyl-3-phenyl-propionamide was isolated as a brown solid. Yield: 48%; mp 58° C.; MS: 350 (M+H)+; $^1$H NMR (300 MHz, $CDCl_3$): δ 8 1.4 (s, 3H), 3.1 (d, J=9 Hz, 1H), 3.6 (d, J=9 Hz, 1H), 3.9 (s, 3H), 6.8–7.8 (m, 9H).

EXAMPLE 13
2-(4-Methoxy-benzenesulfonyl)-2,5-dinethyl-hex-4-enoic acid hydroxyamide Starting from 2-(4-methoxy-phenylsulfanyl)-propionic acid ethyl ester (Example 1) (12 g; 50 mmol) and following the procedure as outlined in Example 9, 12 g of 2-(4methoxy-benzenesulfonyl)-propionic acid ethyl ester was isolated as a semi-solid. yield 100%; MS: 256.1 (M+H)+.

Following the procedure as outlined in Example 12, 2-(4-methoxy-benzenesulfonyl)-2,5-dimethyl-hex-4-enoic acid ethyl ester was prepared, starring from (1 g, 3.6 mmol) of 2-(4-methoxy-benzenesulfonyl)-propionic acid ethyl ester and isoprenyl bromide (1.0 g, 6 mmol). Yield 1.0 g, 81%; Colorless oil; MS: 341 (M+H)+.

Starting from 2-(4-methoxy-benzenesulfonyl)-2,5-dimethyl-hexenoic acid ethyl ester (900 mg, 2.6 mmol) 800 mg (96%) of 2-(4-methoxybenzenesulfonyl)-2,5-dimethyl-hexenoic acid was isolated as a semi solid by following the procedure as outlined in Example 9. MS: 313 (M+H)+.

Starting from 2-(4-methoxy-benzenesulfonyl)-2,5dethyl-hex4noic acid (1.0 g, 3.2 mmol) and following the procedure as outlined in Example 1, 700 mg of 2-(4-methoxy-benzenesulfonyl)-2,5dimethyl-hex-4-enoic acid hydroxyamide was isolated as a low melting solid. Yield: 67%; MS: 328 (M+H)+; $^1$H NMR (300 Mz, $CDCl_3$): δ 1.3 (s, 3H), 1.5 (d, J=6.2 Hz, 6H), 2.5–3.0 (m, 2H), 3.9 (s, 3H), 7.0 (d, J=11 Hz, 2H), 7.8 (d, J=11 Hz, 2H).

EXAMPLE 14
3-(Biphenyl-4-yl)-N-hydroxy-2-(4-methoxy-benzenesulfonyl)-2-methyl-propionamide Following the procedure as outlined in Example 12, 3-(biphenyltyl)-2-(4-methoxy-benzenesulfonyl)-2-methyl-propionic acid ethyl ester was prepared, starting from (2.7 g,10 mmol) of 2-(4-methoxy-benzenesulfonyl)-propionic acid ethyl ester and 4 (chloromethyl)biphenyl (2.5 g, 12 mmol). Yield 4.0 g, 91%; Colorless oil; MS: 438 (M+H)+.

Starting from 3-(biphenyl-4-yl)-2-(4-methoxy-benzenesulfonyl)-2-methyl propionic acid ethyl ester (3 g, 6.8 mmol), 2.5 g (89%) of 3-(biphenylfyl)-2-(4-methoxy-benzenesulfonyl)-2-methyl propionic acid was isolated as a colorless solid by following the procedure as outlined inExample9. mp 161° C.; MS: 411 (M+H)+.

Starting from 3-(biphenyl-4-yl)-2-(4-methoxy-benzenesulfonyl)-2-methyl-propionic acid (2.0 g, 4.8 mmol) and foluowing the procedure as outlined in Example 1, 1.2 g of 3-(biphenyl-4-yl)-N-hydroxy-2-(methoxy-benzenesulfonyl)-2-methyl-propionamide was isolated as colorless solid. Yield: 58%; mp 177° C.; MS: 426 (M+H)+; $^1$H NMR (300 MHz, $CDCl_3$): δ 1.4 (s, 3H), 3.2 (d, J=9 Hz, 1H), 3.7 (d, J=9 Hz, 1H), 3.9 (s, 3H), 7.0 –7.8 (m, 13H), 9.7 (bs, 1H).

EXAMPLE 15
2-(4-methoxy-benzenesulfonyl)-2,5,9-trimethyl-deca-4,8-dienoic acid hydroxyamide Following the procedure as outlined in Example 12, 2-(4-methoxy-benzenesulfonyl)-2,5,9-trimethyl-deca-4,8-dienoic acid ethyl ester was prepared, starting from (2.7 g, 10 mmol) of 2-(4-methoxy-benzenesulfonyl)-propionic acid ethyl ester and geranyl bromide (3.0 g, 13 mmol). Yield 4.0 g, 98%; Colorless oil; MS: 409 (M+H)+.

Starting from 2-(4-methoxy-benzenesulfonyl)-2,5,9-trimethyl-deca-4,8-dienoic acid ethyl ester (3 g, 7.4 mmol), 2.8 g (96%) of 2-(4-methoxy-benzenesulfonyl)-2,5,9-trimethyl-deca-4,8-dienoic acid was isolated as a colorless oil by following the procedure as outlined in Example 9. MS: 379 (M–H)−.

Starting from 2-(4-methoxy-benzenesulfonyl)-2,5,9-trimethyl-deca-4,8-enoic acid (2.0 g, 5.2 mmol) and following the procedure as outlined in Example 1, 1.8 g of 2-(4-methoxy-benzenesulfonyl)2,5,9-timethyl-deca-4,8-enoic acid hydroxyamide was isolated as a colorless oil. Yield: 88%; MS: 396 (M+H)+; $^1$H NMR (300 Mz, $CDCl_3$): δ 1.4 (s, 3H), 1.6 (s, 3H), 1.65 (s, 3H), 1.7 (s, 3H), 2.0–3.1 (m,6 H), 3.9 (s, 3H), 5.5 (m, 2H), 6.98 (d, J=9.0 Hz, 2H), 7.7 (d, J=9.0 Hz, 2H).

EXAMPLE 16
3-Cyclohexyl-N-hydroxy-2-(4-methoxy-benzenesulfonyl)-2-methyl-propionamide Following the procedure as outlined in Example 12, 3-cyclohexyl-2-(4-methoxy-benzenesulfonyl)-2-methyl-propionic acid ethyl ester was prepared, starting from (2.7 g, 10 mmol) of 2-(4-medioxy-benzenesulfonyl)-propionic acid ethyl ester and bromomethylcyclohexane (1.8 g, 10 mmol). Yield 3.5 g, 95%; Yellow oil; MS: 369 (M+H)$^+$.

Starting from 3cyclohexyl-2-(4-methoxy-benzenesulfonyl-2-methyl propionic acid ethyl ester (3 g, 8.1 mmol) 2.5 g (90%) of 3-cyclohexyl-2-(4-methoxy-benzenesulfonyl)-2-methyl propionic acid was isolated as colorless solid by following the procedure as outlined in Example 9. mp 116° C.; MS: 341 (M+H)$^+$.

Starting from 3-cyclohexyl-2-(4-methoxy-benzenesulfonyl)-2-methyl-propionic acid (2.0 g, 5.8 mmol) and following the procedure as outlined in Example 1, 1.1 g of 3-cyclohexyl-N-hydroxy-2-(4-methoxy-benzenesulfonyl)-2-methyl-propionamide was isolated as colorless solid. Yield: 55%; mp 58° C.; MS: 356 (M+H)$^+$; $^1$H NMR (300 MHz, CDCl$_3$) δ 1.4 (s, 3H), 2.3–1.0 (m, 13 H), 3.9 (s, 3H), 7.0 (d, 8.8 Hz, 2H), 7.69 (d, 9.0 Hz, 2H).

EXAMPLE 17
N-Hydroxy-2-(4-methoxy-benzenesulfonyl)-2-methyl-3-[4-(2-piperdin-1-yl-ethoxy)-Phenyl]-propionamide Following the procedure as outlined in example 12, 24methoxy-benzenesulfonyl)-2-methyl 3-[4-(2-piperidin-1-yl-ethoxy)-phenyl]-propionic acid ethyl ester was prepared, starting from (2.7 g, 10 mmol) of 2-(4-methoxy-benzenesulfonyl)-propionic acid ethyl ester and the 4-(2-piperidin-1-yl-ethoxy)-benzyl chloride (2.9 g, 10 mmol). Yield 4.8 g, 98%; Brown oil; MS: 490 (M+H)$^+$.

Starting from 2-(4-methoxy-benzenesulfonyl)-2-methyl-3-[4-(2-piperidin-1-yl-ethoxy)-phenyl]-propionic acid ethyl ester (4.0 gm, 7.9 mmol) 3.5 g (Yield: 94%) of 2-(4-methoxy-benzenesulfonyl)-2-methyl-3-[4-(2-piperidin-1-yl-ethoxy)-phenyl]-propionic acid was isolated as colorless crystals by following the procedure as outlined in example 9. Mp 106° C.; MS: 462.5 (M+H)$^+$.

Starting from 2-(4-methoxy-benzenesulfonyl)-2-methyl-3-[4-(2-piperidin-1-yl-ethoxy)-phenyl]-propionic acid (2.0 g, 4.2 mmol) and following the procedure as outlined in example 1, 1 g of N-hydroxy-2-(4-methoxy-benzenesulfonyl)-2-methyl-3-[4-(2-piperidin-1-yl-ethoxy)-phenyl]-propionamide was isolated as colorless solid. Yield: 1 g, 48%; mp 98° C.; MS: 477 (M+H)$^+$; $^1$H NMR (300 MHz, CDCl$_3$): δ 1.2 (s, 3H), 3.5–1.5 (m, 16 H), 3.9 (s, 3H), 4.4 (m, 1H), 6.5–7.8 (m, 8H), 10.8 (bs, 1H).

EXAMPLE 18
2-4-(2-Azepan-1-yl-ethoxy)-benzyl)-2-(4methoxy-benzenesulfonyl)-propionic acid hydroxyamide Following the procedure as outlined in example 12, 2-[4-(2-azepan-1-yl-ethoxy)-benzyl]-2-(4-methoxy-benzenesulfonyl)-propionic acid ethyl ester was prepared, starting from (2.7 g, 10 mmol) of 2-(4-methoxy-benzenesulfonyl)-propionic acid ethyl ester and the 1-[2-(4-chloromethyl-phenoxy)ethyl]-azepane (3.03 g, 10 mmol). Yield 4.5 g, 90%; Brown oil; MS: 504 (M+H)$^+$.

Starting from 2-[4-(2-azepan-1-yl-ethoxy)-benzyl]-2-(4-methoxy-benzenesulfonyl)-propionic acid ethyl ester (4.0 gm, 7.9 mmol) 3.5 g (Yield: 94 %) of 2-[4-(2-azepan-1-yl-ethoxy)-benzyl]-2 -(4-methoxy-benzenesulfonyl)-propionic acid was isolated as semi-solid by following the procedure as outlined in example 9. MS: 476 (M+H)$^+$.

Starting from 2-[4-(2-azepan-1-yl-ethoxy)-benzyl]-2-(4-methoxy-benzenesulfonyl)-propionic acid (2.0 g, 4.2 mmol) and following the procedure as outlined in example 1, 1 g of 2-[4-(2-azepan-1-yl-ethoxy)-benzyl]-2-(4-methoxy-benzenesulfonyl)propionic acid hydroxyamide was isolated as colorless solid. Yield: 1.8 g, 87%; mp 68° C.; MS: 491 (M+H)$^+$; 1H NMR (300 MDz, CDCl$_3$): δ 1.23 (s, 3H), 3.5–1.7 (m, 18 H), 3.8 (s, 3H), 4.2 (m, 1H), 6.4 –7.89 (m, 8H), 10.9 (bs, 1H).

EXAMPLE 19
2-[4-(2-Azepan-1-yl-ethoxy)-benzyl]-2-(4methoxy-benzenesulfonyl)-pentanoic acid hydroxyamide 2-[4-(2-Azepan-1-yl-ethoxy)-benzyl]-2-(4-methoxy-benzenesulfonyl)-pentanoic acid ethyl ester was prepared according to the general method as outlined in example 12. Starting from 2-(4-methoxy-benzenesulfonyl)-pentanoic acid ethyl ester (3.5 g, 11.7 mmol) and 1-[2-(4-chloromethyl-phenoxy)-ethyl]-azepane (3.9 g, 12.8 mmol). Yield 2.58 g (42%); brown oil; MS: 532.4 (M+H)$^+$.

2-[4-(2-Azepan-1-yl-ethoxy)-benzyl]-2-(4-methoxy-benzetesulfonyl)-pentanoic acid was prepared starting from 2-[4-(2-azepan-1-yl-ethoxy)-benzyl]-2-(4-methoxy-benzenesulfonyl)-pentanoic acid ethyl ester (2 g, 3.76 mmol) dissolved in methanol (300 ml) and 10 N NaOH (15 ml). The resulting mixture was worked up as outlined in example 1. Yield 830 mg (44%); brown solid; mp 55° C.; MS: 504.4 (M+H)$^+$.

Starting from 2-[4-(2-azepan-1-yl-ethoxy)-benzyl]-2-(4-methoxy-benzenesulfonyl)-pentanoic acid (690 mg, 1.37 mmol) and following the procedure as outlined in example 1, 240 mg of 2-[4-(2-azepan-1-yl-ethoxy)-benzyl]-2-(4-methoxy-benzenesulfonyl)-pentanoic acid hydroxyamide was isolated as a yellow solid. Yield 34%; mp 85° C.; MS: 519.2 (M+H)$^+$; $^1$H NMR (300 MHz, DMSO-d$_6$): δ 0.71 (t, J=7.3 Hz, 31), 0.78–1.77 (m, 16 H), 3.04–3.46 (m, 4H), 3.87 (s, 3H), 4.26 (m, 2H) 6.87 (d, J=8.7 Hz, 2H), 7.14 (m, 4H), 7.71 (d, J=9 Hz, 2H), 9.07 (s, 1H), 10 (s, 1H).

EXAMPLE 20
N-Hydroxy-2-(4-methoxy-benzenesulfonyl)-2-methy-3-[4-(2-N,N-diisopropyl amino-ethoxy)-phenyl]-propionamide Following the procedure as outlined in example 12, 2-(4-methoxy-benzenesulfonyl)-2-methyl-3-[4-(2-N,N-iisopropyl anino-ethoxy)-phenyl]-propionic acid ethyl ester was prepared, starting from (5.4 g, 20 mmol) of 2-(4-methoxy-benzenesulfonyl)-propionic acid ethyl ester and the 4-(2-N,N diisopropyl amino-ethoxy)-benzyl chloride (6.1 g, 20 mmol). Yield 8.9 g, 88%; Yellow oil; MS: 506.5 (M+H)$^+$.

Starting from 2-(4-methoxy-benzenesulfonyl)-2-methyl-3-[4-(2-N,N-diisopropyl amino-ethoxy)-phenyl]-propionic acid ethyl ester (4.0 gm, 7.9 mmol) 3.5 g (Yield: 92%) of 2-(4-methoxy-benzenesulfonyl)-2-methyl-3-[4-(2-N,N diisopropyl amino-ethoxy)-phenyl]-propionic acid was isolated as colorless crystals by following the procedure as outlined in example 9. Mp 68° C.; MS: 478.6 (M+H)$^+$.

Starting from 2-(4-methoxy-benzenesulfonyl)-2-methyl-3-[4-(2-N,N-diisopropyl amino-ethoxy)-phenyl]-propionic acid (2.0 g, 4.1 mmol) and following the procedure as outlined in example 1, 1 g of 2-(4-methoxy-benzenesulfonyl)-2-methyl-3-[4-(2-N,N-diisopropyl amino-ethoxy)-phenyl]-propionamide was isolated as colorless solid. Yield: 1 g, 49%; mp 98° C., (Hcl Salt); MS: 493 (M+H)$^+$; $^1$H NMR (300 MHz, CDCl$_3$): δ 1.2 (s, 3H), 1.3 (d,6H), 1.4 (d,6H), 3.5–1.5 (m, 6 H), 3.9 (s, 3H), 4.4 (s, 2H), 6.5–7.8 (m, 8H), 10.8 (bs, 1H).

EXAMPLE 21
N-Hydroxy-2-(4-methoxy-benzenesulfonyl)-2-methyl-3-[4-(2-N,N-diethyl amino-ethoxy)-phenyl]-propionamide Following the procedure as outlined in example 12, 2-(4-methoxy-benzenesulfonyl)-2-methyl-3-[4-(2-N,N-diethyl amino-ethoxy)-phenyl]-propionic acid ethyl ester was prepared, starting from (5.4 g, 20 mmol) of 2-(4-methoxy-benzenesulfonyl)-propionic acid ethyl ester and the 4-(2-N,N-diethyl amino-ethoxy)-benzyl chloride (5.5 g, 20 mnmol). Yield 8.5 g, 89%; Brown oil; MS: 478.6 (M+H)+.

Starting from 2-(4-methoxy-benzenesulfonyl)-2-methyl-3-[4-(2-N,N-diethyl amino-ethoxy)-phenyl]-propionic acid ethyl ester (3.5 gm, 7.7 mmol) 3.0 g (Yield: 85%) of 2-(4-methoxy-benzenesulfonyl)-2-methyl-3-[4-(2-N,N-diethyl amino-ethoxy)-phenyl]-propionic acid was isolated as colorless crystals by following the procedure as outlined in example 9. Mp 96–98° C.; MS: 450.5 (M+H)+.

Starting from 2-(4-methoxy-benzenesulfonyl)2-methyl-3-[4-(2-N,N-diethyl amino-ethoxy)-phenyl]-propionic acid (2.0 g, 4.4 mmol) and following the procedure as outlined in example 1, 1 g of 2-(4-methoxy-benzenesulfonyl)-2-methyl-3-[4-(2-N,N ethyl amino-ethoxy)-phenyl]-propionamide was isolated as colorless solid. Yield: 1 g, 48%; mp 56–59° C. (HCl Salt); MS: 465.5 (M+H)+; $^1$H NMR (300 MHz, CDCl$_3$): δ 1.1 (t, 6H), 1.3 (s,3H), 3.2–3.9 (mn, 8 H), 3.9 (s, 3H), 4.3 (s, 2H), 6.5–7.8 (m, 8H), 10.8 (bs, 1H).

EXAMPLE 22
N-Hydroxy-2-(4-methoxy-benzenesulfonyl)-2-methyl-3-[3-(2-piperidin-1-yl-ethoxy)-phenyl]-propionamide Following the procedure as outlined in example 12, 2-(4-methoxy-benzenesulfonyl)-2-methyl-3-[3-(2-piperidin-1-yl-ethoxy)-phenyl]-propionic acid ethyl ester was prepared, starting from (5.2 g, 20 mmol) of 2-(4-methoxy-benzenesulfonyl)-propidnic acid ethyl ester and the 3-(2-piperidin-1-yl-ethoxy)-benzyl chloride (6.0 g, 20 mmol). Yield 8.2 g, 83%; Brown oil; MS: 490 (M+H)+.

Starting from 2-(4-methoxy-benzenesulfonyl)-2-methyl-3-[3-(2-piperidin-1-yl-ethoxy)-phenyl]-propionic acid ethyl ester (6.0 gm, 12.2 mmol) 4.9 g (Yield: 79%) of 2-(4-methoxy-benzenesulfonyl)-2-methyl-3-[3-(2-piperidin-1-yl-ethoxy)-phenyl]-propionic acid was isolated as colorless crystals by following the procedure as outlined in example 9. Mp 112 ° C.; MS: 462.5 (M+H)+.

Starting from 2-(4-methoxy-benzenesulfonyl)-2-methyl-3-[3-(2-piperidin-1-yl-ethoxy)-phenyl]-propionic acid (3.0 g, 6.5 mmol) and following the procedure as outlined in example 1, 1.8 g of 2-(4-methoxy-benzenesulfonyl)-2-methyl-3-[3-(2-piperidin-1-yl-ethoxy)-phenyl]-propionamide was isolated as colorless solid. Yield: 1.8 g, 58%; mp 74° C.; MS: 477 (M+H)+; $^1$H NMR (300 MHz, CDCl$_3$): δ 1.25 (s, 3H), 1.6–1.8 (m, 6 H), 2.5–3.7 (m, 8H), 3.9 (s, 3H), 4.4 (t, 2H), 6.7–7.8 (m, 8H), 10.8 (bs, 1H).

EXAMPLE 23
3-(4-{3-[4-(3-Chloro-phenyl)-piperain-1-yl]-propoxy}-phenyl)-N-hydroxy-2-(4-m ethoxy-benzenesulfonyl)-2-methyl-propionamide Following the procedure as outlined in example 12, 3-(4-{3-[4-(3-chlorophenyl)-piperazin-1-yl]-propoxy}-phenyl)-2-(4-methoxy-benzenesulfonyl)-2-methyl-propionic acid ethyl ester was prepared, starting from (2.72 g, 10 mmol) of 2-(4-methoxy-benzenesulfonyl)-propionic acid ethyl ester and the 1-[2-(4-chloromethyl-phenoxy)-ethyl]4-(3-chlorophenyl)-piperazine (4.2 g, 11 mmol). Yield 5.5 g, 89%; Brown oil; MS: 616 (M+H)+.

Starting from 3-(4-{3-[4-(3-chloro-phenyl)-piperazin-1-yl]-propoxy}-phenyl)-2-(4-methoxy-benzenesulfonyl)-2-methyl-propionic acid ethyl ester (4.0 gm, 6.5 mmol) 3.0 g (Yield: 78%) of 3-(4-{3-[4-(3-chloro-phenyl)-piperazin-1-yl]-propoxy}-phenyl)-2-(4-methoxy-ben zenesulfonyl)-2-methyl-propionic acid was isolated as colorless crystals by following the procedure as outlined in example 9. Mp 196° C.; MS: 588.1 (M+H)+.

Starting from 3-(4-{3-[4-(3-chloro-phenyl)-piperazin-1-yl]-propoxy}-phenyl)-2-(4-methoxy-benzenesulfonyl)-2-methyl-propionic acid (3.0 g, 5.1 mmol) and following the procedure as outlined in example 1, 1.8 g of 3-(4-{3-[4-(3-chloro-phenyl)-piperazin-1-yl]-propoxy}-phenyl)-N-hydroxy-2-(4-methoxy-benzenesulfonyl)-2-methyl-propionanude was isolated as pale yellow solid. Yield: 1.8 g, 55%; mp 122° C. (HCl Salt); MS: 640 (M+H)+; $^1$H NMR (300 MHz, CDCl$_3$): δ 1.2 (s, 3H), 3.4–1.5 (m, 14 H), 3.9 (s, 3H), 4.5 (m, 2H), 6.5–8.2 (m, 12H), 10.3 (bs, 1H).

EXAMPLE 24
2-(4-Methoxy-benzenesulfonyl)-5-methyl-2-[4-(2-morpholinlyl-ethoxy)-benzyl]-hex-4-enoic acid hydroxyamide To a stirred solution of (4-methoxy-benzenesulfonyl)-acetic acid ethyl ester (5.16 g, 20 mmol), isoprenyl bromide (3.0 g, 20 mmol) and 18-Crown-6 (500 mg) in acetone (250 ml) was added K2CO3 (10 gms, excess) and the mixture refluxed foe 24 hours. At the end, the reaction mixture was filtered and the acetone layer was concentrated. The residue obtained was extracted with chloroform, washed well with water, dried over anhydrous MgSO4, filtered and concentrated. The product obtained was purified by silica-gel column chromatography, eluting with 30% ethy acetate: hexane. The product 2-(4methoxy-benzenesulfonyl)-5-methyl-hex-4-enoic acid ethyl ester was isolated as a colourless oil. Yield: 3.0 g, 93%.

Following the procedure as outlined in example 12, 2-(4-Methoxy-benzenesulfonyl)-5-methyl-2-[4-(2-morpholin-4-yl-ethoxy)-benzyl]-hextenoic acid ethyl ester was prepared, starting from (3.26 g, 10 mmol) of 2-(4-methoxy-benzenesulfonyl)-5-methyl-hex-4-enoic acid ethyl ester and 4-(2-morpholin-1-yl-ethoxy)-benzyl chloride (3.0 g, 11 mmol). Yield 4.5 g, 82%; Brown oil; MS: 546 (M+H)+.

Starting from 2-(4-Methoxy-benzenesulfonyl)-5-methyl-2-[4-(2-morpholin-4-yl-ethoxy)-benzyl]-hex-4-enoic acid ethyl ester (3.0 gm, 5.5 mmol) 2.1 g (Yield: 75%) of 2-(4-Methoxy-benzenesulfonyl)-5-methyl-2-[4-(2-morpholin-4-yl-etoxy)-benzyl]-hex-4-enoic acid was isolated as semi-solid by following the procedure as outlined in example 9. MS: 518.6 (M+H)+.

Starting from 2-(4-Methoxy-benzenesulfonyl)-5-methyl-2-[4-(2-morpholin-4-yl-ethoxy)-benzyl]-hex-4-enoic acid (1.0 g, 1.9 mmol) and following the procedure as outlined in example 1, 450 mg of 2-(4-Methoxy-benzenesulfonyl)-5-methyl-2-[4-(2-morpholin-4-yl-ethoxy)-benzyl]-hex-4-noic acid hydroxyamide was isolated as pale yellow solid. Yield: 450 mg, 45%; mp 92° C. (HCl Salt); MS: 570 (M+H)+; $^1$H NMR (300 MHz, CDCl$_3$): δ 1.3 (d, 3H), 1.65 (d, 2H), 3.5–1.8 (m, 14 H), 3.9 (s, 3H), 4.5 (m, 2H), 5.4 (m, 1H), 6.5–7.9 (m, 8H), 11.5 (bs, 1H).

EXAMPLE 25
N-Hydroxy-2-(4-ethoxy-benzenesulfonyl)-2-methyl-3-[4-(2-N,N-diethyl amino-ethoxy)-phenyl]-propionamide To a stirred solution of 4-hydroxy thiophenol (12.6 g, 100 mmnol) and triethyl amine (15.0 g, 150 mmol) in chloroform (400 ml) 2-bromo ethyipropionate (18. 2 g, 100 mmol) was added drop wise. The reaction mixture was refluxed for 1 hr and cooled to room temperature. The reaction mixture was washed with water, dried and concentrated. 2-(4- hydroxy-phenylsulfanyl)-propionic acid ethyl ester was isolated as colorless oil. Yield: 22.0 g, 99%, MS: 227 (M+H).

To stirred solution of 2-(4-hydroxy-phenylsulfanyl)-propionic acid ethyl ester (11.3 g, 50 mmol), and $K_2CO_3$ (50 g, excess) in acetone (300 ml) ethyl iodide (20 ml, excess) was added and refluxed for 8 hrs. At the end, reaction mixture was filtered and concentrated The residue obtained was extracted with chloroform and washed well with water. It was dried and concentrared. The product, 2-(4-ethoxy-phenylsulfanyl)-propionic acid ethyl ester was isolated as colorless oil. Yield: 12.0 g, 98%; MS: 255 (M+H).

2-(4-Ethoxy-phenylsulfanyl)-propionic acid ethyl ester was converted to 2-(4-ethoxy-phenylsulfonyl)-propionic acid ethyl ester by following the procedure as described in example 9, paragraph 2.

Following the procedure as outlined in example 12, 2-(4-ethoxy-benzenesulfonyl)-2-methyl-3-[4-(2-N,N-diethyl amino-ethoxy)-phenyl]-propionic acid ethyl ester was prepared, starting from (3.5 g, 12.2 mmol) of 2-(4-ethoxy-benzenesulfonyl)-propioni( acid ethyl ester and the 4-(2-N,N-diethyl amino-ethoxy)-benzyl chloride (3.5 g, 12.2 mnmol). Yield 4.8 g, 80%; Brown oil; MS: 492.6 (M+H)$^+$.

Starting from 2-(4-ethoxy-benzenesulfonyl)-2-methyl-3-[4-(2-N,N-diethyl amino-ethoxy)-phenyl]-propionic acid ethyl ester (4.0 gm, 8.1 mmol) 3.2 g (Yield: 80%) of 2-(4-ethoxy-benzenesulfonyl)-2-methyl-3-[4-(2-N,N-diethyl amino-ethoxy)-phenyl]-propionic acid was isolated as colorless semi-solid by following the procedure as outlined in example 9. MS: 464.5 (M+H)$^+$.

Starting from 2-[4-ethoxy-benzenesulfonyl)-2-methyl-3-(4-(2-N,N-diethyl amino-ethoxy)-phenyl]-propionic acid (2.0 g, 4.3 mmol) and following the procedure as outlined in example 1, 1.2 g of 2-(4-ethoxy-benzenesulfonyl)-2-methyl-3-[4-(2-N,Niethyl amino-ethoxy)-phenyl]-propionamide was isolated as colorless low melting solid. Yield: 1.2 g 57%; (HCl Salt); MS: 478.5 (M+H)$^+$; $^1$H NMR (300 MHz, CDCl$_3$): δ 0.9 (t, 3H), 1.1 (t, 6H), 1.3 (s,3H), 3.2–3.9 (m, 8 H), 3.9 (s, 3H), 4.3 (s, 2H), 6.5–7.8 (m, 8H), 10.8 (bs, 1H).

EXAMPLE 26

(4E)-2-(4-Methoxy-benzenesulfonyl)-5,9ethyl-2-[4-(2-morpholin-4-yl-ethoxy) -benzyl]-deca-4,8-dienoic acid hydroxyamide To a stirred solution of (4-methoxy-benzenesulfonyl)-acetic acid ethyl ester (5.16 g, 20 mmol), geranyl bromide (4.2g, 20 mmol) and 18-Crown-6 (500 mg) in acetone (250 ml) was added K2CO3 (10 gms, excess) and the mixture refluxed foe 24 hours. At the end, the reaction mixture was filtered and the acetone layer was concentrated. The residue obtained was extracted with chloroform, washed well with water, dried over anhydrous MgSO$_4$, filtered and concentrated. The product obtained was purified by silica-gel column chromatography, eluting with 30% ethy acetate: hexane. The product 2-(4-methoxy-benzenesulfonyl)-5,9-dimethyl-deca-4,8-dienoic acid ethyl ester was isolated as a colourless oil. Yield: 7.0 g,89%.

Following the procedure as outlined in example 12, 2-(4-Methoxy-benzenesulfonyl)-5,9-dimethyl-2-[4-(2-morpholin-4-yl-ethoxy)-benzyl]-deca-4,8-dienoic acid ethyl ester was prepared, starting from (1.0 g, 2.5 mmol) of 2-(4-methoxy-benzenesulfonyl)-5,9-dimethyl-deca-4,8-dienoic acid ethyl ester and 4-(2-morpholin-1-yl-ethoxy)-benzyl chloride (800 mg, 2.5 mmol). Yield 1.2 g, 76%; Brown oil; MS: 614 (M+H)$^+$.

Starting from 2-(4-Methoxy-benzenesulfonyl)-5,9-dimethyl-2-[4-(2-morpholin-4yl-ethoxy)-benzyl]-deca-4,8-dienoic acid ethyl ester (2.0 gm, 3.2 mmol) 1.5 g (Yield: 80%) of 2-(4-Methoxy-benzenesulfonyl)-5,9-dimethyl-2-[4-(2-morpholin-4-yl-ethoxy)-benzyl]-deca-4,8-dienoic acid was isolated as semi-solid by following the procedure as outlined in example 9. MS: 586.6 (M+H)$^+$.

Starting from 2-(4-Methoxy-benzenesulfonyl)-5,9-dimethyl-2-[4-(2-morpholin-4-yl-ethoxy)-benzyl]-deca-4,8-dienoic acid (1.0 g, 1.7 mmol) and following the procedure as outlined in example 1, 550 mg of (4E)-2-(4-Methoxy-benzenesulfonyl)-5,9-dimethyl-2-[4(2-morpholin-4-yl-ethoxy)-benzyl]-deca-4,8-dienoic acid hydroxyamide was isolated as pale yellow solid. Yield: 550 mg, 53%; mp 61° C. (HCl Salt); MS: 638 (M+H)$^+$.

EXAMPLE 27

2-[4-(2-Diethylamino-ethoxy)-benzyl]-2-(4-methoxy-benzenesulfonyl)-hexanoic acid hydroxyamide 2-[4-(2-Diethylamino-ethoxy)-benzyl]-2-(4-methoxy-benzenesulfonyl)-hexanoic acid ethyl ester was prepared according to the general method as outlined in example 12. Starting from 2-(4-methoxy-benzenesulfonyl)-hexanoic acid ethyl ester (4 g, 12.7 mmol) and [2-(4-chloromethyl-phenoxy)-ethyl]diethylamine (3.38 g, 14 mmol). Yield 8.21 g crude (100%); brown oil; MS: 520.4 (M+H)$^+$.

2-[4-(2-Diethylamino-ethoxy)benzyl]-2-(methoxy-benzenesulfonyl)-hexanoic acid was prepared starting from 2-[4-(2-ethylamino-ethoxy)-benzyl]-2-(4-methoxy-benzenesulfonyl)-hexanoic acid ethyl ester (8 g, 15.4 mmol) dissolved in methanol (200 ml) and 10 N NaOH (30 ml). The resulting mixture was worked up as outlined in example 1. Yield 3.88 g crude (51%); brown oil; MS: 492 (M+H)$^+$.

Starting from 2-[4-(2-diethylamino-ethoxy)-benzyl]-2-(4-methoxy-benzenesulfonyl)-hexanoic acid (3.88 g, 7.89 mmol) and following the procedure as outlined in example 1, 800 mg of 2-[4-(2-diethylamino-ethoxy)-benzyl]-2-(4-methoxy-benzenesulfonyl)-hexanoic acid hydroxyamide was isolated as a yellow powder. Yield 20%; mp 67° C.; MS: 507.4 (M+H)$^+$; $^1$H NMR (300 MHz, DMSO-d$_6$): δ 0.75 (t, J=7.1 Hz, 3H), 1.05 (m, 2 H), 1.23 (t, J=7.2 Hz, 6H) 1.37–1.91 (m, 2H), 3.13 (m, 4H), 3.38–3.51 (m, 4H), 3.87 (s, 3H), 4.3 (t, J=4.8 Hz, 2H), 6.88 (d, J=8.7 Hz, 2H), 7.15 (m, 4H), 7.7 (d, J=9 Hz, 2H), 9.07 (s, 1H), 10.1 (s, 1H)

EXAMPLE 28

N-Hydroxy-2-(4-n-butoxy-benzenesulfonyl)-2-methyl-3-[4 (2-piperidin-1-yl-ethoxy)-phenyl]-propanamide Following the procedure as outlined in example 12, 2-(4-n-butoxy-benzenesulfonyl)-2-methyl-3-[4-(2-piperidin-1-yl-ethoxy)-phenyl]-propionic acid ethyl ester was prepared, starting from (3.1 g, 10 mmol) of 2-(4-n-butoxy-benzenesulfonyl)-propionic acid ethyl ester (Prepared from 2-(4-hydroxy-phenylsulfanyl)-propionic acid ethyl ester and n-butylbromide following the procedure outlined in example 27 )the 4-(2-piperidin-1-yl-ethoxy)-benzyl chloride (3.0 g, 10.1 mmol). Yield 4.5 g, 84%; Brown oil; MS: 532.7 (M+H)$^+$.

Starting from 2-(4-n-butoxy-benzenesulfonyl)-2-methyl-3-[4-(2-piperidin-1-yl-ethoxy)-phenyl]-propionic acid ethyl ester (5.0 gm, 9.4 mmol) 4.2 g (Yield: 88%) of 2-(4-n-butoxy-benzenesulfonyl)-2-methyl-3-[4-(2-piperidin-1-yl-ethoxy)-phenyl]-propionic acid was isolated as colorless solid by following the procedure as outlined in example 9. MS: 504.6 (M+H)$^+$ Starting from 2-(4n-butoxy-benzenesulfonyl)-2-methyl-3-[4-(2-piperidin-1-yl-ethoxy)-phenyl]-propionic acid (3.0 g, 5.9 mmol) and following the procedure as outlined in example 1, 1.3 g of 2-(4n-butoxy-benzenesulfonyl)-2-methyl-3-[4-(2-piperidine-1-yl-ethoxy)-phenyl]-propionamide was isolated as colorless solid. MP. 65 C, Yield: 1.3 g, 42%; (HCl Salt); MS: 478.5 (M+H)⁺; ¹HNMR (300 MHz, CDCl₃): δ 0.9 (t, 3H), 1.2 (s, 3H), 1.3–1.9 (m,10H), 2.8–4.5 (m, 12 H),, 6.8–7.8 (m, 8H), 10.8 (bs, 1H).

EXAMPLE 29
N-Hydroxy-2-(4-methoxy-benzenesulfonyl)-2-methyl-3-[3-(2-N,N-diethyl amino-ethoxy)-phenyl]-propionamide Following the procedure as outlined in example 12, 2-(4-methoxy-benzenesulfonyl)-2-methyl-3-[3-(2-N,N-diethyl amino-ethoxy)-phenyl]-propionic acid ethyl ester was prepared, starting from (5.0 g, 18 mmol) of 2-(4-methoxy-benzenesulfonyl)-propionic acid ethyl ester and the 3-(2-N,N-diethyl amino-ethoxy)-benzyl chloride (4.9 g, 18 mnmol). Yield 8.1 g, 93%; Brown oil; MS: 478.1 (M+H)⁺.

Starting from 2-(4-methoxy-benzenesulfonyl)-2-methyl-3-[3-(2-N,N-diethyl amino-ethoxy)-phenyl]-propionic acid ethyl ester (8.1 gm, 16.9 mmol) 6.7 g (Yield: 88%) of 2-(4-methoxy-benzenesulfonyl)-2-methyl-3-[3-(2-N,N-diethyl amino-ethoxy)-phenyl]-propionic acid was isolated as colorless semi-solid by following the procedure as outlined in example 9. MP: 78–81; MS: 450.1 (M+H)⁺.

Starting from 2-(4-methoxy-benzenesulfonyl)-2-methyl-3-[3-(2-N,N-diethyl amino-ethoxy)-phenyl]-propionic acid (6.7 g, 15 mmol) and following the procedure as outlined in example 1, 1.5 g of 2-(4-methoxy-benzenesulfonyl)-2-methyl-3-[3-(2-NN-diethyl amino-ethoxy)-phenyl]-propionamide was isolated as colorless low melting solid. Yield: 1.5 g, 21%; (HCl Salt); MS: 450.5 (M+H)⁺; ¹H NMR (300 MHz, DMSO-d₆): δ 1.21 (t, 6Hi), 1.26 (s, 3H), 3.18–3.24 (m, 2H), 3.38 (m, 4H), 3.43–3.46 (m, 2H), 3.80 (s, 3H), 4.30 (s,2H), 6.76–6.78 d, 2H), 6.84–7.2 (m,6H), 10.3 (bs, 1H).

EXAMPLE 30
N-Hydroxy-2-(4-methoxy-benzenesulfonyl)-2-methyl-3-[3-(2-morpholin-1-yl-ethoxy)-phenyl]-propionamide Following the procedure as outlined in example 12, 2-(4-methoxy-benzenesulfonyl)-2-methyl-3-[3-(2-morpholin-1-yl-ethoxy)-phenyl]-propionic acid ethyl ester was prepared, starting from (5.2 g, 20 mmol) of 2-(4-methoxy-benzenesulfonyl)-propionic acid ethyl ester and the 3-(2-morpholin-1-yl-ethoxy)-benzyl chloride (6.0 g, 20 mmol). Yield 9.1 g, 93%; Brown oil; MS: 492 (M+H)⁺.

Starting from 2-(4-methoxy-benzenesulfonyl)-2-methyl-3-[3-(2-morpholin-1-yl-ethoxy)-phenyl]-propionic acid ethyl ester (10.0 gm, 20.3 mmol) 8.0 g (Yield: 86%) of 2-(4-methoxy-benzenesulfonyl)-2-methyl-3-[3-(2-morpholin-1-yl-ethoxy)-phenyl]-propionic acid was isolated as colorless crystals by following the procedure as outlined in example 9.; MS: 464.5 (M+H)⁺.

Starting from 2-(4-methoxy-benzenesulfonyl)-2-methyl-3-[3-(2-morpholin-1-yl-ethoxy)-phenyl]-propionic acid (4.55 g, 9.8 mmol) and following the procedure as outlined in example 1, 440 mg of 2-(4-methoxy-benzenesulfonyl)-2-methyl-3-[3-(2-morpholi- 1-yl-ethoxy)-phenyl]-propionamide was isolated as colorless solid. Yield: 440 mg, 9%; mp 63° C.; MS: 479.5 (M+H)⁺; ¹H NMR (300 Mhz, DMSO-d₆): δ 1.26 (s, 3H), 3.18–3.8 (m, 12H), 3.9 (s, 3H), 4.4 (m, 2H), 6.7–8.8 (m, 8H), 10.8 (bs, 1H).

EXAMPLE 31
6-(1,3-Dioxo-1,3-dihydro-isoindol-2-yl)-2-(4-methoxy-benzenesulfonyl)-2-methyl -hexanoic acid hydroxyamide Following the procedure as outlined in Example 9, 6-(1,3-Dioxo-1,3-dihydro-isoindol-2-yl)-2-(4-methoxy-benzenesulfonyl)-2-methyl-hexanoic acid ethyl ester was prepared, starting from (5.0 g, 20 mmol) of 2-(4-methoxy-benzenesulfonyl)-acetic acid ethyl ester and 4-phathalimido bromobutane (5.66 g, 20 mmol). Yield 8.4 g, 97%; Colorless oil; MS: 474 (M+H).

Starting from 6-(1,3-Dioxo-1,3-dihydro-isoindol-2-yl)-2-(4methoxy-benzenesulfonyl)-2-methyl-hexanoic acid ethyl ester (8.4 g, 17.7 mmol) 6.95 g (88%) of 6-(1,3-Dioxo-1,3-dihydro-isindol-2 -yl)-2-(4-methoxy-benzenesulfonyl)-2-methyl-hexanoic acid was isolated as colorless oil by following the procedure as outlined in Example 9. MS: 446 (M–H)⁻.

Starting from 6-(1,3-Dioxo-1,3-dihydro-isoindol-2-yl)-2-(4-methoxy-benzenesulfonyl)-2-methyl-hexanoic acid (4.9 g, 11 mmol) and following the procedure as outlined in Example 1, 3.1 g of 6-(1,3-Dioxo-1,3-dihydro isoindol-2-yl)-2-(4-methoxy-benzenesulfonyl)-2-methyl -hexanoic acid hydroxyamide was isolated as a light brown solid; Yield: 46%; mp 146–148° C.; MS: 461.2 (M+H)⁺; ¹H NMR (300 MHz, DMSO-d₆): δ 1.55 (s, 3H), 1.61–3.77 (m, 8H), 3.82 (s, 3H), 6.92–8.21 (m, 8H), 10.70 (bs,1H), 11.20 (bs,1H).

EXAMPLE 32
3-[4-(2-Diethylamino-ethoxy)-phenyl]-2-(4-furan-2-yl-benzenesulfonyl)-N-hydroxy-2-methyl-propionamide To a stirred solution of 4-bromo thiophenol (19.0 g, 100 mmol) and triethyl amine (15.0 g, 150 mmol) in chloroform (400 ml) 2-bromo ethylpropionate (18. 2 g, 100 mmol) was added drop wise. The reaction mixture was refluxed for 1 hr and cooled to room temperature. The reaction mixture was washed with water, dried and concentrated. 2-(4-bromo-phenylsulfanyl)-propionic acid ethyl ester was isolated as colorless oil. Yield: 28.0 g, 99%, MS: 290 (M+H).

2-(4-bromo-phenylsulfanyl)-propionic acid ethyl ester was converted to 2-(4-bromo-phenylsulfonyl)-propionic acid ethyl ester by following the procedure as described in example 9, paragraph 2.

A mixture of 2-(4-bromo-phenylsulfonyl)-propionic acid ethyl ester (6.4 g, 20 mmol), 2-(tributyl stannyl)furan (7.5g, 21 mmol) and (Ph₃P)₄Pd (500 mg) was refluxed in degassed tolune (250 ml) for 8 hrs. At the end reaction rnixture was filtered through Celite and concentrated. The product was purified by silica gel column chromatography by eluting it with 50% ethylacetate : hexane. Colorless oil. Yield: 5.9 g, 95%, MS: 309 (M+H).

Following the procedure as outlined in example 12, 2-(4-(2-furanyl-benzenesulfonyl)-2-methyl-3-[4-(2-N,N-diethyl amino-ethoxy)-phenyl]-propionic acid ethyl ester was prepared, starting from (3.08 g, 10.0 mmol) of 2-(4-(2-furanyl-benzenesulfonyl)-propionic acid ethyl ester and the 4-(2-N,N-diethyl aminoethoxy)-benzyl chloride (3.5 g, 12.2 mmol). Yield 5.0 g, 97%; Brown oil; MS: 514.6 (M+H)⁺.

Starting from 2-(4-(2-furanyl-benzenesulfonyl)-2-methyl-3-[4-(2-N,Nethyl aminothoxy)-phenyl]-propionic acid ethyl ester (5.1 gm, 10.0 mmol) 3.8 g (Yield: 78 %) of 2-(4-(2-furanyl-benzenesulfonyl)-2-methyl-3-[4-(2-N,N-diethyl amino-ethoxy)-phenyl]-propionic acid was isolated as colorless solid by following the procedure as outlined in example 9. MP: 58 C, MS: 486.5 (M+H)⁺.

Starting from 2-(4-(2-furanyl-benzenesulfonyl)-2-methyl-3-[4-(2-N,N-diethyl amino-ethoxy)-phenyl]-propionic acid (5.0 g, 10.3 mmol) and following the procedure as outlined in example 1, 1.2 g of 2-(4-ethoxy-benzenesulfonyl)-2-methyl-3-[4-(2-N,N-ethyl aminoethoxy)-phenyl]-propionamide was isolated as colorless low melting solid. Yield. 3.2 g, 62%; (HCl Salt); MS: 502 (M+H)⁺; ¹H NMR (300 MHz, CDCl₃): δ 1.23 (t, 6H), 1.4 (s, 2H), 2.8 (q,4H), 3.0 (t, 2 H), 4.1 (t, 2H), 6.5–8.0 (m, 7H).

EXAMPLE 33

N-Hydroxy-2-(4-methoxy-benzenesulfonyl)-2-[4-(2-morpholin-4-yl-ethoxy)-benzyl]-butyramide 2-(4-Methoxy-phenylsulfanyl)-butyric acid ethyl ester was prepared according to the general method as outlined in example 9. Starting from ethyl 2-bromobutyrate (10.71 g, 55 mmol) and methoxythiophenol (7 g, 50 mmol), 5.19 g (40%); clear oil; MS: 255.2 (M+H)+.

2-(4-Methoxy-benzenesulfonyl)-butyric acid ethyl ester was prepared according to the general method as outlined in example 9. Starting from 2-(4-methoxy-phenylsulfanyl)-butyric acid ethyl ester (5 g, 20 mmol). Yield 5.74 g (100%); clear oil; MS: 287.1 (M+H)+.

Following the procedure as outlined in example 12, 2-(4-Methoxy-benzenesulfonyl)-2-[4-(2-morpholin-4-yl-ethoxy)-benzyl]-butyric acid ethyl ester was prepared, starting from (3.5 g, 12.2 mmol) of 2-(4-methoxy-benzenesulfonyl)-butyric acid ethyl ester and the 4-[2-(chloromethyl-phenoxy)-ethyl]-morpholine (2.34 g, 6.7 mmol). Yield 5.7 g, 100%; Brown oil; MS: 506.4 (M+H)+.

Starting from 2-(4-Methoxy-benzenesulfonyl)-2-[4-(2-morpholinyl-ethoxy)-benzyl]-butic acid ethyl ester (5.54 gm, 11 mmol) 2.9 g (Yield: 55%) of 2-(4-Methoxy-benzenesulfonyl)-2-[4-(2-morpholin-4-yl-ethoxy)-benzyl]-butyric acid was isolated as colorless semi-solid by following the procedure as outlined in example 9. MS: 478.3 (M+H)+.

Starting from 2-(4-methoxy-benzenesulfonyl)-2-[4-(2-morpholin-4-yl oxy)-benzyl]-butyric acid (2.6 g, 5.4 mmol) and following the procedure as outlined in example 1, 510 mg of N-hydroxy-2-(4-methoxy-benzenesulfonyl)-2-[4-(2-morpholin-4-yl-ethoxy)-benzyl]-butyramide was isolated as a brown solid. Yield 2%; mp 51° C.; MS: 493.3 (M+H)+; $^1$H NMR (300 MHz, DMSO-d$_6$): δ 0.90 (t, J=7.2 Hz, 3H), 1.69–1.96 (m, 4 H), 2.67 (t, 2H), 3.34 (m, 8H), 3.87 (s, 3H), 4.04 (m, 2H) 6.8 (d, J=8.7 Hz, 2H), 7.14 (m, 4IH), 7.73 (d, J=4.7 Hz, 2H), 9.08 (s, 1H), 10.8 (s, 1H).

EXAMPLE 34

N-Hydroxy-2-(4-methoxy-benzenesulfonyl)-2-[4-(2-piperidin-1-yl-ethoxy)-benzyl]-butyramide Following the procedure as outlined in example 12, 2-(4-Methoxy-benzenesulfonyl)-2-[4-(2-piperidin-1-yl-ethoxy)-benzyl]-butyric acid ethyl ester was prepared, starting from (1.0 g, 3.33 mmol) of 2-(4-methoxy-benzenesulfonyl)-butyric acid ethyl ester and the 1-[2-(4-chloromethyl-phenoxy)-ethyl]-piperidine (0.85 g, 3.36 =mol). Yield 1.07 g, 62%; Brown oil; MS: 504.4 (M+H)+.

Starting from 2-(4-Methoxy-benzenesulfonyl)-2-[4-(2-piperidin-1-yl-ethoxy)-benzyl]-butyric acid ethyl ester (3.7 gm, 7.3 mmol) 2.2 g (Yield: 63 %) of 2-(4-Methoxy-benzenesulfonyl)-2-[(2-piperidin-1-yl- ethoxy)-benzyl]-butyric acid was isolated as colorless semi-solid by following the procedure as outlined in example 9. MS: 476( M+H)+.

Starting from 2-(4-Methoxy-benzenesulfonyl)-2-[4-(2-piperidin-1-yl-ethoxy)-benzyl]-butyric acid (2.2 g, 4.63 mmol) and following the procedure as outlined in example 1, 360 mg of N-Hydroxy-2-(4-methoxy-benzenesulfonyl)-2-[4-(2-piperidin-1-yl-ethoxy)-benzyl]-butyramide was isolated as a brown solid. Yield 16%; mp 75° C.; MS: 491.3 (M+H)+; $^1$H NMR (300 MHz, DMSO-d$_6$): δ 0.90 (t, J=7.1 Hz, 3H), 1.36–1.96 (m, 4 H), 2.4–2.63 (m, 14H), 3.87 (s, 3H), 4.01 (t, J=5.9 Hz, 2H) 6.8 (d, J=8.5 Hz, 2H), 7.11 (m, 4H), 7.71 (d, J=8.8 Hz, 2H), 9.09 (s, 1H), 10.8 (s, 1H)

EXAMPLE 35

2-(4-Methoxy-benzenesulfonyl)-2-[4-(2-morpholin-4-yl-ethoxy)-benzyl]-pentanoic acid hydroxyamide 2-(4-Methoxy-phenylsulfanyl)-pentanoic acid ethyl ester was prepared according to the general method as outlined in example 9. Starting from ethyl 2-bromovalerate (8.23 g, 39.3 mmol) and 4-methoxythiophenol (5 g, 35.7 mmol), 10.46 g (100%); clear oil; MS: 269 (M+H)+.

2-(4-Methoxy-benzenesulfonyl)-pentanoic acid ethyl ester was prepared according to the general method as outlined in example 9. Starting from 2-(4-methoxy-phenylsulfanyl)-pentanoic acid ethyl ester (6.9 g, 27.4 mmol). Yield 7.07 g (86%); clear oil; MS: 300.9 (M+H)+.

Following the procedure as outlined in example 12, 2-(4-Methoxy-benzenesulfonyl)-2-[4-(2-morpholin-4-yl-ethoxy)-benzyl]-pentanoic acid ethyl ester was prepared, starting from (3.0 g, 10.8 mmol) of 2-(4-methoxy-benzenesulfonyl)-pentanoic acid ethyl ester and the 4-[2-(chloromethyl-phenoxy)-ethyl]-morpholine (3.45 g, 11.9 mmol). Yield 3.08 g, 62%; Brown oil; MS: 520.4 (M+H)+.

Starting from 2-(4-Methoxy-benzenesulfonyl)-2-[4-(2-morpholinlyl-ethoxy)-benzyl]-pentanoic acid ethyl ester (2.73 gm, 5.27 mmol) 1.45 g (Yield: 56%) of 2-(4-Methoxy-benzenesulfonyl)-2-[4-(2-morpholin-4-yl-ethoxy)-benzyl]-pentanoic acid was isolated as colorless semi-solid by following the procedure as outlined in example 9. MS: 492.3 (M+H)+.

Starting from 2-(4-methoxy-benzenesulfonyl)-2-[4-(2-morpholin-4-yl-ethoxy)-benzyl]-pentanoic acid (1.01 g, 2.05 mmol) and following the procedure as outlined in example 1, 190 mg of 2-(4-methoxy-benzenesulfonyl)-2-[4-(2-morpholin-4yl-ethoxy)-benzyl]-pentanoic acid hydroxyamide was isolated as a brown solid. Yield 18%; mp 101° C.; MS: 507.4 (M+H)+; $^1$H NMR (300 MHz, DMSO-d$_6$): δ 0.71 (t, J=7 Hz, 3H), 1.58–1.82 (m, 4 H), 3.12–3.98 (m, 12H), 3.87 (s, 3H), 4.35 (t, 2H) 6.89 (d, J=8.7 Hz, 2H), 7.15 (m, 4H), 7.74 (d, J=8.9 Hz, 2H), 9.08 (s, 1H).

EXAMPLE 36

2-[4-(2-Azepan-1-yl-ethoxy)-benzyl]-2-(4Methoxy-benzenesulfonyl)-octanoic acid hydroxyamide 2-(4-Methoxy-phenylsulfanyl)-octanoic acid ethyl ester was prepared according to the general method as outlined in example 9. Starting from ethyl 2-bromooctanoate (11.8 g, 47.3 mmol) and 4-methoxythiophenol (6 g, 43 mmol). Yield: 7.24 g (57%); clear oil; MS: 311.2 (M+H)+, 2-(4-Methoxy-benzenesulfonyl)-octanoic acid ethyl ester was prepared according to the general method as outlined in example 9. Starting from 2-(4-methoxy-phenylsulfanyl)octanoic acid ethyl ester (4.0 g, 13.6 mmol). Yield 3.7 g (83%); clear oil; MS: 343.3 (M+H)+.

Following the procedure as outlined in example 12, 2-[4-(2-Azepan-1-yl-ethoxy)-benzyl]-2-(4-Methoxy-benzenesulfonyl)-octanoic acid ethyl ester was prepared, starting from (1.69 g, 5.18 mmol) of 2-(4-methoxy-benzenesulfonyl)-octanoic acid ethyl ester and the 1-[2-(4-chloromethyl-phenoxy)-ethyl]-azepane (1.73 g, 6.0 mmol). Yield 4.86 g, 99%; Brown oil; MS: 574.5 (M+H)+.

Starting from 2-[4-(2-Azepan-1-yl-ethoxy)-benzyl]-2-(4-Methoxy-benzenesulfonyl)-octanoic acid ethyl ester (4.8 gm, 8.37 mmol) 1.55 g (Yield: 34%) of 2-[4-(2-Azepan-1-yl-ethoxy)-benzyl]-2-(4-Methoxy-benzenesulfonyl)-octanoic acid was isolated as colorless semi-solid by following the procedure as outlined in example 9. MS: 551 (M+H)+.

Starting from 2-[4-(2-Azepan-1-yl-ethoxy)-benzyl]-2-(4-Methoxy-benzenesulfonyl)-octanoic acid (1.09 g, 2.0 mmol) and following the procedure as outlined in example 1, 300 mg of 2-[4-(2-Azepan-1-yl-ethoxy)-benzyl]-2-(4-Methoxy-benzenesulfonyl)-octanoic acid hydroxyamide was isolated as a yellow solid. Yield 27%; mp 65° C.; MS: 561.6 (M+H)$^+$; $^1$H NMR (300 MHz, DMSO-d$_6$): δ 0.81 (t, J=6.6 Hz, 3H), 1.08–1.82 (m,14H), 3.13–3.51 (m, 12H), 3.87 (s, 3H), 4.33 (t, 2H) 6.88 (d, J=8.7 Hz, 2H),7.14 (m,4H), 7.7 (d, J=9 Hz, 2H), 9.06 (s, 1H), 10.28 (s, 1H).

EXAMPLE 37

2-(4-Methoxy-benzenesulfanyl)-octanoic acid hydroxyamide 2-(4-Methoxy-phenylsulfanyl)-octanoic acid ethyl ester was prepared according to the general method as outlined in example 9. Starting from ethyl 2-bromooctanoate (11.8 g, 47.3 mmol) and 4-methoxythiophenol (6 g, 43 mmol). Yield: 7.24 g (57%); clear oil; MS: 311.2 (M+H)$^+$.

Starting from 2-(4-Methoxy-benzenesulfanyl)-octanoic acid ethyl ester (3.1 gm, 10 mmol) 255 g (Yield: 90 %) of 2-(4-Methoxy-benzenesulfanyl)-octanoic acid was isolated as colorless semi-solid by following the procedure as outlined in example 9. MS: 283 (M+H)$^+$.

Starting from 2-(4-Methoxy-benzenesulfanyl)-octanoic acid (4.25 g, 16 mmol) and following the procedure as outlined in example 1, 3.64 g of 2-(4-Methoxy-benzenesulfanyl)-octanoic acid hydroxyamide was isolated as colorless solid. Yield: 76%, MP: 90 C; MS: 298.2 (M+H).

EXAMPLE 38

2-(4-Fluoro-phenylsulfanyl)-octanoic acid hydroxyamide 2-(4-Fluorophenylsulfanyl)-octanoic acid ethyl ester was prepared according to the general method as outlined in example 9. Starting from ethyl 2-bromooctanoate (6.47 g, 24.7 mmol) and 4-fluorothiophenol (3 g, 23.4 mmol). Yield: 6.31 g (90%); clear oil; MS: 299 (M+H)$^+$.

Starting from 2-(4-fluoro-benzenesulfanyl)-octanoic acid ethyl ester (3.1 gm, 10 mmol) 2.89 g (Yield: 100 %) of 2-(4-fluoro-benzenesulfanyl)-octanoic acid was isolated as colorless semi-solid by following the procedure as outlined in example 9. MS: 268.9 (M+H)$^+$.

Starting from 2-(4-fluoro-benzenesulfanyl)-octanoic acid (2.49 g, 9.2 mmol) and following the procedure as outlined in example 1, 2.72 g of 2-(4-fluoro-benzenesulfanyl)-octanoic acid hydroxyamide was isolated as colorless solid. Yield: 99%, MP: 58 C; MS: 284(M–H).

EXAMPLE 39

2-(1-methyl-1H-imidazol-2-ylsulfanyl)-octanoic acid hydroxyamide 2-(1-methyl-1H-imidazol-2-ylsulfanyl)-octanoic acid ethyl ester was prepared according to the general method as outlined in example 9. Starung from ethyl 2-bromooctanoate (12.1 g, 48 mmol) and 1-methyl-2-mercapto imidazole (5 g, 43.8 mnmol). Yield: 12 g (96%); clear oil; MS: 285 (M+)$^+$.

Starting from 2-(1-methyl-1H-imidazol-2-ylsulfanyl)-octanoic acid ethyl ester (12 gm, 42.2 mmol) 10.2 g (Yield: 95%) of 2-(1-methyl-1H-imidazol-2-ylsulfanyl)-octanoic acid was isolated as colorless solid by following the procedure as outlined in example 9. MP: 95 C, MS: 257.1 (M+H)$^+$.

Starting from 2-(1-methyl-1H-imidazol-2-ylsulfanyl)-octanoic acid (7.84 g, 30.6 mmol) and following the procedure as outlined in example 1, 2.77 g of 2-(1-methyl-1H-imidazol-2-ylsulfanyl)-octanoic acid hydroxyamide was isolated as colorless solid. Yield: 33%, MP: 125 C; MS: 272.2 (M+H).

EXAMPLE 40

N-Hydroxy-2-(4-methoxy-benzenesulfonyl)-3-naphthalen-2-yl-propionamide

Following the procedure as outlined in Example 9, 2-(4-methoxy-benzensulfonyl)-3-naphthalen-2-yl-propionic acid ethyl ester was prepared, starting from (5.0 g, 20 mmol) of 2-(4-methoxy-benzenesulfonyl)-acetic acid ethyl ester and 2-bromomethyl naphthalene (4.4 g, 20 mmol). Yield 7.2 g, 91%; Colorless oil; MS: 399 (M+H)$^+$.

Starting from 2-(4-methoxy-benzenesulfonyl)-3-naphthalen-2-yl-propionic acid ethyl ester (3.7 g, 9 mmol) 3.3g (96%) of 2-(4-methoxy-benzenesulfonyl)-3-naphthalen-2-yl-propionoic acid was isolated as colorless oil by following the procedure as outlined in Example 9. MS: 369.1 (M–H)$^-$.

Starting from 2-(4-methoxy-benzenesulfonyl)-3-naphthalen-2-yl-propionic acid (2.2 g, 5.9 mmol) and following the procedure as outlined in Example 1, 820 mg of N-hydroxy-2-(4-methoxy-benzenesulfonyl)-3 -naphthalen-2-yl-propionamide was isolated as a light brown solid; Yield: 36%; mp 161–163° C.; MS: 385.9 (+M)$^+$; $^1$H NMR (300 MHz, CDCl$_3$): δ 3.32 (d, 3–7.0 Hz, 1H), 3.69 (d, J=7.0 Hz, 1H), 3.82 (s, 3H), 5.02 (s, 1H), 6.92–7.89 (a, 11H).

EXAMPLE 41

N-Hydroxy-2-(4-methoxy-phenylmethanesulfonyl)-2-methyl-3-phenyl propionic acid hydroxamide A mixture of 4methoxybenzyl mercaptan ( 7.0g, 45 mmol), ethyl 2-bromopropionate (8.2 g, 46 mmol) and powdered oven dried potassium carbonate ( log, 72 mmol) in 150 mL of acetone was heated at reflux for 18 h. The mixture was cooled, filtered, and the filtrate concentrated. The residue was taken up in 150 mL of methylene chloride, washed with water (150 mL), dried over anhydrous sodium sulfate and evaporated to yield 12 g (99%); colorless liquid; MS 255.1 (M+H). This product is used without further purification.

To an ice cold (5° C.) solution of 2-(4-methoxy-phenylmethanesulfanyl)-propionic acid ethyl ester (5.7g, 21 mmol) in 100 mL CH$_2$Cl$_2$ was added portionwise (7.2g, 40 mmol) of m-chloroperbenzoic acid and the mixture was stirred for 1 h. The reaction was diluted with hexanes (500 mL) and stirred at 25° C. for 30 minute at room temperature. The mixture was filtered and the organic layer treated with saturated aqueous sodium bisulfite (200 mL). The hexanes solution containing the product was washed with water, dned (Na$_2$SO$_4$) and concentrated. Yield 5.5 g (91%); colorless oil; MS 287.1 (M+H)$^+$.

Following the procedure as outlined in Example 9, 2-(4Methoxy-phenylmethanesulfonyl)-2-methyl-3-phenyl-propionic acid ethyl ester was prepared, starting from 2-(4-Methoxy-phenylmethanesulfonyl)-propionic acid ethyl ester (2 g, 7 mmol) and benzyl bromide (1.3 g, 7.7 mmol). Yield 3.0 g, 100%; Low melting solid; MS: 377 (M+H)$^+$.

2-(4-Methoxy-phenylmethanesulfonyl)-2-methyl-3-phenyl-propionic acid was prepared starting from 2-(4-Methoxy-phenylmethanesulfonyl)-2-methyl-3-phenyl-propionic acid ethyl ester (3.5 g, 9.0 mmol) dissolved in methanol (50 ml) and 10 N NaOH (30 ml). The resulting reaction mixture was worked up as outlined in Example 9. Yield 930 mg, 31%. Colorless solid, mp: 106–108 C;. MS: 347 (M–H)$^+$.

Starting from 2-(4-Methoxy-phenylmethanesulfonyl)-2-methyl-3-phenyl-propionic acid (2.7 g, 57.0 mmol) and following the procedure as outlined in example 1, 266 mg of N-Hydroxy-2-(4-methoxy-phenylmethanesulfonyl)-2-methyl-3-phenyl propionic acid hydroxamide was isolated as light colorless solid; Yield 10%; mp 58–59° C.; MS:

364.2 (M+H)⁺; ¹H NMR (300 MHz, DMSO-d$_6$): δ 1.28 (s, 3H), 2.842.88 (d, 1H), 3.75 (s, 3H), 3.81–3.86 (d, 1H), 4.594.63 (d, 1H), 4.694.74 (d, 1H), 6.94–6.98 (d, 2H), 7.19 (m, 2H), 7.29–7.33 (d, 4H), 9.24 (s, 1H), 10.88 (s, 1H).

EXAMPLE 42
5-Methyl-2-(3-methyl-but-2-enyl)-2-(toluene-4-sulfonyl)-hexenoic acid hydroxyamide 5-Methyl-2-(3-methyl-but-2enyl)-2-(toluenesulfonyl)-hex-4-enoic acid ethyl ester was prepared according to general method as outlined in example 9. Starting from ethyl α-(p-tolylsulfonyl)acetate (2.9 g, 10.9 mmol and 4bromo-2-methyl butene (3.42g, 23 mmol). Yield 4.6 g; tan oil; MS 379.2 (M+H)⁺.

5-methyl-2-(3-methyl-but-2-enyl)-2-(toluenefsulfonyl)-hexenoic acid was prepared according to general method as outlined in example 9. Starting from 5-methyl-2-(3-methyl-but-2-enyl)-2-(toluenesulfonyl-hexfnoic acid ethyl ester (4.5g, 11 mmol), ethanol (15 mL) and 10-N sodium hydroxide.

Starting fom 5-methyl-2-(3-methyl-but-2-enyl)-2-(toluenefsulfonyl)-hexfnoic acid (4.1 g, 11 mmol) and following the procedure as outlined in example 1, 1.07 g of 5-Methyl-2-(3-methyl-but-2-enyl)-2-(toluenefsulfonyl)-hex-4-enoic acid hydroxyamide was isolated as colorless solid; Yield: 30%; mp 108–110° C.; MS: 366.2 (M+H)⁺; ¹H NMR (300 MHz, DMSO-d$_6$): δ 61.49 (s, 6H), 1.62 (s, 6H), 2.41 (s, 3H), 2.53–2.63 (m, 4H), 5.00–5.05 (t, 2H), 7.40–7.43 (d, 2H), 7.59–7.62 (d, 2H), 9.04 (s, 1H), 10.80 (s, 1H).

EXAMPLE 43
2-Methyl-2-(2-methyl-furan-3-sulfonyl)-3-phenyl-propionic acid hydroxamide 2-Methyl-2-(2-methyl-furan-3-sulfonyl)-3-phenyl-propionic acid ethyl ester (Prepared from 3-mercapto-2-methylfuran) was prepared according to the general method as outlined in example 9. Starting from 2-(2-methyl-furan-3-ylsulfanyl)-propionic acid ethyl ester (2.9g, 11.9 mmol), benzyl bromide (2.22g, 13 mmol) and potassium carbonate (lOg) in acetone (75 mL). Yield (99%); amber oil; MS 337.1 (M+H)⁺.

2-Methyl-2-(2-methyl-furan-3-sulfonyl)-3-phenyl-propionic acid was prepared according to the general method as outlined in example 9. Starting from 2-(2-methyl-furan-3-ylsulfanyl)-propionic acid ethyl ester (4.8g, 14.3 mmol), dissolved in ethanol (25 niL and 10 N sodium hydroxide (10 mL). Yield 3.7 g (84 %), white solid, MS 307.4 (M–H).

Starting from 2-Methyl-2-(2-methyl-furan-3-sulfonyl)-3-phenyl-propionic acid (3.58 g, 12 mmol) and following the procedure as outlined in example 1, 1.078 g of 2-Methyl-2-(2-methyl-furan-3-sulfonyl)-3-phenyl-propionic acid hydroxyamide was isolated as orange color solid; Yield: 29%; mp 68–70° C.; MS: 324 (M+H)⁺; ¹H NMR (300 MHz, DMSO-d$_6$): δ 1.27 (s, 3H), 2.81–2.86 (d, 1H), 3.33 (s, 3H), 3.61–3.66 (d, 1H), 6.66 (s, IH), 7.19–7.25 (m, 5H), 7.76 (s, 1H), 9.09 (s, 1H), 10.81 (s, 1H)

EXAMPLE 44
2-Methyl-2-(2-methyl-furan-3-sulfonyl)-3-[4-(2-piperidin-1-yl-etoxy)-phenyl]-propionic acid hydroxamide 2-Methyl-2-(2-methyl-furan-3-sulfonyl)-3-[4(2-piperidin-yl-ethoxy)-phenyl]-propionic acid ethyl ester was prepared according to the general method as outlined in example 9. Starting from 2-(2-methyl-furan-3-sulfonyl)-propionic acid ethyl ester (2.4g, 9.8 mmol) and 1-[2-(4-chloromethylphenoxy)-ethyl]-piperidine (2.96g, 10.7 mmol); Yield 2.4 g (92%); amber oil; MS 464.2 (M+H)⁺.

2-Methyl-2-(2-methyl-furan-3-sulfonyl)-3-[4(2-piperidin-1-yl-ethoxy)-phenyl]-propionic acid was prepared according to the general method as outlined in example 1. Starting from 2-methyl-2-(2-methyl-furan-3-sulfonyl)-3-[4-(2-piperidin-1-yl-ethoxy)-phenyl]-propionic acid ethyl ester (2.01 g, 4.5 mmol), dissolved in ethanol (20 mL) and 10 N sodium hydroxide (10 mL). The resulting mixture was worked up as outline in example 9. Yield 2.03g; amber crystals mp 66–68° C.; MS 434 (M–H).

Starting from 2-Methyl-2-(2-methyl-furan-3-sulfonyl)-3-[(2-piperdin-1-yl-ethoxy)-phenyl]-propionic acid (2.03 g, 6.0 mmol) and following the procedure as outlined in example 1, 1.36 g of 2-Methyl-2-(2-methyl-furan-3-sulfonyl)-3-[(2-piperidin-1-ylethoxy)-phenyl]-prpionic acid hydroxyamide was isolated as amber color solid; Yield: 32%; mp 115–117 ° C; MS: 451.1 (M+H)⁺; ¹H NMR (300 MHz, DMSO-d$_6$): δ 1.15–1.22 (m, 2H), (1.75 (s, 3H), 1.78 (s, 3H) 2.98–3.03 (m, 2H), 3.42–3.47 (m, 2H), 3.5 (s, 3H), 6.65 (s, 1H), 6.87–6.90 (d, 2H), 7.12–7.17 (d, 2H), 10.35 (s, 1H), 10.60 (s, 1H), 11.70 (s, 1H).

EXAMPLE 45
2-Methyl-3-[4-(2-piperidin-1-yl-ethoxy)-phenyl-2-(thiophene-2-sulfonyl)-propionic acid hydroxamide 2-Methyl-3-[4-(2-piperidin-1-yl-ethoxy)-phenyl2-(thiophene-2-sulfonyl)-propionic acid ethyl ester was prepared acording to the general method as outlined in example 9. Starting from 2-(thiophene-2-sulfonyl)-propionic acid ethyl ester( prepared from 2-mercaptothiophene and 2-bromopropionic acid ethylester) (4.4 g, 17.7 mnmol) and 1-[2-(4-chloromethylphenoxy)-ethyl]-piperidine (5.3 g, 19.5 mmol); Yield (96%); semi-solid; MS 466.

2-Methyl-3-[4-(2-piperidin-1-yl-ethoxy)-phenyl-2-(thiophene-]1-sulfonyl)-propionic acid was prepared according to the general method as outlined in example 9. Starting from 2-methyl-3-([(2-piperidin-1-yl-ethoxy)-phenyl-2-sulfonyl)-propionic acid ethyl ester (9.8g, 20 mmol), dissolved in ethanol (20 mL) and 10 N sodium hydroxide (20 maL). The resulting mixture was worked up as outline in example 1. Yield 4.5g (49%); white solid mp 170–172° C.; MS 436.3 (M–H).

Starting from 2-Methyl-3-[4-(2-piperidin-1-yl-ethoxy)-phenyl-2-(thiophene-2-sulfonyl)-propionic acid (3.6 g, 8.0 mmol) and following the procedure as outlined in example 1, 345 mg of 2-Methyl-3-[4-(2-piperidin-1-yl-ethoxy)-phenyl-2-(thiophene-2-sulfonyl)-propionic acid hydroxyamide was isolated as light colorless solid; Yield: 10%; mp 115–118° C.; MS: 451.2 (M+H)⁺; ¹H NMR (300 MHz; DMSO-d$_6$): δ 31.29 (s, 3H), 1.66–1.78 (m, 6H), 2.81–2.86 (d, 1H), 2.96–3.99 (m, 4H), 3.39–3.47 (m, 2H), 3.51–3.59 (d, 1H), 4.32 (m, 2H),6.72–6.74 (d 1H), 6.87–6.96 (d, 2H), 7.01–7.20 (m, 3H), 7.31–7.33 (m, 1H), 7.69–7.72 (m, 1H), 7.83–7.84 (m, 1H), 8.07–8.08 (dd, 1H), 8.17 (dd, 1H), 9.0 (s, IH) 10.0 (s, 1H), 10.78 (s, 1H).

EXAMPLE 46
2-(octane-1-sulfonyl)-3-[4-(2-piperidin-yl-ethoxy)-phenyl] propionic acid hydroxamide 2-(Octane-1-sulfonyl)-3-[4-(2-piperidin-yl-ethoxy)-phenyll-propionic acid ethyl ester was prepared according to the general method as outlined in example 9. Starting from 2-(octane-1-sufonyl)-propionic acid ethyl ester (5.0 g, 18 mmol) and 1-[2-(4chloromethylphenoxy)-ethyl]-piperidine (5.6 g, 19.7 mmol); Yield 8.9 g (96%); amber oil, MS 495.

2-(Octane-1-sulfonyl)-3-[4-(2-piperidin-yl-ethoxy)-phenyl]-propionic acid was prepared according to the general method as outlined in example 9. Starting from 2-(octane-1-sulfonyl)-3-[4-(2-piperidin-yl-ethoxy)-phenyl- 3-propionic acid ethyl ester (8.9g, 18 mmol), ethanol (25 mL) and 10 N sodium hydroxide (25 mL). Yield 6.0 g (72%).

Starting from 2-(Octane-1-sulfonyl)-3-[4-(2-piperidin-yl-ethoxy)-phenyl]-propionic acid (3.6 20 g, 7.7 mmol) and following the procedure as outlined in example 1, 3.3 g of 2-(Octane-1-sulfonyl)-3-[4-(2-piperidin-yl-ethoxy)-phenyl]-propionic acid hydroxyamide was isolated as tan solid; Yield: 89%; mp 69–70° C.; MS: 483.2 (M+H)$^+$; $^1$H NMR (300 MHz, DMS O-d$_6$): δ 0.687 (t, 3H), 1.27–1.69 (m, 15H), 2.71–2.75 (d, 1H), 3.51 (s, 3H), 3.65–3.69 (d, 1H), 6.86–6.89 (d, 2H), 7.08–7.11 (d, 2H), 9.16 (s, 1H), 10.70 (s, 1H).

EXAMPLE 47
3-Biphenyl-4yl-2-methyl-2-(1-methyl-1H-imidazole-2-sulfonyl)-propionic acid hydroxyamide 3-Biphenyl-4-yl-2-methyl-2-(1-methyl-1H-imidazole-2-sulfonyl)-propionic acid ethyl ester was prepared according to the general method as outlined in example 9. Starting from 2-methyl-(1-methyl-1H-imidazolesulfonyl)-propionic acid ethyl ester Prepared from (1-Methyl-2-mercapto imidazole and 2-bromo ethyl propionate) (3.0 g, 12.2 mmol) and 4 chloromethylbiphenyl (2.97 g,15 mmol). Yield 5.0 g (99 %); low melting solid; MS 413 (M+H)$^+$.

3-Biphenyl-4yl-2-methyl-2(1-methyl-1H-imidazole-2-sulfonyl)-propionic acid was prepared according to the general method as outlined in example 9. Starting from 3-biphenyl-4-yl-2-methyl2-(1-methyl-1H-imidazole-2-sulfonyl)-propionic acid ethyl ester (5.0g, 11.9 mmol), ethanol (15 mL) and 10 N sodium hydroxide (10 mL). Yield 2.8g (61%); brown solid mp 119–122° C.; MS 385.2 (M+H).

Starting from 3-Biphenyl-4-yl-2-methyl-2-(1-methyl-1H-imidazole-2-sulfonyl)-propionic acid (2.8 g, 7.0 mmol) and following the procedure as outlined in example 1, 112 mg of 3-Biphenyl-4-yl-2-methyl-2-(1-methyl-1H-imiidazole-2-sulfonyl)-propionic acid hydroxyamide was isolated as tan colored solid; Yield: 4%; mp 112° C.; MS: 399.0 (M+H)$^+$; $^1$H NMR (300 Mz, DMSO-d$_6$): δ 0.911 (s, 3H), 3.3 (s, 3H), 3.5 (d, 1H), 4.2 (d, 1H), 6.8 (d, 1H), 6.9 (d, 1H), 7.18–7.66 (m, 5H), 7.30–7.33 (d, 2H), 7.55–7.58 (d, 2H).

EXAMPLE 48
2-Methyl-3-phenyl-2-(thiophene-2-sulfonyl)-propionic acid hydroxyamide 2-Methyl-3-phenyl-2-(thiophene-2-sulfonyl)-propionic acid ethyl ester was prepared according to the general method as outlined in example 9. Starting from 2-(thiophen-2-sulfonyl)-propionic acid ethyl ester (3.0 g, 12 mmol) and benzyl bromide (2.48 g, 15 mmol). Yield 5.2 g (%); tan oil; MS 339.1 (M+H).

2-Methyl-3-phenyl-2-(thiophene-2-sulfonyl)-propionic acid was prepared according to the general method as outlined in example 9. Starting from 2-methyl-3-phenyl-2-(thiophen-2-sulfonyl)-propionic acid ethyl ester (5.0 g, 15 mmol), ethanol (30 mL) and 10 N sodium hydroxide (10 mL). Yield 5.6g MS 310.0 (M+H).

Starting from 2-Methyl-3-phenyl-2-(thiophene-2-sulfonyl)-propionic acid (5.0 g, 16 mmol) and following the procedure as outlined in example 1, 1.8 g of 2-Methyl-3-phenyl-2-(thiophene-2-sulfonyl)-propionic acid hydroxyamide was isolated as colorless solid; Yield: 40%; mp 116–117° C.; MS: 325.9 (M+H)$^+$; $^1$H NMR (300 MHz, DMSO-d$_6$): δ 1.29 (s, 3H), 3.33 (d, 1H), 3.69 (d 1H), 7.18–7.30 (m, 5H), 7.74 (m, 1H), 8.22 (m, 1H), 9.13 (s, 1H), 10.80 (s, 1H),

EXAMPLE 49
2-[8-(1-carboxy-ethanesulfonyl)-octane-1-sulfonyl]-propionic acid hydroxyamide 2-[8-(1-Carboxyl-ethanesulfonyl)-octane-1-sulfonyl]-propionic acid ethyl ester was prepared according to the general method as outlined in example 9. Starting from 2-[4-(1-ethoxycarbonyl-ethylsulfanyl)octylsulfanyl]-propionic acid ethyl ester (10.2 g, 26 mmol) and sodium peroxymonopersulfate (64g, 104 mmol). Yield 9.87g (86%); colorless liquid; MS 442.9 (M+H).

2-[8-(1-Carboxy-ethanesulfonyl)-octane-1-sulfonyl]-propionic acid was prepared according to general method as outline in example 1. Starting from 2-[8-(1-carboxyethanesulfonyl)-octane-1 -suffonyl]-propionic acid ethyl ester (3.0 g 6.8 mmol), ethanol (15 mL) and 10 N sodium hydroxide (15 nm). Yield 2.7 g (98%); wite solid mp 99–102 ° C.; MS 387 (M+NH3)$^+$.

Starting from 2-[8-(1-Carboxy-ethanesulfonyl)-octane-1-sulfonyl]-propionic acid (2.5 g, 6.5 mmol) and following the procedure as outlined in example 1, 641 mg of 2-[8-(1-Carboxy-ethanesulfonyl)-octane-1-sulfonyl]-propionic acid hydroxyamidewas isolated as amber coloured oil.; Yield: 23%; MS: 434.0 M+NH4)$^+$; $^1$H NMR (300 MHz, DMSO-d$_6$): δ 1.27–3.23 (m, 22H), 3.33 (m, 2H), 8.9 (s, 1H), 9.28 (s, 1H).

EXAMPLE 50
2-(4-Bromo-benzenesulfonyl)-2-methyl-3-[4-(2-piperidine-1-yl-ethoxy)-phenyl]-propionic acid hydroxamide 2-(4-Bromo-benzenesulfonyl)-2-methyl-3-[4-(2-piperidine-1-yl-ethoxy)-phenyl]-propionic acid ethyl ester was prepared according to general method as outlined in example 9. Starting from ethyl α-(4-bromophenyl-sulfonyl) acetate (5.0g, 16 mmol) and 1-[2-(4-chloromethylphenoxy)-ethyl]-piperidine (4.97 g, 16 mmol). Yield 6.1 g (71%); tan oil; MS 541.1 (M+H)$^+$.

2-(4-Bromo-benzenesulfonyl)-2-methyl-3-[4-(2-piperidine-1-yl-ethoxy)-phenyl]-propionic acid was prepared according to general method as outlined in example 9. Starting from2-(4-bromo-benzenesulfonyl)-2-methyl-3-[4-(2-piperidine-1-yl-ethoxy)-phenyl]-propionic acid ethyl ester (6.5 g, 20 mmol), ethanol (30 mL) and 10 N sodium hydroxide (15 mL). Yield 6.3 g (100%); yellow solid mp 125–127° C.; MS 512.5 (M+H)$^+$.

Starting from 2-(4-Bromo-benzenesulfonyl)-2-methyl-3-[4-(2-piperdine-1-yl-ethoxy)-phenyl]-propionic acid (6.1 g, 612 mmol) and following the procedure as outlined in example 1, 1.07 g of 2-(4-Bromo-benzenesulfonyl)-2-methyl-3-[4-(2-piperidine-1-yl-ethoxy)-phenyl]-propionic acid hydroxyamide was isolated as light yellow solid; Yield: 17%; MS: 525.4 (M+H)$^+$.

EXAMPLE 51
3-(4-Bromo-phenyl)-N-hydroxy-2-(4-methoxy-benzenesulfonyl)-2-methyl-propionamide Following the procedure as outlined in Example 9, 3-(4-bromo-phenyl)-2-(4-methoxy-benzensulfonyl)-2-methyl-propionic acid ethyl ester was prepared, starting from (3.0 g, 11 mmol) 2-(4-methoxy-benzenesulfonyl)-propionic acid ethyl ester and 4bromobenzyl bromide (3.0 g, 12 mmol). Yield 4.67 g, 96%; Colorless oil; MS: 441 (M+H)$^+$.

3-(4-Bromo-phenyl)-2-(4-methoxy-benzenesulfonyl)-2-methyl-propionic acid was prepared starting from 3-(4-bromo-phenyl)-2-(4-methoxy-benzenesulfonyl)-2-methyl-propionic acid ethyl ester (4.0 g, 9.0 mmol) dissolved in methanol (50 ml) and 10 N NaOH (30 ml). The resulting reaction mixture was worked up as outlined in Example 9. Yield 3.0 g, 78%. Low melting solid. MS: 413 (M+H)$^+$.

Starting from 3-(4-bromo-phenyl)-2-(4-methoxy-benzenesulfQnyl)-methyl-propionic acid (2.7 g, 6.5 mmol) and following the procedure as outlined in example 1, 2.26 g of 3-(4-bromophenyl)-N-hydroxy-2-(4-methoxy-benzenesulfonyl)-2-methyl-propionamide was isolated as light colorless solid; Yield: 81%; mp 86–88° C.; MS: 429.8 $(M+H)^+$; $^1$H NMR (300 MHz, CDCl$_3$): δ 1.42 (s,3H), 1.77 (bs, 1H), 3.26 (d, J=7.0 Hz, 1H), 3.68 (d, J=7.0 Hz, 1H), 3.85 (s, 3H), 7.01–7.76 (m,8H), 9.71–9.88 (bs, 1H).

EXAMPLE 52

N-hydroxy-2-(4-methoxy-benzenesulfonyl)-2-methyl-3-naphthalen-2-yl-propionamide

Following the procedure as outlined in Example 9, 2-(4-methoxy-benzenesulfonyl)-2-methyl-3-naphthalen-2-yl-propionic acid ethyl ester was prepared, starting from (5.4 g, 20 mmol) 2-(4 -methoxy-benzenesulfonyl)-propionic acid ethyl ester and 2-bromomethyl naphthalene (4.4 g, 20 mmol). Yield 8.0 g, 97%; Colorless crystals, mp 182–184° C.; MS: 413 $(M+H)^+$.

Starting from 2-(4-methoxy-benzenesulfonyl)-2-methyl-3-naphthalen-2-yl-propionic acid ethyl ester (4.6 g, 11 mmol) 4.2g (98%) of 2-(4-methoxy-benzenesulfonyl)-2-methyl-3-naphthalen 2-yl-propionic acid was isolated as colorless crystals by following the procedure as outlined in Example 9. mp144–146° C.; MS: 384.9 $(M+H)^+$.

Starting from 2-(4-methoxy-benzenesulfonyl)-2-methyl-3-naphthalen-2-yl-propionic acid (2.4 g, 6.2 mmol) and following the procedure as outlined in Example 1, 1.6 g of N-hydroxy-2-(4-methoxy-benzenesulfonyl)-2-methyl-3-naphthalen-2-yl-propionamide was isolated as a light colorless solid; Yield: 64%; mp 185–187° C.; MS: 400.2 (M+H)+; $^1$H NMR (300 MHz, CDCl$_3$): δ 1.56 (s,3H), 3.28 (d, J=8.0 Hz, 1H), 3.81 (d, J=8Hz, 1H), 3.93 (s,3H), 4.88 (bs, 1H), 7.02–7.92 (m, 11H).

EXAMPLE 53

N-Hydroxy-2-(4-methoxy-benzenesulfonyl)-3-methyl-butyramide 2-(4-Methoxy-phenylsulfanyl)-3-methyl-butyric acid ethyl ester was prepared according to the general method as outlined in Example 1. Starting from ethyl 2-bromo-3-methyl-butanoate (20.9 g, 100 mmol) and 4methoxyben-zenethiol (14.0 g, 100 mmol), 30 g of 2-(4-methoxy-phenylsulfanyl)-3-methyl-butyric acid ethyl ester was isolated. Yield 99%; Light yellow oil; MS: 269 $(M+H)^+$.

Starting from 2-(4-methoxy-phenylsulfanyl)-3-methyl-butyric acid ethyl ester. (2.68 g 10 mmol) and following the procedure as outlined in Example 9 for oxidation, 3 g of 2-(4-methoxy-benzenesulfonyl)-3-methyl-butyric acid ethyl ester was isolated as a colorless solid. yield: 99%; mp 53° C.; MS: 273 $(M+H)^+$.

Starting from 2-(4-methoxy-benzenesulfonyl)-3-methyl-butyric acid ethyl ester (3 g, 10 mmol) 2.7 g (96%) of 2-(4-methoxy-benzenesulfonyl)-3-methyl-butyric acid was isolated as a colorless solid by following the procedure as outlined in Example 9. Mp 96° C.; MS: 273 $(M+H)^+$.

Starting from 2-(4-methoxy-benzenesulfonyl)-3-methyl-butyric acid (2.0 g, 7.34 mmol) and following the procedure as outlined in Example 9, 590 mg of N-hydroxy-2-(4methoxy-benzenesulfonyl)-3-methyl-butyramide was isolated as a colorless solid. Mp 220° C.; Yield 28%; MS: 288 $(M+H)^+$; $^1$H NMR (300 Mz, DMSO$_6$): δ 0.88 (d, J=6.7 Hz, 3H), 1.07 (d, J=6.7 Hz, 3H), 2.09–2.20 (bs, 1H), 3.53 (d, J=9, 1H), 7.12–7.17 (m, 2H), 7.74–7.79 (m, 2H).

EXAMPLE 54

1-(4-Methoxy-benzenesulfonyl)cyclopentanecarboxylic acid hydroxyamide

Following the procedure as outlined in Example 9, 1-(4methoxy-benzenesulfonyl)-cyclopentanecarboxylic acid ethyl ester was prepared, starting from (3.0 g, 11.6 mmol) of 2-(4-methoxy-benzenesulfonyl)-acetic acid ethyl ester and 1,Sdibromobutane (2.4 g, 7.6 mmol). Yield 2.4 g, 78%; Colorless solid, mp 86–88° C.; MS: 313 $(M+H)^+$.

1-(4-Methoxy-benzenesulfonyl)-cyclopentanecarboxylic acid was prepared starting from 1-(4-methoxy-benzenesulfonyl)yclopentanecarboxylic acid ethyl ester (2.2 g, 7.0 mmol) dissolved in methanol (50 ml) and 10 N NaOH (30 ml). The resulting reaction mixture was worked up as outlined in Example 9. Yield 1.66 g, 83%. Colorless solid; mp 112–115° C.; MS: 285 $(M+H)^+$.

Starting from 1-(4-methoxy-benzenesulfonyl)-cyclopentanecarboxylic acid (442 mg, 1.5 mmol) and following the procedure as outlined in Example 1, 410 mg of 1-(4-methoxy-benzenesulfonyl)cyclopentanecarboxylic acid hydroxyamide was isolated as a colorless solid. mp 89–91° C.; Yield 88%; MS: 300 $(M+H)^+$;$^1$H NMR (300 MHz, CDCl$_3$): δ 1.65–1.82 (m, 4H), 2.17–2.42 (m, 4H), 3.87 (s, 3H), 7.0 (d, J=8Hz, 2H), 7.7 (bs, 1H), 7.72 (d, J=8 Hz, 2H), 9.73 (bs, 1H).

EXAMPLE 55

3-(2-Bromo-phenyl)-N-hydroxy-2-(4-methoxy-benzenesulfonyl)-2-methyl-propionamide Following the procedure as outlined in Example 9, 3-(2-bromo-phenyl)-2-(4-methoxy-benzenesulfonyl)-2-methyl-propionic acid ethyl ester was prepared, starting from (2.0 g, 7.3 mmol) of 2-(4-methoxy-benzenesulfonyl)-propionic acid ethyl ester and 2-(bromo)benzyl bromide (2.0 g, 8 mmol). Yield 3.1 g, 87%; Colorless oil; MS: 441 $(M+H)^+$.

3-(2-Bromo-phenyl)-2-(4-methoxy-benzenesulfonyl)-2-methyl-propionic acid was prepared starting from 3-(2-bromo-phenyl)-2-(4-methoxy-benzenesulfonyl)-2-methyl-propionic acid ethyl ester (3.0 g, 68 mmol) dissolved in methanol (50 ml) and 10 N NaOH (30 ml). The resulting reaction mixture was worked up as outlined in Example 9. Yield 1.7 g, 63%. Waxy solid; MS: 414 $(M+H)^+$.

Starting from 3-(2-bromo-phenyl)2-(4-methoxy-benzenesulfonyl)-2-methyl-propionic acid (470 mg, 1.1 mmol) and following the procedure as outlined in Example 9, 380 mg of 3-(2-bromo-phenyl)-N-hydroxy-2-(4-methoxy-benzenesulfonyl)-2-methyl-propionamide was isolated as a colorless solid. mp 93–96° C.; Yield 77%; MS: 429 $(M+H)^+$; $^1$H NMR (300 MHz, CDCl$_3$): δ 1.3 (s, 3H), 3.32 (d, J=7.0 Hz, 1H), 3.69 (d, J=7.0 Hz, 1H), 3.82 (s, 3H), 6.92–7.89 (m, 8H).

EXAMPLE 56

2-(4-methoxy-benzenesulfonyl)-2-methyl-5-phenyl-pentfenoic acid hydroxyamide

Following the procedure as outlined in Example 9, 2-(4-methoxy-benzenesulfonyl)-2-methyl-5-phenyl-penttenoic acid ethyl ester was prepared, startipg from (3.0 g, 11 mmol) 2-(4 methoxy-benzenesulfonyl)-propionic acid ethyl ester and cinnamyl bromide (2.1 g, 11 mmol). Yield 3.51 g, 82%; Colorless oil; MS: 389 $(M+H)^+$.

2-(4-Methoxy-benzenesulfonyl)-2-methyl-5-phenyl-pent-4-enoic acid was prepared starting from 2-(4-methoxy-benzenesulfonyl)-2-methyl-5-phenyl-pent-4-enoic acid ethyl ester (3.0 g, 11 mmol) dissolved in methanol (50 ml) and 10 N NaOH (30 ml). The resulting reaction mixture was worked up as outlined in Example 9. Yield 1.9 g, 68%; yellowish oil; MS: 361 $(M+H)^+$.

Starting from 2-(4-methoxy-benzenesulfonyl)-2-methyl-5-phenyl-pent-4-enoic acid (440 mg, 1.2 mmol) and following the procedure as outlined in Example 1, 420 mg of 2-(4methoxy-benzenesulfonyl)-2-methyl-5-phenyl-pent-4-enoic acid hydroxyamide was isolated as a colorless solid. mp 162–164° C.; Yield 92%; MS: 376 (M+H)$^+$; $^1$H NMR (300 MHz, CDCl$_3$): δ 1.41 (s, 3H), 3.0–3.16 (m, 1H), 3.30 (d, J=1I Hz, 2H), 3.92 (s, 3H), 5.9 - 6.1 (m, 1H), 6.53 (d, J=11 Hz, 1H), 7.1–7.72 (m, 9H), 9.12 (bs,1H).

EXAMPLE 57
2-(4-methoxy-benzenesulfonyl)5-phenyl-2-(3-phenyl-propyl)-pentanoic acid hydroxyamide Following the procedure as outlined in Example 9, 2-(4-methoxy-benzenesulfonyl)-5-phenyl-2-(3-phenyl-propyl)-pentanoic acid ethyl ester was prepared, starting from (4.0 g, 15.8 mmol) 2-(4-methoxy-benzenesulfonyl)-acetic acid ethyl ester and 3-bromopropyl benzene (6.4 g, 32 mmol). Yield 3.7 g, 47%; Colorless oil; MS: 495 (M+H)$^+$.

2-(4-Methoxy-benzenesulfonyl)-5-phenyl-2-(3-phenyl-propyl)-pentanoic acid was prepared starting from 2-(4-methoxy-benzenesulfonyl)-5-phenyl-2-(3-phenyl-propyl)-pentanoic acid ethyl ester (2.0 g, 4 mmol) dissolved in methanol (50 ml) and 10 N NaOH (30 ml). The resulting reaction mixture was worked up as outlined in Example 9. Yield 1.18 g, 63%. Waxy solid; MS: 449.2 (M+H–H$_2$O)$^+$.

Starting from 2-(4-methoxy-benzenesulfonyl)-5-phenyl-2-(3-phenyl-propyl)-pentanoic acid (600 mg, 1.2 mmol) and following the procedure as outlined in Example 1, 420 m; of 2-(4-methoxy-benzenesulfonyl)-5-phenyl-2-(3-phenyl-propyl)-pentanoic acid hydroxyamide was isolated as a colorless solid. Mp 118–120° C.; yield 68%; MS: 482 (M+H)$^+$; $^1$H NMR (300 MHz, CDCl$_3$): δ 1.52–1.68 (m, 2H), 1.74–1.92 (m, 2H), 1.98–2.20 (m, 4H), 2.58 - 2.72 (m,4H), 3.86 (s, 3H), 6.93 (d, J=11 Hz, 2H), 7.02–7.63 (m, 10OH), 7.81 (d, J=11 Hz, 2H).

EXAMPLE 58
2-allyl-2-(4-methoxy-benzenesulfonyl)-pent-4-enoic acid hydroxyamide Following the procedure as outlined in Example 9, 2-allyl-2-(4methoxy-benzenesulfonyl)-pent-4-enoic acid ethyl ester was prepared, starting from (3.0 g, 11.6 mmol) 2-(4-methoxy-benzenesulfonyl)-acetic acid ethyl ester and allyl bromide (4 ml, excess). Yield 3.6 g, 92%; Yellow oil; MS: 338 (M+H)$^+$.

2-Allyl-2-(4-methoxy-benzenesulfonyl)-pentenoic acid was prepared starting from 2-allyl-2-(4-methoxy-benzenesulfonyl)-pent-4-enoic acid ethyl ester (2.2 g, 6.5 mmol) dissolved in methanol (50 ml) and 10 N NaOH (30 ml). The resulting reaction mixture was worked up as outlined in Example 9. Yield 1.76 g, 87%; yellowish oil; MS: 311 (M+H)$^+$.

Starting from 2-allyl-2-(4-methoxy-benzenesulfonyl)-pentAenoic acid (1.5 g, 4.8 mmol) and following the procedure as outlined in Example 1, 1.5 g of 2-allyl-2-(4-methoxy-benzenesulfonyl)-pent-4-enoic acid hydroxyamide was isolated as colorless solid Mp 114–116° C.; Yield 99%; MS: 326 (M+H)$^+$; $^1$H NMR (300 MD, CDCl$_3$): δ 1.62 (s, 1H), 2.70–2.80 (m,4H), 3.9 (s, 3H), 5.16–5.27 (m, 4H), 5.81–5.94 (m, 2H), 7.12 (d,J=8 Hz,2H).

EXAMPLE 59
2-(4-methoxy-benzenesulfonyl)-2-propyl-pentanoic acid hydroxyamide 2-allyl-2-(4-methoxy-benzenesuifony1)-pentenoic acid hydroxyamide (326 mg, 1.0 mmol) (example 26) was dissolved in methanol (50 ml) and hydrogenated over 10% Pd/C (100 mg) at room temperature, under 49 psi pressure for 4 hours. At the end, the reaction mixture was filtered and methanol was removed. The resulting solid was crystallized from methanol. Yield: 250 mg, 75%; MS: 330 (M+H)$^+$; $^1$H NMR (300 MHz, CDCl$_3$): δ 0.92 (t, J=4.0 Hz, 6H), 1.27–1.59 (m, 4H), 1.78–2.02 (m, 4H), 3.86 (s, 3H), 6.04 (bs, 1H), 6.97 (d, J=9Hz, 2H), 7.76 (d, J=9 Hz, 2H).

EXAMPLE 60
2-benzyl-N-hydroxy-2-(4-methoxy-benzenesulfonyl)-3-phenyl-propionamide Following the procedure as outlined in Example 9, 2-benzyl-2-(4-methoxy-benzenesulfonyl)-3-phenyl-propionic acid ethyl ester was prepared, starting from (1.0 g, 3.8 mmol) of 2-(4-methoxy-benzenesulfonyl)-acetic acid ethyl ester and benzylbromide (4 ml, excess). Yield 1.2 g, 72%; Yellow oil; MS: 439 (M+H)$^+$.

2-Benzyl-2-(4-methoxy-benzenesulfonyl)-3-phenyl-propionic acid was prepared starting from 2-benzyl-2-(4-methoxy-benzenesulfonyl)-3-phenyl-propionic acid ethyl ester (1.0 g, 2.2 mmol) dissolved in methanol (50 ml) and 10 N NaOH (30 ml). The resulting reaction mixture was worked up as outlined in Example 9. Yield: 580 mg, 62%; Waxy solid; MS: 409 (M–H)$^-$.

Starting from 2-benzyl-2-(4-methoxy-benzenesulfonyl)-3-phenyI-propionic acid (410 mg, 1 mmol) and following the procedure as outlined in Example 1, 225 mg of 2-benzyl-N-hydroxy-2-(4-methoxy-benzenesulfonyl)-3-phenyl-propionamide was isolated as a waxy solid Yield 52%; MS: 426 (M+H)$^+$; $^1$H NMR (300 MD, CDCl$_3$): δ 3.25 (d, J=14 Hz, 2H), 3.52 (d, J=14 Hz, 2H), 3.9 (s, 3H), 6.93 (d, J=8Hz, 2H), 7.02–7.26 (m, 9H), 7.61 (d, J=8 Hz, 2H), 7.87 (d, J=4Hz, 1H), 9.58 (bs, IH).

EXAMPLE 61
N-hydroxy-2-(4-methoxy-benzenesulfonyl)-2-methyl-3-pyridin-3-yl-propionamide To a stirred solution of 2-(4-methoxy-benzenesulfonyl) propionic acid ethyl ester (2.7 gm, 10 nmmol), 3-picolyl chloride hydrochloride (3.2 g, 20 mmol). and triethyl benzylammonium chloride (1 g) in methylene chloride (400 ml), 10 N NaOH (30 ml) was added. The reaction was continued at room temp for 48 hours. At the end, the organic layer was separated and washed well with water. The organic layer was dried, filtered and concentrated. The crude product obtained was purified by silica-gel column chromatography. The column was eluted with 50% ethyl acetate: hexane. 2-(4-Methoxy-benzensulfonyl)-2-methyl-3-pyridin-3-yl-propionic acid ethyl ester was isolated as brown oil. Yield 3.0 g, 82%; Brown oil; MS: 364 (M+H).

Starting, from 2-(4-methoxy-benzenesulfonyl)-2-methyl3pyrdin-3-yl-propionic acid ethyl ester (2.5 g, 6.8 mmol) 1.8 g (79%) of 2-(4-methoxy-benzenesulfonyl)-2-methyl-3-pyridin-3-yl-propionic acid was isolated as a colorless solid by following She procedure as outlined in Example 9. mp 58° C.; MS: 336 (M+H)$^+$.

Starting from 2-(4-methoxy-benzenesulfonyl)-2-methyl-3-pyridin-3-yl-propionic acid (410 mg, 1 mmol) and following the procedure as outlined in Example 1,225 mg of N-hydroxy-2-(4-methoxy-benzenesulfonyl)-2-methyl-3-pyridin-3-yl-propionamide was isolated as a colorless solid. Yield 52%; mp 98° C.; MS: 351 (M+H)$^+$; $^1$H NMR (300 MHz, CDCl$_3$): δ 1.4 (s, 3H), 3.1 (d, J=9.0, 1H), 3.65 (d, J=9.1, 1H), 3.9 (s, 3H), 7–8.5 (m, 8H).

EXAMPLE 62

2-(4-Methoxy-benzenesulfonyl)-2-pyridin-3-ylmethylecanoic acid hydroxyamide

Starting from 2-(4-methoxy-benzenesulfonyl)-acetic acid ethyl ester (7.5 g, 29 mmol) and 1-bromooctane (6.7 g, 35 mmol) 8 g of the mono octylated compound 2-(4-methoxy-benzenesulfonyl)-decanoic acid ethyl ester was isolated by following the procedure outlined in Example 9. Yield: 8.0 g 74%; MS: 370 (M+H)$^+$.

Following the procedure as outlined in example 29, 2-(4-methoxy-benzenesulfonyl)-2-pyridin-3-ylmethyl-decanoic acid ethyl ester was prepared, starting from (8.0 g, 21.6 mmol) of 2-(4-methoxy-benzenesulfonyl)-decanoic acid ethyl ester and 3-picolyl chloride hydrochloride (4.1 g, 25 mmol). Yield 6.5 g, 68%; Brown oil; MS: 462 (M+H)$^+$.

Starting from 2-(4-methoxy-benzenesulfonyl)-2-pyridin-3-ylmethyl-decanoic acid ethyl ester (5.0 g, 11 mmol), 4.5g (91%) of 2-(4-methoxy-benzenesulfonyl)-2-pyridin-3-ylmethyl-decanoic acid was isolated as a colorless solid by following the procedure as outlined in Example 9. Mp 159° C.; MS: 434 (M+H)$^+$.

Starting from 2-(4-methoxy-benzenesulfonyl)-2-pyridin-3-ylmethyl-decanoic acid (2.5 g, 5.7 mmol) and following the procedure as outlined in Example 1, 1.4 g of 2-(4methoxy-benzenesulfonyl)-2-pyridin-3-ylmethyldecanoic acid hydroxyamide was isolated as colorless solid. Yield: 50%; mp 62° C.; MS: 448 (M+H)$^+$; $^1$H NMR (300 MHz, CDCl$_3$): δ 0.86 (t, 6.9 Hz, 3H), 1.25–2.17 (m, 14 H), 3.3 (d, J=14 Hz, 1H), 3.5 (d, J=14 Hz, 1H), 3.9 (s, 3H), 6.8–8.6 (m, 8H).

EXAMPLE 63

2-(4-Methoxy-benzenesulfonyl)-5-methyl-2-pyridin-3-ylmethyl-hex-4-enoic acid hydroxyamide Following the procedure as outlined in Example 9, 2-(4-methoxy-benzenesulfonyl)-5-methyl-hexenoic acid ethyl ester was prepared, starting from (6.0 g, 23 mmol) 2-(4methoxy-benzenesulfonyl)-acetic acid ethyl ester and isoprenyl bromide (3.0 ga 20 mmol). Yield 6.52 g, 86%; Colorless oil; MS: 327 (M+H)$^+$.

Following the procedure as outlined in Example 29, 2-(4-methoxy-benzenesulfonyl)-5-methyl-2-pyridin-3-ylmethyl-hex-4-enoic acid ethyl ester was prepared, starting from (4.0 g, 12.2 mmol) of 2-(4-methoxy-benzenesulfonyl)-5-methyl-hex-4-enoic acid ethyl ester and 3-picolylchloride hydrochloride (2.1 g, 13 mmol). Yield 4.14 g, 81%; Brown oil; MS: 418 (M+H)$^+$.

2-(4-Methoxy-benzenesulfonyl)-5-methyl-2-pyridin-3-ylmethyl-hex-4-enoic acid was prepared starting from 2-(4-methoxy-benzenesulfonyl)-5-methyl-2-pyridin-3-ylmethyl-hexenoic acid ethyl ester (4.0 g, 9.5 mmol) dissolved in methanol (50 ml) and 10 N NaOH (30 ml). The resulting reaction mixture was worked up as outlined in Example 9. Yield 3.2 g, 87%; ivory solid; mp 117–119° C.; MS: 390 (M+)$^+$.

Starting from 2-(4-methoxy-benzenesulfonyl)-5-methyl-2-pyridin-3-ylmethyl-hex-4-enoic acid (2.1 g, 5.4 mmol) and following the procedure as outlined in Example 1, 1.82 g of 2-(4-methoxy-benzenesulfonyl)-5-methyl-2-pyridin-3-ylmethyl-hex-4-enoic acid hydroxyamide was isolated as a colorless solid. Yield: 82%; mp 89–92° C.; MS: 405 (M+H)$^+$; $^1$H NM (300 MHz, CDCl$_3$): δ 1.63 (s, 3H), 1.76 (s, 3H), 2.62–2.78 (m, 2H), 3.3 (d, J=4.0 Hz, 1H), 3.63 (d, J=4.0 Hz, 1H), 3.82 (s, 3H), 5.26 (m, 1H), 7.12–7.88 (m, 6H), 8.27–8.33 (m, 2H).

EXAMPLE 64

2-Benzyl-4-diisopropylamino-N-hydroxy-2-(4-methoxy-benzenesulfonyl)-butyramide

Following the procedure as outlined in Example 29, 2-benzyl4-diiiopropylamino-2-(4 methoxy-benzenesulfonyl)-butyric acid ethyl ester was prepared, starting from (3.0 g, 8.5 mmol) of 2-(4-methoxy-benzenesulfonyl)-3-phenyl-propionic acid ethyl ester (Example 9) and 2-diisopropylaminoethyl chloride hydrochloride (4.0 g, 20 mmol). Yield 3.2 g, 79%; Ivory solid, mp 89–91° C.; MS: 476.4 (M+H)$^+$.

Starting from 2-benzyl-4-disopropylaniino-2-(4-methoxy-benzenesulfonyl)-butync acid ethyl ester (3.53 gm, 7.5 mmol) 2.8 g (86%) of 2-benzylA-diisopropylamino-2-(4-methoxy-benzenesulfonyl)-butyric acid was isolated as colorless crystals by following the procedure as outlined in Example 9. Mp 136–138° C.; MS: 448.5 (M+H)$^+$.

Starting from 2-benzyl-4-diisopropylamino-2-(4-methoxy-benzenesulfonyl)-butyric acid (1.85 g, 4.1 mmol) and following the procedure as outlined in Example 1, 1.3 g of 2-benzyl-4-diisopropylamino-N-hydroxy-2 -(4-methoxy-benzenesulfonyl)-butyramide was isolated as a low melting waxy solid; Yield: 68%; MS: 463.3 (M+H)$^+$; $^1$H NMR (300 MHz, CDCl$_3$): δ 0.98 (d, J=11 Hz, 6H), 1.16 (d, J=11 Hz, 6H), 1.92 (m, 2H), 2.46 (m, 2H), 2.71 (m, 2H), 3.18 (m, 1H), 3.48 (m, 1H), 3.86 (s, 3H), 6.98 (d, J=8 Hz, 2H), 7.18–7.22 (m, 5H), 7.92 (d, J=8 Hz, 2H), 8.12 (s, 1H).

EXAMPLE 65

3-Cyclohexyl-N-hydroxy-2-(4-methoxy-bcnzenesulfonyl)-2-pyridin-3-ylmethyl-propionamide Following the procedure as outlined in Example 9, 3-cyclohexyl-2-(4methoxy-benzenesulfonyl)-propionic acid ethyl ester was prepared, starting from (4.0 g, 15 mmol) 2-(4-methoxy-benzenesulfonyl)-acetic acid ethyl ester and 1-bromomethyl cyclohexane (2.7 g, 15 mmol). Yield 5.0 g, 94%; Colorless oil; MS: 355 (M+H)$^+$.

Following the procedure as outlined in Example 29, 3-cyclohexyl-2-(4-methoxy-benzenesulfonyl)-2-pyridin-3-ylmethyl-propionic acid ethyl ester was prepared, starting from 3-cyclohexyl-2-(4-methoxy-benzenesulfonyl)-propionic acid ethyl ester(1.5 g, 4.2 mmol) and 3-picolyl chloride (1.0 g, 6 mmol). Yield 1.0 g, 38%; Colorless oil; MS 446 (M+H)$^+$.

Starting from 3-cyclohexyl-2-(4-methoxy-benzenesulfonyl)-2-pyridin-3-ylmethyl-propionic acid ethyl ester (1.3 g, 2.9 mmol) 1.0 g (83%) of 3-cyclohexyl-2-(4-methoxy-benzenesulfonyl)-2-pyridin-3-ylmethyl-propionic acid was isolated as colorless crystals by following the procedure as outlined in Example 9. Mp 92° C. MS: 417.5 (M+H)$^+$ Starting from 3-cyclohexyl-2-(4-methoxy-benzenesulfonyl)-2-pyridin-3-ylmethyl-propionic acid (1.0 g, 2.4 mmol) and following the procedure as outlined in Example 1, 80 mg of 3-cyclohexyl-N-hydroxy-2-(4-methoxy-benzenesulfonyl)-2-pyndin-3-ylmethyl-propionamide was isolated as a colorless hydrochloride salt; Yield: 71%; mp 57–60 ° C; MS: 433 (M+H)+; $^1$H NMR (300 MHz, CDCl$_3$): δ 0.8–2.08 (m, 13 H), 3.3 (d, J=14 Hz, 1H), 3.7 (d, J=14 Hz, 1H), 3.9 (s, 3H), 7.0–8.5 (m, 8H).

EXAMPLE 66

2-(4-Methoxy-benzenesulfonyl)-4-methyl-2-pyrdin-3-yh nethyl-pentoic acid hydroxyamide Following the procedure as outlined in Example 9, 2-(4-methoxy-benzenesulfonyl)-4-methyl-pentanoic acid ethyl ester was prepared, starting from (5.0 g, 20 mmol) 2-(4methoxy-benzenesulfonyl)-acetic acid ethyl ester and 1-bromo-2-methyl propane (2.6 g, 20 mmol). Yield 6.0 g, 95%; Colorless oil; MS: 315 (M+H)+.

Following the procedure as outlined in Example 29, 2-(4-methoxy-benzenesulfonyl) methyl-2-pyridin-3-ylmethyl-penanoic acid ethyl ester was prepared, starting from (3.1 g, 10 mmol) of 2-[(4-methoxy-benzenesulfonyl)-4-methyl pentanoic acid ethyl ester and 3-picolyl chloride hydrochloride (1.8 g, 11 mmol). Yield 3.0 g, 75%; Colorless oil; MS: 406 (M+H)+.

Starting from 2-4-methoxy-benzenesulfonyl)-4-methyl-2-pyrdin-3-ylmethyl-pentanoic acid ethyl ester (1.2 g, 2.9 mmol) 1.0 g (91%) of 2-(4-methoxy-benzenesulfonyl)4-methyl-2-pyridin-3-ylmethyl-pentanoic acid was isolated as colorless crystals by following the procedure as outlined in Example 9. Mp 188–186° C.; MS: 378 (M+H)+.

Starting from 2-(4-methoxy-benzenesulfonyl)-4medyl-2-pyrdin-3-ylmethyl-pentanoic acid (800 mg, 2.1 mmol) and following the procedure as outlined in Example 1, 180 mg of 2-(4-methoxy-benzenesulfonyl)-4-methyl-2-pyridin-3-ylmethyl-pentanoic acid hydroxyamide was isolated as a colorless solid; Yield: 21%; mp 78° C.; MS: 393.4 (M+H)+; $^1$H NMR (300 MHz, CDCl$_3$): δ 0.65 (d, 6.3 Hz, 3H), 0.89 (d, J=6.2 Hz, 3H), 1.7 (m, IH), 2.06 (m, 2H), 3.85 (s, 3H), 6.8–8.5 (m, 10H).

EXAMPLE 67
N-Hydroxy-2-(4-methoxy-benzenesulfonyl)-2-methyl-3-quinolin-6-yl-propionamide Following the procedure as outlined in Example 29, 2-(4-methoxy-benzenesulfonyl)-2-methyl-3-quinolin-6-yl-propionic acid ethyl ester was prepared, starting from (5.2 g, 20 mmol) of 2-(4-methoxy-benzenesulfonyl)-propionic acid ethyl ester and 7-bromomethyl quinoline (4.4 g, 20 mmol). Yield 4.5 g, 54%; Pale yellow solid; mp 86 ° C; MS: 414 (M+H)+.

Starting from 2-(4-methoxy-benzenesulfonyl)-2-methyl-3-quinolin-6yl-propiolic acid ethyl ester ( 3.0 gm, 7.2 mmol) 2.5g (90%) of 2-(4methoxy-benzenesulfonyl)-2-methyl-3uinolin 6-yl-propionic acid was isolated as colorless crystals by following the procedure as outlined in Example 9. mp 106–108° C.; MS: 386.4 (M+H)+.

Starting from 2-(4-methoxy-benzenesulfonyl)-2-methyl-3-quinolin-6-yl-propionic acid (2.0 gm, 5.2 mmol) and following the procedure as outlined in Example 1, 1.2 g of N-hydroxy-2-(methoxy-benzenesulfonyl)-2-methyl-3-quinolin-6-yl-propionamide was isolated as a colorless solid; Yield: 57%; mp 206° C.; MS: 401.4 (M+H)+; $^1$H NMR (300 MHz, CDCl$_3$): δ 1.4 (s, 3H), 3.19 (m, 1H), 3.8 4.0 (m, 4H), 7.1–8.95 (m, 12H).

EXAMPLE 68
2-(4-Methoxy-benzenesulfonyl)-6-phenoxy-2-pyridin-3-yhnethyl-hexanoic acid hydroxyamide Following the procedure as outlined in Example 9, 2-(4-methoxy-benzenesulfonyl)-6-phenoxy-hexanoic acid ethyl ester was prepared, starting from (2.5 g, 10 mmol) 2-(4-methoxy-benzenesulfonyl)-acetic acid ethyl ester and 1-bromophenoxy butane (2.2, 10 ramol). Yield 3.8 g, 93%; Colorless oil; MS: 407 (M+H)+.

Following the procedure as outlined in Example 9, 2-(4-methoxy-benzenesulfonyl)-6-phenoxy-2-pyridin-3-ylmethyl-hexanoic acid ethyl ester was prepared, starting from (3.1 g, 10 mmol) 2-(4-methoxy-benzenesulfonyl)-6-phenoxy-hexanoic acid ethyl ester and 3-picolyl chloride (1.8 g, 11 mmol). Yield 3.5 g, 71%; Colorless oil; MS: 498 (M+H)+.

Starting from 2-(4-methoxy-benzenesulfonyl)-6-phenoxy-2-pyridin-3-ylmethyl-hexanoic acid ethyl ester (3.0 g, 6.0 mmol), 2.8 g (Yield: Quantitative) of 2-(4methoxy-benzenesulfonyl)-6-phenoxy-2-pyridin-3-ylmethyl-hexanoic acid was isolated as colorless crystals by following the procedure as outlined in Example 9. Mp 148–151° C.; MS: 470.5 (M+H)+.

Starting from 2-(4-methoxy-benzenesulfonyl)-6-phenoxy-2-pyridin-3-ylmethyl-hexanoic acid (2.0 g, 4.3 mmol) and following the procedure as outlined in Example 1, 1.5 g of 2-(4-methoxy-benzenesulfonyl)-6-phenoxy-2-pyridin-3-ylmethyl-hexanoic acid hydroxyamide was isolated as a colorless solid; Yield: 72%; mp 68° C.; MS: 485.5 (M+H)+; $^1$H NMR (300 MHz, CDCl$_3$): δ 1.5–2.5 (m, 8H), 3.4 (bs, 2H), 3.8 (s, 3H), 6.8–8.7 (m, 13H).

EXAMPLE 69
2-(4-Methoxy-benzenesulfonyl)-5-methyl-2-pyridin-3-ylmethyl-hexanoic acid hydroxyamide Following the procedure as outlined in Example 9, 2-(4-methoxy-benzenesulfonyl)-5-hexanoic acid ethyl ester was prepared, starting from (10.0 g, 39 mmol) 2-(4methoxy-benzenesulfonyl)-acetic acid ethyl ester and 1-bromo-3-methyl butane ( 6.0 g, 40 mmol). Yield 8.5 g, 62%; Colorless oil; MS: 329 (M+H)+.

Following the procedure as outlined in Example 9, 2-(4-methoxy-benzenesulfonyl)-5-methyl-2-pyridin-3-ylmethyl-hexanoic acid ethyl ester was prepared, starting from (6.0 g, 18 mmol) of 2-(4-methoxy-benzenesulfonyl)-5-methyl-hexanoic acid ethyl ester and picolyl chloride hydrochloride (4.1 g, 25 mmol). Yield 4.5 g, 60%; Brown oil; MS: 420 (M+H)+.

Starting from 2-(4-methoxy-benzenesulfonyl)-5-methyl-2-pyridin-3-ylmethyl-hexanoic acid ethyl ester (3.0 g, 7.1 mmol) 2.6 g (92%) of 2-(4-methoxy-benzenesulfonyl)-5-methyl-2-pyridin-3-ylmethyl-hexanoic acid was isolated as a colorless solid by following the procedure as outlined in Example 9. Mp: 173 C; MS: 392 (M+H)+.

Starting from 2-(4-methoxy-benzenesulfonyl)-5-methyl-2-pyridi-3-ylmethyl-hexanoic acid (1.0 g, 2.5 mmol) and following the procedure as outlined inExample 1, 800 mg of 2-(4-methoxy-benzenesulfonyl)-5-methyl-2-pyridin-3-ylmethyl-hexanoic acid hydroxyamide was isolated as a colorless solid; The hydrochloride was prepared byr passing hydrogen chloride gas through methanol solution of the hydroxyarnide. Yield: 72%; mp 62 ° C (HCl salt); MS: 408 (M+H)+; $^1$H NMR (300 MHz, CDCl$_3$): δ 0.76 (m, 611), 1.2 –2.0 (5H), 3.5 (bq, 2H), 7.1–8.8 (m, 8H), 11.1 (bs,1H).

EXAMPLE 70
2-(4-Methoxy-benzenesulfonyl)-2-pyridin-3-ylmethyl-hexanoic acid hydroxyamide (4-Methoxy-phenylsulfanyl)-acetic acid tert-butyl ester was prepared according to the general method as outlined in Example 1. Starting from the corresponding 1-bromo tert-butyl acetate (5.3 g, 27 mmol) and 4-methoxybenzenethiol (3.7 g, 27 im=ol), 6.4 g of the product was isolated. Yield 98%; Light yellow oil; MS: 255 (M+H)+.

2-(4-Methoxy-benzenesulfonyl)-acetic acid tert-butyl ester was prepared according to the general method as outlined in Example 9. Staring from 2-(4-methoxy-benzenesulfanyl)-acetic acid tert-butyl ester (5.0 g, 20 mmol) and 3-chloroperoxybenzoic acid 57% (12.0g, 40 mmol), 5.3 g of the product was isolated. Yield 92%; Waxy solid; MS: 287.1 (M+H)+.

2-(4-Methoxy-benzenesulfonyl)-pyridin-3-ylpropionic acid tert-butyl ester was prepared according to the procedure as outlined in Example 9. Starting from 2-(4-methoxy-benzenesulfonyl)acetic acid tert-butyl ester (20.0 g, 70.0 mmol) and 3-picolyl chloride (7.28 g, 44.4 mmol), 10.5 g of the product was isolated by silica gel chromatography (50% ethyl acetate: hexane). Yield 63%; white solid; mp 93–94° C.; MS: 378.0 (M+H)+.

2-(4-Methoxy-benzenesulfonyl)-2-pyridin-3-ylmethyl-hexanoic acid tert-butyl ester was prepared according to the procedure as outlined in Example 9. Starting from 2-(4-methoxy-benzenesulfonyl)-pyridin-3-ylpropionic acid tert-butyl ester (2.0 g, 5.3 mmol) and n-butyl bromide (0.73 g, 5.3 mmol), 1.20 g of the product isolated. Yield 52%; yellowish gum; MS: 434.3 (M+H)+.

A mixture of the 2-(4-Methoxy-benzenesulfonyl)-2-pyridin-3-ylmethyl-hexanoic acid tert-butyl ester (1.1 g, 2.5 mmol), in methylene chloride/TFA (1:1) was stirred at room temperature for about 2 hours. The solvents were then evaporated and the 2-T4-methoxy-benzenesulfonyl)-2-pyridin-3-ylmethyl-hexanoic acid was purified by silica gel chromatography (30% methanol/methylene chloride). Yield 0.90 g, 94%; white solid; mp 10 ° C; MS: 376.1 (M–H)−.

2-(4-Methoxy-benzenesulfonyl)-2-pyridin-3-ylmethyl-hexanoic acid hydfoxyamide was prepared according to the method as outlined in Example 1. Starting from 2-(4-methoxy-benzenesulfonyl)-2-pyridin-3-ylmethyl-hexanoic acid (0.31 g, 0.81 mmol) and hydroxylamine hydrochloride (0.70 g, 10 mmol), 0.13 g of the product isolated. Yield 37%; pale yellowish solid; mp 65° C.; MS: 392.9 (MN+H)+; $^1$H NMR (300 MHz, DMSO-d6) 5 0.80 (t, J=7.2 Hz, 3H), 1.10–1.25 (m, 2H), 1.25–1.50 (m, 2H), 1.70–2.00 (m, 2H), 3.53 (d, J =14.4 Hz, 1H), 3.62 (d, J=14.4 Hz, 1H), 3.88 (s, 3H), 7.15 (d, J =8.9 Hz, 2H), 7.71 (d, J =8.9 Hz, 2H), 7.90–8.00 (m, 1H), 8.40–8.45 (m, 1H), 8.70–8.85 (m, 2H), 11.0 (brs, 1H); IR (KBr, cm-l): 3064m, 2958s, 2871m, 1671m.

EXAMPLE 71
2-(4-methoxy-benzenesulfonyl)-2-oct-2-ynyl-decffynoic acid hydroxyamide.

The title compound was prepared according to the procedure as outlined in example 9. Starting from 2-(4-methoxy-benzenesulfonyl)-acetic acid tert-butyl ester (2.86 g, 10 mmol) and 1-bromo-2-octyne (3.80 g, 20 mmol), 4.4 g of the product isolated. Yield 100%; yellowish gum; MS: 446.9 (M+H)+.

2-(4-Methoxy-benzenesulfonyl)-2-oct-2-ynyl-dec4-ynoic acid was prepared according to the method as outlined in example 70. Starting from 2-(4-methoxy-benzenesulfonyl)-2-oct-2-ynyl-decynoic acid tert-butyl ester (4.40 g, 10.0 mmol), 2.0 g of the product isolated. Yield 49%; white solid; mp 61° C.; MS: 345.1 (M–H)−.

2-(4-Methoxy-benzenesulfonyl)-2-oct-2-ynyl-decwynoic acid hydroxyamide was prepared according to the method as outlined in example 1. Starting from 2-(4-methoxy-benzenesulfonyl)-2-oct-2-ynyl-decfynoic acid (0.36 g, 0.81 mmol) and hydroxylamine hydrochloride (0.70 g, 10 mmol), 0.25 g of the product isolated. Yield 62%; white solid; mp 83–84° C.; 462.0 (M+H)+; $^1$H NMR (300 MHz, DMSO-d$_6$) δ 0.82–0.90 (m, 6H), 1.15–1.45 (m, 12H), 1.90–2.05 (m, 4H), 2.86 (brd, J =17.0 Hz, 2H), 3.00 (brd, J=17.0 Hz, 2H), 3.87 (s, 3H), 7.15 (d, J=10.0 Hz, 1H), 7.71 (d, J3=10.0 Hz, IH), 9.20 (brs, 1H), 10.90 (brs, 1H); IR (KBr, cm$^{-1}$): 3344s, 3208m, 2930m, 2870m, 1677s, 1592s; Anal. Calc'd for C$_{25}$H$_{35}$NO$_5$S: C, 65.05; H, 7.64; N, 3.03. Found: C, 65.26; H, 7.68; N, 2.90.

EXAMPLE 72
2-(4-Methoxy-benzenesulfonyl)-2-but-2-ynyl-hextynoic acid hydroxyamide 2-(4Methoxy-benzenesulfonyl)-2-but-2-ynyl-hex4-ynoic acid tert-butyl ester was prepared according to the procedure as outlined in Example 9. Starting from 2-(4methoxy-benzenesulfonyl)-acetic acid tert-butyl ester (2.86 g, 10 mmol) and 1-bromo-2-butyne (2.68 g, 20 mmol), 3.50 g of the product was isolated. Yield 90%; white solid; mp 85–87° C.; MS: 391.0 (M+H)+.

2-(4Methoxy-benzenesulfonyl)-2-but-2-ynyl-hextynoic acid was prepared according to the procedure as outlined in example 70. Starting from 2-(4-methoxy-benzenesulfonyl)-2-but-2-ynyl-hextynoic acid tert-butyl ester (3.0 g, 7.7 mmol), 2.5 g of the product isolated. Yield 97%; white solid; mp 141–143° C.; MS: 333.1 (M–H)−.

2-(4-Methoxy-benzenesulfonyl)-2-but-2-ynyl-hexynoic acid hydroxyamide was prepared according to the method as outlined in example 1. Staring from 2-(4-methoxy-benzenesulfonyl)-2-but-2-ynyl-hexfynoic acid (0.27 g, 0.81 mmol) and hydroxylamine hydrochloride (0.70 g, 10 mmol), 0.23 g of the product was isolated. Yield 89%; white solid; mp 135–137° C.; MS: 349.9 (M+H)+1; $^1$H NMR (300 MHz, DMSO-d6) 5 1.67 (s, 6H), 2.70–3.10 (m, 4H), 3.88 (s, 3H), 7.15 (d, J=10.0 Hz, 2H), 7.71 (d, J =10.0 Hz, 2H), 9.20 (brs, 1H), 10.90 (brs, 1H); IR (KBr, cm-1): 3301s, 3161m, 2922m, 1640m, 1595s, 1500m.

EXAMPLE 73
2-(4-Methoxy-benzenesulfonyl)-2-prop-2-ynyl-pentynoic acid hydroxyamde 2-(4Methoxy-benzenesulfonyl)-2-prop-2-ynyl-pent4ynoic acid tert-butyl ester was prepared according to the procedure as outlined in Example 9. Starting from 2-(4methoxy7, benzenesulfonyl)-acetic acid tert-butyl ester (2.0 g, 7.0 mmol) and propargyl bromide (1.77 g, 15 mmol), 1.90 g of the product was isolated. Yield 75%; white solid; mp 113–1 15° C; MS: 362.1 (M+H)+.

2-(4-Methoxy-benzenesulfonyl)-2-prop-2-ynyl-pent4ynoic acid was prepared according to the procedure as outlined in Example 70. Starting, from 2-(4methoxy-benzenesulfonyl)-2-prop-2-ynyl-pent4-ynoic acid tert-butyl ester (1.70 g, 4.7 mmol), 1.30ga of the product isolated. Yield 90%; white solid; mp 156° C.; MS: 305.1 (M–H)−.

2-(4-Methoxy-benzenesulfonyl)-2-prop-2-ynyl-pent4ynoic acid hydroxyamide was prepared according to the method as outlined in Example 1. Starting from (4methoxy-benzenesulfonyl)-2-prop-2-ynyl-pent-4-ynoic acid (0.25 g, 0.81 minol) and hydroxylamine hydrochloride (0.70 g, 10 mmol), 0.22 g of the product was isolated. Yield 85%; white solid; mp 156° C.; MS: 321.9 (M+H)+; $^1$H NMR (300 MHz, DMSO-d$_6$) δ 2.00–2.13 (m, 2H), 3.00–3.30 (m, 4H), 3.90(s, 3H), 7.01 (d, J=9.0 Hz, 2H), 7.82 (d, J =9.0 Hz, 2H), 8.76 (brs, 1H), 10.65 (brs, 1H); IR (KBr, cm-1): 3392s, 3293s, 3271m, 2955m, 1650s, 1594s; Anal. Calc'd for C$_{15}$H$_{15}$NO$_5$S: C, 56.07; H, 4.70; N, 4.36. Found: C, 55.65; H, 4.67; N, 4.10.

EXAMPLE 74
2-(4-Methoxy-benzenesulfonyl)-2-pyridin-3-ylmethyl-decfynoic acid hydroxyamide The title compound was prepared according to the procedure as outlined in Example 38. Starting from 2-(4-methoxy-benzenesulfonyl)-pyridin-3-ylpropionic acid tert-butyl ester (2.20 g, 5.8 mmol) and 1-bromo-2-octyne (1.14 g, 6 mmol), 2.60 gm of the product isolated. Yield 92%; yellowish gum; MS: 486.0 (M+H)+.

A mixture of the 2-(4-methoxy-benzenesulfonyl)-2-pyridin-3-ylmethyl-decfynoic acid tert-butyl ester (2.60 g, 5.35 mmol), in methylene chloridenTFA (1: 1) is stirred at room temperature for about 2 hours. (Ref. example 70) The solvents are then evaporated and the 2-(4-methoxy-benzenesulfonyl)-2-pyridin-3-ylmethyldecynoic acid was purified by silica gel chromatography (~30% methanoL/ methylene chloride). Yield: 2.0 g, 87%; White solid; mp 146° C.; MS: 428.1 (M−H)⁻.

2-(4-Methoxy-benzenesulfonyl)-2-pyridin-3-ylmethyl-dec4-yrioic acid hydroxyamide was prepared according to the procedure outlined in Example 1. Starting from 2-(4methoxy-benzenesulfonyl)-2-pyridin-3-ylmethyl-decfynoic acid (0.71 g, 1.62 mmol) and hydroxylamine hydrochloride (1.39 g, 20 mmol), 0.48 g of the product was isolated. Yield 67%; off-white solid; mp 65° C.; MS: 445.0 (M+H)⁺; ¹H NMR (300 MHz, DMSO-d₆) δ 0.84 (t, J=6.8 Hz, 3H), 1.10–1.40 (m, 6H), 1.85–2.00 (m, 2H), 2.79 (d, J 17.9 Hz, 1H), 2.90 (d, J=17.9 Hz, 1H), 3.50 (d, J=13.7 Hz, 1H), 3.74 (d, J =13.7 Hz, 1H), 3.89 (s, 3H), 7.19 (d, J=9.0 Hz, 2H), 7.76 (d, J=9.0 Hz, 2H), 7.85–7.89 (m, 1H), 8.37–8.40 (m, 1H), 8.70–8.80 (m, 2H), 11.0 (brs, 1H); IR (KBr, cm-1): 3157m, 3095m, 2954s, 2932s, 2858m, 1671m, 1593s;

Anal. Calc'd for $C_{23}H_{28}N_2O_5S \cdot HCl \cdot 0.9H_2O$: C, 55.56; H, 6.24; N, 5.63.

Found: C, 55.84; H, 6.19; N, 5.59.

EXAMPLE 75
2-(4-Methoxy-benzenesulfonyl)-2-pyridin-3-ylmethyl-pent4fynoic acid hydroxyamide 2-(4-Methoxy-benzenesulfonyl)-2-pyridin-3-ylmethyl-penttynoic acid tert-butyl ester was prepared according to the procedure as outlined in Example 38. Starting from 2-(4-methoxy-benzenesulfonyl)-pyridin-3-ylpropionic acid tert-butyl ester (3.77 g, 10 mmol) and propargyl bromide (1.74 g, 13 mmol), 2.50 g of the product was isolated. Yield 60%; yellowish solid; mp 132–133° C.; MS: 416.0 (M+H)⁺.

2-(4-Methoxy-benzenesulfonyl)-2-pyridin-3-ylmethyl-pentAynoic acid was prepared according to the procedure as outlined in Example 70. Starting from 2-(4-methoxy-benzenesulfonyl)-2-pyridin-3-ylmethyl-pent-4-ynoic acid tert-butyl ester (2. 0 g, 4.8 mmol), 1.2 g of the product isolated. Yield 69%; white solid; mp 119–121° C; MS: 358.1 (M−H)⁻.

2-(4-Methoxy-benzenesulfonyl)-2-pyridin-3-ylmethyl-pent4-ynoic acid hydroxyamide was prepared according to the method as outlined in Example 1. Starting from 2-(4-methoxy-benzenesulfonyl)-2-pyridin-3-ylmethyl-pentfynoic acid (0.29 g, 0.81 mmol) and hydroxylarnine hydrochloride (0.70 m, 10 mmol), 0.065 g of the product was isolated. Yield 25%; off-white solid; mp 70° C.; MS: 375.0 (M+H)⁺; ¹H NMR (300 MHz, DMSO-d₆) δ 1.19 (brs, 1H), 2.90–3.00 (m, 2H), 3.55 (d, J=13.8 Hz, 1H), 3.67 (d, J =13.8 Hz, 1H), 3.89 (s, 3H), 7.18 (d, J=9.0 Hz, 2H), 7.75 (d, J=9.0 Hz, 2H, 7.80–7.89 (m, 1H), 8.35–8.40 (m, 1H), 8.70–8.80 (m, 2H), 11.1 (brs, 1H); IR (KBr, cm-l): 3168m, 3095s, 1670m, 1593s.

EXAMPLE 76
2-(4-Fluoro-benzenesulfonyl)-2-pyridin-3-ylmethyl-hex4-ynoic acid hydroxyamide 2-(4-Fluoro-benzenesulfanyl)-acetic acid tert-butyl ester was prepared according to the procedure as outlined in Example 1. Starting from 4-fluorothiophenol (30.0 g, 230 mmol) and tert-butyl bromoacetate (45.67 g, 230 mmol), 53.4 g of the product was isolated. Yield 100%; pale yellowish oil; MS: 243.1 (M+H)⁺.

2-(4-Fluoro-benzenesulfonyl)-acetic acid tert-butyl ester was prepared according to the general method as outlined in Example 9. Starting from 2-(4-fluoro-benzenesulfanyl)-acetic acid tert-butyl ester (48.4 g, 200 mmol) and 3-chloroperoxybenzoic acid (121.3g (57%), 400 mnmol), 48.0 g of the product was isolated. Yield 88%; pale yellowish oil; MS: 275.1 (M+H)⁺.

The title compound was prepared according to the procedure as outlined in Example 70. Starting from 2-(4-fluoro-benzenesulfonyl)-3-pyridin-3-ylpropionic acid tert-butyl ester (1.83 g, 5.0 mmol) and 1-bromo-2-butyne (0.67 g, 5.0 mmol), 2.18 g of the product was isolated Yield 100%; yellowish gum; MS: 419.2 (M+H)⁺.

2-(4-Fluoro-benzenesulfonyl)-2-pyridin-3-ylmethyl-hex4ynoic acid was prepared according to the method as outlined in Example 38. Starting from 2-(4-fluoro-benzenesulfonyl)-2-pyridin-3-ylmethyl-hex-4-ynoic acid tert-butyl ester (2.1 g, 5.0 mmol), 1.20 g of the product was isolated. Yield 67%; off-white solid; mp 150° C.; MS: 360.2 (M−H)⁻.

2-(4-Fluoro-benzenesulfonyl)-2-pyridin-3-ylmethyl- hex-ynoic acid hydroxyamide was prepared according to the method as outlined in Example 1. Starting from 2-(4fluoro-benzenesulfonyl)-2-pyridin-3-ylmethyl-hextynoic acid (0.29 g, 0.81 mmol) and hydroxylamine hydrochloride (0.70 g, 10 mmol), 0.15 g of the product was isolated. Yield 45%; white solid; mp 190° C.; MS: 377.2 (M+H)⁺; ¹H NIR (300 MHz, DMSO-d₆) δ 1.60 (s, 3H), 2.70–3.00 (m, 2H), 3.53 (d, J=13.8 Hz, IH), 3.74 (d, J3=13.8 Hz, 1H), 7.50–7.58 (m, 2H), 7.80–7.95 (m, 3H), 8.35–8.40(m, 1H), 8.748.79 (m, 2H), 11.1 (brs, 1H); IR (KBr, cm-1): 3154m, 3105s, 3068s, 2875m, 1696s, 1630w, 1590s;

Anal. Calc'd for $C_{18}H_{17}FN_2O_4 \cdot SHCl \cdot 0.5H_2O$: C, 51.24; H, 4.54; N, 6.64.

Found: C, 51.21; H, 4.35; N, 6.46.

EXAMPLE 77
2-(4-Fluoro-benzenesulfonyl)-2-pyridin-3-ylmethyl-decfynoic acid hydroxyamide The title compound was prepared according to the procedure as outlined in Example 9. Starting from 2-(4-fluoro-benzenesulfonyl)-3-pyridin-3-ylpropionic acid tert-butyl ester (1.83 g, 5.0 mnol) and 1-bromo-2-octyne (0.95 g, 5.0 =nnol), 1.80 g of the product was isolated. Yield 56%; yellowish gum; MS: 474.3 (M+H)⁺.

2-(4-Fluoro-benzenesulfonyl)-2-pyridin-3-ylmethyldecfynoic acid was prepared according to the method as outlined in Example 70. Starting from 2-(4-fluoro-benzenesulfonyl)-2-pyridin-3-ylmethyl-dec ynoic acid tert-butyl ester (1.80 g, 3.8 mmol), 1.40 g of the product was isolated. Yield 88%; off-white solid; mp 123–124° C.; MS: 416.3 (M−H)⁻.

2-(4-Fluoro-benzenesulfonyl)-2-pyridin-3-yhmethyl-decwynoic acid hydroxyide was prepared according to the method as outlined in Example 1. Staaing from 2-(4fluoro-benzenesulfonyl)-2-pyridin-3-ylmethyl-decfynoic acid (0.67 g, 1.62 mmol) and hydroxylamine hydrochloride (1.39 g, 20 mmol), 0.22 g of the product was isolated. Yield 29%; white solid; mp 180–182° C.; MS: 433.2 (M+H)⁺; ¹H NMR (300 MHz, DMSO₆) δ 0.84 (t, J=6.8 Hz, 3H), 1.20–1.40 (m, 6H), 1.90–2.05 (m, 2H), 2.75 (d, J=19.9 Hz, 1H), 2.94 (d, J=19.9 Hz, 1H), 3.54 (d, J=13.7 Hz, 1H), 3.75 (d, J =13.7 Hz, 1H), 7.40–7.60(m, 2H), 7.70–8.00 (m, 3H), 8.30–8.40 (m, IH), 8.70–8.80 (m, 2H), 11.1 (brs, 1H); IR (KBr, cm-1): 3154m, 3105s, 3067m, 2957s, 2933s, 2873m, 1690s, 1631m.

Anal. Calc'd for $C_{22}H_sFN_2O_4S \cdot HCl$: C, 56.34; H, 5.59; N, 5.97.

Found: C, 56.18; H, 5.54; N,5.76.

EXAMPLE 78
2-(4-Fluoro-benzenesulfonyl)-2-but-2-ynyl-hexynoic acid hydroxyamide 2-(4-Fluoro-benzenesulfonyl)-2-but-2-ynylhexynoic acid tert-butyl ester was prepared according to the procedure as outlined in Example 9. aSctarting from 2-(4fluoro-benzenesulfonyl)-acetic acid tert-butyl ester (4.87 g, 20 mmol) and 1-bromo-2-butyne (5.36 g, 40 mmol), 6.0 g of the product was isolated. Yield 77%; white solid; mp 85° C.; MS: 379.1 (M+H)$^+$.

2-(4-Fluoro-benzenesulfonyl)-2-but-2-yiiyl-hexynoic acid was prepared according to the procedure as outlined in Example 70, starting from 2-(4fluoro-benzenesulfonyl)2-but-2-ynyl-hex-4-ynoic acid tert-butyl ester (3.50 g, 8.47 mmol), 2.35 g of the product was isolated. Yield 79 %; white solid; mp 129–131° C.; MS: 642.8 (2M–H)$^-$.

2-(4-Fluoro-benzenesulfonyl)-2-but-2-ynyl-hex4ynoic acid hydroxyamide was prepared according to the method as outlined in Example 1. Starting from 2-(4-fluoro-benzenesulfonyl)-2-but-2-ynyl-hex4-ynoic acid (0.26 g, 0.81 mmol) and hydroxylamine hydrochloride (0.70 g, 10 mmnol), 0.21 g of the product was isolated. Yield 77%; white solid; mp 161–163° C.; MS:338.1(M+H)$^+$; $^1$H NMR (300 MHz, DMSO-d$_6$) o 1.67(s, 6H), 2.80–3.10 (m, 4H), 7.51 (dd, J=9.0, 9.0 Hz, 2H), 7.87 (m, 2H), 9.26 (brs, 1H), 10.95 (brs, 1H); IR (KBr, cm-1): 3336s, 3245r, 168 Is, 1589m, 1493m;
Anal. Calc'd for C$_{16}$H$_{16}$FNO$_4$S: C, 56.96; H, 4.78; N, 4.15. Found: C, 56.59; H, 4.75; N, 4.04.

EXAMPLE 79

2-(4-Methoxy-benzenesulfonyl)-5-methyl-2-(3-methyl-but-2-enyl)-hexenoic acid hydroxyamide Following the procedure as outlined in Example 9, 2-(4-methoxy-benzenesulfonyl)-5-methyl-2-(3-methyl-but-2-enyl)-hexAenoic acid ethyl ester was prepared, starting from (5.0 g, 20 mmol) 2-(4methoxy-benzenesulfonyl)-acetic acid ethyl ester and isoprenyl bromide (6.0 g, 40 mmol). Yield 7.0 g, 88%; Colorless oil; MS: 395 (M+H)$^+$.

Starting from 2-(4-methoxy-benzenesulfonyl)-5-methyl-2-(3-methyl-but-2-enyl)-hex-4-enoic acid ethyl ester (3.5 g, 9 mmol), 3.3 g (97%) of 2-(4methoxy-benzenesulfonyl)-5-methyl-2-(3-methyl-but-2-enyl)-hex-4-enoic acid was isolated as a colorless oil by following the procedure as outlined in Example 9. MS: 365 (M–H)$^-$.

Starting from 2-(4-methoxy-benzenesulfonyl)-5-methyl-2-(3-methyl-but-2-enyl)-hexenoic acid (2.6 g, 7.0 mmol) and following the procedure as outlined in Example 1, 1.36 g of 2-(4-methoxy-benzenesulfonyl)-5-methyl-2-(3-methyl-but-2-enyl)-hex-4-enoic acid hydroxyamide was isolated as a colorless solid. Yield: 67%; mp 93–96° C.; Ms: 393 (M+H)+; $^1$H NMR (300 MHz, CDCl$_3$): δ 1.68 (s, 6H), 1.73 (s, 6H), 2.72 (m, 4H), 3.82 (s, 3H), 5.12 (m, 2H), 6.92 (d, J=8 Hz, 2H), 7.33 (bs, 1H), 7.72 (d, J=8 Hz, 2H), 9.71 (bs, 1H).

EXAMPLE 80

2-(4-methoxy-phenylsulfanyl)-heptanoic acid hydroxyamide.

2-(4-Methoxy-phenylsulfanyl)-heptanoic acid ethyl ester (13.8 g, 98%) was prepared according to the general method as outlined in example 1 starting from ethyl 2-bromoheptanoate (11 g, 47 mmol) and 4methoxythiophenol (6 g, 42.8 mmol), as a yellow oil; MS: 297.2 (M+H)$^+$.

2-(4-Methoxy-phenylsulfanyl)-heptanoic acid was prepared starting with 2-(4-methoxy-phenylsulfanyl)-heptanoic acid ethyl ester (4 g, 13.5 mmol) dissolved in methanol (300 ml) and 10 N NaOH (25 ml). The resulting reaction mixture was worked up as outlined in example 1. Yield 3 g (83%). yellow oil. MS: 267.1 (M–H)$^-$.

Starting from 2-(4-methoxy-phenylsulfanyl)-heptanoic acid (2.49 g, 9.32 mmol) and following the procedure as outlined in example 1, 1.83 g of 2-4-(methoxy-phenylsulfanyl)-heptanoic acid hydroxyamide was isolated as an off white solid Mp 90–95° C.; Yield 70%; MS: 284.0 (M+H)$^+$; $^1$H NMR (300 MHz, DMSO-d$_6$): δ 0.826 (t, J=6.9 Hz, 3H), 1.135–1.76 (m, 8H), 3.35 (m, 1H), 3.82 (s, 3H), 6.91–7.49 (m, 4H).

EXAMPLE 81

(49A) 2R*-(4-methoxy-phenyl-S*-sulfnyl)-heptanoic acid hydroxyamide and
(49B) 2S*-(4-methoxy-phenyl-R*-sulfinyl)-heptanoic acid hydroxyamide Starting from 2-(4-methoxy-phenylsulfanyl)-heptanoic acid hydroxyamide (1.69 g, 6 mmol) and following the procedure outlined in example 5, the two diastereomers of 2-(4-methoxy-phenylsulfanyl)-heptanoic acid hydroxyamide were separated on a silica gel column using 75% ethyl acetate:hexanes. The less polar isomer, 2R*-(4-methoxy-phenyl-S*-sulfiryl)-heptanoic acid hydroxyamide was isolated as a white powder. Yield: 390 mg (22%); mp 115° C.; MS: 300.0 (M+H)$^+$; $^1$H NMR (300 MHz, DMSO-d$_6$): 0.828 (t, J=6.2 Hz, 3H), 1.18–1.23 (m, 6H), 1.73–1.99 (m, 2H), 3.11–3.15 (m, 1H), 3.82 (s, 3H), 7:09–7.61 (m, 4H). The more polar isomer, 2S*-(4-methoxy-phenyl-R*-sulfmyl)-heptanoic acid hydroxyamide was isolated as a gray solid. Yield: 200 mg (11%); mp 112° C.; MS: 300.0 (M+H)$^+$,$^1$H NMR (300 MHz, DMSO-d$_6$): δ 0.754 (t, J=6.9 Hz, 3H), 1.014–1.121 (m, 6H), 1.58–1.89 (m, 2H), 3.10–3.15 (m, 1H), 3.834 (s, 3H), 7.13–7.65 (m, 4H).

EXAMPLE 82

2-(4-methoxy-benzenesulfonyl)-2-methyl-3-[4-(2-morpholinyl-ethoxy)-phenyl]-propionic hydroxyamide hydrochloride.

Following the procedure as outlined in example 12, 2-(4-methoxy-benzenesulfonyl)-2-methyl-3-[4-(2-morpholin-1-yl-ethoxy)-phenyl]-propionic acid ethyl ester was prepared, starting from (4.0 g, 15 mmol) of 2-(4-methoxy-benzenesulfonyl)-propionic acid ethyl ester and 4-(morpholin-1-yl-ethoxy)-benzyl chloride hydrochloride (2.9 g, 10 mmol). Yield 4.8 g, 98%; Brown oil; MS: 492 (M+H)$^+$.

Starting from 2-(4-methoxy-benzenesulfonyl)-2-methyl-3-[4(2-morpholin-1-yl-ethoxy)-phenyl]-propionic acid ethyl ester (4.0 gm, 8.1 mmol) 3.2 g (Yield: 84 %) of 2-(4methoxy-benzenesulfonyl)-2-methyl-3-[4-(2-morpholin-1-yl-ethoxy)-phenyl]-propionic acid was isolated as colorless crystals by following the procedure as outlined in example 9. Mp 171° C.; MS: 464 (M+H)$^+$.

Starting from 2-(4-methoxy-benzenesulfonyl)-2-methyl-3-[4(2i-morpholin-1-yl-ethoxy)-phenyl]-propionic acid (4.0 g, 8.6 mmol) and following the procedure as outlined in example 1, 2.5 g of 2-(4-methoxy-benzenesulfonyl)-2-methyl-3-[4-(2-morpholin-1-yl-ethoxy)-phenyl]-propionic hydroxyamide was isolated as colorless solid. The hydrochloride salt was prepared by reacting the free base with methanolic hydrogen chloride at 0° C. Yield: 2.5 g, 60%; mp 98° C.; MS: 479 (M+H)$^+$; $^1$H NlvR (300 Mdz, CDCl$_3$): 1.36 (s, 3H), 3.8 –12.6 (m, 16 H), 3.9 (s, 3H), 4.1–4.3 (m, 1H), 6.6 (d, J=8 Hz, 2H), 6.96 (d, J=9 Hz, 2H), 7.1 (d, 8 Hz, 2H), 7.84 (d, 9 Hz, 2H), 10.8 (bs, 1H).

EXAMPLE 83

1-Benzyl-4-(4-methoxy-benzenesulfonyl)-piperidine-4carboxylic Acid hydroxyamide

To a stirred solution of 4-methoxybenzenethiol (2.8 gin, 20 miol) and anhydrous K$_2$CO$_3$ (10 gm, excess) in dry acetone (100 ml), α-bromo ethyl acetate (3.3 gm, 20 mmol) was added in a round bottom flask and the reaction mixture was heated at reflux for 8 hours with good stirring. At the end, the reaction mixture was allowed to cool and the potassium salts were filtered off and the reaction mixture was concentrated. The residue was extracted with chloroform and washed with H$_2$O and 0.5 N NaOH solution. The organic layer was her washed well with water, dried over MgSO$_4$, filtered and concentrated. (4-methoxy-phenylsulfanyl)-acetic acetic acid ethyl ester was isolated as pale yellow oil. Yield: 4.4 g (100%), MS; 227 (M+H)$^+$.

To a stirred solution of 60% 3-chloroperoxybenzoic acid (14.0 gm, 40 mmol) in methylene chloride (100 ml) at 0° C., (4-methoxy-phenylsulfany1)-acetic acid ethyl ester (4.4 g, 20 mmol) in CH$_2$Cl$_2$ (15 ml) was added slowly. The reaction mixture turned cloudy and was stirrd at room temperature for 6 hours. The reaction mixture was then diluted with hexanes (300 ml) and stirred for 15 minutes. The solids were filtered off and Na$_2$SO$_3$ solution was added to the organic layer which was stirred for at least 3 hours before the mixture was extracted with CHCl$_3$ and washed with H$_2$O. The organic layer was dried over MgSO$_4$, filtered and concentrated and the colorless (4-methoxy-phenylsulfonyl)-acetic acid ethyl ester was isolated as an oil. Yield: 100%; MS: 259.1 (M+H)$^+$.

To a stirred solution of diethanol armine (10.5 g,100 mmol), and anhydrous K,)CO$_3$ (30 gm, excess) in dry acetone (250 ml), benzyl bromide (17.2 gm, 100 mmnol) was added in a round is bottom flask and the reaction mixture was heated at reflux for 8 hours with good stirring. At the end, the reaction mixture was allowed to cool and the potassium salts were filtered off and the reaction mixture was concentrated. The residue was extracted with chloroform and washed with H$_2$O. The organic layer was fuirther washed well with water, dried over MaSO$_4$, filtered and concentrated. Colorless oil. Yield: 19.0 g,97%; MS: 196 (M+H).

N-B enzyldiethanolarnine (9.75 g,50 mmol) was dissolved in saturated methanolic hydrochloric acid and concentrated to dryness. The hydrocltloride thus formed was dissolved in methylene chloride (300 ml) and thionyl chloride (20 g, excess) was added dropwise and stirred at room temperature for I hr. At the end reaction mixture was concentrated to dryness and the product bis-(2-chloroethyl)-benzyl amine hydrochloride wasp used for further transformation with out any purification. Yield: 13.0 g, 97%; Mp: MS: 232 (M+H).

To a stirred solution of bis-(2-chloro-ethyl)-benzyl amine hydrochloride (6.6 g, 24.7 mmol), 18-Crown-6 (500 mg), and anhydrous K$_2$CO$_3$ (30 gmn, excess) in dry acetone (250 ml), (4-methoxy-phenylsulfonyl)-acetic acid ethyl ester (6.12 gm, 24 mmol) was added in a round bottom flask and the reaction mixture was heated at reflux for 16 hours with good stirig. At the end, the reaction miixture was allowed to cool and the potassium salts were filtered off and the reaction mixture was concentrated. The residue was extracted with chloroform and washed with H$_2$O. The organic layer was furher washed well with water, dried over MgSO$_4$, fitered and concentrated. The dark brown reaction mixture was purified by silica gel couinn chromatography by eluting it with 30% ethylace tate: hexane and the product 4-(4-Methoxy-benzenesulfonyl)-1-benzyl-piperidine-4-carboxylic acid ethyl ester was isolated as Brown oil. Yield: 6.0 g, 60%; MS: 418 (M+H).

4-(4-Methoxy-benzenesulfonyl)-1-benzyl-piperidine-4-carboxylic acid ethyl ester (5.0 g, 11.9 mmnol) was dissolved in MeOHTHF (1:1, 200 ml) and stirred at room temperature for 72 hrs. At the end reaction mixture was concentrated and the product was nuetralised with con. Hcl by dissolving it in water (200 ml). After the nuetralition reaction mixture was concentrated to dryness. Ice cold water (100 ml) was added to the solid and filtered. The product 4-(4-Methoxy-benzenesulfonyl)-1-benzyl-piperidine-4-carboxylic acid was dried at 50 C and taken to next step with out any purification. Colorless solid Yield: 3.2 g, 69% ; MS: 390 (M+H).

To a stirred solution of 4-(4-Methoxy-benzenesulfonyl)-1-benzyl-piperidine-4-carboxylic acid (2.0 g, 5.1 mmol) and DMF (2 drops) in CH$_2$Cl$_2$ (100 ml) at OC, oxalyl chloride (1.0 gm, 8 mmol) was added in a drop-wise manner. After the addition, the reaction mixture was stirred at room temperature for 1 hour. Simultaneously, in a separate flask a mixture of hydroxylainine hydrochloride (2.0 gm, 29 mmol) and triethylamine (5 ml, excess) was stirred in THF:water (5:1, 30 ml) at 0° C. for 1 hour. At the end of 1 hour, the oxalyl chloride reaction mixture was concentrated and the pale yellow residue was dissolved in 10 ml of CH$_2$Cl$_2$ and added slowly to the hydroxylamine at 0° C. The reaction mixture was stirred at room temperature for 24 hours and concentrated. The residue obtained was extracted with chloroform and washed well with water. The product obtained was purified by silica gel column chromatography and eluted with chloroform the product 4-(4-Methoxy-benzenesulfonyl)-1-benzyl-piperidinefcarboxylic acid hydroxyamide was isolated as a colorless solid. mp 90–95° C.; Yield, 1.2 g, 48%; MS: 405 (M+H)$^+$; $^1$H NMR (300 MHz, DMSO-d$_6$): 8 2.29 (m, 3H), 2.76–2.79 (m, 2H), 3.43 (m, 4H),4.30 (s, 2H), 7.14–7.17 (d,2H), 7.50–7.73 (m, 5H), 9.37 (s,lH), 10.53 (s,lH), 11.18 (s,1H).

EXAMPLE 84

4-(4-methoxy-benzenesulfonyl)-1-(3-methoxy-benzyl)-piperidine-4-carloxylic acid hydroxyamide 2-[(2-Hydroxy-ethyl)-(3-methoxy-benzyl)-amino]-ethanol was prepared according to the general method as outlined in example 83. Starting from diethanolamine ( 3.1 g, 29.5 mmol) and 3-methoxybenzyl chloride (5 g, 31.9 mmol). Yield 9.28 g, (99 %); yellow oil; MS: 226 (M+H).

3-Methoxybenzyl-bis-(2-chloro-ethyl)-amine was prepared according to the general method as outlined in example 83. Starting from 3-Methoxy-benzyl diethanolamine (4.4 g, 20 mmol). Yield 4.5 g (93 %); yellow solid mp 86–88 C; MS: 263. (M+H)$^+$.

4-(4-Methoxy-benzenesulfonyl)-1-(3-methoxy-benzy1) piperidinecarboxylic acid ethyl ester was prepared according to the general method as outlined in example 83. Starting from 4-(methoxy-benzenesulfonyl)-acetic acid ethyl ester (5.0 g, 22 mmol) and bis- (2-chloro ethyl)-(3-methoxy-benzyl)-amine (8.0 g, 23.5 mmol). Yield 2.4 g (24 %); low melting solid; MS: 447.9 (M+H)$^+$.

4-(4-Methoxy-benzenesulfonyl)1-(3-methoxy-benzyl)-piperidine4carboxylic acid was prepared starting from 4-(4-Methoxy-benzenesulfonyl)-1-(3-methoxy-benzyl) piperidine-4-carboxylic acid ethyl ester (2.4g, 5.36 mmol) dissolve in methanol (30 mL), 10 N sodium hydroxide (10 mL), tetrahydrohydrofuran (20 mL). The resulting reaction mixture was worked up as outlined in example 83. Yield 710 mg (32%). white solid mp 199° C., MS: 419.9 (M+H)$^+$.

Starting from 4-(4-methoxy-benzenesulfonyl)-1-(3-methoxy-benzyl)-piperidine-4-carboxylic acid (830 mg, 1.98 mmol) and following the procedure as outlined in example 83, 190 mg of 4-(4-methoxy-benzenesulfonyl)-1-(3-methoxy-benzyl)-piperidine-4-carboxylic acid hydroxamide was isolated as a white solid. mp 130° C.; Yield 20.4%; MS: 435.0 (M+H)$^+$; $^1$H NMR (300 MHz, DMSO-d$_6$): δ 2.24–2.32(m, 2H), 2.51(d, 2H), 2.73–2.83 (m, 2H), 3.37 (d, 2H), 3.76 (s, 3H), 3.88 (s, 3H), 4.32 (s, 2H), 7.01–7.77 (m,8H), 9.38 (s, 1H0, 10.1 (s, 1H).

EXAMPLE 85
1-(3,4-dichlorobenzyl)-4-(4-methoxy-benzenesulfonyl)-piperidine-4-carboxylic acid hydroxamide 2-[(2-Hydroxy-ethyl)-(3,4-dichloro-benzyl)-amino]-ethanol was prepared according to the general method as outlined in example 83. Stariing from diethanolamine (4.84 g, 46 mmol) and 3,4-dichlorobenzyl chloride (9.0 g, 46 mmol). Yield 13.8 g (99 %); colorless oil; MS: 264.3 (M+H)$^+$.

3,4-Dichlorobenzyl-bis-(2-chloro-ethyl)-amine was prepared according to the general method s as outlined in example 83. Starting from 3,4-dichiorobenzyl diethanolamine (10.7 g, 41 mmol). Yield 99%; yellow solid mp 218–220° C.; MS: 301.8 (M+H)$^+$.

1-(3,4-Dichloro-benzyl)4-(methoxy-benzenesulfonyl)-piperidinecarboxylic acid ethyl ester was prepared according to the general method as outlined in example 83. Starting from 4-(methoxy-benzenesulfony-1)-acetic acid ethyl ester (2.9 g, 11 mmol) and 3,Sdichlorobenzy1-bis(2-chloroethyl)-amine (3.4 g, 11 mmol). Yield 5.9 g (60 %); brown oil; MS: 494.5 (M+H)$^+$.

1-(3,4-Dicoro-benzyl)-4-(4-methoxy-benzenesulfulfonyl)-piperidine-4-carboxylic acid was prepared starting from 1-(3,4-dichloro-benzyl)-4-(methoxy-benzenesulfonyl)-piperidine-4-carboxylic acid ethyl ester (5.0 g, 10 mmol) dissolved in methanol (50 mL), 10 N sodium hydroxide (15 mL) and tetrahydrofuran (75 mL). The resulting reaction mixture was worked up as outlined in example 83. Yield 2.94 g (62%), MS: 458.3 (M+H)$^+$.

Starting from 1-(3,4-dichlorobenzyl)-4-(4-methoxy-benzenesulfonyl)-piperidine-4-carboxylic acid (2.67g, 5.8 mmol) and following the procedure as outlined in example 83, .2 g of 1-(3,4-dichlorobenzyl) -4-(4-methoxy-benzenesulfonyl)-piperidine-4-carboxylic acid hydroxamide was isolated as a white solid. mp 192–195° C.; Yield 10%; MS 472.9 (M+H)$^+$; $^1$H NMR (300 MHz, DMSO-d$_6$): δ 2.20–2.28 (m, 2H), 2.76–2.79 (m, 2H), 3.43–3.44 (m, 4H), 4.30 (s, 2H), 7.14–7.17 (d, J=0.030, 2H), 7.50–7.73 (d, J=0.02,7, 1H), 7.65–7.68 (d, J=0.029, 2H), 7.72–7.75 (d, J=0.027, 2H), 7.87 (s, 1H), 9.37 (s, IH), 10.53 (s, 1H), 11.18 (s, 1H).

EXAMPLE 86
4-(4-methoxy-benzenesulfonyl)-1-(4-methylbenzyl)-piperidine-4-carboxylic acid hydroxamide 2-[(2-Hydroxy-ethyl)-(4-methyl-benzyl)-amino]-ethanol was prepared according to the general method as outlined in example 83. Staring from diethanolamine (4.8 g, 46 mmol) and 4-methylbenzyl chloride (8.5 g, 46 mmol). Yield 9.8 g (99%); MS: 209.9 (M+H)$^+$.

4-Methylbenzyl-bis-(2-chloro-ethyl)-amine was prepared according to the general method as outlined in example 83. Starting from 4-methyl-benzyl diethanolamine (6 g, 20 mmol). Yield 5.2 g (84 %); yellow solid mp 145–147° C.; MS: 245.9 (M+H)$^+$.

4-(4-Methoxy-benzenesulfonyl)-1-(4-methyl-benzyl) piperidine4carboxylic acid ethyl ester was prepared according to the general method as outlined in example 83. Starting from 4-(methoxy-benzenesulfonyl)-acetic acid ethyl ester (7.0 g, 27 mmol) and 4-methyl-bis-(2-chloro-ethyl)-amine (5.0 g, 17 mmol). Yield 4.64 g (63%); low melting solid; MS: 431.9 (M+H)$^+$.

4-(4-Methoxy-benzenesulfonyl)1-(4-methyl-benzyl)-piperidine-4-carboxylic acid was prepared starting from 4-(4-methoxy-benzenesulfonyl)-piperidine4carboxylic acid ethyl ester (4.3 g, 9.9 mmol) dissolve in methanol (30 mL), 10 N sodium hydroxide (10 mL), tetrahydrohydrofiran (20 mL). The resulting reaction mixture was worked up as outlined in example 83. Yield 1.6 g (40%). white solid mp 207–208° C., MS: 404.3 (M+H)$^+$.

Starting from 4-(4-methoxy-benzenesulfonyl)-1-(4-methylbenzyl)-piperidine-4-carboxylic acid (1.59 g, 3.9 mmol) and following the procedure as outlined in example 83, .505 g of 4-(4-methoxy-benzenesulfonyl)-1-(4-methylbenzyl)-piperidine-4-carboxylic acid hydroxamide was isolated as a white solid. mp 176–177° C.; Yield 32%; MS: 419.0 (M+H)$^+$; $^1$H NMR (300 MHz, DMSO-d$_6$): δ 2.24–2.32 (m, 2H), 2.51(t, 3H), 2.73–2.90 (m, 2H), 3.35–3.50 (m, 4H), 3.87 (s, 3H), 4.24 (s, 2H), 7.13–7.17 (d, J=.039, 2H), 7.,3–7.60 (d, J=.036, 2H), 7.38–7.41 (d, J=0.025, 2H), 7.65–7.68 (d, J=0.039, 2H).

EXAMPLE 87
4-(4-methoxy-benzene-sulfonyl)-1-napthalene-2-yl-methylpiperidine-4-carboxylic acid hydroxamide 2-[(2-Hydroxy-ethyl)-(2-napthyl-2-ylmethyl)-amino]-ethanol was prepared according to the general method as outlined in example 83. Starting from diethanolamine (6.18 g, 59 mmol) and 2-(bromomethyl)napthalene (10 g, 45 mmol). Yield 12.7 g (96 %); yellow solid mp 162–164° C.; MS: 246.0 (M+H)$^+$.

2-Napthyl-2-ylmethyl-bis-(2-chloro-ethyl)-anmine was prepared according to the general method as outlined in example 83. Starting from 2-napthyl-ylmethyl-diethanol amine (10 g, 36 mmol). Yield 9.1 g (79%); brown solid mp 124–126° C.; MS: 281.9 (M+H)$^+$.

4-(4-Methoxy-benzenesulfonyl)-napthalene-ylmethyl-piperiddine-4-carboxylic acid ethyl ester was prepared according to the general method as outlined in example 83. Stang from 4-(methoxy-benzenesulfonyl)-acetic acid ethyl ester (8.4 g, 32 mmol) and 1-napdialene-ylmethyl bis-(2-chloro-ethyl)-amine ((8.6 g, 27 mmol). Yield 6.5 g (52 %); low melting solid; MS: 440.0 (M+H)$^+$.

4-(4-Methoxy-benzenesulfonyl)-1-napthalene-ylmethyl-piperidine-4-carboxylic acid was prepared starting from 4-(4-methoxy-benzenesulfonyl)-napthalene-ylmethyl-piperidine-4-carboxylic acid ethyl ester (6.3g, 13 mmol) dissolved in methanol (30 mL), 10 N sodium hydroxide (30 mL) and tetrahydrofuran (30 mL). The resulting reaction miixture was worked up as outlined in example 83. Yield 2.3 g (36%). yellow solid mp 226–228° C., MS: 440.0 (M+H)$^+$.

Starting from 4-(4-methoxy-benzenesulfonyl)-1-napthalene-2-yl-methylpiperidine-4-carboxylic acid (2.18g, 5.0 mmol) and following the procedure as outlined in example 83, .753 g of 4-(4-methoxy-benzene-sulfonyl)-1-napthalene-2-yl-methylpiperidine-4-carboxylic acid hydroxamide was isolated as a off white solid. mp 168–170° C.; Yield 31%; MS 455.0 (M+H)$^+$; H NMR (300 MHz, DMSO-d$_6$): δ 2.29–2.33 (m, 2H), 2.86–2.89 (m, 2H), 3.42–3.46 (m, 4H), 3.85 (s, 3H), 4.46 (s, 2H), 7.13–7.16 (d, J=0.030, 2H), 7.56–7.64 (m, 3H), 7.65–7.68 (d, J=0.030, 2H), 7.98–8.00 (m, 3H), 8.21 (s, 1H), 10.70 (s, 1H), 11.20 (s, 1H).

EXAMPLE 88
1-Biphenyl-4-ylmethyl-4-(4-methoxy-benzenesulfonyl) piperidine-4-carboxylic acid hydroxamide 2-[(2-Hydroxy-ethyl)-(1-biphenylfylmethyl))-amino]-ethanol was prepared according to the general method as outlined in example 83. Starting from diethanol amine (5.2 g, 49 mmol) and 4-(chloromethyl)biphenyl (10 g, 49 mmol). Yield 9.98 g (66 %); white solid mp 160–162° C.; MS: 271.9 (M+H)$^+$. This was converted to the dichloride as outlined in example 83

1-Biphenyl-4-ylmethyl-4-(4-methoxy-benzenesulfonyl)-piperidine-4-carboxylic acid ethyl ester was prepared according to the general method as outlined in example 83. Starting from 4-(methoxy-benzenesulfonyl)-acetic acid ethyl ester (2.85 g, 11 mmol) and l-biphenyl4-ylmethyl-bis-(2chloro-ethyl)-amine (3.4 g, 11 mmol). Yield 2.1 g, (39 %); beige solid, mp 176–178° C., MS: 494.1 (M+H)$^+$.

1-Biphenyl-4-ylmethyl-4-(4-methoxy-benzenesulfonyl)-piperidine-4-carboxylic acid was prepared starting from 1-biphenyl-4-ylmethyl-(4-methoxy-benzenesulfonyl)-piperidine-4-carboxylic acid ethyl ester (5.7g, 12 mmol) dissolved in ethanol (20 mL), tetrahydrofuran (20 mL) and 10 N sodium hydroxide (10 mL). The resulting reaction mixture was worked up as outlined in example 83. Yield 2.1g (39% ) MS: 465.8 (M+H)$^+$.

Starting from 1-biphenyl-4-ylmethyl-4-(methoxy-benzenesulfonyl)-piperidine-4-carboxylic acid (1.0 g, 2.2 mmol and following the procedure as outlined in example 83, .132g of 1-biphenyl-4-ylmethyl-4-(4-methoxy-benzenesulfonyl)piperidine-4-carboxylic acid hydroxamide was isolated as a tan solid. mp168° C.; Yield 20%; MS: 440.9 (M+H)$^+$; $^1$H NMR (300 ML, DMSO-d$_6$): δ 2.30–2.35 (m, 2H), 2.83–2.87 (m, 2H), 3.35–3.5 (m, 4H), 3.87 (s, 3H), 7.15–7.721 (d, J=0.059 Hz, 2H), 7.49–7.65 (m, 5H), 7.68–7.74(d, J=.06 Hz, 2H), 9.3 (s, 1H), 10.3 (s, 1H), 11.15 (s, 1H).

EXAMPLE 89

4-(4-methoxy-benzene-sulfonyl)-1-(3-methyl-but-2-enyl) piperidine4carboxylic acid hydroxamide 2-[(2-Hydroxy-ethyl)-1-(3-methyl-but-2-enyl)-amino]-ethanol was prepared according to the general method as outlined in example 83. Starting from diethanol amine (4.1 g, 39 mmol) and 4-bromo-2-methyl-butene (6.0 g, 40 mmol). Yield ( 98 %); brown oil; MS: 173.8 (M+H)$^+$.

1-(3-methyl-but-2-enyl)]-bis-(2-chloro-ethyl)-amine was prepared according to the general method as outlined in example 83. Starting from 2-[(2-hydroxy-ethyl)-1-(3-methyl-but-2-enyl)-amino]-ethanol (10.4g, 50 mmol). Yield 10.5g (99%); brown solid; MS: 210.3 (M+H)

4(4-Methoxy-benzenesulfonyl)-1-(3-methyl-but-2enyl)-piperidine-4-carboxylic acid ethyl ester was prepared according to the general method as outlined in example 1. Starting from 4-(methoxy-benzenesulfonyl)-acetic acid ethyl ester (11.32 g, 44 mmol) and 3-methyl-but-2-enyl)-bis-(2-chloroethyl)-amme ( 10.4 g, 50 mmol). Yield 6.2 g (36 %); brown oil; MS: 395.6 (M+H)$^+$.

4-(4-Methoxy-benzenesulfonyl)-1-(3-methyl-but-2-enyl) piperidine-4-carboxylic acid was prepared starting from 4-(4-methoxy-benzenesulfonyl)-1-(3-methyl-but-2-enyl)-piperidine-4-carboxylic acid ethyl ester (6.2g, 16 mmol) dissolved in ethanol (15 mL), 10 N sodium hydroxide (10 mL) and tetahydrofuiran (75 mL). The resulting reaction mixture was worked up as outlined in example 83. Yield 1.2 g (21%). brown solid mp 196–197 ° C, MS: 367.9 (M+H)$^+$.

Starting from 4-(4-methoxy-benzenesulfonyl)-1-(3-methyl-but-2-enyl)-piperidine-4-carboxylic acid (1.0 g. 3.0 mmol) and following the procedure as outlined in example 83, .110 mg of 4-(4-methoxy-benzene-sulfonyl)-1-(3-methyl-but-2-enyl)piperidine-4-carboxylic acid hydroxamide was isolated as a yellow solid. mp 142–145° C.; Yield 12%; MS: 382.9 (M+H)$^+$; $^1$H NMR (300 MHz, DMSO-d$_6$): δ 1.67 (s, 3H), 1.79 (s, 3H), 2.18–2.23 (m, 2H), 2.66–2.73 (m, 2 H), 3.37–3.46 (m, 2H), 3.67–3.69 (m, 2H), 5.19–5.24 (m, 1H), 7.15–7.18 (d, J=0.03, 2H), 7.67–7.70 (d, J=0.030, 2H), 9.34 (s, 1H), 9.88 (s, IH),.11.15 (s, 1H).

EXAMPLE 90

1-(Bromo-benzyl)-4-(4-methoxy-benzenesulfonyl)-piperidine-4-carboxylic acid hydroxyamide 2-[(4-Bromobenzyl)-(2-hydroxy-ethyl)-amino]-ethanol was prepared according to the general method as outlined in example 83. Starting from diethanolamine (22.5 g, 150 mnmol). and 4-bromobenzyl bromide (25 g, 100 mmol). Yield 33.66g, (99%); yellow oil; MS: 273.8 (M+H)$^+$.

(4-Bromo-benzyl)-bis-(2-chloro-ethyl)-amine was prepared according to the general method as outlined in example 83. Starting from 2-[(4-bromobenzyl)-(2-hydroxy-ethyl)-amino]-ethanol (33.28 g, 122 mmol). Yield 47 g, (99%); brown solid; mp 125 ° C; MS: 309.8 (M+H)$^+$.

1-(4-Bromo-benzyl)-4-(4methoxy-benzenesulfonyl)-piperidine-4-carboxylic acid ethyl ester was prepared according to the general method as outlined in example 83. Staring from 4-(methoxy-benzenesulfonyl) acetic acid ethyl ester (8.6 g, 33.5 mmol) and (4-bromobenzyl)-bis-(2-chloroethyl)-amine (13.3 g, 38.6 mmol). Yield 17 g (44%); brown oil; MS: 497.8 (M+H)$^+$.

1-(4-Bromo-benzyl)-4-(4-methoxy-benzenesulfonyl)-piperidine-4-carboxylic acid was prepared starting from 1-(4-bromo-benzyl)-4-(4-methoxy-benzenesulfonyl)-piperidine-4-carboxylic acid ethyl ester (16.5 g, 33.3 mmol) dissolved in TBF:methanol 3:1 and 10 N NaOH (20 ml). The resulting reaction mixture was worked up as outlined in example 83. Yield 6.18 g (40%); tan solid; mp 215° C.; MS: 469.7 (M+H)$^+$.

Starting from 1-(4-Bromo-benzyl)-4-(4-methoxy-benzenesulfonyl)-piperidine-4-carboxylic acid (1.95 g, 4.2 mmol) and folowing the procedure as outlined in example 83, 1.29 g of 1-(4-bromo-benzyl)-4-(4-methoxy-benzenesulfonyl)-piperidine-4-carboxylic acid hydroxamide was isolated as an off white solid. Yield 60%; mp 180° C.; MS: 484.7 (M+H)$^+$; $^1$H NMR (300 MHz, DMSO-d$_6$): δ 2.18–2.29 (m, 2H), 2.46 (d, 2H), 2.74–2.89 (m, 2H), 3.39 (d, 2H), 3.87 (s, 3H), 4.28 (s, 2H), 7.18 (d, J=17 Hz, 2H), 7.49 (d, J=8.1 Hz, 2H), 7.65–7.68 (m, 4H), 9.37 (s, 1H), 10.5 (s, 1H).

EXAMPLE 91

4-(4-methoxy-benzenesulfonyl)-1-(3-phenyl-propyl)-piperidine-4-carboxylic acid hydroxyamide 2-[(2-Hydroxy-ethyl)-(3-phenyl-propyl)-amino]-ethanol was prepared according to the general method as outlined in example 83. Starting from diethanolamine (15.8 g, 151 mmol). and 1-bromo-3-phenylpropane (20 g, 101 mmol). Yield 21.31 g, (95%); yellow oil; MS: 223.9 (M+H)$^+$.

Bis-(2-Chloro-ethyl)-(3-phenyl-propyl)-amine was prepared according to the general method as outlined in example 83. Starting from 2-[(2-hydroxy-ethyl)-(3-phenyl-propyl)-amino]-ethanol (20.32 g, 90.7 mmol). Yield 24.9 g (92%); brown oil; MS: 259.8 (M+H)$^+$.

4-(4-Methoxy-benzenesulfonyl)-1-(3-phenyl-propyl)-piperidine-4-carboxylic acid ethyl ester was prepared according to the general method as outlined in example 83. Starting from from 4-(methoxy-benzenesulfonyl) acetic acid ethyl ester (12 g, 46.5 mmol) and bis-(2-chloro-ethyl)-(3-phenyl-propyl)-amine (24.8 g, 93.8 mmol). Yield 11.24 g (54%); brown oil; MS: 446 (M+H)$^+$.

4-(4-Methoxy-benzenesulfonyl)-1-(3-phenyl-propyl)-piperidine-4-carboxylic acid was prepared starting from 4-(4-Methoxy-benzenesulfonyl)-1(3-phenyl-propyl)-piperidine-4-carboxylic acid ethyl ester (10.74 g, 24.13 mmol) dissolved in THF:methanol 3:1 and 10 N NaOH (40 ml). The resulting reaction mixture was worked up as outlined in example 83. Yield 4.67 g (47%); off white powder, mp 203° C.; MS: 418.2 (M+H)$^+$.

Starting from 4-(4-methoxy-benzenesulfonyl)-1-(3-phenyl-propyl)-piperidine-4-carboxylic acid (4.37 g, 10.4 mmol) and following the procedure as outlined in example 83, 1.64 g of 4-(4-methoxy-benzenesulfonyl)-1-(3-phenyl-propyl)-piperidine-4-carboxylic acid hydroxyamide was isolated as an off white solid. Yield 37%; mp 143° C.; MS: 432.9 (M+H)$^+$; $^1$H NMR (300 MHz, DMSO-d$_6$): δ 1.92–1.97 (m, 2H), 2.18–2.29 (m, 2H), 2.47 (d, 2H), 2.58 (t, J=7.7 Hz, 2H), 2.6–2.73 (m, 2H), 3.0–3.06 (m, 2H), 3.60 (d, J =12.3 Hz, 2H), 3.87 (s, 2H), 7.15–7.30 (m, 7 H), 7.68, (d, J=9 Hz, 2H), 9.3 (s, 1H), 10.1 (s, 1H).

EXAMPLE 92
1-Tert-butyl-4-(4-methoxy-benzenesulfonyl)-piperidine-4-carboxylic acid hydroxyamide tert-Butyl-bis-(2-chloroethyl)-amine was prepared according to the general method as outlined in example 83. Starting from 1-tert-butyl-diethanolamine (6 g, 37.2 mmol). Yield 11.15 g, (99%); white solid; MS: 197.8 (M+H)$^+$.

1-tert-Butyl-4-(4-methoxy-benzenesulfonyl)-piperidine-4-carboxylic acid ethyl ester was prepared according to the general method as outlined in example 83. Starting from 4-(methoxy-benzenesulfonyl) acetic acid ethyl ester (10 g, 38.76 mmol) and tert-butyl-bis-(2-chloro-ethyl)-amine (5.25 g, 22.53 mmol). Yield 5.37 g, (62%); brown oil; MS: 384 (M+H)$^+$.

1-tert-Butyl-4-(4-methoxy-benzenesulfonyl)-piperidine-4-carboxylic acid was prepared starting from 1-tert-butyl-4-(4-methoxy-benzenesulfonyl)-piperidine-4-carboxylic acid ethyl ester (5.37 g 14 mmol) dissolved in methanol (300 ml) and 10 N NaOH (23 ml). The resulting reaction mixture was worked up as outlined in example 83. Yield 1.52 g (30.6%); white powder; mp 204° C.; MS: 356 (M+H)$^+$.

Starting from 1-tert-butyl-4-(4-methoxy-benzenesulfonyl)-piperidine-4-carboxylic acid (320 mg, 0.9 mmol) and following the procedure as outlined in example 83, 190 mg of 1-tert-butyl-4-(4-methoxy-benzenesulfonyl)-piperidine-4-carboxylic acid hydroxyamide was isolated as a green solid. Yield 52%; mp 40° C.; MS: 371.1 (M+H)$^+$; $^1$H NMR (300 Mz, DMSO d): δ 1.29 (s, 9H), 1.54 (m, 2H), 1.66 (m, 2H), 2.39 (m, 2H), 2.98 (m, 2H), 3.88 (s, 3H), 7.18 (d, 2H), 7.67 (d, 2H).

EXAMPLE 93
1-Butyl-4-(4-methoxy-benzenesulfonyl)-piperidine-4-carboxylic acid hydroxyamide Butyl-bis-(2-chloro-ethyl)-amine was prepared according to the general method as outlined in example 83. Starting from N-butyldiethanolamine (6 g, 37.2 mmol). Yield 11.3 g, (99%); white powder; mp 165° C.; MS: 197.9 (M+H)$^+$.

1-Butyl-4-(4-methoxy-benzenesulfonyl)-piperidine-4-carboxylic acid ethyl ester was prepared according to the general method as outlined in example 83. Startng from 4-(methoxy-benzenesulfonyl) acetic acid ethyl ester (5 g, 19.38 mmol) and butyl-bis-(2-chloroethyl)-amine (4.52 g, 19.38 mmol). Yield 6.86 g, (93%); brown oil; MS: 384 (M+H)$^+$.

1-Butyl-4-(4-methoxy-benzenesulfonyl)-piperidine-4-carboxylic acid was prepared starting from 1-butyl-4-(4-methoxy-benzenesulfonyl)-piperidine-4-carboxylic acid ethyl ester (6.42 g 16.8 mmol) dissolved in methanol (200 ml) and 10 N NaOH (20 ml). The resulting reaction mixture was worked up as outlined in example 83. Yield 1.6 g (27%); white powder; mp 206° C.; MS: 356.4 (M+H)$^+$.

Starting from 1-butyl-4-(4-methoxy-benzenesulfonyl)-piperidine-4-carboxylic acid (1.51 g, 4.3 mmol) and following the procedure as outlined in example 83, 200 mg of 1-butyl(4-methoxy-benzenesulfonyl)-piperidine4-carboxylic acid hydroxyamide was isolated as an off white solid. Yield 9.3%; mp 75° C.; MS: 371.1 (M+H)$^+$; $^1$H NMR (300 MHz, DMSO-d$_6$): δ 0.87 (t, J=7.2 Hz, 3H), 1.27 (m, 2H), 1.59 (m, 2H), 2.27 (m, 2H), 2.45 (m, 2H), 2.50 (m, 2H), 2.65 (m, 2H), 2.97 (m, 2H) 3.88 (s, 3H), 7.18 (d, 2H), 7.69 (d, 2H).

EXAMPLE 94
1-Cyclooctyl-4-(4-methoxy-benzenesulfonyl)-piperidine-4-carboxylic acid hydroxyamide Cyclooctyl-bis-(2-chloro-ethyl)-amine was prepared according to the general method as outlined in example 83. Starting from N-cyclooctyldiethanolamine (6 g, 28 mmnol). Yield 10 g, (99%); off white solid; mp 158° C.; MS: 251.9 (M+H)$^+$.

1-Cyclooctyl-4-(4-methoxy-benzenesulfonyl)-piperidine-4-carboxylic acid ethyl ester was prepared according to the general method as outlined in example 83. Stting from 4-(methoxy-benzenesulfonyl) acetic acid ethyl ester (5 g, 19.4 mmol) and cyclooctyl-bis-(2-chloro-ethyl)-amine (5.57 g, 19.4 mmol). Yield 8.2 g, (96%); brown oil; MS: 438 (M+H)$^+$.

1-Cyclooctyl-4-(4-methoxy-benzenesulfonyl)-piperidine-4-carboxylic acid was prepared starting from 1-cyclooctyl-4-(4-methoxy-benzenesulfonyl)-piperidine-4-carboxylic acid ethyl ester (8 g, 183 mmol) dissolved in methanol (200 ml) and 10 N NaOH (25 ml). The resulting reaction mixture was worked up as outlined in example 83. Yield 2.36 g (32%); white powder; mp 180° C.; MS: 410 (M+H)$^+$.

Starting from 1-Cyclooctyl-4-(4-methoxy-benzenesulfonyl)-piperidine-4-carboxylic acid (2.26 g, 5.53 mmol) and following the procedure as outlined in example 83, 570 mg of 1-cyclooctyl-4-(4-methoxy-benzenesulfonyl)-piperidine-4-carboxylic acid hydroxyamide was isolated as a white powder. Yield 22%; mp >200° C.; MS: 425 (M+H)$^+$; $^1$H NMR (300 MHz, DMSO-d$_6$): δ 1.42–1.66 (m, 14H), 1.83 (m, 2H), 2.33 (m, 2H), 2.67 (m, 2H), 3.30–3.51 (m, 3H) 3.88 (s, 3H) 7.17 (d, 2H), 7.66 (d, 2H).

EXAMPLE 95
1-Ethyl-4-(4-methoxy-benzenesulfonyl)-piperidine-4-carboxylic acid hydroxyamide 1-Ethyl-4-(4-methoxy-benzenesulfonyl)-piperidine-4-carboxylic acid ethyl ester was prepared according to the general method as outlined in example 83. Starting from 4-(methoxy-benzenesulfonyl) acetic acid ethyl ester (3 g, 11.6 mmol) and ethyl-bis-(2-chloro-ethyl)-amine (2.39g, 11.6 mmol). Yield 3.09 g, (75%); low melting brown solid; MS: 356 (M+)$^+$.

1-Ethyl-4-(4-methoxy-benzenesulfonyl)-piperidine-4-carboxylic acid was prepared staring from 1 -ethyl-4-(4-methoxy-benzenesulfonyl)-piperidinencarboxylic acid ethyl ester (2.42 g, 6.8 mmol) dissolved in methanol (100 ml) and 10 N NaOH (15 ml). The resulting reaction mixture was worked up as outlined in example 83. Yield 1.29 g (58%);-white solid; mp 209° C.; MS: 328 (+M)$^+$.

Starting from 1-ethyl-4-(4-methoxy-benzenesulfonyl)-piperidine-4-carboxylic acid (1.23 g, 3.76 mmol) and following the procedure as outlined in example 83, 1.02 g of 1-ethyl-4-(4-methoxy-benzenesulfonyl)-piperidine-4-carboxylic acid hydroxyamide was isolated as an off white powder. Yield 80%; mp 85° C.; MS: 343 (M+H)+; $^1$H NEM (300 M , DMSO d$_6$): δ 0.926 (t, J=7.1 Hz, 3H), 1.68–1.89 (m, 4H), 2.05–2.24 (ne, 4H), 2.73 (q, 2H), 3.85 (s, 3H), 7.07 (d, 2H), 7.64 (d, 2H).

EXAMPLE 96
1-Isopropyl-4-(4-methoxy-benzenesulfonyl)-piperidine-4-carboxylic acid hydroxyamide 1-Isopropyl-4-(4-methoxy-benzenesulfonyl)-piperidine-4-carboxylic acid ethyl ester was prepared according to the general method as outlined in example 83. Starting from 4-(methoxy-benzenesulfonyl) acetic acid ethyl ester (5.7 g, 22.2 mmol) and isopropyl-bis-(2-chloro-ethyl)-amine (4.9 g, 22.2 mmol). Yield 5.64 g, (68%); low melting brown solid; MS: 370 (M+H)$^+$.

1-Isopropyl-4-(4-methoxy-benzenesulfonyl)-piperidine-4-carboxylic acid was prepared starting from 1-isopropyl-4-(4-methoxy-benzenesulfonyl)-piperidine-4-carboxylic acid ethyl ester (5.6 g, 15.2 mmol) dissolved in methanol (75 ml) and 10 N NaOH (25 ml). The resulting reaction mixture was worked up as outlined in example 83. Yield 2.18 g (42%); white powder; mp 204° C.; MS: 341.9 (M+H)$^+$.

Starting from 1-isopropyl-4-(4-methoxy-benzenesulfonyl)-piperidine-4carboxylic acid (2.13 g, 6.25 mmol) and following the procedure as outlined in example 83, 590 mg of 1-isopropyl-4-(4-methoxy-benzenesulfonyl)-piperidine-4-carboxylic acid hydroxyamide was isolated as a white powder. Yield 2.4%; mp 75° C.; MS: 357 (M+H)+; $^1$H NMR (300 MD, DMSO-d$_6$): δ 1.21 (d, J=6.6 Hz, 6H), 2.33–3.53 (m, 9H), 3.88 (s, 3H), 7.16 (d, 2H), 7.66 (d, 2H).

EXAMPLE 97
1-Methyl-4-(4-methoxy-benzenesulfonyl)-piperidine-4-carboxylic acid hydroxyaride 1-Methyl-4-(4-methoxy-benzenesulfonyl)-piperidine-4-carboxylic acid ethyl ester was prepared according to the general method as outlined in example 83. Starting from 4(methoxy-benzenesulfonyl) acetic acid ethyl ester (3 g, 11.6 mmol) and methyl-bis-(2-chloro-ethyl)-amine (2.2g, 11.6 mmol). Yield 3.09 g, (75%); low melting brown solid; MS: 342 (M+H)$^+$.

1-Methyl-4-(4-methoxy-benzenesulfonyl)-piperidine-4-carboxylic acid was prepared starting from 1-methyl-(4-methoxy-benzenesulfonyl)-piperidine-4-carboxylic acid ethyl ester (8.7 g, 25.6 mmol) dissolved in methanol (300 ml) and 10 N NaOH (35 ml). The resulting reaction mixture was worked up as outlined in example 83. Yield 3.23 g (41%); white solid; mp 204° C.; MS: 313.9 (M+H)$^+$.

Starting from 1-methyl-4-(4-methoxy-benzenesulfonyl)-piperidine-4-carboxylic acid (2.0 g, 6.38 mmol) and following the procedure as outlined in example 83, 1. 10 g of 1-methyl-4-(4-methoxy-benzenesulfonyl)-piperidine-4-carboxylic acid hydroxyamide was isolated as a yellow powder. Yield 53%; mp 89° C.; MS: 329 (M+H)$^+$; $^1$H NMR (300 MHz, DMSO-d$_6$): δ 1.67–1.76 (m, 2H), 1.85–1.96 (m, 2H), 2.05 (s, 3H), 2.17 (d, J3=11.4 Hz, 2H), 2.57 (d, J=10.4 Hz, 2H) 3.83 (s, 3H), 7.02 (d, 2H), 7.62 (d, 2H).

EXAMPLE 98
1-Benzyl-4-(4-butoxy-benzenesulfonyl)-piperidine-4-carboxylic acid hydroxyamide 1-Benzyl-4-(butoxy-benzenesulfonyl)-piperidine-4-carboxylic acid ethyl ester was prepared according to the general method as outlined in example 83. Starting from from 4-(butoxy-benzenesulfonyl) acetic acid ethyl ester (6 g, 20 mmol) and bis-(2-chloro-ethyl)-benzylamine (10 g, 30 mmol). Yield 5.15 g (56%); yellow oil; MS: 460 (M+H)$^+$.

1-Benzyl-4-(4-butoxy-benzenesulfonyl)-piperidine-4-carboxylic acid was prepared starting from 1-benzyl-4-(4-butoxy-benzenesulfonyl)-piperidine-4-carboxylic acid ethyl ester (5.1 g, 11.1 mmol) dissolved in TBF:methanol 3:1 and 10 N NaOH (10 ml). The resulting reaction mixture was worked up as outlined in example 83. Yield 2.66 g (56%); off white solid; mp 210° C.; MS: 432 (M+H)$^+$.

Starting from 1-benzyl-(4-butoxy-benzenesulfonyl)-piperidine-4-carboxylic acid (2.61 g, 6.06 mmol) and following the procedure as outlined in example 83, 860 mg of 1-benzyl-4-butoxy-benzenesulfonyl)-piperidine-4-carboxylic acid hydroxyamide was isolated as an off white powder. Yield 32%; mp 144° C.; MS: 446.9 (M+H)$^+$; $^1$H NMR (300 MHZ, DMSO-d$_6$): δ 0.94 (t, J=7.3 Hz, 3H), 1.44,(q, J=7.5 Hz, 2H), 1.70 (q, 2H), 2.28–2.32 (m, 2H), 2.50 (d, 2H), 2.74–2.83 (m, 2H), 3.35 (d, 2H), 4.08 (t, J =6.3 Hz, 2H), 4.34 (s, 2H), 7.13 (d, J=8.7, 2H), 7.45 (s, 3H), 7.54 (s, 2H), 7.74 (d, J =8.7, 2H), 9.35 (s, 1H), 10.7 (s, 1H).

EXAMPLE 99
1-(4-Fluoro-benzyl)-4-(4-methoxy-benzenesulfonyl)-piperidine-4-carboxylic acid hydroxyamide 1-(4-Fluoro-benzyl)-4-(4-methoxy-benzenesulfonyl)-piperidinecarboxylic acid ethyl ester was prepared according to the general method as outlined in example 83. Starting from 4-(methoxy-benzenesulfonyl) acetic acid ethyl ester (18.8 g, 72.8 mmol) and (4-fluoro-benzyl)-bis-(2-chloro-ethyl)-amine (20.8 g, 73 mmol). Yield 25 g (79%); brown oil; MS: 436.9 (M+H)$^+$.

1-(4-Fluoro-benzyl)-4-(4-methoxy-benzenesulfonyl)-piperidine4-carboxylic acid was prepared starting from 1-(4-fluoro-benzyl)-4-(4-methoxy-benzenesulfonyl)-piperidine-4-carboxylic acid ethyl ester (17.4 g, 40 mmol) dissolved in THF:methanol 3:1 and 10 N NaOH (40 ml). The resulting reaction mixture was worked up as outlined in example 83. Yield 10.8 g (66%); colorlesssolid; mp 154° C.; MS: 408 (M+H)$^+$.

Starting from 1-(4-Fluoro-benzyl)-4-(4-methoxy-benzenesulfonyl)-piperidine-4-carboxylic acid (8.14 g, 20 mmol) and following the procedure as outlined in example 83, 4.3 g of 1-(4-fluoro-benzyl)4-(4-methoxy-benzenesulfonyl)-piperidine-4-carboxylic acid hydroxyamide was isolated as an off white solid. Yield 51 %; mp 176–178° C.; MS: 484.7 (M+H)$^+$; $^1$H NMR (300 MHz, DMSO-d$_6$): δ 2.12–2.20 (m, 2H), 2.64–2.79 (m, 2H), 3.32–3.45 (m, 4H), 3.87 (s, 3H), 4.31 (s, 2H), 7.14–7.19 (d, J=17 Hz, 2H), 7.27–7.33 (d, J=8.1 Hz, 2H), 7.50–7.54 (d, 2H), 7.65–7.68 (d, 2H), 9.38 (s, 1H), 9.75 (s, 1H).

EXAMPLE 100
1-(4-Fluoro-benzyl)-4-(4-butoxy-benzenesulfonyl)-piperidine-4-carboxylic acid hydroxyamide 1-(4-Fluoro-benzyl)-4-(4-butoxy-benzenesulfonyl)-piperidine-4-carboxylic acid ethyl ester was prepared according to the general method as outlined in example 83. Starting from from 4-(butoxy-benzenesulfonyl) acetic acid ethyl ester (6 g, 20 mmol) and (4-fluoro-benzyl)-bis-(2-chloro-ethyl)-amine (5.73 g, 20 mmol). Yield 8.2 g (86%); yellow oil; MS: 478 (M+H)$^+$.

1-(4-Fluoro-benzyl)-4-(4-butoxy-benzenesulfonyl)-piperidine-4-carboxylic acid was prepared starting from 1-(4-Fluoro-benzyl)-4-(4-butoxy-benzenesulfonyl)-piperdine-4-carboxylic acid ethyl ester (4.77 g, 10 mmol) dissolved in TBF:methanol 3:1 and 10 N NaOH (10 ml). The resulting reaction mixture was worked up as outlined in example 83. Yield 3.5 g (79%); off white solid; mp 114° C.; MS: 450 (M+H)$^+$.

Starting from 1-(4-Fluoro-benyl)-4-(4-butoxy-benzenesulfonyl)-piperdine-4-carboxylic acid (2.24 g, 5.0 mmol) and following the procedure as outlined in example 83, 200 mg of 1-(4-Fluoro-benzyl)-4-(4-butoxy-benzenesulfonyl)-piperidine-4-carboxylic acid hydroxyamide was isolated as an off white powder. Yield 9%; mp 112° C.; MS: 465.9 (M+H)$^+$; $^1$H NMR (300 MHz, DMSO-d$_6$): δ 0.94 (t, J=7.3 Hz, 3H), 1.35–1.50 (m, 2H), 1.68–1.77

(m, 2H), 2.20–2.28 (m, 2H), 2.66–2.77 (m, 2H), 3.77–3.78 (m, 4H), 4.064.10 (m, 2H), 4.19 (s, 2H), 7.14–7.19 (d, J=8.7, 2H), 7.27–7.33 (d, 2H), 7.50–7.54 (d, 2H), 7.65–7.68 (d, 2H), 9.34 (s, 1H), 10.55 (s, 1H).

EXAMPLE 101

4-(4-methoxy-benzenesulfonyl)-1-(4-medthoxy-benzyl)-piperidine-4 -carboxylic acid hydroxyamide 2-[(2-Hydroxy-ethyl)-(4-methoxy-benzyl)-amino]-ethanol was prepared according to the general method as outlined in example 83. Starting from diethanolamine (12.0 g, 114 mmol) and 4-methoxybenzyl chloride (14.2 g, 100 mmol). Yield 17.5 g, (77 %); yellow oil; MS: 226 (M+H).

4-Methoxybenzyl-bis-(2-chloroethyl)-amine was prepared according to the general method as outlined in example 83. Starting from 4-Methoxy-benzyl diethanolamine (10 g, 44 mmol). Yield 10 g (75 %); yellow solid mp 55 C; MS: 263.1 (M+H)$^+$.

4-(4-Methoxy-benzenesulfonyl)-1-(4-methoxy-benzyl) piperidine-4-carboxylic acid ethyl ester was prepared according to the general method as outlined in example 83. Starting from 4-(methoxy-benzenesulfonyl)-acetic acid ethyl ester (5.0 g, 20 mmol) and bis- (2-chloro ethyl)-(4-methoxy-benzyl)-amine (7.0 g, 22 mmol). Yield 5.0 g (56 %); low melting solid; MS: 448.5 (M+H)$^+$.

4-(4-Methoxy-benzenesulfonyl)-1-(4-methoxy-benzyl)-piperidine-4-carboxylic acid was prepared starting from 4-(4-Methoxy-benzenesulfonyl)-1-(4-methoxy-benzyl) piperidine-4-carboxylic acid ethyl ester (4.2g, 10 mmol) dissolve in methanol (30 mL), 10 N sodium hydroxide (10 mL), tetrahydrohydrofimran (20 mL). The resulting reaction mixture was worked up as outlined in example 83. Yield 3.0 g (71 %). white solid mp 190 IC, MS: 420.4 (M+H)$^+$.

Starting from 4-(4-methoxy-benzenesulfonyl)-1-(4-methoxy-benzyl)-pipeidine-4-carboxylic acid (2.0 g, 4.7 mmol) and following the procedure as outlined in example 83, 1.2 g of 4(4 methoxy-benzenesulfonyl)-1-(methoxy-benzyl)-piperidine-4-carboxylic acid hydroxamide was isolated as a white solid. mp 175° C. (HCl); Yield: 1.2 g, 59 %; MS: 433.0 (M+H)$^+$; $^1$HMR (300 Mz, DMSO-d$_6$): δ 1.8 (m, 4H), 2.3(m, 2H), 2.73 (m, 2H), 3.37 (d, 2H), 3.76 (s, 3H), 3.88 (s,3H), 6.87 ( d, 2H), 7.11 (d, 2H), 7.21 (d, 2H), 7.65 (d, 2H),9.2 (bs, 1H), 10.9 (bs, 1H).

EXAMPLE 102

4-(4-methoxy-benzenesulfonyl)-1-[2-(4-methoxyphenyl)-ethyl]-piperidine-4-carboxylic acid hydroxyamide 2-{(2-Hydroxy-ethyl)-[2-(4-methoxy-phenyl)ethyl]-amino}-ethanol was prepared according to the general method as outlined in example 83. Starting from diethanolamine (10.0 g, excess). and 1-(2-chloroethyl)-4-methoxybenzene (8.5 g, 50 mmol). Yield 11 g, (92%); yellow oil; MS: 240 (M+H)$^+$.

The corresponding dichloride, bis-(2-chloro-ethyl)-(4-methoxyphenyl-2-ethyl)-amine was prepared according to the general method as outlined in example 83. Starting from 2-{(2-hydroxy-ethyl)-[2-(4-methoxy-phenyl)-ethyl]-amino}-ethanol (10 g, 41.8 mmol). Yield 11 g (95%); brown oil; MS: 277.2 (M+H)$^+$.

4-(4-methoxy-benzenesulfonyl)-1-[2-(4-methoxyphenyl)-ethyl]-piperidine-4-carboxylic acid ethyl ester was prepared according to the general method as outlined in example 83. Starting from from 4-(methoxy-benzenesulfonyl) acetic acid ethyl ester (5.0 g, 20 mmol) and bis-(2-chloro-ethyl)-(4-methoxyphenyl-2-ethyl)-amine (6.4 g, 20 mmol). Yield 6.0 g (65%); brown oil; MS: 462.5 (M+H)$^+$.

4-(4-methoxy-benzenesulfonyl)-1-[2-(4-methoxyphenyl)-ethyII-piperidine-4-carboxylic acid was prepared starting from 4-(4methoxy-benzenesulfonyl)-1-[2-(4methoxyphenyl)-ethyl]-piperidine-4-carboxylic acid ethyl ester (5.0, 10.8 mmol) dissolved in THF:methanol 3:1 and 10 N NaOH (40 ml). The resulting reaction mixture was worked up as outlined in example 83. Yield 4.0 g (85%o); off white powder; mp 205 ° C; MS: 434.5 (M+H)$^+$.

Starting from 4-(4-methoxy-benzenesulfonyl)-1-[2-(4-methoxyphenyl)-ethyl]-piperidine-4-carboxylic acid (1.5 g, 3.46 mmol) and following the procedure as outlined in example 83, 900 mg of 4-(4-methoxy-benzenesulfonyl)-1-[2-(4-methoxyphenyl)-ethyl]-piperidirne-4-carboxylic acid hydroxyamide was isolated as an off white solid. Yield 58%; mp 206° C. (HCl); MS: 449.5 (M+H)$^+$; $^1$H NMR (300 MHz, DMSO-d$_6$): 5 2.3 (m, 2H), 2.5 (m, 3H), 2.8 (m, 2H), 2.95 (m, 2H), 3.25 (m, 2H), 3.4 (m,4H), 3.60 (d, J =12.3 Hz, 2H), 3.77 (s, 3H),3.99 (s, 3H), 6.9 (d, 2H), 7.1–7.25, (q, 4H), 7.7 (d, 2H), 9.3 (s, 1H), 10.6 (s, 1H).

EXAMPLE 103

4-(4-methoxy-benzenesulfonyl)-1-(2-phenyl-ethyl)-piperidine-4-carboxylic acid hydroxyamide 2-[(2-Hydroxy-ethyl)-(2-phenyl-ethyl)-amino]-ethanol was prepared according to the general method as outlined in example 1. Starting from diethanolamine (6.0 g, 57). and 2-bromo-ethylbenzene (9.0 g, 48.3 mmol). Yield 9 g, (90%); yellow oil; MS: 210 (M+H)$^+$.

Bis-(2-Chloro-ethyl)-(2-phenyi-ethyl)-anine was prepared according to the general method as outlined in example 83. Starting from 2-[(2-Hydroxy-ethyl)-(2-phenyl-ethyl)-amino]-ethanol (8.5 g, 40.6 mmol). Yield 11 g (95%); brown oil; MS: 247.1 (M+H)$^+$.

4-(4-methoxy-benzenesulfonyl)-1-(2-phenyl-ethyl)-piperidine-4-carboxylic acid ethyl ester was prepared according to the general method as outlined in example 83. Starting from from 4-(nethoxy-benzenesulfonyl) acetic acid ethyl ester (5.0 g, 20 mmol) and bis-(2-chloro-ethyl)-(2-phenyl-ethyl)-amine (5.6 g, 20 mmol). Yield 5.5 g (63%); brown oil; MS: 432.5 (M+H)$^+$.

4-(4-methoxy-benzenesulfonyl)-1-(2-phenyl-ethyl)-piperidine-4-carboxylic acid was prepared starting from 4-(4methoxy-benzenesulfonyl)-1-(2-phenyl-ethyl)-piperidine-4-carboxylic acid ethyl ester (3.0 g, 6.9 mmol) dissolved in THF:methanol 3:1 and 10 N NaOH (40 ml). The resulting reaction mixture was worked up as outlined in example 83. Yield 2.0 g (72%); off white powder; mp 208° C.; MS: 404.5 (M+H)$^+$.

Starting from 4-(4-methoxy-benzenesulfonyl)-1-(2-phenyl-ethyl)-piperidine-4-carboxylic acid (1.5 g, 3.7 mmol) and following the procedure as outlined in example 83, 900 mg of 4-(4-methoxy-benzenesulfonyl)-1-(2-phenylethyl)-piperdine-4-carboxylic acid hydroxyamide was isolated as an off white solid. Yield 58%; mp 205° C. (HCl); MS: 419.4 (M+H)$^+$; $^1$H N (300 MHz, DMSO-d$_6$): δ 2.3 (m, 2H), 2.5 (m, 3H), 2.8 (m, 2H), 2.95 (m, 2H), 3.25 (m, 2H), 3.4 (m,4H), 3.9 (s, 3H),7.22–7.8 (m, 9H), 10.6 (s, IH), 11.2 (bs, 1H).

EXAMPLE 104

4-(4-n-Butoxy-benzenesulfonyl)-1-(4-methoxy-benzyl)-piperdine-4-carboxylic acid hydroxyamide 4-(4-n-Butoxy-benzenesulfonyl)-1-(4-methoxy-benzyl) piperidine-4-carboxylic acid ethyl ester was prepared according to the general method as outlined in example 83. Starting from 4(n-Butoxy-benzenesulfonyl)-acetic acid ethyl ester (2.5 g, 10 mmol) and bis- (2-chloro ethyl)-(4-methoxy-benzyl)-amine (3.0 g, 10 mmol). Yield 3.5 g (71 %); low melting solid; MS: 490.5 (M+H)$^+$.

4(4-n-Butoxy-benzenesulfonyl)-1-(4-methoxy-benzyl)-piperidine-4-carboxylic acid was prepared starting from 4-(4-Butoxy-benzenesulfonyl)-1-(4-methoxy-benzyl) piperidine-4-carboxylic acid ethyl ester (3.0 g, 6.1 mmol) dissolve in methanol (30 mL), 10 N sodium hydroxide (10 mL), tetrahydrohydrofuran (20 mL). The resulting reaction mixture was worked up as outlined in example 83. Yield 1.5 g (53%). white solid mp 207° C., MS: 462.5 (M+H)⁺.

Starting from 4-(4-n-Butoxy-benzenesulfonyl)-1-(4-methoxy-benzyl)-piperidine-4-carboxylic acid (1.0 g, 2.1 mmol) and following the procedure as outlined in example 83, 1.2 g of 4(4-Butoxy-benzenesulfonyl)-1-(4-methoxy-benzyl)-piperidine-4-carboxylic acid hydroxamide was isolated as a white solid. mp 173° C. (HCl); Yield: 800 mg, 77%; MS: 477.5 (M+H)⁺; $^1$H NMR (300 MHz, DMSO-$d_6$): δ 0.9 (t, 3H), 1.4 (m, 2H), 1.7 (m,2H), 2.3 (m, 2H), 2.5 (m, 2H), 2.7 (m, 2H), 3.3 (m, 2H), 3.5(m, 2H), 4.1 (t, 2H), 4.3 (m, 2H), 6.97 ( d, 2H), 7.14 (d, 2H), 7.48 (d, 2H), 7.7 (d, 2H), 9.4 (bs, 1H), 10.9 (bs, 1H).

EXAMPLE 105

4-(4-Methoxy-benzenesulfony )-1-(3-phenoxy-propyl)-pipendine-4-carboxyllc acid hydroxyamide 2-[(2-Hydroxy-ethyl)-(3-phenoxy-propyl)-amino]-ethanol was prepared according to the general method as outlined in example 83. Starting from diethanolamine (15.8 g, 151 mmol). and 3-Phenoxypropyl bromide (21.5 g, 100 mmol). Yield 21.31 g, (95%); yellow oil; MS: 238.1 (M+H)⁺.

Bis-(2-Chloro-ethyl)-(3-phenoxy-propyl)-amine was prepared according to the general method as outlined in example 83. Stariing from 2-[(2-hydroxy-ethyl)-(3-phenoxy-propyl)-amlino]-ethanol (20.0 g, 84 mmol). Yield 24.0 g (91%); brown oil; MS: 277.8 (M+H)⁺.

4-(4-Methoxy-benzenesulfonyl)-1-(3-phenoxy-propyl)-piperidine-4-carboxylic acid ethyl ester was prepared according to the general method as outlined in example 83. Starting from from 4-(methoxy-benzenesulfonyl) acetic acid ethyl ester (5.2 g, 20 mmol) and bis-(2chloro-ethyl)-(3-phenoxy-propyl)-amine (7.0 g, 22 mmol). Yield 6.5 g (70%); brown oil; MS: 462.5 (M+H)⁺.

4-(4-Methoxy-benzenesulfonyl)-1-(3-phenoxy-propyl)-piperidine-4-carboxylic acid was prepared starting from 4-(4-Methoxy-benzenesulfonyl)-1-(3-phenoxy-propyl)-piperidine-4-carboxylic acid ethyl ester (4.2 g, 9.1 mmol) dissolved in THF:Methanol 3:1 and 10 N NaOH (40 ml). The resulting reaction mLxture was worked up as outlined in example 83. Yield 3.0 g (75%); off white powder; mp 195° C.; MS: 434.5 (M+H)⁺.

Starting from 4-(4-methoxy-benzenesulfonyl)-1-(3-phenoxy-propyl)-piperidine-4-carboxylic acid (2.5 g, 5.77 mmol) and following the procedure as outlined in example 83, 1.2 g of 4-(4-methoxy-benzenesulfonyl)-1-(3-phenoxy-propyl)-piperidine-4-carboxylic acid hydroxamide was isolated as an off white solid. Yield 46%; mp 101° C.; MS: 448.5 (M+H)⁺; $^1$H NMR (300 MHi, DMSO-$d_6$): δ 2.18 (m, 2H), 2.3 (m, 2H), 2.58 (m, 2H), 2.6–2.73 (m, 2H), 3.0–3.06 (m, 2H), 3.60 (m 2H), 3.87 (s, 3H), 4.01 (t, 2H), 6.9 - 7.7 (m, 9H), 9.33 (bs, 1H), 10.28 (bs, 1H).

EXAMPLE 106

4-(4-n-Butoxy-benzenesulfonyl)-1-(3-phenoxy-propyl)-piperidine-4-carboxylic acid hydroxyamide 4-(4n-Butoxy-benzenesulfonyl)-1-(3-phenoxy-propyl)-piperidie-4-carboxylic acid ethyl ester was prepared according to the general method as outlined in example 83. Starting from from 4-(butoxy-benzenesulfonyl) acetic acid ethyl ester (3.0 g, 10 mmol) and bis-(2-chloro-ethyl)-(3-phenoxy-propyl)-amine (3.0 g, 11 mmol). Yield 4.5 g (89%); brown oil; MS: 504.6 (M+H)⁺.

4-(4n-Butoxy-benzenesulfonyl)-1-(3-phenoxy-propyl)-piperidine-4-carboxylic acid was prepared starting from 4-(4-n-Butoxy-benzenesulfonyl)-1-(3-phenoxy-propyl)-piperidine4-carboxylic acid ethyl ester (4.0 g, 7.9 mmol) dissolved in THF:Methanol 3:1 and 10 N NaOH (40 ml). The resulting reaction mixture was worked up as outlined in example 83. Yield 3.0 g (79%); off white powder; mp 191° C.; MS: 476.5 (M+H)⁺.

Starting from 4-(4-n-butoxy-benzenesulfonyl)-1-(3-phenoxy-propyl)-piperidine-4-carboxylic acid (700 mg, 1.4 mmol) and following the procedure as outlined in example 83, 300 mg of 4-(4-n-butoxy-benzenesulfonyl)-1-(3-phenoxy-propyl)-piperidine-4-carboxylic acid hydroxyamide was isolated as an off white solid. Yield 43%; mp 84° C.; MS: 491.5 (M+H)⁺; $^1$H NMR (300 MHz, DMSO-$d_6$): δ 0.9 (t, 3H), 1.5 (m, 2H),l1.8 (m, 2H), 2.18 (m, 2H), 2.3 (m, 2H), 2.58 (m, 2H), 2.6–2.73 (m, 2H), 3.2 (m, 2H), 3.40 (m 6H), 3.97 (t, 2H), 4.1 (t, 2H), 6.9–7.7 (m, 9H), 10.7 (bs, 1H), 11.28 (bs, 1H).

EXAMPLE 107

4-(4-methoxy-benzenesulfonyl)-1-(2-phenoxy-ethyl)-piperidine-4-carboxylic acid hydroxyamide 2-[(2-Hydroxy-ethyl)-(2-phenoxy-ethyl)-aminol-ethanol was prepared according to the general method as outlined in example 83. Starting from diethanolarine (15.0 g, 150). and 2chloro-phenetol (15.6 g, 100 mmol). Yield 18 g, (80%); Colorless oil; MS: 226 (M+H)⁺.

Bis-(2-Chioro-ethyl)-(2-phenoxy-ethyl)-amine was prepared according to the general method as outlined in example 83. Starting from 2-[(2-Hydroxy-ethyl)-(2-phenoxy-ethyl)-amino]-ethanol (20.0 g, 88.8 mmol). Yield 25 g (94%); brown oil; MS: 263.1 (M+H)⁺.

4-(4-methoxy-benzenesulfonyl)-1-(2-phenoxy-ethyl)-piperidine-4-carboxylic acid ethyl ester was prepared according to the general method as outlined in example 83. Starting from from 4-(methoxy-benzenesulfonyl) acetic acid ethyl ester (5.0 g, 20 mmol) and bis-(2-chloro-ethyl)-(2-phenoxy-ethyl)-amine (6.0 g, 20 mnmol). Yield 5.8 g (64%); brown oil; MS: 448.5 (M+H)⁺.

4-(4-methoxy-benzenesulfonyl)-1-(2-phenoxy-ethyl) piperidine-4-carboxylic acid was prepared starting from 4-(4-methoxy-benzenesulfonyl)-1-(2-phenyl-ethoxy)-piperidine-4-carboxylic acid ethyl ester (5.0 g, 11.1 mmol) dissolved in T° F:methanol 3:1 and 10 N NaOH (40 ml). The resulting reaction mixture was worked up as outlined in example 83. Yield 3.0 g (63%); off white powder, mp 235° C.; MS: 420.5 (M+H)⁺.

Starting from 4-(4-methoxy-benzenesulfonyl)-1-(2-phenoxy-ethyl)-piperidine-4-carboxylic acid (2.5 g, 5.9 mmol) and following the procedure as outlined in example 83, 1.3 g of 4-(4-methoxy-benzenesulfonyl)-1-(2-phenoxy-ethyl)-piperidine-4-carboxylic acid hydroxyamide was isolated as an off white solid. Yield 50%; mp 168–172 ° C (HCI); MS: 435.4 (M+H)⁺; $^1$H NMR (300 MHz, DMSO-$d_6$): δ 2.3 (m, 2H), 2.5 (m, 2H), 2.9 (m, 2H), 3.4 (m, 4H), 3.5 (m, 2H), 3.7 (m,2H), 3.9 (s, 3H), 4.4 (m, 2H), 6.9 - 7.8 (m, 9H), 9.3 (s, 1H), 10.2 (bs, 1H), 11.3 (s, 1H).

EXAMPLE 108

4-(4-n-Butoxy-benzenesulfonyl)-1-(2-phenoxy-ethyl)-piperidine-4-carboxylic acid hydroxyamide 4-(4-Butoxy-benzenesulfonyl)-1-(2-phenoxy-ethyl)-piperidine-4-carboxylic acid ethyl ester was prepared according to the general method as outlined in example 83. Starting from from 4-(methoxy-benzenesulfonyl) acetic acid ethyl ester (2.5 g, 10 mmol) and bis-(2-chloro-ethyl)-(2-phenoxy-ethyl)-amine (2.98 g, 10 mmol). Yield 3.0 g (69%); brown oil; MS: 490.6 (M+H)⁺.

4-(4-n-Butoxy-benzenesulfonyl)-1-(2-phenoxy-ethyl)-piperidine-4-carboxylic acid was prepared starting from 4-(4n-butoxy-benzenesulfonyl)-1-(2-phenyl-ethoxy)-piperidine-4-carboxylic acid ethyl ester (2.5 g, 5.76 mmol) dissolved in THF:methanol 3:1 and 10 N NaOH (40 ml). The resulting reaction mixture was worked up as outlined in example 83. Yield 1.5 g (56%); off white powder; mp 204° C.; MS: 462.5 (M+H)+.

Starting from 4-(4n-butoxy-benzenesulfonyl)-1-(2-phenoxy-ethyl)-piperidine-4-carboxylic acid (1.0 g, 2.16 mmol) and following the procedure as outlined in example 83, 600 mg of 4-(4-butoxy-benzenesulfonyl)-1-(2-phenoxy-ethyl)-piperidine-4-carboxylic acid hydroxyamide was isolated as an off white solid. Yield 58%; mp 112° C. (HCl); MS: 477.4 (M+H)+; $^1$H NMR (300 MHz, DMSO-d$_6$): δ 0.942 (t, 3H), 1.4 (m, 2H), 1.7 (m, 2H), 2.3 (m, 2H), 2.5 (m, 4H), 2.8 (m, 2H), 2.9–3.4 (m, 4H), 3.3 (m, 4H), 4.2 (t, 2H), 4.4 (m, 2H), 6.9–7.7 (m, 9H), 9.4 (s, 1H), 10.5 (bs, 1H), 11.3 (s, 1H).

EXAMPLE 109

4-(4-Methoxy-benzenesulfonyl)-1-[4-(2-piperidin-1-yl-ethoxy)-benzyl]-piperidine-4-carboxylic acid hydroxyamide Bis-(2-chloro-ethyl)-[4-(2-piperidin-1-yl-ethoxy)-benzyl]-aiine was prepared according to the general method as outlined in example 83. Starting from diethanolainine (15.0 g, 150). and 4-(2-pipeddin-1-yl-ethoxy)-benzyl chloride (5.9 g, 20 mmol). Yield 5.5 g, (85%); Brown semi-solid; MS: 323 (M+H)+.

Bis-(2-chloro-ethyl)-[4-(2-piperidin-1-yl-ethoxy)-benzyl]-amine was prepared according to the general method as outlined in example 83. Starting from 2-[(2-Hydroxy-ethyl)-[4-(2-piperidin-1-yl-ethoxy)-benzyl]-amine (3.22 g, 10 mmol). Yield 4.0 g (92%); brown semi-solid; MS: 361.1 (M+H)+.

4-(4-Methoxy-benzenesulfonyl)-1-[4-(2-piperidin-1-yl-ethoxy)-benzyl]-piperidine-4-carboxylic acid ethyl ester was prepared according to the general method as outlined in example 83. Starting from from 4(methoxy-benzenesulfonyl) acetic acid ethyl ester (5.0 g, 20 mmol) and Bis-(2-chloro-ethyl)[4-(2-piperidin-1-yl-ethoxy)-benzyll-amine (8.6 g, 20 mmol). Yield 6.0 g (55%); brown oil; MS: 545.7 (M+H)+.

4-(4-Methoxy-benzenesulfonyl)-1-[4-(2-piperidin- 1-yl-ethoxy)-benzyl]-piperidine-4-carboxylic acid was prepared starting from 4-(4-Methoxy-benzenesulfonyl)-1-[4-(2-piperidin-1-yl-ethoxy)-benzyl]-piperidine-4-carboxylic acid ethyl ester (5.4 g, 10 mmol) dissolved in TBF:methanol 3:1 and 10 N NaOH (40 ml). The resulting reaction mixture was worked up as outlined in example 83. Yield 4.0 g (77%); off white powder, mp 174° C.; MS: 517.6 (M+H)+.

Starting from 4-(4-Methoxy-benzenesulfonyl)-1-[4-(2-piperidin-1-ylethoxy)-benzyl]-piperidine-4 -carboxylic acid (3.5 g, 6.78 mmol) and following the procedure as outlined in example 83, 1.8 g of 4-(4-Methoxy-beenzenesulfonyl)-1-[4-(2-piperidin- 1-yl-ethoxy)-benzyl]-piperidine-4-carboxylic acid hydroxy amide was isolated as an pale yellow solid. Yield 49%; mp 114° C. (HCl); MS: 532 (M+H)+; $^1$H NMR (300 M , DMSO-dd: δ 1.41.6 (m, 411), 1.9 (m, 2H), 5 2.3 (m, 2H), 2.8 (m, 2H), 3.4 (m, 4H), 3.9 (s, 3H), 4.2 (m, 1H), 6.9–7.8 (m, 8H), 9.1 (s, 1H), 10.8 (bs, 1H).

EXAMPLE 110

N-Hydroxy-2-(4-methoxy-benzenesulfonyl)-propionamide
Step A: Coupling of 2-bromo-propionic acid to hydroxylamine resin.

4-O-Methylhydroxylamine-phenoxymethyl-copoly (styrene-1%-divinylbenzene)-resin[1] (2 g, 1.1 meq/g) was placed in a peptide synthesis vessel (Chemglass Inc. Part Number CG-1866) and suspended in DMF (20 mL). 2-Bromopropionic acid (0.6 nL, 3.0 eq.) 1-hydroxybenzotriazole hydrate (HOBt, 1.8 g, 6.0 eq.) and 1,3-diisopropylcarbodlimide (DIC, 1.4 mL, 4.0 eq.) were added. The reaction was shaken on an orbital shaker at room temperature for 2–16 hours. The reaction was filtered and washed with DMF (3×20 mL). A sample of resin was removed and subjected to the Kaiser test. If the test showed the presence of free amine (resin turned blue) the coupling described above was repeated, otherwise the resin was washed with DICM (3×20 mL), MeOH (2×20 mL), and DCIM (2×20 mL). (A wash consisted of addition of the solvent and agitation either by nitrogen bubbling or shaking on the orbital shaker for 1–5 minutes, then filtration under v[acun). The resin was dried in vacuo at room temperature.

A sample of resin (5–20 mg) was subjected to cleavage with DCM (0.5 AL) and TFA (0.5 mL) for 1 hour at room temperature. The reaction was filtered and the resin washed with DCM (1×1 mL). The filtrate and the washing were combined and concentrated in vacuo on a Savant SpeedVac Plus. Methanol (1 mL) was added and the mixture concentrated. The product was then characterized by H$^1$NMR, (DMSO d-$_6$) δ 4.54 (q, 1H), 1.83 (d, 3H).

Step B: Displacement of bromide with 4-methoxybenzenethiol.

The N-Hydroxy-2-bromo-propionamide resin prepared in Step A (0.35 g, 1.1 meq/g) was placed in a 20 mL scintillation vial and suspended in THF (2 mL). 4-Methoxybenzenethiol (0.23 mL, 5.0 eq.), sodium iodide (288 mog, 5.0 eq.) and 1,8-diazabicyclo[5.4.0]undec-7ene (DBU, 0.17 mL, 3.0 eq.) were added. The reaction was shaken at room temperature for 12–16 hours. The reaction mixture was poured into a polypropylene syringe barrel fitted with a polypropylene frit, filtered and washed with DMF (2×2 mL), DMF:water 9:1 (2×2 mL), DMF (2 mL), MeOH (2×2 mL), and DCM (2×2 mL). The resin was dried in vacuo at room temperature.

Step C: Oxidation of sulfide to sulfoxide.

N-Hydroxy-2-(4-methoxy-benzenesulfanyl)-propionamide resin prepared in Step B (175 mg, 1.1 meq/g) was suspended in DCM (3.0 mnL) and 70% tert-butylhydroperoxide (1.0 mL) and benzenesulfonic acid (50 mg) were added. The reaction mixture was shaken on an orbital shaker at room temperature for 12–24 hours. The reaction was filtered and washed with DCM (2×2 mL), DMF (2×2), MEOH (2×2mL), and DCM (2×2 mL). The resin was driedin vacuo at room temperature.

Step D: Oxidation of sulfide to sulfone.

N-Hydroxy-2-(4-methoxy-benzenesulfanyl)-propionamide resin prepared in Step B (175 mg, 1.1 meq/g) was suspended in DCM (3.0 mL) and mCPBA (180 mg) was added. The reaction mixture was shaken on an orbital shaker at room temperature for 12–24 hours. The reaction was filtered and washed with DCM (2×2 mL), DMF (2×2 mL), MeOH (2×2 mL), and DCM (2×2 mL). The resin was dried in vacuo at room temperature.

Step E: Cleavage of N-Hydroxy-2-(4-methoxy-benzenesulfonyl)-propionamide from resin.

The N-Hydroxy-2-(4-methoxy-benzenesulfonyl)-propionamide resin prepared in Step D (73 mg, 1.2 meq/g) was suspended in DCM (1.0 mL) and TFA (1.0 mnL) was added. The reaction was shaken for 1 hour at room temperature. The reaction was filtered and the resin washed with DCM (2×1 mL). The filtrate and the washing were combined and concentrated to dryness on a Savant SpeedVac Plus. Methanol (1 mL) was added and the mixture concentrated.

84% @ 215 nm; ¹H NMR (DMSO-d-6) δ 10.75 (brs, 1 H), 7.95 (brs, 1 H), 7.71 (dd, 2 H), 7.16 (dd, 2 H), 3.87 (s, 3 H), 3.83 (q, 1 H), 1.26 (d, 3 H).

The hydroxamic acids of Examples 111–113 are synthesized using appropriate starting materials and following the steps in example 110.

EXAMPLE 111

N-Hydroxy-2-(4-methoxy-benzenesulfanyl)-propionamide. 72% @ 215 nm

N-Hydroxy-2-(4-methoxy-benzenesulfmyl)-propionamide. 76% @ 215 nm; ¹H NMR (DMSO d-6) δ 10.90 & 10.60 (brs, 1 H), 7.95 (brs, 1 H) 7.61 & 7.52 (dd, 2 H), 7.15 & 7.10 (dd, 2 H), 3.83 & 3.82 (s, 3 H), 3.42 & 3.28 (q 1H), 1.23 & 0.97 (d, 3H).

EXAMPLE 112

N-Hydroxy-2-(3-methyl-butane-1-sulfanyl)-propionamide. 74% @ 215 nm.

N-Hydroxy-2-(3-methyl-butane-1-sulfanyl)-propionamide. ¹H NMR (DMSO d-6) δ 10.8 (brs 1 H), 7.95 (brs, 1 H), 3.45 & 3.31 (q, 1 H), 2.71 –2.50 (m, 2 H), 1.71–1.46 (m, 3 H), 1.33 & 1.25 (d, 3 H), 0.94–0.82 (m, 6 H)

EXAMPLE 113

N-Hydroxy-2-(3-methyl-butane-1-sulfonyl)-propionamide. 84% @ 215 nm.

EXAMPLE 114

N-hydroxy-3-methyl-2-(naphthalen-2-ylsulfanyl)-butyramide

Step A: Coupling of 2-bromo-3-methyl-butyric acid to hydroxylamine resin.

4-O-Methylhydroxylamine-phenoxymethyl-copoly (styrene-1%-divinylbenzene)-resin[1] (5 g, 1.1 meq/g) was placed in a peptide synthesis vessel and suspended in DMF (40 mL). 2-Bromo-3-methyl-butyric acid (9.96 g, 10.0 eq.) and DIC (9.04 mL, 10.5 eq.) were added. The reaction was shaken on an orbital shaker at room temperature for 2–16 hours. The reaction was filtered and washed with DMF (3×20 mL). A sample of resin was removed and subjected to the Kaiser test. If the test showed the presence of free amine (resin turned blue) the coupling described above was repeated, otherwise the resin was washed with DCM (3×20 mL), MeOH (2×20 mL), and DCM (2×20 mL). The resin was dried in vacuo at room temperature.

Step B: Displacement of bromide with 2-naphthalenethiol.

The 2-bromo hydroxymate resin prepared in Step A (0.15 g, 1.1 meq/g) was placed in a 20 mL scintillation vial and suspended in THF (2 mL). 2-Naphthalenethiol (138 mg, 5.0 eq.), sodium iodide (129 mg, 5.0 eq.) and 1,8diazabicyclo (5.4.0]undec-7-ene (DBU, 0.078 mL, 3.0 eq.) 5 were added. The reaction was shaken at room temperature for 12–16 hours. The reaction mixture was poured into a polypropylene syringe barrel fitted with a polypropylene frit, filtered and washed with DMF (2×2 mL), DMF:water 9:1 (2×2 mL), DMF (2 mL), MeOH (2×2 mL), and DCM (2×2 mL). The resin was dried in vacua at room temperature.

Step C: Oxidation of sulfide to sulfoxide.

2-(2-Naphthalenesulfanyl)-N-hydroxypropionamide resin prepared in Step B (175 mg, 1.1 meqig) was suspended in DCM (3.0 mL) and 70% tert-butylhydroperoxide (1.0 mL) benzenesulfonic acid (50 mg) were added. The reaction mixture was shaken on an orbital shaker at room temperature for 12–24 hours. The reaction was filtered and washed with DCM (2×2 mL), DMF (2×2 mL), MeOH (2×2 mL), and DCM (2×2 mL). The resin was dried in vacuo at room temperature.

Step D: Oxidation of sulfide to sulfone.

2-(2-Naphthalenesulfanyl)-N-hydroxypropionamide resin prepared in Step B (175 mg, 1.1 meqlg) was suspended in DCM (3.0 mL) and mCPBA (180 mg) was added. The reaction mixture was shaken on an orbital shaker at room temperature for 12–24 hours. The reaction was filtered and washed with DCM (2×2 mL), DMF (2×2 mL), MeOH (2×2 mL), and DCM (2×2 mL). The resin was dried in vacuo at room temperature.

Step E: Cleavage of N-Hydroxy-3-methyl-2-(naphthalen-2-ylsulfanyl)-butyramide from resin.

The 2-(2-Naphthalenesulfanyl)-N-hydroxypropionamide resin; prepared in Step B (73 mg, 1.2 meq/g) was suspended in DCM (1.0 mL) and TFA (1.0 mL) was added. The reaction was shaken for 1 hour at room temperature. The reaction was filtered and the resin washed with DCM (2×1 mL). The filtrate and the washing were combined and concentrated to dryness on a Savant SpeedVac Plus. Methanol (1 mL) was added and the mixture concentrated.

83% @ 215 nm; LCMS (API-electrospray) m/z 276 (M+H)[1]; ¹H NMR (DMSO d-6) δ 10.7 (brs, 1 H), 7.91 (brs, 1 H), 7.91–7.81 (m, 4 H), 7.55–7.45 (m, 3 H), 3.41 (d, 1 H), 2.09–1.97 (m, 1 H), 1.05 (d, 3 H), 0.97 (d, 3 H).

The hydroxamic acids of Examples 115–118 are synthesized using appropriate starting materials and following the steps in example 114:

EXAMPLE 115

N-Hydroxy-3-methyl-2-(naphthalen-2-ylsulfanyl) butyramide. 67% @ 215 nm.

EXAMPLE 116

N-Hydroxy-3-methyl-2-(naphthalen-2-ylsulfonyl)-butyramide. 97% @ 215 nm; LCMS (API-electrospray) m/z 308 (M+H)⁺.

EXAMPLE 117

N-Hydroxy-3-methyl-2-phenethylsulfanyl-butyramide. 93% @ 215 nm; LCMS (API-electrospray) m/z 254 (M+H)⁺.

EXAMPLE 118

N-Hydroxy-3-methyl-2-phenethylsulfonyl-butyramide. 97% @ 215 nm; LCMS (API-electrospray) m/z 286 (M+H)⁺.

EXAMPLE 119

(1-Hydroxycarbamoyl-propane-1-sulfanyl)-acetic acid methyl ester

Step A: Coupling of 2-bromobutyric acid to hydroxylamine resin.

4-O-Methylhydroxylamine-phenoxymethyl-copoly (styrene-1%-divinylbenzene)-resin[1] (5 g, 1.1 meq/g) was placed in a peptide synthesis vessel and suspended in DMF (40 mL). 2-Bromobutyric acid (3.0 g, 3.0 eq.) HOBt (4.86 g, 6.0 eq.) and DIC (3.75 mL, 4.0 eq.) were added. The reaction was shaken on an orbital shaker at room temperature for 2–16 hours. The reaction was filtered and washed with DMF (3×20 mL). A sample of resin was removed and subjected to the Kaiser test. If the test showed the presence of free amine (resin turned blue) the coupling described above was repeated, otherwise the resin was washed with DCM (3×20 mL), MEOH (2×20 mL), and DCM (2×20 mL). The resin was dried in vacuo at room temperature.

Step B: Displacement of bromide with methyl thioglycolate.

The 2-bromo hydroxymate resin prepared in Step A (0.45 g, 1.1 meq/g) was placed in a 20 mL scintillation vial and suspended in THF (2 mL). Methyl thioglycolate (286 mg, 5.0 eq.), sodium iodide (404 mg, 5.0 eq.) and 1,8-diazabicyclo(5.4.0]undec-7-ene (DBU, 0.24 mL, 3.0 eq.) were added. The reaction was shaken at room temperature for 12–16 hours. The reaction mixture was poured into a polypropylene syringe barrel fitted with a polypropylene frit, filtered and washed with DMF (2×2 mL), DMF:water 9:1 (2×2 mL), DMF (2 mL), MeOH (2×2 mL), and DCM (2×2 mL). The resin was dried in vacuo at room temperature.
Step C: Oxidation of sulfide to sulfoxide.

(1-Hydroxycarbamoyl-propane-1-sulfanyl)-acetic acid methyl ester resin prepared in Step B (150 mg, 1.1 meq/g) was suspended in DCM (3.0 mL) and 70% tert-butylhydroperoxide (1.0 mL) benzenesulfonic acid (50 mg) were added. The reaction mixture was shaken on an orbital shaker at room temperature for 12–24 hours. The reaction was filtered and washed with DCM (2×2 mL), DMF (2×2 mL), MeOH (2×2 mL), and DCM (2×2 mL). The resin was dried in vacuo at room temperature.
Step D: Oxidation of sulfide to sulfone.

(1-Hydroxycarbamoyl-propane-1-sulfanyl)-acetic acid methyl ester resin prepared in Step B (150 mg, 1.1 meq/g) was suspended in DCM (3.0 mL) and mCPBA (180 mg) was added. The reaction mixture was shaken on an orbital shaker at room temperature for 12–24 hours. The reaction was filtered and washed with DCM (2×2 mL), DMF (2×2 mL), MeOH (2×2 mL), and DCM (2×2 mL). The resin was dried in vacuo at room temperature.
Step E: Cleavage of (1-Hydroxycarbamoyl-propane-1-sulfanyl)-acetic acid methyl ester from resin The (1-Hydroxycarbamoyl-propane-1-sulfanyl)-acetic acid methyl ester resin prepared in Step B (150 mg, 1.2 meq/g) was suspended in DCM (1.0 mL) and TFA (1.0 mL) was added. The reaction was shaken for 1 hour at room temperature. The reaction was filtered and the resin washed with DCM (2×1 mL). The filtrate and the washing were combined and concentrated to dryness on a Savant Speed-Vac Plus. Methanol (1 mL) was added and the mixture concentrated. LCMS (API-electrospray) m/z 228 (M+Na)$^+$.

The hydroxamic acids of Examples 120–124 are synthesized using appropriate starting materials and following the steps in example 119.

EXAMPLE 120
(1-Hydroxycarbamoyl-propane-1-sulfonyl)-acetic acid hydroxyamide. LCMS (API-electrospray) m/z 224 (M+H)$^+$.

EXAMPLE 121
(1-Hydroxycarbamoyl-propane-1-sulfinyl)-acetic acid hydroxy amide. 100% @ 220 nm; LCMS (API-electrospray) m/z 240 (M+H)$^+$.

EXAMPLE 122
(1-Hydroxycarbamoyl-propane-1 -sulfanyl)-propionic acid hydroxyamide.

$^1$H NMR (DMSO d-6) δ 10.7 (brs, 1 H), 4.03 (t, 2 H), 2.95 (q, 1 H), 2.75–2.70 (m, 1 H), 2.60–2.54 (m, 1 H), 1.74I.66 (m, 2 H), 1.58–1.50 (m, 4 H), 1.32 (sextet, 2 H), 0.88 (t, 3 H), 0.85 (t, 3 H); LCMS (API-electrospray) m/z 264 (M+H)$^+$.

EXAMPLE 123
(1-Hydroxycarbamoyl-propane-1-sulfinyl)-propionic acid hydroxyamide. 83% @ 220 nm; LCMS (API-electrospray) m/z 280 (M+H)$^+$.

EXAMPLE 124
(1-Hydroxycarbamoyl-propane-1-sulfonyl)-propionic acid hydroxyamide. 100% @ 220 nm;

EXAMPLE 125
2-(4-Hydroxybenzenesulfanyl)-N-hydroxy-3-phenyl-propionamide
Step A: Coupling of 2-bromo-3-phenyl-propionic acid to hydroxylamine resin.

4-O-Mediylhydroxylamine-phenoxymethylcopoly (styrene-l%-divinylbenzene)-resin$^1$ (5 g, 1.2 meq/g) was placed in a peptide synthesis vessel and suspended in DMF (40 mL). 2-Bromo-3-phenyl-propionic acid (3.5 g, 3.0 eq.) HOBt (4.4 g, 6.0 eq.) and DIC (3.4 mL, 4.0 eq.) were added. The reaction was shaken on an orbital shaker at room temperature for 2–16 hours. The reaction was filtered and washed with DMF (3×20 mL). A sample of resin was removed and subjected to the Kaiser tesL If the test showed the presence of free amine (resin turned blue) the coupling described above was repeated, otherwise the resin was washed with DCM (3×20 mL), MeOH (2×20 mL), and DCM (2×20 mL). The resin was dried in vacuo at room temperature.
Step B: Displacement of bromide with 4-hydroxythiophenol.

The 2-bromo hydroxymate resin prepared in Step A (0.33 g, 1.2 meq/g) was placed in a 20 mL scintillation vial and suspended in THF (2 mL). 4-Hydroxythiophenol (250 mg, 5.0 eq.), sodium iodide (297 mg, 5.0 eq.) and 1,8diazabicyclo[5.4.0]undec-7-ene (DBU, 0.18 mL, 3.0 eq.) were added. The reaction was shaken at room temperature for 12–16 hours. The reaction mixture was poured into a polypropylene syringe barrel fitted with a polypropylene frit, filtered and washed with DMF (2×2 mL), DMF:water 9:1 (2×2 mL), DME (2 mL), MeOH (2×2 mL), and DCM (2×2 mL). The resin was dried in vacuo at room temperature.
Step C: Oxidation of sulfide to sulfoxide.

2-(4-Hydroxybenzenesulfanyl)-N-hydroxy-3-phenyl-propionamide resin prepared in Step B (110 mg, 1.1 meq/g) was suspended in DCM (3.0 mL) and 70% tert-butylhydroperoxide (0.73 mL) benzenesulfonic acid (36 mg) were added. The reaction mixture was shaken on an orbital shaker at room temperature for 12–24 hours. The reaction was filtered and washed with DCM (2×2 mL), DMF (2×2 ml), MeOH (2×2 mL), and DCM (2×2 mL). The resin was dried in vacuo at room temperature.
Step D: Oxidation of sulfide to sulfone.

2-(4-Hydroxybenzenesulfanyl)-N-hydroxy-3-phenyl-propionamide resin prepared in Step B (110 mg, 1.1 meq/g) was suspended in DCM (3.0 mL) and 3nCPBA (132 mg) was added. The reaction mixture was shaken on an orbital shaker at room temperature for 12–24 hours. The reaction was filtered and washed with DCM (2×2 mL), DME (2×2 mL), MeOH (2×2 mL), and DCM (2×2 mL). The resin was dried in vacuo at room temperature.
Step E: Cleavaage of 2-(4-Hydroxybenzenesulfanyl)-N-hydroxy-3-phenyl-propionamide from resin.

The 2-(4-Hydroxybenzenesulfanyl)-N-hydroxy-3-phenyl-propionamide resin prepared in Step B (110 mg, 1.2 meq/g) was suspended in DCM (1.0 mL) and TFA (1.0 mL) was added. The reaction was shaken for 1 hour at room temperature. The reaction was filtered and the resin washed with DCM (2×1 mL). The filtrate and the washing were combined and concentrated to dryness on a Savant Speed-Vac Plus. Methanol (1 ) was added and the mixture concentrated. 84% @ 215 nm; $^1$H NMR (OMSO d-6) δ 10.41 (brs, 1 H), 7.95 (brs (1 H), 7.30–7.15 (m, 5 H), 7.10 (dd, 2 H), 6.75 (dd, 2 H), 3.53 (q, 1 H), 3.05 (dd, 1 H), 2.79 (dd, 1 H).

The hydroxamic acids of Examples 126–130 are synthesized using appropriate starting materials and following the steps in example 125.

EXAMPLE 126

2-(4-Hydroxybenzenesulfinyl)-N-hydroxy-3-phenyl-propionamide. 73% @ 215 nm;

EXAMPLE 127

2-(4Hydroxybenzenesulfonyl)-N-hydroxy-3-phenyl-propionamide. 77% @ 215 nm; $^1$H NMR (DMSO d-6) δ 10.50 (brs, 1 H), 7.95 (brs, 1 H), 7.68–7.57 (m, 2 H), 7.28–7.17 (m, 3 H), 7.08–7.98 (m, 2 H), 6.95–6.87 (m, 2 H), 3.96 (t, 1 H), 3.02 (d, 2 H).

EXAMPLE 128

2-(4-Acetylamino-benzenesulfanyl)-N-hydroxy-3-phenyl-propionamide. 86% @ 215 nm; $^1$H NMR (DMSO d-6) δ 10.50 (brs, 1 H), 10.03 (brs, 1 H), 8.13 (brs, 1 H), 7.56–7.12 (m, 9 H), 3.67 (q, 1 H), 3.08 (dd, 1 H), 2.84 (dd, 1 H), 2.04 (s,3 H)

EXAMPLE 129

2-(4-Acetylamino-benzenesufanyl)-N-hydroxy-3-phenyl-propionarnide.173% @ 215 nm.

EXAMPLE 130

2-(4-Acetylamino-benzenesulfonyl)-N-hydroxy-3-phenyl-propionamide. 95% @ 215 nm;

EXAMPLE 131

4-Hydroxycarbamoyl-4-(4-methanesulfanyl-phenylsulfanyl)-butyric acid methyl ester Step A: Coupling of 2-bromo-5-methyl glutaric acid to hydroxylamine resin.

4-O-Methylhydroxylanie-phenoxymethyl-copoly (styrene-1%-divinylbenzene)-resin$^1$ (4.5 g, 1.2 meq/g) was placed in a peptide synthesis vessel and suspended in DMF (40 mL). S-2-Bromo-5-methyl glutarate (3.87 g, 3.0 eq.) HOBt (4.4 g, 6.0 eq.) and DIC (3.4 mL, 4.0 eq.) were added. The reaction was shaken on an orbital shaker at room temperature for 2–16 hours. The reaction was filtered and washed with DMF (3×20 mL). A sample of resin was removed and subjected to the Kaiser test. If the test showed the presence of free amine (resin turned blue) the coupling descnbed above was repeated, otherwise the resin was washed with DCM (3×20 mL), MeOH (2×20 mL), and DCM (2×20 mL). The resin was dried in vacuo at room temperature.

Step B: Displacement of bromide with 4-hydroxythiophenol.

The 2-bromo hydroxymate resin prepared in Step A (0.22 g, 1.2 meq/g) was placed in a 20 mL scintillation vial and suspended in THF (2 mL). 4(Methylthio)thiophenol (206 mg, 5.0 eq.), sodium iodide (197 mg, 5.0 eq.) and 1,8-diazabicyclo[5.4.0]undec-7-ene (DBU, 0.12 mL, 3.0 eq.) were added. The reaction was shaken at room temperature for 12–16 hours. The reaction mixture was poured into a polypropylene syringe barrel fitted with a polypropylene frit, filtered and washed with DMF (2×2 mL), DMF:water 9:1 (2×2 mL), DMF (2 mL), MeOH (2×2 mL), and DCM (2×2 mL). The resin was dried in vacuo at room temperature.

Step C: Oxidation of sulfide to sulfoxide.

4-Hydroxycarbamoyl-4-(4-methanesulfanyl-phenylsulfanyl)-butyric acid methyl ester resin prepared in Step B (73 mg, 1.1 meq/g) was suspended in DCM (1.5 mL) and 70% tert-butylhydroperoxide (0.49 mL) benzene-sulfonic acid (24 mg) were added. The reaction mixture was shaken on an orbital shaker at room temperature for 12–24 hours. The reaction was filtered and washed with DCM (2×2 mL), DMF (2×2 mL), MeOH (2×2 mL), and DCM (2×2 mL). The resin was dried in vacuo at room temperature.

Step D: Oxidation of sulfide to sulfone.

4-Hydroxycarbamoyl-4-(4-methanesulfanyl-phenylsulfanyl)-butync acid methyl ester resin prepared in Step B (73 mg, 1.1 meq/g) was suspended in DCM (1.5 mL) and mCPBA (87 mg) was added. The reaction mixture was shaken on an orbital shaker at room temperture for 12–24 hours. The reaction was filtered and washed with DCM (2×2 mL), DMF (2×2 mL), MeOH (2×2 mL), and DCM (2×2 mL). The resin was dried in vacua at room temperature.

Step E: Cleavage of 4-Hydroxycarbamoyl-4-(4-methanesulfanyl-phenylsulfanyl)-butyric acid methyl ester from resin.

The 4-Hydroxycarbamoyl-4-(4-methanesulfanyl-phenylsulfanyl)-butyric acid methyl ester resin prepared in Step B (73 mg, 1.2 meq/g) was suspended in DCM (1.0 mL) and TFA (1.0 naL) was added. The reaction was shaken for 1 hour at room temperature. The reaction was filtered and the resin washed with DCM (2×1 mL). The filtrate and the washing were combined and concentrated to dryness on a Savant SpeedVac Plus. Methanol (1 mL) was added and the mixture concentrated. 77% @ 215 nm; LCMS (API-electrospray) m/z 316 (M+H)$^+$.

The hydroxamic acids of Examples 132–139 are synthesized using appropriate starting materials and following the steps in example 131.

EXAMPLE 132

4-Hydroxycarbamoyl-4-(4-methanesulfinyl-phenylsulfinyl)-butyric acid hydroxyamide. 79% @ 215 nm; LCMS (API-electrospray) m/z 348 (M+H)$^+$.

EXAMPLE 133

4-Hydroxycarbamoyl-4-(4-methanesulfonyl-phenylsulfonyl)-utyric acid hydroxyamide. 78% @ 215 nm; LCMS (API-electrospray) m/z 380 (M+H)$^+$.

EXAMPLE 134

4-Hydroxycarbamoyl-4-(4-bromo-benzenesulfanyl)-buyric acid hydroxyamide. 93% @ 215 nm.

EXAMPLE 135

4-Hydroxycarbamoyl-4-(4-bromo-benzenesulfinyl)-butyric acid hydfoxyamide. 80% @ 215 nm.

EXAMPLE 136

4-Hydroxycarbamoyl-4-(4-bromo-benzenesulfonyl)-butyric acid hydroxyamide. 77% @ 215 nm.

EXAMPLE 137

4-Hydroxycarbamoyl-4-(2-trifluoromethyl-benzenesulfanyl)-butyic acid hydroxyamide. 93% @ 215 nm.

EXAMPLE 138

4-Hydroxycarbamoyl-4-(2-triuoromethyl-benzenesulfmyl)-butyric acid hydroxyamide. 72% @ 215 nm.

EXAMPLE 139

4-Hydroxycarbamoyl-4-(2-trifiuoromethyl-benzenesulfonyl)-butyric acid hydroxyamide. 90% @ 215 nm.

EXAMPLE 140

2-(3-methoxy-benzenesulfanyl)decanoic acid hydroxamide

Step A: Coupling of 2-bromo-decanoic acid to hydroxylarnine resin.

4-O-Methylhydroxylamine-phenoxymethylcopoly (styrene-1%-divylbenzene)-resin[1] (4.5 g, 1.2 meq/g) was placed in a peptide synthesis vessel and suspended in DMF (40 mL). 2-Bromo-decanoic acid (4.07 g, 3.0 eq.) HOBt (4.4 g, 6.0 eq.) and DIC (3.4 mL, 4.0 eq.) were added. The reaction was shaken on an orbital shaker at room temperature for 2–16 hours. The reaction was filtered and washed with DMF (3×20 mL). A sample of resin was removed and subjected to the Kaiser test. If the test showed the presence of free amine (resin turned blue) the coupling described above was repeated, otherwise the resin was washed with DCM (3×20 mL), MEOH (2×20 mL), and DCM (2×20 mL). The resin was dried in vacuo at room temperature.

Step B: Displacement of bromide with 3-methoxy-benzenethiol.

The 2-bromo hydroxymate resin prepared in Step A (0.22 g, 1.2 meq/g) was placed in a 20 mL scintillation vial and suspended in THF (2 mL). 3-Methoxy-benzenethiol (185 mg, 5.0 eq.), sodium iodide (197 mg, 5.0 eq.) and 1,8-diazabicyclo[5.4.0]undec-7-ene (DBU, 0.12 mL, 3.0 eq.) were added. The reaction was shaken at room temperature for 12–16 hours. The reaction mixture was poured into a polypropylene syringe barrel fitted with a polypropylene frit, filtered and washed with DMF (2×2 mL), DMF:water 9:1 (2×2 mL), DMF (2 mL), MeOH (2×2 mL), and DCM (2×2 mL). The resin was dried in vacua at room temperature.

Step C: Oxidation of sulfide to sulfoxide.

2-(3-Methoxy-benzenesulfanyl)decanoic acid hydroxamide resin prepared in Step B (73 mg, 1.1 meq/g) was suspended in DCM (1.5 mL) and 70% tert-butylhydroperoxide (0.49 mL) benzenesulfonic acid (24 mg) were added. The reaction mixture was shaken on an orbital shaker at room temperature for 12–24 hours. The reaction was filtered and washed with DCM (2×2 mL), DMF (2×2 mL), MeOH (2×2 mL), and DCM (2×2 mL). The resin was dried in vacuo at room temperature.

Step D: Oxidation of sulfide to sulfone.

2-(3-Methoxy-benzenesulfanyl)decanoic acid hydroxamide resin prepared in Step B (73 mg, 1.1 meq/g) was suspended in DCM (1.5 mL) and mCPBA (87 mg) was added. The reaction mixture was shaken on an orbital shaker at room temperature for 12–24 hours. The reaction was filtered and washed with DCM (2×2 mL), DMF (2×2 mL), MeOH (2×2 mL), and DCM (2×2 mL). The resin was dried in vacuo at room temperature.

Step E: Cleavage of 2-(3-methoxy-benzenesulfanyl) decanoic acid hydroxamide from resin.

The 2-(3-methoxy-benzenesulfanyl)decanoic acid hydroxamide resein prepared in Step B (73 mg, 1.2 meq/g) was suspended in DCM (1.0 mL) and TFA (1.0 mL) was added. The reaction was shaken for 1 hour at room temperature. The reaction was filtered and the resin washed with DCM (2×1 mL). The filtrate and the washing were combined and concentrated to dryness on a Savant SpeedVac Plus. Methanol (1 mL) was added and the mixture concentrated. 89% @ 215 nm.

The hydroxamic acids of Examples 141–145 are synthesized using appropriate starting materials and following the steps in example 140.

EXAMPLE 141.

2-(3-Methoxy-benzenesulfinyl)decanoic acid hydroxamide. 96% @ 215 nm.

EXAMPLE 142

2-(3-Methoxy-benzenesulfonyl)decanoic acid hydroxamide. 96% @ 215 nm.

EXAMPLE 143

2-(4-methanesulfanyl-benzenesulfanyl)decanoic acid hydroxamide. 85% @ 215 nm; LCMS (API-electrospray) m/z 342 (M+H)$^+$.

EXAMPLE 144

2-(4-methanesulfinyl-benzenesulfinyl)decanoic acid hydroxamide. 86% @ 215 nm; LCMS (API-electrospray) m/z 374 (M+H)$^+$.

EXAMPLE 145

2-(4-methanesulfonyl-benzenesulfonyl)decanoic acid hydroxamide. 92% @ 215 nm.

EXAMPLE 146

3-benzyloxy-N-hydroxy-2-(4-methanesulfanyl-benzenesulfanyl)-propionamide

Step A: Coupling of 2-bromo-3-benzyloxy propionic acid to hydroxylamine resin.

4-O-Methylhydroxylamine-phenoxymethyl-opoly (styrene-1%-divinylbenzene)-resin[1] (4.5 g, 1.2 meq/g) was placed in a peptide synthesis vessel and suspended in DMF (40 mL). S-2-Bromo-3-benzyloxy-propionic acid (4.2 g, 3.0 eq.) HOBT (4.4 g, 6.0 eq.) and DIC (3.4 mL, 4.0 eq.) were added. The reaction was shaken on an orbital shaker at room temperature for 2–16 hours. The reaction was filtered and washed with DMF (3×20 mL). A sample of resin was removed and subjected to the Kaiser test. If the test showed the presence of free amine (resin turned blue) the coupling, described above was repeated, otherwise the resin was washed with DCM (3×20 mL), MeOH (2×20 mL), and DCM (2×20 mL). The resin was dried in vacuo at room temperature.

Step B: Displacement of bromide with 4-(methylthio) thiophenol.

The 2-bromo hydroxymate resin prepared in Step A (0.22 g, 1.2 meq/g) was placed in a 20 mL scintillation vial and suspended in THF (2 mL). 4(Methylthio)thiophenol (206 mg, 5.0 eq.), sodium iodide (197 mg, 5.0 eq.) and 1,8-diazabicyclo[5.4.0]undec-7-ene (DBU, 0.12 mL, 3.0 eq.) were added. The reaction was shaken at room temperature for 12–16 hours. The reaction mixture was poured into a polypropylene syringe barrel fitted with a polypropylene frit, filtered and washed with DMF (2×2 mL), DMF:water 9:1 (2×2 mL), DMF (2 mL), MeOH (2×2 mL), and DCM (2×2 mL). The resin was dried in vacuo at room temperature.

Step C: Oxidation of sulfide to sulfoxide.

3-Benzyloxy-N-hydroxy-2-(4-methanesulfanyl-benzenesulfanyl)-propionamide resin prepared in Step B (73 mg, 1.1 meq/g) was suspended in DCM (1.5 mL) and 70% tert-butylhydroperoxide (0.49 mL) benzenesulfonic acid (24 mg) were added. The reaction mixture was shaken on an orbital shaker at room temperature for 12–24 hours. The reaction was filtered and washed with DCM (2×2 mL), DMF (2×1.5 mL), MeOH (2×2 mL), and DCM (2×2 mL). The resin was dried in vacuo at room temperature.

Step D: Oxidation of sulfide to sulfone.

3-Benzyloxy-N-hydroxy-2-(4methanesulfanyl-benzenesulfanyl)-propionamide resin prepared in Step B (73 mg, 1.1 meq/g) was suspended in DCM (1.5 mL) and mCPBA (87 mg) was added. The reaction mixture was shaken on an orbital shaker at room temperature for 12–24 hours. The reaction was filtered and washed with DCM (2×2 mL), DMF (2×2 mL), MeOH (2×2 mL), and DCM (2×2 mL). The resin was dried in vacuo at room temperature.

Step E: Cleavage of 3-benzyloxy-N-hydroxy-2-(4-methanesulfanyl-benzenesulfanyl)-propionamide from resin.

The 3-benzyloxy-N-hydroxy-2-(4-methanesulfanyl-benzenesulfanyl)-propionamide resin prepared in Step B (73 mg, 1.2 meq/g) was suspended in DCM (1.0 mnL) and TFA (1.0 mL) was added. The reaction was shaken for 1 hour at room temperature. The reaction was filtered and the resin washed with DCM (2×1 mL). The filtrate and the washing were combined and concentrated to dryness on a Savant SpeedVac Plus. Methanol (1 mL) was added and the mixture concentrated. 76% @ 215 nm; LCMS (API-electrospray) m/z 350 (M+H)$^+$.

The hydroxamic acids of Examples 147–151 are synthesized using appropriate starting materials and following the steps in example 146.

EXAMPLE 147

3-Benzyloxy-N-hydroxy-2-(4-methanesulfinyl-benzenesulfmyl)-propionamide. 70% @ 215 ni; LCMS (API-electrospray) m/z 382 (M+H)$^+$.

EXAMPLE 148

3-Benzyloxy-N-hydroxy-2-(4-methanesulfonyl-benzenesulfonyl)-propionamide. 63% @ 215 nm; LCMS (API-electrospray) m/z 414 (M+H)$^+$.

EXAMPLE 149

3-Benzyloxy-N-hydroxy-2-(2-chloro-benzylsulfanyl)-propionamide. 90% @ 215 nm.

EXAMPLE 150

3-Benzyloxy-N-hydroxy-2-(2-chloro-benzylsulfinyl)-propionamide. 70% @ 215 nm.

EXAMPLE 151

3-B enzyloxy-N-hydroxy-2-(2chlorobenzylsulfonyl)-propionamide. 72% @ 215 nm.

EXAMLE 152

2-(2 -bromo-benzenesulfanyl)-N-hydroxy-3-(3H-bimdazol ayl)-propionamide
Step A: Coupling of 2-bromo-3-(3H-imidazol-4-yl)-propionic acid to hydroxylamine resin.

4-O-Methylhydroxylamine-phenoxymethylcopoly (styrene-1%-divinylbenzene)-resin[1] (4.5 g, 1.2 meq/g) was placed in a peptide synthesis vessel and suspended in DMF (40 mL). S-2-Bromo-3-(3H-imidazol-4-yl)-propionic acid (3.55 g, 3.0 eq.) HOBt (4.4 g,, 6.0. eq.) and DIC (3.4 mL, 4.0 eq.) were added. The reaction was shaken on an orbital shaker at room temperature for 2–16 hours. The reaction was filtered and washed with DMF (3×20 mL). A sample of resin was removed and subjected to the Kaiser test. If the test showed the presence of free amine (resin turned blue) the coupling described above was repeated, otherwise the resin was washed with DCM (3×20 mL), MeOH (2×20 mL), and DCM (2×20 mL). The resin was dried in vacuo at room temperature.

Step B: Displacement of bromide with 2-bromothiophenol.

The 2-bromo hydroxymate resin prepared in Step A (0.22 g, 1.2 meq/g) was placed in a 20 mL scintillation vial and suspended in THF (2 mL). 2-Bromothiophenol (249 mg, 5.0 eq.), sodium iodide (197 mg, 5.0 eq.) and 1,8-diazabicyclo (5.4.0]undec-7-ene (DBU, 0.12 mL, 3.0 eq.) were added The reaction was shaken at room temperature for 12–16 hours. The reaction mixture was poured into a polypropylene syringe barrel fitted with a polypropylene frit, filtered and washed with DMF (2×2 mL), DMF:water 9:1 (2×2 mL), DMF (2 mL), MeOH (2×2 mL), and DCM (2×2 mL). The resin was dried in vacuo at room temperature.

Step C: Oxidation of sulfide to sulfoxide.

2-(2-Bromo-benzenesulfanyl)-N-hydroxy-3-(3H-imidazol-4-yl)-propionamide resin prepared in Step B (73 mg, 1.1 meq/g) was suspended in DCM (1.5 mL) and 70% tert-butylhydroperoxide (0.49 mL) benzenesulfonic acid (24 mg) were added. The reaction mixture was shaken on an orbital shaker at room temperature for 12–24 hours. The reaction was filtered and washed with DCM (2×2 mL), DMF (2×2 mL), MeOH (2×2 mL), and DCM (2×2 mL). The resin was dried in vacuo at room temperature.

Step D: Oxidation of sulfide to sulfone.

2-(2-Bromo-benzenesulfanyl)-N-hydroxy-3-(3H-imidazolfyl)-propionamnide resin prepared in Step B (73 mg, 1.1 meq/g) was suspended in DCM (1.5 mL) and mCPBA (87 mg) was added. The reaction mixture was shaken on an orbital shaker at room temperature for 12–24 hours. The reaction was filtered and washed with DCM (2×2 mL), DMF (2×2 mL), MeOH (2×2 mL), and DCM (2×2 mL). The resin was dried in vacuo at room temperature.

Step E: Cleavage of 2-(2-bromo-benzenesulfanyl)-N-hydroxy-3-(3H-imidazol-4-yl)-propionamide from resin.

The 2-(2-bromo-benzenesulfanyl)-N-hydroxy-3-(3H-imidazol-4-yl)-propionamide resin prepared in Step B (73 mg, 1.2 meq/g) was suspended in DCM (1.0 mL) and TFA (1.0 mL) was added. The reaction was shaken for 1 hour at room temperature. The reaction was filtered and the resin washed with DCM (2×1 mL). The filtrate and the washing were combined and concentrated to dryness on a Savant SpeedVac Plus. Methanol (1 mL) was added and the mixture concentrated. 86% @ 215 nm.

The hydroxamic acids of Examples 153–154 are synthesized using appropriate starting materials and following the steps in example 152.

EXAMPLE 153

2-(4-bromo-benzenesulfinyl)-N-hydroxy-3-(3H-imidazol-4-yl)-propionamide. 69% @ 215 nm

EXAMPLE 154

2-(4-chloro-benzenesulfonyl)-N-hydroxy-3-(3H-imidazol-4-yl)-propionamide.

EXAMPLE 155

2-(3-fluorophenylsulfanyl)-5-guanidino-pentanoic acid hydroxyamide
Step A: Coupling of 2-bromo-5-guanidino-pentanic acid to hydroxylamine resin.

4-O-Methylhydroxylamine-phenoxymethyl-copoly (styrenee-1%-divinylbenzene)-resin[1] (4.5 g, 1.2 meq/q) was placed in a peptide synthesis vessel and suspended in DMF (40 mL). S-2-Bromo-5-guanidino-pentanic acid (3.85 g, 3.0 eq.) HOBt (4.4 g, 6.0 eq.) and DIC (3.4 mL, 4.0 eq.) were added. The reaction was shaken on an orbital shaker at room temperature for 2–16 hours. The reaction was filtered and washed with DUF (3×20 mL). A sample of resin was removed and subjected to the Kaiser test. If the test showed the presence of free amine (resin turned blue) the coupling described above was repeated; otherwise the resin was washed with DCM (3×20 mL), MeOH (2×20 mL), and DCM (2×20 mL). The resin was dried in vacua at room temperature.

Step B: Displacement of bromide with 3-fluorothiophenol.

The 2-bromo hydroxymate resin prepared in Step A (0.22 g, 1.2 meqog) was placed in a 20 mL scintillation vial and suspended in TBF (2 mL). 3-Fluorothiophenol (169 mg, 5.0 eq.), sodium iodide (197 mg, 5.0 eq.) and 1,8-diazabicyclo [5.4.0]undec-7-ene (DBU, 0.12 mL, 3.0 eq.) were added. The reaction was shaken at room temperature for 12–16 hours. The reaction mixture was poured into a polypropylene syringe barrel fitted with a polypropylene frit, filtered and washed with DMF (2×2 mL), DMF:water 9:1 (2×2 mL), DMF (2 mL), MeOH (2×2 mL), and DCM (2×2 mL). The resin was dried in vacuo at room temperature.

Step C: Oxidation of sulfide to sulfoxide.

2(3-Fluorophenylsulfanyl)-5-guanidino-pentanoic acid hydroxyamide resin prepared in Step B (73 mg, 1.1 meq/g) was suspended in DCM (1.5 mL) and 70% tert-butylhydroperoxide (0.49 mL) benzenesulfonic acid (24 mg) were added. The reaction mixture was shaken on an orbital shaker at room temperature for 12–24 hours. The reaction was filtered and washed with DCM (2×2 mL), DMF (2×2 mL), eOH (2×2 mL), and DCM (2×2 mL). The resin was dried m vacuo at room temperature.

Step D: Oxidation of sulfide to sulfone.

2-(3-Fluorophenylsulfanyl)-5-guanidino-pentanoic acid hydroxyamide resin prepared in Step B (73 mg, 1.1 meq/g) was suspended in DCM (1.5 mL) and mCPBA (87 mg) was added. The reaction mixture was shaken on an orbital shaker at room temperature for 12–24 hours. The reaction was filtered and washed with DCM (2×2 mL), DMF (2×2 mL), MeOH (2×2 mL), and DCM (2×2 mL). The resin was dried in vacuo at room temperature.

Step E: Cleavage of 2-(3-fluorophenylsulfanyl)-5-guanidino-pentanoic acid hydroxyamide from resin.

The 2-(3-fluorophenylsulfanyl)-5-guanidino-pentanoic acid hydroxyamide resin prepared in Step B (73 mg, 1.2 meq/g) was suspended in DCM (1.0 mL) and TFA (1.0 mL) was added. The reaction was shaken for 1 hour at room temperature. The reaction was filtered and the resin washed with DCM (2×1 mL). The filtrate and the washing were combined and concentrated to dryness on a Savant Speed-Vac Plus. Methanol (1 mL) was added and the mixture concentrated. 93% @ 215 nm.

The hydroxarnic acids of Examples 156–159 are synthesized using appropriate stariing materials and following the steps in example 155:

EXAMPLE 156

2-(3-Fluorophenylsulfinyl)-5-guanidino-pentanoic acid hydroxyamide. 80% @ 220 nm; LCMS (API-electrospray) m/z 317 (M+H)$^+$.

EXAMPLE 157

2-(2-Bromosulfanyl)-5-guanidino-pentanoic acid hydroxyamide. 92% @ 220 nm; $^1$H NMR (DMSO d-6) δ 10.90 (brs, 2 H), 10.41 (brs, 1H), 7.95 (brs, 1 H), 7.66–7.14 (m, 5 H), 3.72 (q, 1 H), 3.13 (q, 2 H), 1.90–1.66 (m, 2 H), 1.58–1.43 (2 H).

EXAMPLE 158

2-(2-Bromosulfinyl)-5-guanidino-pentanoic acid hydroxyamide. 79% @ 220 nm; LCMS (API-electrospray) m/z 379 (M+H)$^+$.

EXAMPLE 159

2-(2-Bromosulfonyl)-5-guanidino-pentanoic acid hydroxyamide. $^1$H NMR (DMSO d-6) δ 8.03–7.45 (m, 5 H), 4.52 (q, 1 H), 3.16 (q, 2 H), 2.07–1.90 (m, 2 H), 1.66–1.59 (2 H).

EXAMPLE 160

2-(2,5-dichlorobenzenesulfanyl)-octanoic acid hydroxyamide

Step A: Coupling of 2-bromo-octanoic acid to hydroxylamine resin.

4-O-Methylhydroxylamine-phenoxymethylcopoly (styrene-1%-divinylbenzene)-resin[1] (10.0 g, 1.2 meq/g) was placed in a peptide synthesis vessel and suspended in DMF (80 mL). 2-Bromo-octanoic acid (8.4 g, 3.0 eq.) HOBt (8.8 g, 6.0 eq.) and DIC (7.2 mL, 4.0 eq.) were added. The reaction was shaken on an orbital shaker at room temperature for 2–16 hours. The reaction was filtered and washed with DMF (3×20 mL). A sample of resin was removed and subjected to the Kaiser test. If the test showed the presence of free amine (resin turned blue) the coupling described above was repeated, otherwise the resin was washed with DCM (3×20 mL), MeOH (2×20 mL), and DCM (2×20 mL). The resin was dried in vacuo at room temperature.

Step B: Displacement of bromide with 2,5-dichlorothiophenoi.

The 2-bromo hydroxymate resin prepared in Step A (0.45 g, 1.2 meq/g) was placed in a 20 mL scintillation vial and suspended in THF (6 mL). 2,5-Dichlorothiophenol (483 mg, 5.0 eq.), sodium iodide (404 mg, 5.0 eq.) and 1,8-diazabicyclo[5.4.0]undec-7-ene (DBU, 0.24 mL, 3.0 eq.) were added. The reaction was shaken at room temperature for 12–16 hours. The reaction mixture was poured into a polypropylene syringe barrel fitted with a polypropylene frit, filtered and washed with DMF (2×2 mL), DMF:water 9:1 (2×2 mL), DIMF (2 mL), MeOH (2×2 mL), and DCM (2×2 mL). The resin was dried in vacuo at room temperature.

Step C: Oxidation of sulfide to sulfoxide.

2-(2,5-Dichlorobenzenesulfanyl)-octanoic acid hydroxyamide resin prepared in Step B (150 mg, 1.1 meq/g) was suspended in DCM (3.0 mL) and 70% tert-butylhydroperoxide (1.0 mL) benzenesulfonic acid (50 mg) were added. The reaction mixture was shaken on an orbital s shaker at room temperature for 12–24 hours. The reaction was filtered and washed with DCM (2×2 mL), DMF (2×2 mL), MeOH (2×2 mL), and DCM (2×2 mL). The resin was dried n vacuo at room temperature.

Step D: Oxidation of sulfide to sulfone.

2-(2,5-Dichlorobenzenesulfanyl)-octanoic acid hydroxyamide resin prepared in Step B (150 mg, 1.1 meq/g) was suspended in DCM (3.0 mL) and mCPBA (180 mg) was added. The reaction mixture was shaken on an orbital shaker at room temperature for 12–24 hours. The reaction was filtered and washed with DCM (2×2 mL), DMF (2×2 mL), MeOH (2×2 mL), and DCM (2×2 mL). The resin was dried in vacuo at room temperature.

Step E: Cleavage of 2-(2,5-dichlorobenzenesulfanyl)-octanoic acid hydroxyamide from resin.

The 2-(2,5-dichlorobenzenesulfanyl)-octanoic acid hydroxyamide resin prepared in Step B (73 mg, 1.2 meq/g) was suspended in DCM (1.0 mL) and TFA (1.0 mL) was added. The reaction was shaken for 1 hour at room temperature. The reaction was filtered and the resin washed with DCM (2×1 mL). The filtrate and the washing were combined and concentrated to dryness on a Savant SpeedVac Plus. Methanol (1 mL) was added and the mixture concentrated. 92% @ 215 nm; $^1$H NMR (DMSO d-6) δ 10.96 (brs, 1 H), 9.26 (brs, 1 H), 7.93–7.76 (m, 3 H), 4.07 (q, 1 H), 2.041.85 (m, 1 H), 1.78–1.64 (m, 1 H), 1.32–1.09 (m, 8 H), 0.81 (t, 3 H).

The hydroxamic acids of Examples 161–167 are synthesized using appropriate starting materials and following the steps in example 160.

EXAMPLE 161

2-(2,5-Dichlorobenzenesulfonyl)-octanoic acid hydroxyamide. 96% @ 215 nm.

EXAMPLE 162

2-(3-Methoxybenzenesulfanyl)-octanoic acid hydroxyamide 86% @ 220 nm; LCMS (API-electrospray) m/z 298 (M+H)$^+$.

EXAMPLE 163
2-(3-Methoxybenzenesulfinyl)-octanoic acid hydroxyamide 96% @ 220 nm.

EXAMPLE 164
2-(3-Methoxybenzenesulfonyl)tanoic acid hydroxyamide 83% @ 220 nm.

EXAMPLE 165
2-(3,4-Dimethoxybenzenesulfanyl)-octanoic acid hydroxyamide 87% @ 215 nm; LCMS (API-electrospray) m/z 328 (Mt)$^+$.

EXAMPLE 166
2-(3,4-Dimethoxybenzenesulfinyl)-octanoic acid hydroxyamide 90% @ 215 nm.

EXAMPLE 167
2-(3,4-Dimethoxybenzenesulfonyl)-octanoic acid hydroxyamide 87% @ 215 nm.

The hydroxamic acid compounds of Examples 168–198 are synthesized using appropriate starting materials and following the steps in example 160. The crude products are dissolved in DMSO:methanol (1:1, 2 mL) and purified by reverse phase HPLC under the conditions described below: Column: ODS-A, 20 mm×50 mm, 5 µm particle size (YMC, Inc. Wilmington, N.C.)

| Solvent Gradient | Time | Water | Acetonitrile |
| --- | --- | --- | --- |
|  | 0.0 | 95 | 5 |
|  | 25 min. | 5 | 95 |
| Flow Rate: 15 mL/min. | | | |

EXAMPLE 168
2-(2-Benzimidazol-2-ylsulfanyl)-octanoic acid hydroxyamide 81% @ 215 nm; LCMS (API-electrospray) m/z 308 (M+H)$^+$.

EXAMPLE 169
2-(2-Benzooxazol-2-ylsulfanyl)-octanoic acid hydroxyamide 72% @ 215 nm; LCMS (API-electrospray) m/z 309 (M+H)$^+$.

EXAMPLE 170
2-(2-Benzothiazol-2-ylsulfanyl)-octanoic acid hydroxyamide 72% @ 215 nm; LCMS (API-electrospray) m/z 325 (+H)$^+$.

EXAMPLE 171
2-(2-Pyridine-2-sulfanyl)-octanoic acid hydroxyamide 76% @ 215 nm; LCMS (API-electrospray) m/z 269 (M+H)$^+$.

EXAMPLE 172
2-(4-Phenyl-thiazole-2-sulfanyl)-octanoic acid hydroxyamide 97% @ 215 nm; LCMS (API-electrospray) m/z 336 (M+H)$^+$.

EXAMPLE 173
2-(2-Pyridin-2-yl-ethylsulfanyl)-octanoic acid hydroxyaride 84% @ 215 nm; LCMS (API-electrospray) m/z 297 (M+H)$^+$.

EXAMPLE 174
2-(2-Phenyl-5H-tetrazol-5-ylsulfanyl)-octanoic acid hydroxyanide 67% @ 215 nm; LCMS (API-electrospray) m/z 338 (M+H)$^+$.

EXAMPLE 175
2-(2-Pyrazin-2-yl-ethylsulfanyl)-octanoic acid hydroxyamide 98% @ 215 nm; LCMS (API-electrospray) m/z 298 (M+H)$^+$.

EXAMPLE 176
2-(1-Methyl-1H-tetrazol-5-ylsulfanyl)-octanoic acid hydroxyamide 66% @ 215 nm; LCMS (API-electrospray) m/z 274 (M+H)$^+$.

EXAMPLE 177
2-(2-Benzimidazol-2-ylsulfinyl)-octanoic acid hydroxyamide 81% @ 215 nm.

EXAMPLE 178
2-(2-Pyridine-2-sulfinyl)-octanoic acid hydroxyamide 76% @ 215 nm;.

EXAMPLE 179
2-(4-Phenyl-thiazole-2-sulfinyl)-octanoic acid hydroxyamide 78% @ 215 nn.

EXAMPLE 180
2-(2-Pyrazin-2-yl-ethylsulfinyl)-octanoic acid hydroxyamide 96% @ 215 nm; LCMS (API-electrospray) m/z 314 (M+H)$^+$.

EXAMPLE 181
2-(3-Oxy-1H-benzimidazole-2-sulfonyl)-octanoic acid hydroxyamide 63% @ 215 nm; LCMS (API-electrospray) m/z 356 (M+H)$^+$.

EXAMPLE 182
2-(4-Phenyl-thiazole-2-sulfonyl)-octanoic acid hydroxyamide 70% @ 215 nm; LCMS (API-electrospray) m/z 383 (M+H)$^+$.

EXAMPLE 183
2-[2-(1-Oxy-pyridin-2-yl)-ethanesulfonyl]cctanoic acid hydroxyamide 77% @ 215 nm; LCMS (API-electrospray) m/z 345 (M+H)$^+$.

EXAMPLE 184
3-(1-Hydroxycarbamoyl-heptsulfanyl)-benzoic acid hydroxyamide. 100% @ 220 nm; LCMS (API-electrospray) m/z 312 (M+H)$^+$.

EXAMPLE 185
3-[4(1-Hydroxycarbamoyl-heptyl]sulfanyl)-phenyl]-propionic acid hydroxyamide. 90% @ 220 nm; LCMS (API-electrospray) m/z 340 (M+H)$^+$.

EXAMPLE 186
2-(Thiazol-2-ylsulfanyl)-octanoic acid hydroxyamide. 75% @ 215 nm; LCMS (API-electrospray) m/z 275 (M+H)$^+$.

EXAMPLE 187
2-(2,5-Dioxo-imidazolidin-4-ylmethylsulfanyl)octanoic acid hydroxyamide. 98% @ 215 nm; LCMS (API-electrospray) m/z 304 (M+H)$^+$.

EXAMPLE 188
3-(1-Hydroxycarbamoyl-heptylsulfmyl)-benzoicacid hydroxyamide. 84% @ 220 nm; LCMS (API-electrospray) m/z 328 (M+H)$^+$.

EXAMPLE 189
3-[4-(1-Hydroxycarbamoyl-heptylsulfinyl)-phenyl]-propionic acid hydroxyamide. 78% @ 220 nm; LCMS (API-electrospray) m/z 356 (M+H)$^+$.

EXAMPLE 190
2-(Quinoline-8-sulfinyl)-octanoic acid hydroxyamide. 87% @ 220 nm; LCMS (API-electrospray) m/z 335 (M+H)$^+$.

EXAMPLE 191
2-(Naphthalen-2-ylcarbamoylmethanesulfimyl)-cmtanoic acid hydroxyamide. 83% @ 220 nm; LCMS (API-electrospray) m/z 391 (M+H)$^+$.

EXAMPLE 192
3-(1-Hydroxycarbamoyl-heptylsulfonyl)-benzoic acid hydroxyamide. 72% @ 215 nm.

EXAMPLE 193
3-[4-(1-Hydroxycarbamoyl-heptylsulfonyl)-phenyl]-propionic acid hydroxyamide. 67% @ 215 nm.

EXAMPLE 194
2-(1H-Imidazole-2-sulfonyl)-octanoic acid hydroxyamide. 95% @ 215 nm; LCMS (API-electrospray) m/z 290 (M+H)$^+$.

EXAMPLE 195
2-(Thiazol-2-ylsulfonyl)-octanoic acid hydroxyamde. 91% @ 215 nm; LCMS (API-electrospray) m/z 307 (M+H)$^+$.

EXAMPLE 196
2-(Quinoline-8-sulfonyl)-octanoic acid hydroxyamde. 94% @ 220 nm; LCMS (API-electrospray) m/z 351 (M+H)$^+$.

EXAMPLE 197
2-(Naphthalen-2-ylcarbamoylmethanesulfonyl)-octanoic acid hydroxyamide. 79% @ 220 nm; LCMS (API-electrospray ) m/z 407 (M+H)$^+$.

EXAMPLE 198
2-(2,5-Dioxo-inidazolidinyl methylsulfonyl)-octanoic acid hydroxyamide. 97% @ 215 nm.

EXAMPLE 199
Step A: Displacement of bromide with 4-fluorothiophenol.

The 2-bromo hydroxymate resin prepared in Example 160, Step A (9.4 g, 1.2 meq/g) was placed in a peptide synthesis vessel and suspended in TBF (50 mL). 4Fluorothiophenol (6.6 g, 5.0 eq.), sodium iodide (7.7 g, 5.0 eq.) and 1,8-diazabicyclo[5.4.0]undec-7-ene (DBU, 4.6 mL, 3.0 eq.) were added. The reaction was shaken at room temperature for 12–16 hours, then filtered and washed with DMF (2×30 mL), DMF:water 9:1 (2×30 mL), DMF (30 mL), MeOH (2×20 mL), and DCM (2×20 mL). The resin was dried in vacuo at room temperature.

Step B: Coupling of 2-(4-fluorobenzenesulfanyl)octanoic acid hydroxyamnide resin with benzyl alcohol.

2-(4-Fluorobenzenesulfanyl)-octanoic acid hydroxyamide resin prepared in Step A (330 mg, 1.1 meq/g) was suspended in DMF (2.0 mL) and benzyl alcohol (731 mg, 15 eq.) and sodium hydride (237 mg, 15 eq.) were added. The reaction was heated to 80° C. for 15 hours while shaking on an orbital shaker. After cooling to room temperature the mixture was filtered and washed with DMF (2×2 mL), DMF:water 9:1 (2×3 mL), MeOH (2×2 mL), and DCM (2×2 mL). The resin was dried in vacuo at room temperature.

Step C: Oxidation of sulfide to sulfoxide.

2-(4-Benzyloxy-phenylsulfanyl)-octanoic acid hydroxyamide resin prepared in Step B (110 mg, 1.1 meq/g) was suspended in DCM (2.2 mL) and 70% tert-butylhydroperoxide (0.73 mL) benzenesulfonic acid (36 mg) were added. The reaction mixture was shaken on an orbital shaker at room temperature for 12–24 hours. The reaction was filtered and washed with DCM (2×2 mL), DMF (2×2 mL), MeOH (2×2 mL), and DCM (2×2 mL). The resin was dried in vacuo at room temperature.

Step D: Oxidation of sulfide to sulfone.

2-(4-Benzyloxy-phenylsulfanyl)-octanoic acid hydroxyamide resin prepared in Step B (110 mg, 1.1 meq/g) was suspended in DCM (2.2 mL) and mCPBA (132 mg) was added. The reaction mixture was shaken on an orbital shaker at room temperature for 12–24 hours. The reaction was filtered and washed with DCM (2×2 mL), DMF (2×2 mL), MeOH (2×2 mL), and DCM (2×2 mL). The resin was dried in vacuo at room temperature.

Step E: Cleavage of 2-(4-benzyloxy-benzenesulfanyl)-octanoic acid hydroxyamide from resin.

The 2-(4-benzyloxy-phenylsulfanyl)octanoic acid hydroxyamide resin prepared in Step B (110 mg, 1.2 meq/g) was suspended in DCM (1.0 mL) and TFA (1.0 mL) was added The reaction was shaken for 1 hour at room temperature. The reaction was filtered and the resin washed with DCM (2×1 mL). The filtrate and the washing were combined and concentrated to S dryness on a Savant SpeedVac Plus. Methanol (1 mL) was added and the mixture concentrated. The crude product was dissolved in DMSO:methanol (1:1, 2 mL) and purified by reverse phase HPLC under the conditions described below:

Column: ODS-A, 20mm×50 mm, 5 $\mu$m particle size (YMC, Inc. Wilmington, N.C.)

| Solvent Gradient | Time | Water | Acetonitrile |
| --- | --- | --- | --- |
| | 0.0 | 95 | 5 |
| | 25 min. | 5 | 95 |
| Flow Rate: 15 mL/min. | | | |

2-(4-Benzyloxy-phenylsulfanyl)-octanoic acid hydroxyamide 100% @ 215 nm; LCMS (API-electrospray) m/z 374 (M+H)$^+$.

The hydroxamic acid compounds of Examples 200–220 are synthesized using appropriate starting materials and following the steps in example 199:

EXAMPLE 200
2-(4-Butoxy-benzenesulfanyl)-octanoic acid hydroxyamide 100% @ 215 nm; LCMS (API-electrospray) m/z 374 (M+H)$^+$.

EXAMPLE 201
2-[(2-Piperazine-1-yl-ethoxy)-benzenesulfanyl]-octanoic acid hydroxyamide 98% @ 215 nm; LCMS (API-electrospray) m/z 340 (M+H)$^+$.

EXAMPLE 202
2-[4-(5-Hydroxy-pentyloxy)-phenylsulfanyl]-octanoic acid hydroxyamide 65% @ 215 nm.; LCMS (API-electrospray) mlz 370 (M+H)$^+$.

EXAMPLE 203
2-[4-(3-Pyridin-2-yl-propoxy)-benzenesulfanyl]-octanoic acid hydroxyamide 95% @ 215 nm; LCMS (API-electrospray) m/z 403 (M+H)$^+$.

EXAMPLE 204
2-(4-Benzyloxy-phenylsulfinyl)octanoic acid hydroxyamide 100% @ 215 nm

EXAMPLE 205
2-(4-Butoxy-benzenesulfinyl)-octanoic acid hydroxyamide 98% @ 215 nm.

EXAMPLE 206
2-[4-(2-Piperazine-1-yl-ethoxy)-benzenesulfmyl]-octanoic acid hydroxyamide 98% @ 215 nm.

EXAMPLE 207
2-[4-(3-Pyridin-2-yl-propoxy)-benzenesulfinyl]-octanoic acid hydroxyamide 99% @ 215 nm.

EXAMPLE 208
2-(4-Benzyloxy-phenylsulfonyl)-octanoic acid hydroxyamide 100% @ 215 nm

EXAMPLE 209
2-(4-Butoxy-benzenesulfonyl)-octanoic acid hydroxyamide100% @ 215 nm.

EXAMPLE 210
2-[4-(2-Piperazine-1-yl-ethoxy)-benzenesulfonyll-octanoic acid hydroxyamide 97% @ 215 nm.

EXAMPLE 211
2-[4-(3-Pyridin-2-yl-propoxy)-benzenesulfonyl]-octanoic acid hydroxyamide 100% @ 215 nm.

EXAMPLE 212
2-[4-(1-Methyl-pyrrolidin-3-yloxy)-benzenesulfanyl]-octanoic acid hydroxyamide 91% @ 215 nm; LCMS (APIelectrospray) m/z 367 (M+H)+.

EXAMPLE 213
2-[4-(1-Ethyl-propoxy)-benzenesulfanyl]-octanoic acid hydroxyamide 100% @ 215 nm; LCMS (API-electrospray) m/z 354 (M+)+.

EXAMPLE 214
2-[4-(Tetrahydro-pyran-4-yloxy)-benzenesulfanyl]-octanoic acid hydroxyamide 97% @ 215 nm; LCMS (API-electrospray) m/z 368 (M+H)+.

EXAMPLE 215
2-[4-(1-Methyl-pyrrolidin-3-yloxy)-benzenesulfmyl]-octanoic acid hydroxyamide 96% @ 215 nm.

EXAMPLE 216
2-[4-(1-Ethyl-propoxy)-benzenesulfmyl]-octanoic acid hydroxyamide 97% @ 215 nm.

EXAMPLE 217
2-[(Tetrahydro-pyran-4-yloxy)-benzenesulfinyl]-octanoic acid hydroxyamide 97% @ 215 nm.

EXAMPLE 218
2-[4-(1-Methyl-pyrrolidin-3-yloxy)-benzenesulfonyl]-octanoic acid hydroxyamide 96% @ 215 nm.

EXAMPLE 219
2-[4-(1-Ethyl-propoxy)-benzenesulfonyl] octanoic acid hydroxyamide 100% @ 215 nm.

EXAMPLE 220
2-[4-(Tetrahydro-pyranyloxy)-benzenesulfonyl]-octanoic acid hydroxyamide 100% @ 215 nm.

EXAMPLE 221
Step A: Displacement of bromide with 4-bromothiophenol.

The 2-bromo-octanoic acid hydroxymate resin prepared in Example 160, Step A (5.0 g, 1.1 meq/g) was placed in a peptide synthesis vessel and suspended in THF (60 mL). 4 Bromothiophenol (5.2 g, 5.0 eq.), sodium iodide (4.1 g, 5.0 eq.) and 1,8-diazabicyclo[5.4.0]undec-7-ene (DBU, 2.5 mL, 3.0 eq.) were added. The reaction was shaken at room temperature for 12–16 hours, then filtered and washed with DMF (2×30 mL), DMF:water 9:1 (2×30 mL), DMF (30 mL), MeOH (2×30 mL), and DCM (2×30 mL). The resin was dried in vacuo at room temperature.

Step B: Oxidation of sulfide to sulfoxide.

2-(4-Bromobenzenesulfanyl)-octanoic acid hydroxyamide resin prepared in Step A (4.4 g, 1.1 meq/g) was suspended in DCM (60 mL) and 70% tert-butylhydroperoxide (30 mL) benzenesulfonic acid (1.5 g) were added. The reaction mixture was shaken on an orbital shaker at room temperature for 12–24 hours. The reaction was filtered and washed with DC (2×30 mL), DMF (2×30 mL), MeOH (2×30 mL), and DCM (2×30 mL). The resin was dried in vacuo at room temperature.

Step C: Oxidation of sulfide to sulfone.

2-(4-Bromobenzenesulfanyl)-octanoic acid hydroxyamide resins prepared in Step B (4.4 g, 1.1 meq/g) was suspended in DCM (60 mL) and mCPBA (5.2 g) was added. The reaction mixture was shaken on an orbital shaker at room temperature for 12–24 hours. The reaction was filtered and washed with DCM (2×30 mL), DMF (2×30 mL), MeOH (2×30 mL), and DC (2×30 mL). The resin was dried in vacuo at room temperature.

Step D: Coupling of 2-(4-bromobenzenesulfinyl)-octanoic acid hydroxyamide resin with 4-chlorobenzeneboronic acid.

2-(4-Bromobenzenesulfmyl)-octanoic acid hydroxyamide resin prepared in Step B (150 mg, 1.1 meq/g) was suspended in DME (2.0 mL) and nitrogen gas bubbled through the suspension for 1–2 minutes. 4-Chlorobenzeneboronic acid (51.6 mg, 2 eq.), tetrakis(triphenylphosphine) palladium(0) (19.07 mg, 0.1 eq.) and sodium carbonate (2 M solution, 0.825 mL, 10 eq.) were added. The reaction was heated to 80° C. for 8 hours while shaking on an orbital shaker. After cooling to room temperature the mixture was filtered and washed with DME (2×2 mL), DMF:water 9:1 (2×3 mL), MeOH (2×2 mL), and DCM (2×2 mL). The resin was dried in vacuo at room temperature.

Step E: Cleavage of 2-(4'-chloro-biphenyl-1-sulfnyl) octanoic acid hydroxyamide from resin.

The 2-(4'-chloro-biphenylsulfnyl)-octanoic acid hydroxyamide resin prepared in Step D (150 mg, 1.1 meq/g) was suspended in DCM (1.0 mL) and TFA (1.0 mL) was added. The reaction was shaken for 1 hour at room temperature. The reaction was filtered and the resin washed with DCM (2×1 mL). The filtrate and the washing were combined and concentrated to dryness on a Savant SpeedVac Plus. Methanol (1 mL) was added and the mire concentrated. The crude product was dissolved in DMSO:methanol (1:1, 2 mL) and purified by reverse phase HPLC under the conditions described below:

Column: ODS-A, 20mm×50 mm, 5 μm particle size (YMC, Inc. Wilmington, N.C.)

| Solvent Gradient | Time | Water | Acetonitrile |
|---|---|---|---|
|  | 0.0 | 95 | 5 |
|  | 25 min. | 5 | 95 |
| Flow Rate: 15 mL/min. | | | |

2-(4'-Chloro-biphenylfsulfmnyl)-octanoic acid hydroxyamide 96% @ 215 nm; LCMS (API-electrospray) m/z 394 (M+H)+.

The hydroxamic acid compounds of Exmples 222–224 are synthesized using appropriate starting materials and following the steps in example 221:

EXAMPLE 222
2-[4-(5-Chloro-thiophen-2-yl)-benzenesulfmnyl]-octanoic acid hydroxyamide 100% @ 215 nm; LCMS (API-electrospray) m/z 400 (M+H)+.

EXAMPLE 223
2-(4'-Chloro-biphenylsulfonyl)-octanoic acid hydroxyamide 94% @ 215 nm; LCMS (API-electrospray) m/z 410 (M+H)+.

EXAMPLE 224
2-[4-(5-Chloro-thiophen-2-yl)-benzenesulfonyl]ctanoic acid hydroxyamide 85% @ 215 nm; LCMS (API-electrospray) m/z 416 (M+H)+.

EXAMPLE 225
Step A: Coupling of 2-(4-bromobenzenesulfanyl)-Octanoic acid hydroxyamide resin with N-(3-aminopropyl)-morpholine.

2-(4-Bromobenzenesulfanyl)-octanoic acid hydroxyamide resin prepared in Example 199, Step A (100 mg, 1.1 meq/g) was suspended in dioxane (2.0 mL) and nitrogen gas bubbled through the suspension for 1–2 minutes. N-(3-Aminopropyl)-morpholine (346 mg, 20 eq.), tris (dibenzylideneacetone)-dipalladium(0) (22 mg, 0.2 eq.), (S)-(−)-2,2'-bis(diphenylphosphino)-1,1'-binaphthyl((S)-BINAP, 60 mg, 0.8 eq.) and sodium tert-butoxide (207 mg, 18 eq.) were added. The reaction was heated to 80° C. for 8 hours while shaking on an orbital shaker. After cooling to room temperature the mixture was filtered and washed with DMF (2×2 mL), DME:water 9:1 (2×3 mL), MeOH (2×2 mL), and DCM (2×2 mL). The resin was dried in vacuo at room temperature.

Step B: Cleavage of 2-[4-(3-morpholin-4-yl-propylamino)-phenylsulfanyl]-octanoic acid hydroxyamide from resin.

The 2-[4-(3-morpholin-4-yl-propylamino)-phenylsulfanyl]-octanoic acid hydroxyamide resin prepared in Step A (100 mg, 1.1 meq/g) was suspended in IJM (1.0 mL) and TFA (1.0 mL) was added. The reaction was shaken for 1 hour at room temperature. The reaction was filtered and the resin washed with DCM (2×1 mL). The filtrate and the washing were combined and concentrated to dryness on a Savant SpeedVac Plus. Methanol (1 mL) was added and the mixture concentrated. The crude product was dissolved in DMSO:methanol (1:1, 2 mL) and purified by reverse phase HPLC under the conditions described below:

Column: ODS-A, 20mm×50 mm, 5 µm particle size (YMC, Inc. Wilmington, N.C.)

| Solvent Gradient | Time | Water | Acetonitrile |
|---|---|---|---|
| | 0.0 | 95 | 5 |
| | 25 min. | 5 | 95 |
| Flow Rate: 15 mL/min. | | | |

2-[4-(3-morpholin-4-yl-propylamino)-phenylsulfanyl]-octanoic acid hydroxyamide 88% @ 215 nm; LCMS (API-electrospray) m/z 410 (M+H)+.

The hydroxamic acid compounds of Examples 226–231 are synthesized using appropriate stardng materials and following the steps in this example:

EXAMPLE 226
2-[4-(Biphenylylamino)-phenylsulfanyl]-octanoic acid hydroxyamide 95% @ 215 mm; LCMS (API-electrospray) m/z 435 (M+H)+.

EXAMPLE 227
2-[4-(Pyridin-4-ylamino)-phenylsulfanyl]-octanoic acid hydroxyamide 97% @ 215 nm; LCMS (API-electrospray) m/z 360 (M+H)+.

EXAMPLE 228
2-(4-Cyclopentylamino-phenylsulfanyl)octanoic acid hydroxyamide 77% @ 215 nm; LCMS (API-electrospray) m/z 351 (M+H)+.

EXAMPLE 229
2-(4-Methylamino-phenylsulfanyl)octanoic acid hydroxyamide 99% @ 215 nm; LCMS (API-electrospray) m/z 297 (M+H)+.

EXAMPLE 230
2-(4-Piperidin-1-yl-phenylsulfanyl)-octanoic acid hydroxyamide 72% @ 215 nm; LCMS (API-electrospray) m/z 351 (M+H)+.

EXAMPLE 231
2-(4-Piperazin-1-yl-phenylsulfanyl)-octanoic acid hydroxyamide 74% @ 215 nm; LCMS (API-electrospray) m/z 352 (M+H)+.

EXAMPLE 232
Step A: Displacement of bromide with 4hydroxythiophenol.

The 2-bromo-octanoic acid hydroxymate resin prepared in Example 160, Step A (15.0 g, 1.1 meq/g) was placed in a peptide synthesis vessel and suspended in THF (120 mL). 4-Hydroxythiophenol (11.3 g, 5.0 eq.), sodium iodide (13.5 g, 5.0 eq.) and 1,8-diazabicyclo(5.4.0]undec-7-ene (DBU, 8.1 mL, 3.0 eq.) were added. The reaction was shaken at room temperature for 12–16 hours, then filtered and washed with DMF (2×60 mL), DMF:water 9:1 (2×60 mL), DMF (60 mL), MeOH (2×60 mL), and DCM (2×60 mL). The resin was dried in vacuo at room temperature.

Step B: Coupling of 2-(4-hydroxybenzenesulfanyl)-octanoic acid hydroxyamide resin with benzene sulfonyl chloride.

2-(4-Hydroxybenzenesulfanyl)-octanoic acid hydroxyamide resin prepared in Step A (240 mg, 1.2 meq/g) was suspended in DCM (3.0 mL). Benzene sulfonyl chloride (225 mg, 5 eq.), and triethylamine (0.06 mL, 2 eq.) were added. The reaction was shaken on an orbital shaker at room temperature for 8 hours, then filtered and washed with DME (2×2 mL), DMF:water 9:1 (2×3 mL), MeOH (2×2 mL), and DCM (2×2 mL). The resin was dried in vacuo at room temperature.

Step C: Oxidation of sulfide to sulfoxide.

Benzenesulfonic acid 4-(1-hydroxycarbamoyl-heptylsulfanyl)-phenyl ester resin prepared in Step B (80 mg, 1.2 meq/g) was suspended in DCM (3 mL) ,and 70% tert-butylhydroperoxide (1 mL) benzenesulfonic acid (23 mg) were added. The reaction mixture was shaken on an orbital shaker at room temperature for 12 –24 hours. The reaction was filtered and washed with DCM (2×3 mL), DMF (2×3 mL), MeOH (2×3 mL), and DCM (2×3 mL). The resin was dried in vacuo at room temperature.

Step D: Oxidation of sulfide to sulfone.

Benzenesulfonic acid 4-(1-hydroxycarbamoyl-heptylsulfanyl)-phenyl ester resin prepared in Step B (80 mg, 1.2 meq/g) was suspended in DCM (3 mL) and mCPBA (84 mg) was added. The reaction mixture was shaken on an orbital shaker at room temperature for 12–24 hours. The reaction was filtered and washed with DCM (2×3 mL), DNF (2×3 mL), MeOH (2×3 mL), and DCM (2×3 mL). The resin was dried in vacuo at room temperature.

Step E: Cleavage of benzenesulfonic acid 4(1-hydroxycarbamoyl-heptylsulfanyl)-phenyl ester resin.

The benzenesulfonic acid 4-(1-hydroxycarbamoyl-heptylsulfanyl)-phenyl ester resin prepared in Step B (80 mg, 1.2 meq/g) was suspended in DCM (1.0 mL) and TFA (1.0 mL) was added The reaction was shaken for 1 hour at room temperature. The reaction was filtered and the resin washed with DCM (2×1 mL). The filtrate and the washing were combined and concentrated to dryness on a Savant SpeedVac Plus. Methanol (1 mL) was added and the mixture concentrated The crude product was dissolved in DMSO:methanol (1:1, 2 mL) and purified by reverse phase HPLC under the conditions described below:

Column: ODS-A, 20 mm×50 mm, 5 µm particle size (YMC, Inc. Wilmington, N.C.)

| Solvent Gradient | Time | Water | Acetonitrile |
|---|---|---|---|
| | 0.0 | 95 | 5 |
| | 25 min. | 5 | 95 |
| Flow Rate: 15 mL/min. | | | |

Benzenesulfonic acid 4-(1-hydroxycarbamoyl-heptylsulfanyl)-phenyl ester 91% @ 215 nm; LCMS (API-electrospray) m/z 424 (M+H)$^+$.

The hydroxamic acid compounds of Examples 233–240 are synthesized using appropriate starting materials and following the steps in example 232:

EXAMPLE 233

2,5-Dichloro-thiophene-3-sulfonic acid 4-(1-hydroxycarbamoyl-heptylsulfanyl)-hydroxyamide 98% @ 215 mm; LCMS (API-electrospray) m/z 498 (M+H)$^+$.

EXAMPLE 234

Ethanesulfonic acid 4(1-hydroxycarbamoyl-heptylsulfanyl)-hydroxyamide. 72% @ 215 nm LCMS (API-electrospray) m/z 376 (M+H)$^+$.

EXAMPLE 235

5-Chloro-1,3-dimethyl-1H-pyrazolesulfonic acid 4-(I-hydroxycarbamoyl-heptylsulfinyl)-hydroxyamide 99% @ 215 nm; LCMS (API-electrospray) m/z 492 (M+H)$^+$.

EXAMPLE 236

2,5-Dichloro-thiophene-3-sulfonic acid 4(1-hydroxycarbamoyl-heptylsulfinyl)-hydroxyamide 96% @ 215 nm; LCMS (API-electrospray) m/z 514 (M+H)$^+$.

EXAMPLE 237

5-Pyridin-2-yl-thiophene-2-sulfonic acid 4(1-hydroxycarbamoyl-heptylsulfinyl)-hydroxy amide 96% @ 215 nm; LCMS (API-electrospray) m/z 523 (M+H)$^+$.

EXAMPLE 238

2-Nitro-benzenesulfonic acid 4-(1-hydroxycarbamoyl-heptylsulfonyl)-hydroxyamide 97% @ 215 nm; LCMS (API-electrospray) m/z 501 (M+H)$^+$.

EXAMPLE 239

3-Bromo-2-chloro-thiophene-2-sulfonic acid 4-(1-hydroxycarbamoyl-heptylsulfonyl)-hydroxyamide 97% @ 215 nm; LCMS (API-electrospray) m/z 576 (M+H)$^+$.

EXAMPLE 240

Benzo[1,2,5]thiadiazole4sulfonic acid 4-(1-hydroxycarbamoyl-heptylsulfonyl)-hydroxyamide 83% @ 215 nm; LCMS (API-electrospray) m/z 514 M+H)$^+$.

EXAMPLE 241

1-Benzyl-4-(4-benzyloxy-benzenesulfonyl)-piperidinefcarboxylic acid hydroxyamide To a stirred solution of 4-methoxybenzenethiol (2.8 gm, 20 mmol) and anhydrous $K_2CO_3$ (10 gm, excess) in dry acetone (100 ml), α-bromo ethyl acetate (3.3 gm, 20 mmol) was added in a round bottom flask and the reaction mixture was heated at reflux for 8 hours with good stirring. At the end, the reaction mixture was allowed to cool and the potassium salts were filtered off and the reaction mixture was concentrated. The residue was extracted with chloroform and washed with $H_2O$ and 0.5 N NaOH solution. The organic layer was further washed well with water, dried over $MgSO_4$, filtered and concentrated. (4-methoxy-phenylsulfanyl)-acetic acetic acid ethyl ester was isolated as pale yellow oil. Yield: 4.4 g (100%); MS; 227 (M+H)$^+$ To stirred solution of (4-methoxy-phenylsulfanyl)-acetic acid ethyl ester (4.4 g, 20 mmol), anhydrous $K_2CO_3$ (10 gm excess) in dry acetone (100 ml) benzyl bromide (3.5 g, 20 mmol) was added and refluxed for 4 hrs. At the end, reaction mixture was filtered, concentrated and the residue was extracted with chloroform It was washed well with water, dried and concentrated. The crude product obtained was converted to (4-benzyloxy-phenylsulfonyl)-acetic acid ethyl ester by oxidaizing with m-chloro perbenzoic acid as described in the example 83. Low melting solid. Yield: 6.6 g, 97%; MS: 335 M+1)

To a stirred solution of bis-(2-chloro-ethyl)-benzyl amine hydrochloride (6.6 g, 24.7 mmol), 18-Crown-6 (500 mg), and anhydrous $K_2CO_3$ (30 gm, excess) in dry acetone (250 ml), (4-benzyloxy-phenylsulfonyl)-acetic acid ethyl ester (8.01 gm, 24 mmol) was added in a round bottom flask and the reaction mixture was heated at reflux for 16 hours with good stirling. At the end, the reaction mixture was allowed to cool and the potassium salts were filtered off and the reaction mixture was concentrated. The residue was extracted with chloroform and washed with $H_2O$. The organic layer was further washed well with water, dried over $MgSO_4$, filtered and concentrated. The dark brown reaction mixture was purified by silica gel coumn chromatography by eluting it with 30% ethylacetate: hexane and the product 4-(4-Benzyloxy-benzenesulfonyl)-1-benzyl-piperidine-4-carboxylic acid ethyl ester was isolated as Brown oil. Yield: 6.5 g, 55%; MS: 494 (M+H)

4-(4-Benzyloxy-benzenesulfonyl)-1-benzyl-piperidine-4-carboxylic acid ethyl ester (5.0 g, 10.1 mmol) was dissolved in MeOH/THF (1:1, 200 ml) and stirred at room temperature for 72 hrs. At the end reaction mixture was concentrated and the product was nuetralised with con. HCl by dissolving it in water (200 ml). After the nuetralization reaction mixture was concentrated to dryness. Ice cold water (100 ml) was added to the solid and filtered. The product 4-(4-Benzyloxy-benzenesulfonyl)-1-benzyl-piperidinecarboxylic acid was dried at 50° C. and taken to next step with out any purification. Colorless solid. MP: 66–68; Yield: 4.3 g,91%; MS: 466 (M+H)

Starting from 4-(4-Benzyloxy-benzenesulfonyl)-1-benzyl-piperidine-4-carboxylic acid (4.65 g, 10.0 mmol) and following the procedure outlined in example 83, 1.1 g of 4-(4-Benzyloxy-benzenesulfonyl)-1-benzyl-piperidinefarboxylic acid hydroxyamide was isolated as a colurless solid. Yield 21%; mp 89 ° C.; MS: 481.1 1H NMIR (300 MIz, DMSO-$d_6$): δ2.27 (m, 3H), 2.76–2.79 (m, 2H), 3.43 (m, 4H),4.30 (s, 2H), 7.14–7.17 (d,2H), 7.50–7.73 (m, 5H), 9.37 (s,1H), 10.53 (s,1H), 11.18 (s,1H).

EXAMPLE 242

4-(4-Butoxy-benzenesulfonyl)-1-[4-(2-piperidin-1-yl-ethoxy)-benzyl]-piperidine-4-carboxylic acid hydroxyamide from 2-[(2-Hydroxy-ethyl)-[4-(2-piperidin-1-yl-ethoxy)-benzyl]-amine was prepared according to the general method outlined in example 83 starting from diethanolamine (15.0 g, 150). and 4-(2-piperidin-1-yl-ethoxy)-benzyl chloride (5.9 g, 20 mmol). Yield 5.5 g, (85%); Brown semi-solid; MS: 323 (M+H)⁺

Bis-(2-cloro-ethyl)-[4(2-piperidin-1-yl-ethoxy)-benzyl]-amine was prepared according to the general method outlined in example 83 starting from 2-[(2-Hydroxy-ethyl)-[4(2-piperidin-1-yl-ethoxy)-benzyl]-amine (3.22 g, 10 mmol). Yield 4.0 g (92%); brown semi-solid; MS: 361.1 (M+H)⁺

4-(4-Butoxy-benzenesulfonyl)-1-[4-(2-piperidin-1-yl-ethoxy)-benzyl]-piperidine-4-carboxylic acid ethyl ester was prepared according to the general method outlined in example 83 starting from from 4-(butoxy-benzenesulfonyl) acetic acid ethyl ester (6.0 g, 20 =mol) and Bis-(2-chloro-ethyl)-[4-(2-piperidin-1-yl-ethoxy)-benzyl]-amine (8.6 &, 20 mmol). Yield 8.0 g (68%); brown oil; MS: 587.7 (M+H)⁺

4(4-Butoxy-benzenesulfonyl)-1-[4-(2-piperidin-1-yl-ethoxy)-benzyl]-piperidine-4-carboxylic acid was prepared starting from 4-(4-Butoxy-benzenesulfonyl)-1-[4-(2-piperidin-1-yl-ethoxy)-benzyl]-piperidine-4 -carboxylic acid ethyl ester (5.8 g, 10 mmol) dissolved in TBF:methanol 3:1 and 10 N NaOH (40 ml). The resulting reaction mixture was worked up as outlined in example 83. Yield 4.8 g (86%); Spongy brown solid; mp 98° C.; MS: 559.6 (M+H)⁺

Starting from 4-(4-butoxy-benzenesulfonyl)-1-[4-(2-piperidin-1-yl-ethoxy)-benzyl]-piperidine-4-carboxylic acid (5.5 g, 10 mmol) and following the procedure outlined in example 83, 2.4 g of 4-(4-butoxy-benzenesulfonyl)-1-[4-(2-piperidin-1-yl-ethoxy)-benzyl]-piperidine-4-carboxylic acid hydroxy amidewas isolated as a pale yellow solid. Yield 41%; mp 155° C. HCl); MS: 574 (M+H)⁺; ¹H NMR (300 MHz, DMSO-d₆): δ 0.9 (t, 3H), 1.1–1.8 (m, 6H), 1.9 (m, 4H), 2.3 (m, 4H), 2.8 (m, 6H), 3.2–3.6 (m, 8H), 4.2 (m, 2H), 6.9 - 7.8 (m, 8H), 9.1 (s, 1H), 10.8 (bs, 1H).

EXAMPLE 243
4(4-Butoxy-benzenesulfonyl)-1-[3-(2-morpholinyl-1-ylthoxy)-benzyl]-piperidine-4-carboxylic acid hydroxyamide Bis-(2-hydroxy-ethyl)-[3-(2-morpholin-1-yl-ethoxy)-benzyl]-amine was prepared according to the general method outlined in example 83 starting from diethanolamine (15.0 g, 150). and 3-(2-morpholin-1-yl-ethoxy)-benzyl chloride (5.9 g, 20 mmol). Yield 6.2 g, (95%); Brown semi-solid; MS: 325 (M+H)⁺

Bis-(2-chloroethyl)-[3-(2-morpholin-1-ylethoxy)-benzyl]-amine was prepared according to the general method outlined in example 83 starting from Bis-(2-Hydroxy-ethyl)- [3-(2-morpholin-1-yl-ethoxy)-benzyl]-amine (3.24 g, 10 mmol). Yield 4.0 g (92%); brown semi-solid; MS: 363.1 (M+H)⁺

4(4-Butoxy-benzenesulfonyl)-1-[3-(2-morpholin-1-yl-ethoxy)-benzyl]-piperidine-4-carboxylic acid ethyl ester was prepared according to the general method outlined in example 83 starting from from 4-(butoxy-benzenesulfonyl) acetic acid ethyl ester (6.0 g, 20 mmol) and Bis-(2-chloro-ethyl)-[3-(2-morpholin-1-ylethoxy)-benzyl]-amine (8.6 g, 20 mmol). Yield 8.5 g (72%); brown oil; MS: 589.7 (M+H)⁺

4-(4-Butoxy-benzenesulfonyl)-1-[3-(2-morpholin-1-yl-ethoxy)-benzyl]-piperidine-4-carboxylic acid was prepared starting from 4-(4-Butoxy-benzenesulfonyl)-1-[3-(2-morpholin-1 -yl-ethoxy)-benzyl]-piperidine-4-carboxylic acid ethyl ester (5.8 g, 10 mmol) dissolved in THF:methanol 3:1 and 10 N NaOH (40 ml). The resulting reaction mixture was worked up as outlined in example 83. Yield 4.8 g (85%); Spongy brown solid; MS: 561.6 (M+H)⁺

Starting from 4-(4-butoxy-benzenesulfonyl)- 1-[3-(2-morpholin-1-yl-ethoxy)-benzyl]-piperidine-4-carboxylic acid (5.6 g, 10 mmol) and following the procedure outlined in example 83, 4.02 g of 4-(4-butoxy-benzenesulfonyl)-1-[3-(2-morpholin-1-yl-ethoxy)-benzyl]-piperidine-4-carboxylic acid hydroxy amidewas isolated as a pale yellow solid. Yield 62%; mp 123° C. (HCl); MS: 576 (M+H)⁺; ¹H NMR (300 MHz, DMSO-d₆): δ 0.9 (t, 3H), 1.4 (m, 2H), 1.8 (t, 2H), 2.34.7 (m, 24H), 7.0–7.8 (m, 8H), 9.1 (s, 1H), 10.8 (bs, 1H).

EXAMPLE 244
1-Methyl-4-(4-butoxy-benzenesulfonyl)-piperidine-4-carboxylic acid hydroxyamide 1-Methyl-4-(4-butoxy-benzenesulfonyl)-piperidine-4-carboxylic acid ethyl ester was prepared according to the general method outlined in example 83 starting from 4-(butoxy-benzenesulfonyl) acetic acid ethyl ester (3 g, 10 mmol) and methyl-bis-(2-chloro-ethyl)amine (2.2g, 11.6 mmol). Yield 4.0 g, (98%); low melting brown solid; MS: 384 (M+H)⁺

1-Methyl-4-(4butoxy-benzenesulfonyl)-piperidine-4-carboxylic acid was prepared starting from 1-methyl-4-(4-butoxy-benzenesulfonyl)-piperidine-4-carboxylic acid ethyl ester (7.6 g, 20 minol) dissolved in methanol (300 ml) and 10 N NaOH (35 ml). The resulting reaction mixture was worked up outlined in example 83. Yield 6.0 g (84%); white solid; mp 195° C.; MS: 356.4 (M+H)⁺

Starting from 1-methyl-4-(4-butoxy-benzenesulfonyl)-piperidinecarboxylic acid (4.0 g, 11.2 mmol) and following the procedure outlined in example 83, 3.9 g of 1-methyl4-(4-butoxy-benzenesulfonyl)-piperidine-4-carboxylic acid hydroxyaride was isolated as a yellow powder. Yield 85%; mp 118° C.; MS: 371 (M+H)⁺; ¹H NMR (300 MHz, DMSO-d₆): δ 0.9 (t, 3H), 1.45 (q, 2H), 1.8 (q, 2H), 2.1 (s, 3H), 2.3 (d, J =11.4 Hz, 2H), 2.5–3.7 (m, 8H), 4.1 (t, 2H), 7.16 (d, 2H), 7.67 (d, 2H)

EXAMPLE 245
1-Ethyl-4-(4-butoxy-benzenesulfonyl)-piperidine-4-carboxylic acid hydroxyamide 1-Ethyl-4-(4-butoxy-benzenesulfonyl)-piperidine-4-carboxylic acid ethyl ester was prepared according to the general method outlined in example 83 starting from 4-(butoxy-benzenesulfonyl) acetic acid ethyl ester (3 g, 10 mmol) and ethyl-bis-(2-chloro-ethyl)-amine (2.2 g, 10.6 mmol). Yield 3.5 g, (88%); low melting brown solid; MS: 398 (M+H)⁺

1-Ethyl-4-(4-butoxy-benzenesulfonyl)-piperidine-4-carboxylic acid was prepared starting from 1-ethyl-4-(4-butoxy-benzenesulfonyl)-piperidine-4-carboxylic acid ethyl ester (.7.94 g, 20 mmol) dissolved in methanol (300 ml) and 10 N NaOH (35 ml). The resulting reaction mixture was worked up as outlined in example 83. Yield 6.5 g (88%); white solid; mp 162° C.; MS: 370 (M+H)⁺

Startng from 1-ethyl-4-(4-butoxy-benzenesulfonyl)-piperidine-4-carboxylic acid (3.7 g, 10 mmol) and following the procedure outlined in example 83, 3.2 g of 1-ethyl(4-butoxy-benzenesulfonyl)-piperidine-4 -carboxylic acid hydroxyamide was isolated as a yellow powder. Yield 76%; mp 98° C.; MS: 385 (M+H)⁺; ¹H NMR (300 MHz, DMSO-d₆): δ 0.9 (t, 3H), 1.2 (t, 3H), 1.46 (q, 2H), 1.9 (q, 2H), 2.3 (d, J=11.4 Hz, 2H), 2.5–3.6 (m, 10H), 4.1 (t, 2H), 7.16 (d, 2H), 7.67 (d, 2H)

EXAMPLE 246
1-n-Butyl-4-(4-butoxy-benzenesulfonyl)-piperidine-4-carboxylic acid hydroxyamide 1-n-Butyl-4-(4-butoxy-benzenesulfonyl)-piperidine-4-carboxylic acid ethyl ester was prepared according to the general method outlined in example 83 starting from 4-(butoxy-benzenesulfonyl) acetic acid ethyl ester (3 g, 10 mmol) and n-butyl-bis-(2-chloro-ethyl)-amine (2.0g, 10.1 mmol). Yield 3.8 g, (89%); low melting brown solid; MS: 426 (M+H)$^+$ 1-n-Butyl-4-(4-butoxy-benzenesulfonyl)-piperidine-4-carboxylic acid was prepared starting from 1-n-Butyl-4-(4-butoxy-benzenesulfonyl)-piperidine-4-carboxylic acid ethyl ester (8.5 g, 20 mmol) dissolved in methanol (300 ml) and 10 N NaOH (35 mL). The resulting reaction mixture was worked up as outlined in example 83. Yield 7.5 g (88%); white solid; mp 182° C.; MS: 398 (M+H)$^+$ Starting from 1-n-butyl-4-(4-butoxy-benzenesulfonyl)-piperidine-4-carboxylic acid (3.9 g, 10 mmol) and following the procedure outlined in example 83, 1.8 g of 1-n-butyl-4-(4-butoxy-benzenesulfonyl)-piperidine-4-carboxylic acid hydroxyamide was isolated as a yellow powder. Yield 40%; mp 121° C.; MS: 413 (M+H)$^+$; $^1$H NMR (300 MHz, DMSO-d$_6$): δ 0.9–1.0 (m, 6H), 1.2–1.8 (m, 8H), 2.2–2.8 (m, 8H), 3.03.6 (m, 4H), 4.2 (t, 2H), 7.16 (d, 2H), 7.67 (d, 2H), 9.3 (bs,1H), 10.3 (bs,1H), 11.1 (bs,1H).

EXAMPLE 247

[4-(4-Chloro-phenoxy)-phenylsulfanyl]-acetic acid ethyl ester

A mixture of 4-bromo chlorobenzene (1.92 g, 10 mmol), (4-Hydroxy-phenylsulfanyl)-acetic acid ethyl ester (2.12 g, 10 mmol), sodium hydride (460 mg, 10 mmol) and copper (u) chloride (500 mg) was refluxed in anhydrous pyridine (50 ml) for 12 hrs. The reaction mixture was carefilfly quenched with ice cold water and acidified with concentrated HCl. The product was extracted with choroform, washed well with water; dried and concentrated The product was purified by silica gel column chromatography by eluting with 30% ethyl acetate:hexane. Yield 2.5 g (77%); Colorless low melting solid; MS: 323 (M+H)$^+$. Alternatively the title compound may be prepared from 4-(4-chloro-phenoxy)-benzenethiol and bromo ethyl acetate as described in example 83.

EXAMPLE 248

[4-(4-Chloro-phenoxy)-benzenesulfonyl]-acetic acid ethyl ester

[4-(4-Chloro-phenoxy)-benzenesulfonyl]-acetic acid ethyl ester was prepared according to the general method outlined in example 83 starting from [(4-chloro-phenoxy)-phenylsulfanyl]-acetic acid ethyl ester (3.23g, 10 mmol) and oxone (10 g). Yield 3.5g (99%); oil; MS: 356EI (M+H)$^+$

EXAMPLE 249

4-[4-(4-chloro-phenoxy)-benzenesulfonyl]1-methyl-piperidine-4-carboxylic acid hydroxyamide 4-[4-(4-Chloro-phenoxy)-benzenesulfonyl]-1-methyl-piperidinecarboxylic acid ethyl ester was prepared according to the general method outlined in example 83 starting from [4-(4-chloro-phenoxy)-benzenesulfonyl]-acetic acid ethyl ester ( 2.0g, 5.6mmol) and mechlorethanmine hydrochloride (Aldrich), (1.9 g, 10 mmol). Yield 2g ( 81%); brown oil; MS:438 (M+H)$^+$ 4-[4-(4-Chloro-phenoxy)-benzenesulfonyl]-1-methyl-piperidine-4-carboxylic acid was prepared starting from 4-[4-(4-chloro-phenoxy)-benzenesulfonyl]-1-methyl-piperidine-4-carboxylic acid ethyl ester (4.3 g, 10 mmol) dissolved in THF:methanol (3:1 150 ml) and 10 N NaOH (100 ml). The resulting reaction mixture was worked up as outlined in example 83. Yield 3.5 g (86 %); white solid; mp 185° C.; MS:410(M+H)$^+$ Starting from 4-[4-(4-chloro-phenoxy)-benzenesulfonyl]-1-methyl-piperidine-4-carboxylic acid (1.0 g, 2.4 mmol) and following the procedure outlined in example 83, 460 mg of 4-[4-(4-chloro-phenoxy)benzenesulfonyl]1-methyl-piperidine-4-carboxylic acid hydroxyamide was isolated as a HCl salt, a white powder. Yield 41%; mp 52° C.; MS: 426 (M+H)$^+$; $^1$H NMR (300 MHz, DMSO-d$_6$): δ 1.3 (s, 3H), 2.2–2.9 (m, 6H), 3.5 (bd, 2H), 7.2–7.9 ( m, 8H), 8.1 (s, 1H), 11.0 (bs, 1H).

EXAMPLE 250

4-[4-(4-chloro-phenoxy)-benzenesulfonyl]1-ethyl-piperidine-4-carboxylic acid hydroxyamide 4-[4-(4-Chloro-phenoxy)-benzenesulfonyl]-1-ethyl-piperidine-4-carboxylic acid ethyl ester was prepared according to the general method outlined in example 83 starting from [4-(4-chloro-phenoxy)-benzenesulfonyl]-acetic acid ethyl ester (4 g, 11.3 mmol) and ethyl-bis-(2-chloro-ethyl)-amine (2.32 g, 16.9 mmol). Yield 3.36 g (66%); brown oil; MS: 452.0 (M+H)$^+$ 4-[4-(4-Chloro-phenoxy)-benzenesulfonyl]-1-ethyl-piperidine-4-carboxylic acid was prepared starting from 4-[4-(4-chloro-phenoxy)-benzenesulfonyl]-1-ethyl-piperidine-4-carboxylic acid ethyl ester (3.02 g, 6.7 mmol) dissolved in THF:methanol (3: 1150 ml) and 10 N NaOH (20 ml). The resulting reaction mixture was worked up as outlined in example 83. Yield 1.8 g (65%); white solid; mp 184° C.; MS: 423.9 (M+H)$^+$ Starting from 4-[4-(4-chloro-phenoxy)-benzenesulfonyl]-1-ethyl-piperidine-4-carboxylic acid (1.75 g, 4.14 mmol) and following the procedure outlined in example 83,,650 mg of 4-[4-(4-chloro-phenoxy)-benzenesulfonyl]1-ethyl-piperidine-4-carboxylic acid hydroxyamide was isolated as a HCl salt, a white powder. Yield 33%; mp 158° C.; MS: 438.9 (M+H)$^{30}$ ; $^1$H NMR (300 MHz, DMSO-d$_6$): δ 1.78 (t, J=7.23 Hz, 3H), 2.23–2.27 (m, 2H), 2.51–2.73 (m, 4H), 3.04 (m, 2H), 3.81 (d, J=24 Hz, 2H), 7.16–7.27 (m, 4H), 7.50–7.57 (m, 2H), 7.76 (d, J =7 Hz, 2H), 9.34 (s, 1H), 9.85 (s, 1H).

EXAMPLE 251

1-Butyl-4-(4-(4-chloro-phenoxy)-benzenesulfonyl-piperidine-4-carboxylic acid hydroxyamide 1-Butyl-4-[4-(4-chloro-phenoxy)-benzenesulfonyl]-piperidine-4-carboxylic acid ethyl ester was prepared according to the general method outlined in example 83 starting from [4-(4-chloro-phenoxy)-benzenesulfonyl]-acetic acid ethyl ester (6 g, 18.3 mmol) and butyl-bis-(2-chloro-ethyl)-amine (5.2 g, 22 mmol). Yield 3.3 g (38%); yellow oil; MS: 480 (M+H)$^+$ 1-Butyl-4-[4-(4-chloro-phenoxy)-benzenesulfonyl]-piperidine-4-carboxylic acid was prepared staing from 1-butyl-4-[4-(4chloro-phenoxy)-benzenesulfonyl]-piperidine-4-carboxylic acid ethyl ester (3.3 g, 6.9 mmol) dissolved in THF:methanol (3:1 150 ml) and 10 N NaOH (25 ml). The resulting reaction mixture was worked up as outlined in example 83. Yield 2.08 g (67%); white solid; mp 201° C.; MS: 451.9 (M+H)$^+$ Starting from 1-butyl-4-[4-(4-chloro-phenoxy)-benzenesulfonyl]-piperidine-4-carboxylic acid (2 g, 4.43 mmnol) and following the procedure outlined in example 83, 630 mg of 1-butyl-4-[4-(4-chloro-phenoxy)-benzenesulfonyl]-piperidine-4-carboxylic acid hydroxyamide was isolated as a HCl salt, a white solid. Yield 31%; mp 212° C.; MS: 466.9 (M+H)+; $^1$NMR (300 MHz, DMSO-d$_6$): δ 0.87 (t, J=7.3 Hz, 3H), 1.32 (m, 2H), 1.60 (m, 2H), 2.21 (m, 2H), 2.50 (m, 2H), 2.70 (q, 2H), 3.00 (m, 2H), 3.57 (d, 2H), 7.16–7.26 (m, 4H), 7.49–7.56 (m, 2H), 7.77 (d, J=9 Hz, 2H), 9.34 (s, 1H), 10.13 (s, 1H).

EXAMPLE 252
1-Benzyl-4-[4-(4-chloro-phenoxy)-benzenesulfonyl]-piperidine-4-carboxylic acid hydroxyamide 1-Benzyl-[4-(4chloro-phenoxy)-benzenesulfonyl]-piperidine-4-carboxylic acid ethyl ester was prepared according to the general method outlined in example 83 starting from [4-(4-chloro-phenoxy)-benzenesulfonyl]-acetic acid ethyl ester (6 g, 16.9 mmol) arid bis-(2-chloro-ethyl)-benzyl amine (6.44 g, 24 mnmol). Yield 2.21 g (25%); yellow oil; MS: 513.9 (M+H)$^+$ 1-Benzyl-4-[4-(4chloro-phenoxy)-benzenesulfonyl]-piperidine-4-carboxylic acid was prepared starting from 1-benzyl-4-[4-(4chloro-phenoxy)-benzenesulfonyl]-piperidine-4-carboxylic acid ethyl ester (2.11 g, 4.1 mmol) dissolved in TBF:methanol (3:1 150 ml) and 10 N NaOH (20 ml). The resulting reaction mixture was worked up as outlined in example 83. Yield 1.11 g (56%); white solid; mp 201° C.; MS: 485.9 (M+H)$^+$ Starting from 1-benzyl-4-[4-(4chloro-phenoxy)-benzenesulfonyl]-piperdine-4-carboxylic acid (1 g, 2.06 mmol) and following the procedure outlined in example 83, 430 mg of 1-benzyl-4-[(4-chlorophenoxy)-benzenesulfonyl]-piperidine-4-carboxylic acid hydroxyamide was isolated as a HCl salt, an off white solid. Yield 39%; mp 90.4° C.; MS: 500.9 (M+H)$^+$; $^1$H NMR (300 MHz, DMSO-d$_6$): δ 2.18–2.30 (m, 2H), 2.73–2.81 (m, 4H), 3.36 (d, 2H), 4.28 (d, J=4.5 Hz, 2H), 7.15–7.25 (m, 4H), 7.43–7.48 (m, 3H), 7.51–7.56 (m, 4H), 7.74 (d, J=9 Hz, 2H), 9.53 (s, 1H), 10.47 (s, 1H).

EXAMPLE 253
[4-(3-methyl-butoxy)-phenylsulfanyl]-acetic acid ethyl ester

To stirred solution of (4-Hydroxy-phenylsulfanyl)-acetic acid ethyl ester (2.12 g, 10 mmol), K$_2$CO$_3$ (anhydrous, 10 g) and 1-bromo-3-methyl butane (3 g, excess) was added in boiling acetone. The reaction mixture was refluxed for 24 hrs and cooled to room temperature. The reaction mixture was filtered and concentrated. The residue obtained was extracted with chloroform; washed well with water and concentrated. The crude product obtained was taken to next step with out purification. Yield 2.7 g (94%); (M+H)$^+$283.

EXAMPLE 254
[4-(3-methyl-butoxy)-phenylsulfonyl]-acetic acid ethyl ester

[4-(3-methyl-butoxy)-phenylsulfonyl]-acetic acid ethyl ester was prepared according to the general method outlined in example 83 starting from [4-(3-methyl-butoxy)-phenylsulfanyl]-acetic acid ethyl ester (2.8 g, 10 mmol) and oxone (10 g). Yield 3.0g ( 99%); oil; MS: 314EI (M+H)$^+$

EXAMPLE 255
1-Benzyl-4-[4-(3-methyl-butoxy)-benzenesulfonyl]-piperidine-4-carboxylic acid hydroxyamide 1-Benzyl-4-[4-(3-methyl-butoxy)-benzenesulfonyl]-piperidine-4-carboxylic acid ethyl ester was prepared according to the general method outlined in example 83 starting from [4-(3-methyl-butoxy)-phenylsulfonyl]-acetic acid ethyl ester (6.2 g, 20 mnmol) and bis-(2-chloro-ethyl)-benzyl amine (6.44 g, 24 mmol). Yield 8 g (84%); yellow oil; MS: 474 (M+H)$^+$ 1-Benzyl-4-[4-(3-methyl-butoxy)-benzenesulfonyl]-piperidine-4-carboxylic acid was prepared starting from 1-Benzyl[4-(3-methyl-butoxy)-benzenesulfonyl]-piperidine-4-carboxylic ethyl ester (4.7 g, 10 mmol) dissolved in THF:methanol (3:1 150 ml) and 10 N NaOH (20 ml). The resulting reaction mixture was worked up as outlined in example 83. Yield 3 g (67%); white solid; mp 182° C.; MS: 446 (M+H)$^+$ Starting from 1-Benzyl-[4-[(3-methyl-butoxy)-benzenesulfonyl]-piperidine-4-carboxylic acid (2.2 g, 5 mmol) and following the procedure outlined in example 83, 1.82 g of 1-Benzyl-4-[4-(3-methyl-butoxy)-benzenesulfonyl]-piperidine-4-carboxylic acid hydroxyamnide was isolated as a HCl salt, an off white solid. Yield 73%; mp 106 ° C; MS: 498 (M+H)$^+$; $^1$H NMR (300 MHz, DMSO-d$_6$): δ 0.8 (d, 6H), 1.5 (m,1H), 1.6–2.0 (m, 6H), 2.73–2.81 (m, 4H), 3.5 (d, 2H), 4.28 (d, J=4.5 Hz, 2H), 7.15–7.25 (m, 4H), 7.43–7.48 (m, 3H), 7.51–7.56 (m, 4H), 7.74 (d, J=9 Hz, 2H), 9.53 (s, 1H), 10.47 (s, 1H).

EXAMPLE 256
1-Butyl-4-[4-(3-methyl-butoxy)-benzenesulfonyl]-piperidine-4-carboxylic acid hydroxyamide 1-Butyl-4-[4-(3-methyl-butoxy)-benzenesulfonyl]-piperidine-4-carboxylic acid ethyl ester was prepared according to the general method outlined in example 83 starting from [4-(3-methyl-butoxy)-phenylsulfonyl]-acetic acid ethyl ester (6.2 g, 20 mmol) and butyl-bis-(2-chloro-ethyl)-amine (5.2 g, 22 =mol). Yield 7 g (79%); yellow oil; MS: 440 (M+H)$^+$ 1-Butyl-4-[4-(3-methyl-butoxy)-benzenesulfonyl]-piperidine-4-carboxylic acid was prepared starting from 1-Butyl-4-[4(3-methyl-butoxy)-benzenesulfonyl]-piperidine4-carboxylic ethyl ester (4.4 g, 10 mmol) dissolved in TBF:methanol (3:1 150 ml) and IO N NaOH (20 ml). The resulting reaction mixture was worked up as outlined in example 83. Yield 3.2 g (77%); white solid; mp 188° C.; MS: 412 (M+H)$^+$ Starting from 1-Butyl-4-[4-(3-methyl-butoxy)-benzenesulfonyl]-piperidinewcarboxylic acid (2.0 g, 5 mmol) and following the procedure outlined in example 83, 1.6 g of 1-Butyl-[4-(3-methyl-butoxy)-benzenesulfonyl]-piperidine-4-carboxylic acid hydroxyamide was isolated as a HCl salt, an off white solid. Yield 69%; mp 201° C.; MS: 464 (M+H)$^+$.

EXAMPLE 257
[4-(2-Ethyl-butoxy)-phenylsulfanyl]-acetic acid ethyl ester

To stirred solution of (4Hydroxy-phenylsulfanyl)-acetic acid ethyl ester (2.12 g, 10 mmol), K$_2$CO$_3$ (anhydrous, 10 g) and 1-bromo-2-ethyl butane (3 g, excess) was added in boiling acetone. The reaction mixture was refluxed for 24 hrs and cooled to room temperature. The reaction mixture was filtered and concentrated. The residue obtained was extracted with chloroform; washed well with water and concentrated. The crude product obtained was taken to next step without purification. Yield 2.8 g.(94%); (M+H)$^+$297.

EXAMPLE 258
[4(2-Ethyl-butoxy)-phenylsulfonyl]-acetic acid ethyl ester

[4-(2-Ethyl-butoxy)-phenylsulfonyl]-acetic acid ethyl ester was prepared according to the general method outlined in example 83 starting from [4-(2-ethyl-butoxy)-phenylsulfanyl]-acetic acid ethyl ester (2.96 g, 10 mmol) and oxone (10 g). Yield 3.1g ( 99%); oil; MS: 329EI (M+H)$^+$

EXAMPLE 259
1-Benzyl4-[4-(2-ethyl-butoxy)-benzenesulfonyl]-piperidine-4-carboxylic acid hydroxyamide 1-Benzyl4-[4-(2-ethyl-butoxy)-benzenesulfonyl]-piperidine-4-carboxylic acid ethyl ester was prepared according to the general method outlined in example 83 starting from [4(2-ethyl-butoxy)-phenylsulfonyl]-acetic acid ethyl ester (6.4 g, 20 mmol) and bis-(2-chloro-ethyl)-benzyl amine (6.44 g, 24 mmol). Yield 8 g (82%); yellow oil; MS: 488 (M+H)$^+$ 1-Benzyl-4-[4-(2-ethyl-butoxy)-benzenesulfonyl]-piperidine-4-carboxylic acid was prepared starting from 1-Benzyl-4-[4-(2-ethyl-butoxy)-benzenesulfonyl]-piperidine-4-carboxylic ethyl ester (4.8 g, 10 mmol) dissolved in THF:methanol (3:1 150 ml) and 10 N NaOH (20 ml). The resulting reaction mixture was worked up as outlined in example 83. Yield 4 g (87%); Semi solid; MS: 460 (M+H)$^+$ Starting from 1-Benzyl-4-[4-(2-ethyl-butoxy)-benzenesulfonyl]-piperidine-4-carboxylic acid (2.2 g, 5 mmol) and following the procedure outlined in example 83, 1.02 g of 1-Benzyl-4-[4-(2-ethyl-butoxy)-benzenesulfonyl]-piperidine-4-carboxylic acid hydroxyamide was isolated as a HCl salt, an off white solid. Yield 40%; mp 114° C.; MS: 512 (M+H)$^+$.

EXAMPLE 260
4-(4-butoxy-benzenesulfonyl)-1-(3-methoxy-benzyl)-piperidine-4-carboxylic acid hydroxyamide 4-(4-Butoxy-benzenesulfonyl)-1-(3methoxy-benzyl)-piperidine-4-carboxylic acid ethyl ester was prepared according to the ceneral method outlined in example 83 starting from 4-(4-butoxy-benzenesulfonyl)-acedic acid ethyl ester (20 g, 77.5 mmol) and bis-(2-chloro-ethyl)-(3-methoxy-benzyl)-amine (34 g, 116 mmol). Yield 9.53 g (25%); brown oil; MS: 490.2 (M+H)$^+$ 4-(4-Butoxy-benzenesulfonyl)-1-(3-methoxy-benzyl)-piperdine-4-carboxylic acid was prepared stariing from 4-(4methoxy-benzenesulfonyl)-1-(3-methoxy-benzyl)-piperidine-4-carboxylic acid ethyl ester (2.61 g, 5.34 mmol) dissolved in THF:methanol (3:1 150 ml) and 10 N NaOH (15 ml). The resulting reaction mixture was worked up asoutlined in example 83. Yield 1 g (41%); brown solid; mp 175° C.; MS: 462.0 (M+H)$^+$ Starting from 4-(4butoxy-benzenesulfonyl)-1-(3-methoxy-benzyl)-piperidine-4-carboxylic acid (900 mg, 1.95 mmol) and following the procedure outlined in example 83, 200 mg of 4-(4-butoxy-benzenesulfonyl)-1-(3-methoxy-benzyl)-piperidine-4-carboxylic acid hydroxamide was isolated as a HCl salt, a brown powder. Yield 20%; mp 137° C.; MS: 477.0 (M+H)$^+$; $^1$H NMR (300 MHz, DMSO-d$_6$): δ0.96 (t, J=7.11 Hz, 3H), 1.48 (m, 2H), 1.73 (m, 2H), 2.27 (m, 2H), 2.47 (m, 2H), 2.78 (m, 2H), 3.35 (m, 2H), 3.77 (s, 2H), 4.08 (t, J=6.3 Hz, 3H), 4.32 (s, 2H), 7.03 (t, 2H), 7.15 (m, 3H), 7.36 (t, J=7.8 Hz, 1H), 7.64 (d, J=9 Hz, 2H), 9.36 (s, 1H), 10.22 (s, 1H).

EXAMPLE 261
4-(4-Methoxy-benzenesulfonyl)-1-(thiophen-2-yl-benzyl)-piperidine-4-carboxylic acid hydroxyamide 4-(4-Methoxy-benzenesulfonyl)-1-(4thiophen-2-yl-benzyl)-piperidine-4-carboxylic acid ethyl ester was prepared starting from 1-(4-Bromo-benzyl)-4-(4-methoxy-benzensulfonyl)-piperidine-4-carboxylic acid ethyl ester (3 g, 6.05 mmol) and 2-(tributylstannyl)-thiophene (6.8 g, 18.14 mmol) in the presence of tetrakis palladium (0) in boiling tolune. Yield 1.58 g (52%); brown solid; mp 130° C.; MS: 500 (M+H)$^+$ 4-(4-Methoxy-benzenesulfonyl)-1-(4-thiophen-2-yl-benzyl)-piperidine-4-carboxylic acid was prepared starting from 4-(4-methoxy-benzenesulfonyl)-1-(4-thiophen-2-yl-benzyl)-piperidine-4-carboxylic acid ethyl ester (1.3 g, 2.61 mmol) dissolved in THF:methanol (3:1 150 ml) and 10 N NaOH (20 ml). The resulting reaction rnlxture was worked up as outlined in example 83. Yield 950 mg (77%); brown solid; mp 235° C.; MS: 471.8 (M+H)$^+$ Starting from 4-(4-methoxy-benzenesulfonyl)-1-(4-thiophen-2-yl-benzyl)-piperidine-4-carboxylic acid (920 mg, 1.95 mmol) and following the procedure outlined in example 83, 510 mg of 4-(4-methoxy-bernzenesulfonyl)-1-(4-thiophen-2-yl-benzyl)-piperidine-4-carboxylic acid hydroxyamide was isolated as a HCl salt, a brown solid. Yield 50%; mp 166° C.; MS: 486.9 (M+H)$^+$; $^1$H NMR (300 MHz, DMSO-d$_6$): δ2.12–2.21 (m, 2H), 2.50 (m, 2H), 2.78 (m, 2H), 3.39 (m, 2H), 3.87 (s, 3H), 4.29 (d, 2H), 7.17 (m, 3H), 7.54–7.75 (m, 8H), 9.36 (s, 1H), 10.07 (s, 1H)

EXAMPLE 262
4-(4-methoxy-benzenesulfonyl)-1-(4-pyridin-2-yl-benzyl)-piperidine-4-carboxylic acid hydroxyamide 4-(4-Methoxy-benzenesulfonyl)-1-(4-pyridin-2-yl-benzyl)-piperidine-4-carboxylic acid ethyl ester was prepared according to the general method outlined in example 261. Starting from 1-(4-Bromo-benzyl)4-(4-methoxy-benzensulfonyl)-piperidine-4-carboxylic acid ethyl ester (4.65 g, 9.38 mmol) and 2-(tributylstannyl)-pyridine (12.08 g, 32.8 mmol). Yield 2.79 g (60%); brown oil; MS: 495.1 (M+H)$^+$ 4-(4-Methoxy-benzenesulfonyl)-1-(4-pyridin-2-yl-benzyl)-piperidine-4-carboxylic acid was prepared starting from 4-(4-medtoxy-benzenesulfonyl)-1-(4-pyridin-2-yl-benzyl)-piperidine-4-carboxylic acid ethyl ester (1.83 g, 3.7 mmol) dissolved in ThF:methanol (3:1 150 ml) and 10 N NaOH (10 ml). The resulting reaction mixture was worked up as outlined in example 83. Yield 1.38 g (80%); off white solid; mp 217° C.; MS: 466.9 (M+H)$^+$ Starting from 4-(4-methoxy-benzenesulfonyl)-1-(4-pyridin-2-yl-benzyl)-piperidine-4-carboxylic acid (1.32 g, 2.83 mmol) and following the procedure outlined in example 83, 480 mg of 4-4-(methoxy-benzenesulfonyl)-1-(4-pyridin-2-yl-benzyl)-piperidine-4-carboxylic acid hydroxyamide was isolated as a HCl salt, a white powder. Yield 33%; mp 214° C.; MS: 482.0 (M+H)$^+$; $^1$H NMR (300 MHz, DMSO-d$_6$): δ 2.30 (m, 2H), 2.80 (m, 2H), 3.42 (d, J=12.5 Hz, 2H), 3.75 (m, 2H), 3.88 (s, 3H), 4.36 (s, 2H), 7.15 (d, J=8.9 Hz, 2H), 7.59–7.74 (m, 4H), 7.84–7.95 (m, 3H), 8.55 (d, J=8.1 Hz, 1H), 8.79 (s, 1H), 9.14 (s, 1H), 10.68 (s, 1H), 11.17 (s, 1H)

EXAMPLE 263
1-(3,4-Dichlorobenzyl)-4-(4-butoxy-benzenesulfonyl)-piperidine-4-carboxylic acid hydroxyamide 4-(4-Butoxy-benzenesulfonyl)-1-(3,4-dichloro-benzyl)-piperidine-4-carboxylic acid ethyl ester was prepared according to the general method outlined in example 83. Starting from (4-butoxy-benzenesulfonyl)acetic acid ethyl ester (13.2g 44 mmol) (3,4dichloro-benzyl)-bis-(2-chloro-ethyl)-amine (14.3g, mmol). Yield 14.1g (60%), white solid, MP 86° C.; MS: 527.9 (M+H)$^+$ 1-(3,4-dichlorobenzyl)-4-(4-butoxy-benzenesulfonyl)-piperidine-4-carboxylic acid was prepared starting from 4-(4-Butoxy-benzenesulfonyl)-1-(3,4-dichloro-benzyl)-piperidine-4-carboxylic acid ethyl ester (14.0 g, 26.5 mmol) dissolved in THF:Methanol (100: 50 ml) and 10 N NaOH (20 ml). The resulting reaction mixture was worked up as outlined in example 83. Yield 7.87 (60%); off white solid; mp 239 ° C; MS: 501.9 (M+H)$^+$ Starting 1-(3,4-dichlorobenzyl)-4-(4-butoxy-benzenesulfonyl)-piperidine-4-carboxylic acid (7.7g, 15.5 mmol) and following the procedure outlined in example 83, 4.05g of 1-(3,4-dichlorobenzyl)-4-(4-butoxy-benzenesulfonyl)-piperidine-4-carboxylic acid hydroxyamide was isolated as a HCl salt, white solid. Yield 48%; mp 256.8° C.; MS: 514.9 (M+H)$^+$; $^1$H NMR (300 MHz, DMSO-d$_6$): δ 0.94 (t, 3H), 1.38–1.48 (q, 2H), 1.68–1.75 (q, 2H), 2.27 (m, 4H),2.72 (m, 2H), 4.10 (t, 2h), 4.24 (s, 2H), 7.12–7.15 (d, J=8.9, 2H), 7.51–7.53 (d, J=8.1, 1H), 7.63–7.65 (d, J=8.8, 2H), 7.72–7.75 (d, J=9.9, 2H), 7.87 (s, 1H), 9.36 (s, 1H), 10.5 (s, 1H), 11.2 (s, 1H)

EXAMPLE 264

[4-(4-Chloro-benzyloxy)benzenesulfonyl]-1-methylpiperidine-4-carboxylic acid hydroxamide

[4-(4Chloro-benzyloxy)-benzenesulfonyl-1-methylpiperidine-4-carboxylic acid ethyl ester was prepared according to the general method outlined in example 83 starting from [4-(4-chloro-benzyloxy)-benzenesulfonyl]-acetic acid ethyl ester (13.79g, 37 mmol) and 4-(4-chloro-benzyloxy)-bis-(2- chloro-ethyl)-amine (8.7g, 45 mmol). Yield 10.9 (65%); brown oil; MS: 451.9 (M+H)⁺

[4-(4-Chloro-benzyloxy)-benzenesulfonyl-1-methylpiperidine-4-carboxylic acid was prepared starting from [4-(4-Chloro-benzyloxy)-benzenesulfonyl]-1-methylpiperidine-4-carboxylic acid ethyl ester (10.7 g, 24 mmol) dissolved in THF:Methanol (75: 75 ml) and 10 N NaOH (20 ml). The resulting reaction mixture was worked up as outlined in example 83. Yield 4.9 g (50%); off white solid; MS: 426.2 (M+H)⁺

Starting from [4-(4-Chloro-benzyloxy)-benzenesulfonyl-1-nethylpiperidine-4-carboxylic acid (4.9 g, 12 mmol) and following the procedure outlined in example 83, 1.2g of [4-(4-Chloro-benzyloxy)-benzenesulfonyl]-1-methylpiperidine-4-carboxylic acid hydroxamide was isolated as a HCl salt, off white solid. Yield 24%; mp 117.8° C.; MS: 438.9 M+H)⁺; ¹H NMR (300 MHz, DMSO-d₆): δ 2.2 (m, 2H), 2.49 (m, 4H), 2.5 (s, 3 H), 2.6 (m, 2H), 5.2 (s, 2H), 7.25–7.23 (d, t=8.7, 2H), 7.5 (d, t=2.7, 4H), 7.68–7.71 (d, t=9.6, 2H), 9.33 (s, 1H), 10.11 (s, 1H)

EXAMPLE 265

4-(4-Butoxy-benzenesulfonyl)-1-(3-phenoxy-benzyl)-piperidine-4-carboxylic acid hydroxamide 4-(4-Butoxy-benzenesulfonyl)-1-(3-phenoxy-benzyl)-piperidine-4-carboxylic acid ethyl ester was prepared according to the general method outlined in example 83 starting from 4-(4-butoxy-benzenesulfonyl)-acetic acetic acid ethyl ester (10.1 g, 34 mmol) and 1-(3-phenoxy-benzyl)-bis-(2-chloro-ethyl)-amine (18 g, 50 mnmol). Yield 8.9 (49%); brown oil; MS: 552.1 (M+H)⁺

4-(4-Butoxy-benzenesulfonyl)-1-(3-phenoxy-benzyl)-piperidine-4-carboxylic acid was prepared starting from 4-(4-butoxy-benzenesulfonyl)-1-(3-phenoxy-benzyl)-piperidine-4-carboxylic ethyl ester (10.7 g, 24 mmol) dissolved in THF.Methanol (75: 50 ml) and 10 N NaOH (20 ml). The resulting reaction mixture was worked up as outlined in example 83. Yield 5.0 g (76%); off white solid; MS: 524.3 (M+H)⁺

Starting from 4-(4-Butoxy-benzenesulfonyl)-1-(3-phenoxy-benzyl)-piperidine-4-carboxylic acid (5.9 g, 11 mmol) and following the procedure outlined in example 83, 0.39g of 4-(4-butoxy-benzenesulfonyl)-1-(3-phenoxy-benzyl)-piperidine-4-carboxylic acid hydroxamide was isolated as a HCl salt, tan solid. Yield 11%; mp 92.5° C.; MS: 539.1 (M+H)⁺; ¹H N (300 MHz, DMSO-d₆): δ 0.93–0.97 (t, J=3.6, 3H), 1.49 (m, 2H), 1.73 (m, 2H), 2.51 (m, 4H), 4.09 (t, 2H), 4.29 (bs, 2H), 7.06–7.10 (d, J=12, 2H), 7.13–7.15 (m, 3H), 7.39–7.42 (d, 2H), 7.63–7.66 (d, 2H), 9.50 (s, 1H), 9.98 (s, 1H)

EXAMPLE 266

[4-(4-Chloro-benzyloxy)-benzenesulfonyl]-1-(4-methylbenzyl)-piperidine-4-carboxylic acid hydroxamide

[4-(4-Chloro-benzyloxy)-benzenesulfonyl]-1-(4-methylbenzyl)-piperidine-4-carboxylic acid ethyl ester was prepared according to the general method outlined in example 83 starting from [1-(4-chloro-benzyloxy)-benzenesulfonyl]-acedic acid ethyl ester (5.47g, 15 mmol) and 1-(4-methyl-benzyl)-bis-(2-chloro-ethyl)-amine (5.23 g, 18 mmol). Yield 8.0 (96%); brown oil; MS: 542.0 (M+H)

[4-(4-Chloro-benzyloxy)-benzenesulfonyl]-1-(4-methylbenzyl)-piperidine-4-carboxylic acid was prepared starting from [4-(4-Chloro-benzyloxy)-benzenesulfonyl]-1-(4-methylbenzyl)-piperidine-4-carboxylic acid ethyl ester (7.9 g, 124 mmol) dissolved in THF:Methanol (50: 50 ml) and 10 N NaOH (20 ml). The resulting reaction mixture was worked up as outlined in example 83. Yield 4.6g (61%); off white solid, mp 204° C.; MS: 514.2 (M+H)⁺

Starting from [4-(4-Chlorobenzyloxy)-benzenesulfonyl]-1-(4-methylbenzy])-pipendine-4-carboxylic acid (4.2 g, 8 rnmol) and following the procedure outlined in example 83, 1.3 g of [4-(4-Chloro-benzyloxy)-benzenesulfonyl]-1-(4-methylbenzyl)-piperidine-4-carboxylic acid hydroxamide was isolated as a HCl salt, yellow solid Yield 29%; mp 172 ° C; MS: 528.9 (M+H)⁺; ¹H NMR (300 MH, DMSO-d₆): δ

EXAMPLE 267

4-(4-Butoxy-benzenesulfonyl)-1-(4-methylbenzyl)-piperidine-4-carboxylic acid hydroxamide 4-(4-Butoxy-benzenesulfonyl)-1-(4-methylbenzyl)-piperidine-4-carboxylic acid ethyl ester was prepared according to the general method outlined in example 83 starting 4-(4-Butoxy-benzenesulfonyl)-acetic acid ethyl ester (5.47 g, 15 mmol) and 1-(4-methyl-benzyl)-bis-(2-chloro-ethyl)-amine (15.3 g, 51 mmol). Yield 10.1 (57%); white solid, MP 93° C.; MS: 474.1 (M+H)⁺

4-(4-Butoxy-benzenesulfonyl)-1-(4-methylbenzyl)-piperidine-4-carboxylic acid was prepared starting from 4-(4-Butoxy-benzenesulfonyl)-1-(4-methylbenzyl)-piperidine-4-carboxylic ethyl ester (10.0 g, 22 mmol) dissolved in THF:Methanol (50:50 ml) and 10 N NaOH (20 ml). The resulting reaction mixture was worked up as outlined in example 83. Yield 7.2 g (72%); off white solid, mp 244° C.; MS: 446.3 (M+H)⁺

Starting from 4-(4-Butoxy-benzenesulfonyl)-1-(4-methylbenzyl)-piperidine-4-carboxylic acid (6.6 g, 1.5 mmol) and following the procedure outlined in example 83, 2.06g of 4-(4-Butoxy-benzenesulfonyl)-1-(4-methylbenzyl)-piperidine-4-carboxylic acid hydroxamide was isolated as a HCl salt, yellow solid. Yield 28%; mp 137° C.; MS: 461.3 (M+H)⁺; ¹H NMR (300 MHz, DMSO-d₆): δ 0.91–0.964 (t, J=7.3, 3H), 1.41 (m, 2H), 1.70 (m, 4H), 1.79 (t, s, 3H), 2.52 (m, 2H), 2.76 (m, 2H), 3.33 (bd, 2H), 4.10 (t, 2H), 4.22 (d, 2H), 7.12–7.14 (d, J=8.7, 2H), 7.25–7.28 (d, J=8.1, 2H), 7.42–7.45 (d, J=7.8, 2H), 7.63–7.65 (d, J=8.7, 2H), 10.31 (s, 1H), 10.75 (bs, 1H)

EXAMPLE 268

4-(4-Butoxy-benzenesulfonyl)-1-(4-cyano-benzyl)-piperidine-4-hydroxamide carboxylic acid hydroxamide 4-(4-Butoxy-benzenesulfonyl)-1-(4-cyano-benzyl)-piperidine-4-carboxylic acid ethyl ester was prepared according to the general method outlined in example 83 starting 4(4-Butoxy-benzenesulfonyl)-acetic acid ethyl ester (5.29 g, 17.6 mmol) and 1-(4-cyano-benzyl)-bis-(2-chloro-ethyl)amine (6.19 g, 21 mmol). Yield 6.8 g (80%); tan oil; MS: 485.0 (M+H)⁺

4-(4-Butoxy-benzenesulfonyl)-1-(4-cyanobenzyl)-piperidine-4-carboxylic acid was prepared starting from 4-(4-Butoxy-benzenesulfonyl)-1-(4-cyanobenzyl)-piperidine-4-carboxylic ethyl ester (10.0 g, 124 mmol) dissolved in THF:Methanol (75: 50 ml) and 10 N NaOH (20 ml). The resulting reaction mixture was worked up as outlined in example 83. Yield .7g (11%); off white solid; MS: 456.0 (M+H)+

Starting from 4-(4-Butoxy-benzenesulfonyl)-1-(4-cyanobenzyl)-piperidine-4-carboxylic acid (0.600 g, 1.2 mmol) and following the procedure outlined in example 83, .21g of 4-(4-Butoxy-benzenesulfonyl)-1-(4-cyano-benzyl)-piperidine-4-carboxylic acid hydroxamide was isolated as a HCl salt, off white solid. Yield 34%; mp 241.6° C.; MS: 472.0 (M+H)+; $^1$H NMR (300 MHz, DMSO-d$_6$): δ 0.915–0964 (t, J=7.2, 3H), 1.51 (q, 2H),,1.75 (q, 2H), 2.27 (m, 2H), 2.49 (m, 4H), 4.11–4.19 (t, 2H), 4.37 (s, 1H), 7.12–7.15 (d, J=8.7, 2H), 7.63–7.66 (d, J=9, 2H), 7.72–7.74 (d, J=7.8, 2H), 9.36 (s, 1H), 10.23 (s, 1H), 11.16 (s, 1H)

EXAMPLE 269

4-(4-Butoxy-benzenesulfonyl)-1-pyridin-4-ylmethyl-piperidine-4-carboxylic acid hydroxamide 4-(4-Butoxy-benzenesulfonyl)-1-pyridin-4-ylmethyl-piperidine-4-carboxylic acid ethyl ester was prepared according to the general method outlined in example 83 starting with 4-(4-Butoxy-benzenesulfonyl)-acetic acid ethyl ester (6.0 g, 20.0 mmol) and pyridin-4-ylmethyl-bis-(2-chloro-ethyl)- amine.
(4.89 g, 21 inmol). Yield 4.5 g (48%); Brown oil; MS: 461.0 (M+H)+

4-(4-Butoxy-benzenesulfonyl)-1-pyridin-4-ylmethyl-piperidine-4-carboxylic acid was prepared starting from 4-(4-Butoxy-benzenesulfonyl)-1-pyridin-4-ylmethyl-piperidine-4-carboxylic acid ethyl ester (3.0 g, 6.5 mmol) dissolved in TBF:Methanol (75: 50 ml) and 10 N NaOH (20 ml). The resulting reaction mixture was worked up as outlined in example 83. Yield 1.2 g (42%); off white solid; MS: 433.0 (M+H)+

Staring from 4-(4-Butoxy-benzenesulfonyl)-1-pyridin-4-ylmethyl-piperidine-4-carboxylic acid (0.864 mg, 2.0 mmol) and following the procedure as outlined in example 83, 600 mg of 4 (4-Butoxy-benzenesulfonyl)-1-pyridin-4-ylmethyl-piperidine-4-carboxylic acid hydroxyamide was isolated as a HCl salt, off white solid. Yield 67%; mp 118° C.; MS: 447.9 (M+H)+; $^1$H NMR (300 MHZ, DMSO-d$_6$): d0.94 (t, 3H), 1.11 (t, 1H), 1.23 (t, 1H), 1.44 (m, 1H), 1.73 (m, 1H),2.34 (m, 2H), 2.78 (m, 2H), 3.10 (m, 2H), 3.38 (m, 2H), 4.08 (t, 2H), 4.42 (br s, 2H), 7.13 (d, 2H), 7.64 (d, 2H), 7.94 (d, 2H), 8.82(d, 2H), 11.2 (br s, 1H), 11.4 (br s, References:
1 Rickter, L. S.; Desai, M. C. Tetrahedron Letters, 1997, 38, 321–322.

The subject compounds of the present invention were tested for biological activity according to the following procedures.

In Vitro Gelainase Assay

The assay is based on the cleavage of the thiopeptide substrate ((Ac-Pro-Leu-Gly(2 mercapto-4 methyl-pentanoyl)-Leu-Gly-OEt), Bachem Bioscience) by the enzyme, gelatinase, releasing the substrate product which reacts calorimetrically with DTNB ((5,5'-dithio-bis(2-nitrobenzoic acid)). The enzyme activity is measured by the rate of the color increase.

The thiopeptide substrate is made up fresh as a 20 mM stock in 100% DMSO and the DTNB is dissolved in 100% DMSO as a 100 mM stock and stored in dark at room temperature. Both the substrate and DTNB are diluted together to 1 mM with substrate buffer (50 mM HEPES pH 7.5, 5 mM CaCl$_2$) before use. The stock of human neutrophil gelatinase B is diluted with assay buffer (50 mnM HEPES pH 7.5, 5 mM CaCl$_2$, 0.02% Brij) to a final concentration of 0.15 mnM.

The assay buffer, enzyme, DTNB/substrate (500 μM final concentration) and vehicle or inhibitor are added to a 96 well plate (total reaction volume of 200 μl) and the increase in color is monitored spectrophotometrically for 5 minutes at 405 nm on a plate reader.

The increase in OD$_{405}$ is plotted and the slope of the line is calculated which represents the reaction rate.

The linearity of the reaction rate is confirmed ($r^2$>0.85). The mean (x±sem) of the control rate is calculated and compared for statistical significance (p<0.05) with drug-treated rates using Dunnett's multiple comparison test Dose-response relationships can be generated using multiple doses of drug and IC$_{50}$ values with 95% CI are estimated using linear regression (IPRED, HTB).

References: Weingarten, H and Feder, J., Spectrophotometric assay for vertebrate collagenase, Anal. Biochem. 147,437440 (1985).

In Vitro Collazenase Assay

The assay is based on the cleavage of a peptide substrate ((Dnp-Pro-Cha-Gly-Cys(iNe)-His-Ala-Lys(NMa)-NH$_2$), Peptide International, Inc.) by collag,enase releasing the fluorescent NMa group which is quantitated on the fluorometer. Dnp quenches the NiIa fluorescence in the intact substrate. The assay is run in HCBC assay buffer (50 ImM HEPES, pH 7.0, 5 mM Ca$^{+2}$, 0.02% Brij, 0.5% Cysteine), with human recombinant fibroblast collagenase (truncated, mw=18,828, WAR, Radnor). Substrate is dissolved in methanol and stored frozen in 1 mM aliquots. Collagenase is stored frozen in buffer in 25 M aliquots. For the assay, substrate is dissolved in HCBC buffer to a final concentration of 10 μM and collagenase to a final concentration of 5 nM. Compounds are dissolved in methanol, DMSO, or HCBC. The methanol and DMSO are diluted in HCBC to <1.0%. Compounds are added to the 96 well plate containing enzyme and the reaction is started by the addition of substrate.

The reaction is read (excitation 340 nm, emission 444 nm) for 10 min. and the increase in fluorescence over time is plotted as a linear line. The slope of the line is calculated and represents the reaction rate.

The linearity of the reaction rate is confirmed ($r^2$>0.85). The mean (x±sem) of the control rate is calculated and compared for statistical significance (p<0.05) with drug-treated rates using Dunnett's multiple comparison test. Dose-response relationships can be generated using multiple doses of drug and IC$_{50}$ values with 95% CI are estimated using linear regression (IPRED, HTB).

References: Bickett, D. M. et al., A high throughput fluorogenic substrate for interstitial collagenase (MMp-1) and gelatinase (MMP-9), Anal. Biochem. 212,58–64 (1993).

Procedure for Measuring TACE Ambition

Using 96-well black microtiter plates, each well receives a solution composed of 10 μL TACE (Inmunex, final concentration 1 μg/mL), 70 μL Tris buffer, pH 7.4 containing 10% glycerol (final concentration 10 mM), and 10 μL of test compound solution in DMSO (final concentration 1 μM, DMSO concentration <1%) and incubated for 10 minutes at room temperature. The reaction is initiated by addition of a fluorescent peptidyl substrate (final concentration 100 μM to each well and then shaking on a shaker for 5 sec.

The reaction is read (excitation 340 nm, emission 420 nm) for 10 min. and the increase in fluorescence over time is plotted as a linear line. The slope of the line is calculated and represents the reaction rate.

The linearity of the reaction rate is confined ($r^2 > 0.85$). The mean (xtsem) of the control rate is calculated and compared for statistical significance ($p < 0.05$) with drug-treated rates using Dunnett's multiple comparison test. Dose-response relationships can be generate using multiple doses of drug and $IC_{50}$ values with 95% CI are estimated using linear regression The results obtained following these standard experimental test procedures are presented in the following table.

| | IC 50 (nM or % inhibition at 1 micromolar or 10 micromolar (*)) | | | |
|---|---|---|---|---|
| Example | MMP 1 | MMP 9 | MMP 13 | TACE |
| 1 | NT | 559.6 | 193.3 | 31.62% |
| 2 | NT | 10.50% | 0% | 403 |
| 3 | NT | 308.9 | 169.4 | 27.43% |
| 4 | 371 | 22.20% | 17.10% | 21% |
| 5 | NT | 7.7 | 4.7 | 25% |
| 6 | 267 | 21.4 | 15.6 | 40.43% |
| 7 | 844 | 72.9 | 42.1 | 33% |
| 8 | NT | 346 | 307.9 | 47% |
| 9 | 313 | 107 | NT | 20.30% |
| 10 | 8% | 128 | 64 | 54.75% |
| 11 | 18.80% | 2925 | 319 | 942 |
| 12 | 100 | 10.8 | 11 | 15.50% |
| 13 | 239 | 11 | 14 | 626 |
| 14 | 158 | 23 | 8 | 17.18% |
| 15 | 285 | 17 | 4 | 137 |
| 16 | 325 | 9 | 24 | 180 |
| 17 | 238.6 | 8.9 | 1.4 | 41.00% |
| 18 | 540 | 18.9 | 11.5 | 29.2% |
| 19 | 446 | 95.8 | 4.8 | 33.1% |
| 20 | 423 | 14.6 | 18.7 | 31% |
| 21 | 318 | 13.2 | 15.3 | 39% |
| 22 | 219 | 3.2 | 2.5 | 30% |
| 23 | 593 | 7.9 | 4.0 | 40.6% |
| 24 | 413 | 20.9 | 31.3 | 47.5 |
| 25 | 262 | 26.7 | 8.0 | NT |
| 26 | 304.6 | 6.3 | 3.2 | 34.6 |
| 27 | 629 | 106 | 30.1 | NT |
| 28 | 761 | 3.1 | 2.0 | 30.6% |
| 29 | 297 | 4.3 | 3.6 | 41% |
| 30 | 397 | 8.1 | 5.7 | 25.2% |
| 31 | 162 | 15.2 | 5.7 | 688 |
| 32 | 13.7 | 3.7 | 1.0 | NT |
| 33 | 318 | 53.9 | 18.4 | 23.9% |
| 34 | 519.8 | 34.7 | 26.1 | 28.1% |
| 35 | 455.8 | 233.6 | 48.2 | 44.9 |
| 36 | 622 | 83.8 | 20.7 | 826 |
| 37 | 9% | 31.6% | 14.3% | 87 |
| 38 | 48.3% | 1.7% | 5.8% | 55.1% |
| 39 | 29.4% | 35.2% | 26.6% | 69.4 |
| 40 | 583 | 197 | 14 | 160 |
| 41 | 100 | 10.8 | 11 | 15.50% |
| 42 | 262 | 50.9 | 6.2 | 36.5 |
| 43 | 66.1% | 34.7% | 55.5% | 46.6% |
| 44 | 47.1% | 36.9% | 39.5% | 14.9% |
| 45 | 49% | 48.6% | 36.7% | 20.4% |
| 46 | 78.9% | 79.12% | 84.7% | 1.4% |
| 47 | 17.1% | 12.9% | 7.12% | 3.3% |
| 48 | 99.1% | 79.1% | 85.4% | 51.1% |
| 49 | 10.1% | 23.7% | 54.6% | NT |
| 50 | 51.1 | 58.4 | 10.6 | NT |
| 51 | 178.1 | 10.4 | 13.1 | 48.14% |
| 52 | 139.3 | 7.9 | 9.1 | NT |
| 53 | 647.9 | 27.80% | 188 | 52.57% |
| 54 | 110 | 66 | 21 | 55.10% |
| 55 | 303 | 10 | 7 | 21.70% |
| 56 | 299 | 16 | 12 | 65% |
| 57 | 258 | 332 | 191 | 16.57% |
| 58 | 211 | 35 | 39 | 7.70% |
| 59 | 30.20% | 447 | 141 | 24.86% |
| 60 | NT | 184 | NT | 23.60% |
| 61 | 258 | 38 | 22 | 17.21% |
| 62 | 522 | 174 | 43 | 669 |
| 63 | 156 | 9 | 3 | 203 |
| 64 | 40.90% | 25.60% | 36.70% | 29.70% |
| 65 | 1000 | 63 | 13 | 42.21% |
| 66 | 1600 | 131 | 226 | 42.33% |
| 67 | 364 | 2.3 | 43.7 | 690 |
| 68 | 297 | 29 | 27 | 522 |
| 69 | 574.5 | 120.2 | 90 | 41.32% |
| 70 | 1139 | 88.80% | 127 | 764 |
| 71 | 1000 | 63 | 13 | 42.21% |
| 72 | 117 | 11 | 1 | 51.64% |
| 73 | 300 | 141 | 12 | 20.17% |
| 74 | 138.1 | 9.2 | 4.3 | 47.86% |
| 75 | 672.3 | 83.4 | 32.7 | 23.77% |
| 76 | 805 | NT | 500 | NT |
| 77 | 205.5 | NT | 170 | NT |
| 78 | 262 | 560 | 34 | 24.58% |
| 79 | 25 | 0.54 | 0.4 | 805 |
| 80 | 22.1% | 26% | 63.6% | 191 |
| 81a | 2036 | 230.9 | 43.9 | 27.1 |
| 81b | 3765 | 154 | 15.7 | 228 |
| 82 | 237.6 | 19.4 | 5.1 | 34.5% |
| 83 | 492 | 10.2 | 2.0 | 229 |
| 84 | 519 | 8.8 | 2.0 | 213 |
| 85 | 450 | 5.8 | 1.5 | 115 |
| 86 | 494 | 16.8 | 1.5 | 222 |
| 87 | 368 | 5.0 | 1.6 | 170.7 |
| 88 | 1329 | 12.8 | 3.1 | 610 |
| 89 | 1389 | 38.6 | 7.0 | 49% |
| 90 | 598 | 10.3 | 2.2 | 71.9 |
| 91 | 1929 | 13.3 | 10.8 | 503 |
| 92 | 59.6% | 649 | 148 | 9.7 |
| 93 | 56.3% | 452 | 38 | 15.8% |
| 94 | 2640 | 138 | 28.6 | 22.9 |
| 95 | 3681 | 364 | 33.1 | 25.4% |
| 96 | 4437 | 374 | 33.8 | 18.1 |
| 97 | 5109 | 484 | 43.7 | 20.20% |
| 98 | 2383 | 3.8 | 1.2 | 154 |
| 99 | 656 | 16.2 | 2.4 | 250 |
| 100 | 4729 | 19.1 | 5.3 | 39.5% |
| 101 | 642 | 12.3 | 2.1 | 197 |
| 102 | 662 | 33.7 | 1.9 | 53% |
| 103 | 1306 | 45.1 | 8.8 | 470 |
| 104 | 2610 | 3.1 | 1.4 | 208 |
| 105 | 1214 | 44.2 | 4.1 | 50.2% |
| 106 | 3788 | 5.1 | 0.9 | 631 |
| 107 | 629 | 26.8 | 2.5 | 293 |
| 108 | 2896 | 5.4 | 1.7 | 270 |
| 109 | 393 | 2.7 | 2.5 | 386 |
| 241 | 48.2%* | 2.7 | 15.8 | 277 |
| 242 | 1950 | 2 | 1.3 | 581 |
| 243 | 2181 | 1.9 | 1.5 | 506 |
| 244 | 3417 | 9.8 | 1.5 | 594 |
| 245 | 7062 | 43.4 | 2.2 | 51.95%* |
| 246 | 50.30%* | 28.3 | 2.4 | 880 |
| 249 | 1412 | 2 | 1.6 | 270 |
| 250 | 1717 | 1.6 | 0.8 | 413 |
| 251 | 1067 | 0.8 | 0.9 | 301 |
| 252 | 801 | 1.1 | 0.9 | 278 |
| 255 | 2558 | 3.6 | 1.5 | 565 |
| 256 | 10000 | 7.2 | 2.9 | 43.01%* |
| 259 | 3160 | 14.3 | 5.3 | 39%* |
| 260 | 1495 | 2.9 | 1.3 | 272 |
| 261 | 513 | 10.9 | 2.7 | 273 |
| 262 | 422 | 6.1 | 2.3 | 298 |
| 263 | 3669 | 20.3 | 5.2 | 57.70%* |
| 264 | 4293 | 2.9 | 3.1 | 182 |
| 265 | 1944 | 9.3 | 7.8 | 1037 |
| 266 | 4746 | 6 | 5.7 | 421 |
| 267 | 3620 | 5.4 | 2.3 | 508 |

-continued

IC 50 (nM or % inhibition at 1 micromolar or 10 micromolar (*))

| Example | MMP 1 | MMP 9 | MMP 13 | TACE |
|---------|-------|-------|--------|------|
| 268 | 2292 | 2.8 | 1.1 | 278 |
| 269 | 2071 | 2.2 | 1.4 | 296 |

Compounds prepared by solid phase synthesis Data: for Examples 110 to 240

| Example No | MMP 1 | MMP 9 | MMP 13 % inhibition at 0.2 μM (HTS) | MMP 13 % inhibition at 0.2 μM (manual) | TACE % inhibition at 1 mM |
|---|---|---|---|---|---|
| 110 | | | 75 | | 17.6 |
| 111 | | | 10 | | 40.4 |
| 112 | | | 50 | | 33.7 |
| 113 | | | 0 | | 13.1 |
| 114 | | | 0 | | 0 |
| 115 | | | 0 | | 0 |
| 116 | | | 0 | | 9.1 |
| 117 | | | 7 | | 8.1 |
| 118 | | | 24 | | 16.7 |
| 119 | | | 0 | | 7.8 |
| 120 | | | 31 | | 19.9 |
| 121 | | | 0 | | 6.1 |
| 122 | | | 0 | | 3.1 |
| 123 | | | 0 | | 2.5 |
| 124 | | | 0 | | 0 |
| 125 | | | 5 | | 2.3 |
| 126 | | | 25 | | 10.4 |
| 127 | | | 47 | | 29.2 |
| 128 | 1.9 mM | 213 nM | 91 | 255 nM | 19.31 |
| 129 | | | 90 | | 32.77 |
| 130 | | | 28 | | 27.9 |
| 131 | | | 71 | | 20.73 |
| 132 | | | 71 | | 20.76 |
| 133 | | | 53 | | 22.04 |
| 134 | | | 25 | | −9.31 |
| 135 | | | 79 | | 42.67 |
| 136 | | | 89 | | 42.69 |
| 137 | | | 83 | | 13.35 |
| 138 | | | 20 | | 5.284 |
| 139 | | | 8 | | 28.05 |
| 140 | | | 29 | | −4.22 |
| 141 | | | 32 | | 11.76 |
| 142 | | | 69 | | 54.27 |
| 143 | | | 53 | | 43.9 |
| 144 | | | 38 | | 19.7 |
| 145 | | | 45 | | 2.5 |
| 146 | | | 68 | | 7.317 |
| 147 | | | 73 | | 11.95 |
| 148 | | | 15 | | 43.46 |
| 149 | | | 13 | | 4.408 |
| 150 | | | 54 | | 1.818 |
| 151 | | | 6 | | 5.927 |
| 152 | | | 9 | | 10.03 |
| 153 | | | 12 | | 11.8 |
| 154 | | | 89 | | 13.14 |
| 155 | | | 31 | | −18.62 |
| 156 | | | 23 | | −2.09 |
| 157 | | | 19 | | 13.7 |
| 158 | | | 33 | | −7.48 |
| 159 | | | 49 | | 5.852 |
| 160 | | | 14 | | −3.57 |
| 161 | | | 0 | | 12.7 |
| 162 | | | 13 | | 0 |
| 163 | | | 84 | | 9.515 |
| 164 | | | 74 | | 62.69 |
| 165 | | | 71 | | 73.7 |
| 166 | | | 9 | | 4.16 |
| 167 | | | 27 | | 8.961 |
| 168 | | | 21 | | 3.688 |

| Example No. | MMP 13 % inhibition at 36 nM (HTS) | MMP 13 % inhibition at 0.36 mM (HTS) | MMP 13 % inhibition at 3.6 mM (HTS) | TACE IC$_{50}$ nM | TACE % inhibition at 1 mM |
|---|---|---|---|---|---|
| 169 | 28 | 40 | 72 | | 41.7 |
| 170 | 32 | 49 | 90 | | 25.5 |
| 171 | 31 | 38 | 48 | | 16.6 |
| 172 | 34 | 32 | 42 | | 29.4 |
| 173 | 18 | 46 | 56 | | 25.5 |
| 174 | 10 | 19 | 40 | | 27.7 |
| 175 | 16 | 20 | 37 | | 32.9 |
| 176 | 6 | 5 | 16 | | 26.6 |
| 177 | 5 | 1 | 9 | | 38.5 |
| 178 | −10 | 74 | 39 | | 26 |
| 179 | 12 | 32 | 60 | | 42.7 |
| 180 | 14 | 19 | 45 | | 34.4 |
| 181 | 6 | 35 | 62 | | 15.7 |
| 182 | −9 | −8 | 7 | | 28.6 |
| 183 | −6 | 12 | 70 | | 34.6 |
| 184 | 16 | 24 | 44 | | 24.8 |
| 185 | 9 | 0 | 23 | | 7.21 |
| 186 | −14 | −4 | 35 | | 19.5 |
| 187 | −14 | −12 | 20 | | 85.5 |
| 188 | −27 | −24 | 4 | | 16.2 |
| 189 | −30 | −18 | −9 | | 14. |
| 190 | −35 | −28 | −13 | | 38.3 |
| 191 | −45 | −3 | 22 | | 2.9 |
| 192 | −32 | 5 | 61 | | 33.2 |
| 193 | −32 | −15 | 56 | | 14.9 |
| 194 | −17 | −8 | 5 | | 5.4 |
| 195 | −9 | −2 | 10 | | 27.0 |
| 196 | −18 | 1 | 11 | | 35.7 |
| 197 | −33 | −26 | −3 | | 17.8 |
| 198 | −39 | −7 | 15 | | 17.1 |
| 199 | −10 | −7 | 30 | | −1.0 |
| 200 | | | | | 37.9 |
| 201 | | | | | 50.9 |
| 202 | | | | | 10.6 |
| 203 | | | | | 32.8 |
| 204 | | | | | 7.75 |
| 205 | | | | | 84.0 |
| 206 | | | | | 89.8 |
| 207 | | | | | −6.3 |
| 208 | | | | | 67.7 |
| 209 | | | | | 31.2 |
| 210 | | | | | 52.2 |
| 211 | | | | | 20.7 |
| 212 | | | | | 56.0 |
| 213 | | | | | −17.5 |
| 214 | | | | | 11.03 |
| 215 | | | | 895 | 60.12 |
| 216 | | | | | 2.49 |
| 217 | | | | | 55.1 |
| 218 | | | | 380 | 68.7 |
| 219 | | | | | 7.3 |
| 220 | | | | 256 | 53.1 |
| 221 | | | | 146 | 98.9 |
| 222 | | | | 212 | 89.3 |
| 223 | | | | 226 | 107.3 |
| 224 | | | | 404 | 75.0 |

-continued

| Example No. | MMP 13 % inhibition at 36 nM (HTS) | MMP 13 % inhibition at 0.36 mM (HTS) | MMP 13 % inhibition at 3.6 mM (HTS) | TACE IC$_{50}$ nM | TACE % inhibition at 1 mM |
|---|---|---|---|---|---|
| 225 |  |  |  | 96.6 | 114.3 |
| 226 | 28 | 22 | 28 |  | 2.2 |
| 227 | 15 | −16 | −22 |  | 7.3 |
| 228 | 37 | 28 | 65 |  | 6.8 |
| 229 | 29 | 17 | 33 |  | 34.4 |
| 230 | 29 | 31 | 26 | 700 | 72.1 |
| 231 | 23 | 13 | 5 |  | 41.6 |
| 232 | 30 | 17 | 42 |  | 20.8 |
| 233 | 33 | 29 | 46 |  | 19.8 |
| 234 | 26 | 28 | 40 |  | 18.4 |
| 235 | 59 | 70 | 70 |  | 48.3 |
| 236 | 44 | 44 | 64 |  | 35 |
| 237 | 55 | 65 | 72 |  | 38.2 |
| 238 | 22 | 11 | 24 | 930 | 54.4 |
| 239 | 54 | 74 | 83 |  | 45.9 |
| 240 | 48 | 51 | 46 |  | 40.3 |

Compounds of this invention may be administered neat or with a pharmaceutical carrier to a patient need thereof. The pharmaceutical carrier may be solid or liquid.

Applicable solid carriers can include one or more substances which may also act as flavoring agents, lubricants, solubilizers, suspending agents, fillers, glidants, compression aids or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such a solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferable sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

The compounds of this invention may be administered rectally in the form of a conventional suppository. For administration by intranasal ror intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semi-solid emulsions of either the oil in water or water in oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient Other occlusive devices are known in the literature.

The dosage to be used in the treatment of a specific patient suffering from a disease or condition in which MMPs and TACE are involved must be subjectively determined by the attending physician. The variables involved include the severity of the dysfunction, and the size, age, and response pattern of the patient. Treatment will generally be initiated with small dosages less than the optimum dose of the compound. Thereafter the dosage is increased until the optimum effect under the circumstances is reached. Precise dosages for oral, parenteral, nasal, or intrabronchial administration will be determined by the administering physician based on experience with the individual subject treated and standard medical principles.

Preferably the pharmaceutical composition is in unit dosage form, e.g., as tablets or capsules. In such form, the composition is subdivided in unit dose containing appropriate quantities of the active ingredient; the unit dosage form can be packaged compositions, for example packed powders, vials, ampoules, prefilled syringes or sachets containing liquids. The unit dosage form can be, for example, a capsule or tablet itself, or it can be the appropriate number of any such compositions in package form.

What is claimed is:

1. A compound according to formula I

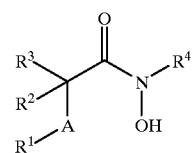

I wherein:
R$^1$ is alkyl of 1 to 18 carbon atoms, optionally substituted with one or two groups selected independently from R$^5$;
alkenyl of 3 to 18 carbon atoms having 1 to 3 double bonds, optionally substituted with one or two groups selected independently from R$^5$;
alkynyl of 3 to 18 carbon atoms having 1 to 3 triple bonds, optionally substituted with one or two groups selected independently from R$^5$;
aryl of 6 to 10 carbon atoms, optionally substituted with one or two groups selected independently from R$^5$;

cycloalkyl of 3 to 8 carbon atoms, optionally substituted with one or two groups selected independently from $R^5$;

saturated or unsaturated 5 to 10 membered mono or bicyclic heterocycle containing one heteroatom selected from O, S or $NR^7$, optionally substituted with one or two groups selected independently from $R^5$;

or heteroaryl-$(CH_2)_{0-6}$- wherein the heteroaryl group is 5 to 6 membered with one or two heteroatoms selected independently from O, S, and N and may be optionally substituted with one or two groups selected independently from $R^5$;

A is —S—, —SO— or $SO_2$—;

$R^2$ and $R^3$, taken with the carbon atom to which they are attached, form a 5 to 7 membered heterocyclic ring containing O, S or N—$R^7$ optionally having one or two double bonds;

$R^4$ is hydrogen,
alkyl of 1 to 6 carbon atoms, optionally substituted with one or two groups selected independently from $R^5$;
alkenyl of 3 to 18 carbon atoms having 1 to 3 double bonds, optionally substituted with one or two groups selected independently from $R^5$;
alkynyl of 3 to 18 carbon atoms having 1 to 3 triple bonds, optionally substituted with one or two groups selected independently from $R^5$;
phenyl or naphthyl optionally substituted with one or two groups selected independently from $R^5$;
$C_3$ to $C_8$ cycloalkyl or bicycloalkyl optionally substituted with one or two groups selected independently from $R^5$;
saturated or unsaturated 5 to 10 membered mono or bicyclic heterocycle containing one heteroatom selected from O, S or $NR^7$, optionally substituted with one or two groups selected independently from $R^5$;

$R^5$ is H, $C_7$–$C_{11}$ aroyl, $C_2$–$C_6$ alkanoyl, $C_1$ to $C_{12}$ alkyl, $C_2$ to $C_{12}$ alkenyl, $C_2$–$C_{12}$ alkynyl, F, Cl, Br, I, CN, CHO, $C_1$–$C_6$ alkoxy, aryloxy, heteroaryloxy, $C_3$–$C_6$ alkenyloxy, $C_3$–$C_6$ alkynyloxy, $C_1$–$C_6$ alkoxyaryl, $C_1$–$C_6$ alkoxyheteroaryl, $C_1$–$C_6$ alkylamino-$C_1$–$C_6$ alkoxy, $C_1$–$C_2$ alkylene dioxy, aryloxy-$C_1$–$C_6$ alkyl amine, $C_1$–$C_{12}$ perfluoro alkyl, $S(O)_n$—$C_1$–$C_6$ alkyl, $S(O)_n$-aryl where n is 0, 1 or 2; OCOO $C_1$–$C_6$ alkyl, OCOaryl, OCONR$^6$, COOH, COO $C_1$–$C_6$ alkyl, COaryl, CONR$^6$R$^6$, CONHOH, NR$^6$R$^6$, $SO_2$NR$^6$R$^6$, NR$^6SO_2$aryl, —NR$^6$CONR$^6$R$^6$, NHSO$_2$CF$_3$, SO$_2$NHheteroaryl,SO$_2$NHCOaryl, CONHSO$_2$-$C_1$–$C_6$ alkyl, CONHSO$_2$aryl, SO$_2$NHCOaryl, CONHSO$_2$-$C_1$–$C_6$ alkyl, CONHSO$_2$aryl, NH$_2$, OH, aryl, heteroaryl, $C_3$ to $C_8$ cycloalkyl; or saturated or unsaturated 5 to 10 membered mono or bicyclic heterocycle containing one heteroatom selected from O, S or $NR^7$, wherein $C_1$–$C_6$ alkyl is straight or branched, heteroaryl is a 5–10 membered mono or bicyclic heteroaryl group having 1 to 3 heteroatoms selected independently from O, S or $NR^7$ and aryl is phenyl or naphthyl, optionally substituted by 1 or 2 groups selected from halogen, cyano, amino, nitro, $C_1$–$C_6$ alkyl, $C_1$–$C_6$ alkoxy, or hydroxy;

$R^6$ is H, $C_1$ to $C_{18}$ alkyl optionally substituted with OH; $C_3$ to $C_6$ alkenyl, $C_3$ to $C_6$ alkynyl, $C_1$ to $C_6$ perfluoro alkyl, $S(O)_n$—$C_1$–$C_6$ alkyl $S(O)n$ aryl where n is 0, 1 or 2; or COheteroaryl, wherein heteroaryl is a 5–10 membered mono or bicyclic heteroaryl group having 1 to 3 heteroatoms selected independently from 0, S or $NR^7$ and aryl is phenyl or naphthyl, optionally substituted by 1 or 2 groups selected from halogen, cyano, amino, nitro, $C_1$–$C_6$ alkyl, $C_1$–$C_6$ alkoxy, or hydroxy;

and $R^7$ is $C_7$-$C_{11}$ aroyl, $C_2$–$C_6$ alkanoyl, $C_1$–$C_{12}$ perfluoro alky, $S(O)_n$-$C_1$–$C_6$-alkyl, $S(O)_n$- aryl where n is 0, 1 or 2; COO-$C_1$–$C_6$-alkyl, COOaryl, CONHR$^6$, CONR$^6$R$^6$, CONHOH, SO$_2$NR$^6$R$^6$, SO$_2$CF$_3$, SO$_2$NHheteroaryl, SO$_2$NHCOaryl, CONHSO-$C_1$-$C_6$-alkyl, CONHSO$_2$aryl, aryl, or heteroaryl, where aryl is phenyl or naphthyl, optionally substituted by 1 or 2 groups selected independently from halogen, cyano, amino, nitro, $C_1$–$C_6$ alkyl, $C_1$–$C_6$ alkoxy, or hydroxy; and heteroaryl is a 5–10 membered mono or bicyclic heteroaryl group having 1 to 3 heteroatoms selected independently from O, S or N-$C_1$-$C_6$ alkyl;

alkyl of 1 to 18 carbon atoms, optionally substituted with one or two groups selected independently from $R^5$;

alkenyl of 3 to 18 carbon atoms having from 1 to 3 double bonds, optionally substituted with one or two groups selected independently from $R^5$;

alkynyl of 3 to 18 carbon atoms having from 1 to 3 triple bonds, optionally substituted with one or two groups selected independently from $R^5$;

arylalkyl of 7 to 16 carbon atoms, wherein aryl is optionally substituted with one or two groups selected independently from $R^5$;

heteroarylalkyl wherein alkyl is from 1 to 6 carbon atoms and heteroaryl contains 1 or 2 heteroatoms selected from O, S or N and is optionally substituted with one or two groups selected independently from $R^5$;

biphenylalkyl of 13 to 18 carbon atoms, wherein biphenyl is optionally substituted with one or two groups selected independently from $R^5$;

arylalkenyl of 8 to 16 carbon atoms, wherein aryl is optionally substituted with one or two groups selected independently from $R^5$;

cycloalkylalkyl or bicycloalkylalkyl of 4 to 12 carbon atoms, wherein the cycloalkyl or bicycloalkyl group is optionally substituted with one or two groups selected independently from $R^5$;

saturated or unsaturated mono or bicyclic heterocycle containing one heteroatom selected from O, S or N-$C_1$–$C_6$ alkyl, optionally substituted with one or two groups selected independently from $R^5$; or $R^8R^9$N-$C_1$-$C_6$-alkoxyaryl-$C_1$–$C_6$-alkyl where $R^8$ and $R^9$ are independently selected from $C_1$–$C_6$ alkyl or $R^8$ and $R^9$ together with the interposed nitrogen forms a 5–7 membered saturated heterocyclic ring optionally containing an oxygen atom, wherein the aryl group is phenyl or naphthyl;

or a pharmaceutically acceptable salt thereof.

2. A compound according to claim 1 wherein:

$R^1$ is alkyl of 1 to 18 carbon atoms, optionally substituted with one or two groups selected independently from $R^5$;

alkenyl of 3 to 18 carbon atoms having 1 to 3 double bonds, optionally substituted with one or two groups selected independently from $R^5$;

alkynyl of 3 to 18 carbon atoms having 1 to 3 triple bonds, optionally substituted with one or two groups selected independently from $R^5$;

aryl of 6 to 10 carbon atoms, optionally substituted with one to two groups selected independently from $R^5$;

cycloalkyl of 3 to 8 carbon atoms, optionally substituted with one to two groups selected independently from $R^5$;

saturated or unsaturated mono or bicyclic heterocycle of from 5 to 10 members containing one heteroatom selected from O, S or $NR^7$, optionally substituted with one to two groups selected independently from $R^5$;

or heteroaryl-$(CH_2)_{0-6}$- wherein the heteroaryl group is 5 to 6 membered with one or two heteroatoms selected independently from O, S, and N and may be optionally substituted with one or two groups selected independently from $R^5$;

A is —S—, —SO— or $SO_2$—;

$R^2$ and $R^3$, taken with the carbon atom to which they are attached, form a 5 to 7 membered heterocyclic ring containing O, S or N—$R^7$ optionally having one or two double bonds;

$R^4$ is hydrogen,
alkyl of 1 to 6 carbon atoms, optionally substituted with one or two groups selected independently from $R^5$;
alkenyl of 3 to 18 carbon atoms having 1 to 3 double bonds, optionally substituted with one or two groups selected independently from $R^5$;
alkynyl of 3 to 18 carbon atoms having 1 to 3 triple bonds, optionally substituted with one or two groups selected independently from $R^5$;
phenyl or naphthyl optionally substituted with one or two groups selected independently from $R^5$;
$C_3$ to $C_8$ cycloalkyl or bicycloalkyl optionally substituted with one or two groups selected independently from $R^5$;

$R^5$ is H, F, Cl, Br, I, CN, CHO, $C_7$-$C_{11}$ aroyl, $C_2$-$C_6$ alkanoyl, $C_1$ to $C_{12}$ alkyl, $C_2$ to $C_{12}$ alkenyl, $C_2$-$C_{12}$ alkynyl, $C_1$-$C_6$ alkoxy, aryloxy, heteroaryloxy, $C_3$-$C_6$ alkenyloxy, $C_3$-$C_6$ alkynyloxy, $C_1$-$C_6$ alkoxyaryl, $C_1$-$C_6$ alkoxyheteroaryl, $C_1$-$C_6$-alkylamino-$C_1$-$C_6$ alkoxy, $C_1$-$C_2$-alkylene dioxy, aryloxy-$C_1$-$C_6$ alkyl amine, $C_1$-$C_{12}$ perfluoro alkyl, $S(O)_n$-$C_1$-$C_6$ alkyl, $S(O)_n$-aryl where n is 0, 1 or 2; $OCOO$-$C_1$-$C_6$ alkyl, OCOOaryl, $OCONR^6$, COOH, COO-$C_1$-$C_6$ alkyl, COOaryl, $CONR^6R^6$, CONHOH, $NR^6R^6$, $SO_2NR^6R^6$, $NR^6SO_2aryl$, $NR^6CONR^6R^6$, $NHSO_2CF_3$, $SO_2NH$heteroaryl, $SO_2NHCO$aryl, $CONHSO_2$-$C_1$-$C_6$ alkyl, $CONHSO_2$aryl, $NH_2$, OH, aryl, heteroaryl, $C_3$ to $C_8$ cycloalkyl; or saturated or unsaturated 5 to 10 membered mono or bicyclic heterocycle containing one heteroatom selected from O, S or $NR^7$;

wherein heteroaryl is a 5–10 membered mono or bicyclic heteroaryl group having 1 to 3 heteroatoms selected independently from O, S or $NR^7$ and aryl is phenyl or naphthyl, optionally substituted by 1 or 2 groups selected independently from halogen, cyano, amino, nitro, $C_1$-$C_6$ alkyl, $C_1$-$C_6$ alkoxy, or hydroxy;

$R^6$ is H, $C_1$ to $C_{18}$ alkyl optionally substituted with OH; $C_3$ to $C_6$ alkenyl, $C_3$ to $C_6$ alkynyl, $C_1$ to $C_6$ perfluoro alkyl, S(O), alkyl or aryl where n is 0, 1, or 2; or COheteroaryl;

wherein heteroaryl is a 5–10 membered mono or bicyclic heteroaryl group having 1 to 3 heteroatoms selected independently from O, S or $NR^7$ and aryl is phenyl or naphthyl, optionally substituted by 1 or 2 groups selected from halogen, cyano, amino, nitro, $C_1$-$C_6$ alkyl, $C_1$-$C_6$ alkoxy, or hydroxy;

and $R^7$ is $C_7$-$C_{11}$ aroyl, $C_2$-$C_6$ alkanoyl, $C_1$-$C_{12}$ perfluoro alkyl, $S(O)_n$-alkyl, $S(O)_n$-aryl where n is 0, 1 or 2; COOalkyl, COOaryl, $CONHR^6$, $CONR^6R^6$, CONHOH, $SO_2NR^6R^6$, $SO_2CF_3$, $SO_2NH$heteroaryl, $SO_2NHCO$aryl, $CONHSO_2$alkyl, $CONHSO_2$aryl, aryl, heteroaryl; wherein $C_1$-$C_6$ alkyl is straight or branched, heteroaryl is a 5–10 membered mono or bicyclic heteroaryl group having 1 to 3 heteroatoms selected independently from 0, S or $NR^7$ and aryl is phenyl or naphthyl, optionally substituted by 1 or 2 groups selected from halogen, cyano, amino, nitro, $C_1$-$C_6$ alkyl, $C_1$-$C_6$ alkoxy, or hydroxy;

alkyl of 1 to 18 carbon atoms, optionally substituted with one or two groups selected independently from $R^5$;

alkenyl of 3 to 18 carbon atoms having from 1 to 3 double bonds, optionally substituted with one or two groups selected independently from $R^5$;

alkynyl of 3 to 18 carbon atoms having from 1 to 3 triple bonds, optionally substituted with one or two groups selected independently from $R^5$;

arylalkyl of 7 to 16 carbon atoms, wherein aryl is optionally substituted with one or two groups selected independently from $R^5$;

heteroarylalkyl wherein alkyl is from 1 to 6 carbon atoms and heteroaryl contains 1 or 2 heteroatoms selected from O, S or N and is optionally substituted with one or two groups selected independently from $R^5$;

biphenylalkyl of 13 to 18 carbon atoms, wherein biphenyl is optionally substituted with one or two groups selected independently from $R^5$;

arylalkenyl of 8 to 16 carbon atoms, wherein aryl is optionally substituted with one or two groups selected independently from $R^5$;

cycloalkylalkyl or bicycloalkylalkyl of 4 to 12 carbon atoms, wherein cycloalkyl or bicycloalkyl is optionally substituted with one or two groups selected independently from $R^5$;

saturated or unsaturated mono or bicyclic heterocycle containing one heteroatom selected from O, S or N-$C_1$-$C_6$ alkyl, optionally substituted with one or two groups selected independently from $R^5$;

$R^8R^9N$-$C_1$-$C_6$-alkoxyaryl-$C_1$-$C_6$-alkyl where $R^8$ and $R^9$ are independently selected from $C_1$-$C_6$ alkyl or $R^8$ and $R^9$ together with the interposed nitrogen forms a 5–7 membered saturated heterocyclic ring optionally containing an oxygen atom, wherein the aryl group is phenyl or naphthyl;

or a pharmaceutically acceptable salt thereof.

3. A compound according to claim 2 wherein $R^1$ is phenyl, naphthyl, alkyl of 1–18 carbon atoms or heteroaryl such as pyridyl, thienyl, imidazolyl or furanyl, optionally substituted with $C_1$-$C_6$ alkyl, $C_1$-$C_6$ alkoxy, $C_6$-$C_{10}$ aryloxy, heteroaryloxy, $C_3$-$C_6$ alkenyloxy, $C_3$-$C_6$ alkynyloxy, halogen; or $S(O)_n$-$C_1$-$C_6$alkyl $C_1$-$C_6$ alkoxyaryl or $C_1$-$C_6$ alkoxyheteroaryl;

A is —S—, O— or —$SO_2$—;

$R^2$ and $R^3$, taken with the carbon atom to which they are attached, form a 5 to 7 membered heterocyclic ring containing O, S or N—$R^7$ optionally having one or two double bonds;

$R^4$ is hydrogen,
alkyl of 1 to 6 carbon atoms, optionally substituted with one or two groups selected independently from $R^5$;
alkenyl of 3 to 18 carbon atoms having 1 to 3 double bonds, optionally substituted with one or two groups selected independently from $R^5$;
alkynl of 3 to 18 carbon atoms having 1 to 3 triple bonds, optionally substituted with one or two groups selected independently from $R^5$;

phenyl or naphthyl optionally substituted with one or two groups selected independently from $R^5$;

$C_3$ to $C_8$ cycloalkyl or bicycloalkyl optionally substituted with one or two groups selected independently from $R^5$;

$R^5$ is H, $C_7$-$C_{11}$ aroyl, $C_2$-$C_6$ alkanoyl, $C_1$ to $C_{12}$ alkyl, $C_2$ to $C_{12}$ alkenyl, $C_2$-$C_{12}$ alkynyl, F, Cl, Br, I, CN, CHO, $C_1$-$C_6$ alkoxy, aryloxy, heteroaryloxy, $C_3$-$C_6$ alkenyloxy, $C_3$-$C_6$ alkynyloxy, $C_1$-$C_6$ alkylamino-$C_1$-$C_6$ alkoxy, $C_1$-$C_2$ alkylene dioxy, aryloxy-$C_1$-$C_6$ alkyl amine, $C_1$-$C_{12}$ perfluoro alkyl,$S(O)_n$-$C_1$-$C_6$ alkyl, $S(O)_n$-aryl where n is 0, 1 or 2; OCOO $C_1$-$C_6$ alkyl, OCOOaryl, OCONR$^6$, COOH, COO $C_1$-$C_6$ alkyl, COOaryl, CONR$^6$R$^6$, CONHOH, NR$^6$R$^6$, SO$_2$NR$^6$R$^6$, NR$^6$SO$_2$aryl, —NR$^6$CONR$^6$R$^6$, NHSO$_2$CF$_3$, SO$_2$NHheteroaryl,SO$_2$NHCOaryl, CONHSO$_2$-$C_1$-$C_6$ alkyl, CONHSO$_2$aryl, SO$_2$NHCOaryl, CONHSO$_2$-$C_1$-$C_6$ alkyl, CONHSO$_2$aryl, NH$_2$, OH, aryl, heteroaryl, $C_3$ to $C_8$ cycloalkyl; saturated or unsaturated 5 to 10 membered mono or bicyclic heterocycle containing one heteroatom selected from O, S or NR$^7$, wherein $C_1$-$C_6$ alkyl is straight or branched, heteroaryl is a 5–10 membered mono or bicyclic heteroaryl group having 1 to 3 heteroatoms selected independently from O, S or NR$^7$ and aryl is phenyl or naphthyl, optionally substituted by 1 or 2 groups selected from halogen, cyano, amino, nitro, $C_1$-$C_6$ alkyl, $C_1$-$C_6$ alkoxy, or hydroxy;

$R^6$ is H, $C_1$ to $C_{18}$ alkyl optionally substituted with OH; $C_3$ to $C_6$ alkenyl, $C_3$ to $C_6$ alknyl, $C_1$ to $C_6$ perfluoro alkyl, $S(O)_n$alkyl or aryl where n is 0, 1 or 2; or COheteroaryl; wherein heteroaryl is a 5–10 membered mono or bicyclic heteroaryl group having 1 to 3 heteroatoms selected independently from O, S or NR$^7$ and aryl is phenyl or naphthyl, optionally substituted by 1 or 2 groups selected from halogen, cyano, amino, nitro, $C_1$-$C_6$ alky, $C_1$-$C_6$ alkoxy, or hydroxy;

and $R^7$ is $C_7$-$C_{11}$ aroyl, $C_2$-$C_6$ alkanoyl, $C_1$-$C_{12}$ perfluoro alkyl, $S(O)_n$-alkyl, $S(O)_n$-aryl where n is 0, 1 or 2; COOalkyl, COaryl, CONHR$^6$, CONR$^6$R$^6$, CONHOH, SO$_2$NR$^6$R$^6$,SO$_2$CF$_3$, SO$_2$iNheteroaryl, SO$_2$NHCOaryl, CONHSO$_2$alkyl, CONHSO$_2$aryl, aryl, or heteroaryl; where aryl is phenyl or naphthyl, optionally substituted by 1 or 2 groups selected independently from halogen, cyano, amino, nitro, $C_1$-$C_6$ alkyl, $C_1$-$C_6$ alkoxy, or hydroxy; and heteroaryl is a 5–10 membered mono or bicyclic heteroaryl group having 1 to 3 heteroatoms selected independently from O, S or N-$C_1$-$C_6$ alkyl; alkyl of 1 to 18 carbon atoms, optionally substituted with one or two groups selected independently from $R^5$;

alkenyl of 3 to 18 carbon atoms having from 1 to 3 double bonds, optionally substituted with one or two groups selected independently from $R^5$;

alkynyl of 3 to 18 carbon atoms having from 1 to 3 triple bonds, optionally substituted with one or two groups selected independently from $R^5$;

arylalkyl of 7 to 16 carbon atoms, optionally substituted with one or two groups selected independently from $R^5$;

heteroarylalkyl wherein alkyl is from 1 to 6 carbon atoms and heteroaryl contains 1 or 2 heteroatoms selected from O, S or N and is optionally substituted with one or two groups selected independently from $R^5$;

biphenylalkyl of 13 to 18 carbon atoms, optionally substituted with one or two groups selected independently from $R^5$;

arylalkenyl of 8 to 16 carbon atoms, optionally substituted with one or two groups selected independently from $R^5$;

cycloalkylalkyl or bicycloalkylalkyl of 4 to 12 carbon atoms, optionally substituted with one or two groups selected independently from $R^5$;

saturated or unsaturated mono or bicyclic heterocycle containing one heteroatom selected from O, S or NR-$C_1$-$C_6$ alkyl, optionally substituted with one or two groups selected independently from $R^5$;

$R^8R^9N$-$C_1$-$C_6$-alkoxyaryl-$C_1$-$C_6$-alkyl where $R^8$ and $R^9$ are independently selected from $C_1$-$C^6$ alkyl or $R^8$ and $R^9$ together with the interposed nitrogen forms a 5–7 membered saturated heterocyclic ring optionally containing an oxygen atom, wherein the aryl group is phenyl or naphthyl;

or a pharmaceutically acceptable salt thereof.

4. A method of inhibiting pathological condition or disorder mediated by matrix metalloproteinases in mammals which comprises administration to a mammal in need thereof a therapeutically effective amount of a matrix metalloproteinase inhibiting compound of the formula

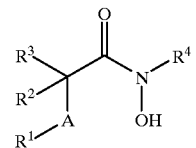

I wherein:

$R^1$ is alkyl of 1 to 18 carbon atoms, optionally substituted with one or two groups selected independently from $R^5$;

alkenyl of 3 to 18 carbon atoms having 1 to 3 double bonds, optionally substituted with one or two groups selected independently from $R^5$;

alkynyl of 3 to 18 carbon atoms having 1 to 3 triple bonds, optionally substituted with one or two groups selected independently from $R^5$;

aryl of 6 to 10 carbon atoms, optionally substituted with one or two groups selected independently from $R^5$;

cycloalkyl of 3 to 8 carbon atoms, optionally substituted with one or two groups selected independently from $R^5$;

saturated or unsaturated 5 to 10 membered mono or bicyclic heterocycle containing one heteroatom selected from O, S or NR$^7$, optionally substituted with one or two groups selected independently from $R^5$;

or heteroaryl-$(CH_2)_{0-6}$- wherein the heteroaryl group is 5 to 6membered with one or two heteroatoms selected independently from O, S, and N and may be optionally substituted with one or two groups selected independently from $R^5$;

A is —S—, —SO— or SO$_2$—;

$R^2$ and $R^3$, taken with the carbon atom to which they are attached, form a 5 to 7 membered heterocyclic ring containing O, S or N—$R^7$ optionally having one or two double bonds;

$R^4$ is hydrogen, alkyl of 1 to 6 carbon atoms, optionally substituted with one or two groups selected independently from $R^5$;

alkenyl of 3 to 18 carbon atoms having 1 to 3 double bonds, optionally substituted with one or two groups selected independently from $R^5$;

alkynyl of 3 to 18 carbon atoms having 1 to 3 triple bonds, optionally substituted with one or two groups selected independently from $R^5$;

phenyl or naphthyl optionally substituted with one or two groups selected independently from $R^5$;

$C_3$ to $C_8$ cycloalkyl or bicycloalkyl optionally substituted with one or two groups selected independently from $R^5$;

saturated or unsaturated 5 to 10 membered mono or bicyclic heterocycle containing one heteroatom selected from O, S or $NR^7$, optionally substituted with one or two groups selected independently from $R^5$;

$R^5$ is H, $C_7$-$C_{11}$ aroyl, $C_2$-$C_6$ alkanoyl, CI to $C_{12}$ alkyl, $C_2$ to $C_{12}$ alkenyl, $C_2$-$C_{12}$ alkynyl, F, Cl, Br, I, CN, CHO, $C_1$-$C_6$ alkoxy, aryloxy, heteroaryloxy, $C_3$-$C_6$ alkenyloxy, $C_3$-$C_6$ alkynyloxy, $C_1$-$C_6$ alkoxyaryl, $C_1$-$C_6$ alkoxyheteroaryl, $C_1$-$C_6$ alkylamino-$C_1$-$C_6$ alkoxy, $C_1$-$C_2$ alkylene dioxy, aryloxy-$C$-$C_6$ alkyl amine, $C_1$-$C_{12}$ perfluoro alkyl, $S(O)_n$-$C_1$-$C_6$ alkyl, $S(O)_n$-aryl where n is 0, 1 or 2; OCOO $C_1$-$C_6$ alkyl, OCOOaryl, OCONR$^6$, COOH, COO $C_1$-$C_6$ alkyl, COOaryl, CONR$^6$R$^6$, CONHOH, NR$^6$R$^6$, SO$_2$NR$^6$R$^6$, NR$^6$SO$_2$aryl, -NR$^6$CONR$^6$R$^6$, NHSO$_2$CF$_3$, SO$_2$NHheteroaryl, SO$_2$NHCOaryl, CONHSO$_2$-$C_1$-$C_6$ alyl, CONHSO$_2$aryl, SO$_2$NHCOaryl, CONHSO$_2$-$C_1$-$C_6$ alkyl, CONHSO$_2$aryl, NH$_2$, OH, aryl, heteroaryl, $C_3$ to $C_8$ cycloalkyl; or saturated or unsaturated 5 to 10 membered mono or bicyclic heterocycle containing one heteroatom selected from O, S or $NR^7$, wherein $C_1$-$C_6$ alkyl is straight or branched, heteroaryl is a 5–10 membered mono or bicyclic heteroaryl group having 1 to 3 heteroatoms selected independently from O, S or $NR^7$ and aryl is phenyl or naphthyl, optionally substituted by 1 or 2 groups selected from halogen, cyano, amino, nitro, $C_1$-$C_6$ alkyl, $C_1$-$C_6$ alkoxy, or hydroxy;

$R^6$ is H, $C_1$ to $C_{18}$ alkyl optionally substituted with OH; $C_3$ to $C_6$ alkenyl, $C_3$ to $C_6$ alkynyl, $C_1$ to $C_6$ perfluoro alkyl, $S(O)_n$-$C_1$-$C_6$ alkyl $S(O)$, aryl where n is 0, 1 or 2;, or COheteroaryl, wherein heteroaryl is a 5–10 membered mono or bicyclic heteroaryl group having 1 to 3 heteroatoms selected independently from O, S or $NR^7$ and aryl is phenyl or naphthyl, optionally substituted by 1 or 2 groups selected from halogen, cyano, amino, nitro, $C_1$-$C_6$ alkyl, $C_1$-$C_6$ alkoxy, or hydroxy;

and $R^7$ is $C_7$-$C_{11}$ aroyl, $C_2$-$C_6$ alkanoyl, $C_1$-$C_{12}$ perfluoro alkyl, S(O)n-$C_1$-$C_6$-alkyl, $S(O)_n$-aryl where n is 0, 1 or 2; COO-$C_1$-$C_6$-alkyl, COOaryl, CONHR$^6$, CONR$^6$R$^6$, CONHOH, SO$_2$NR$^6$R$^6$, SO$_2$CF$_3$, SO$_2$NHheteroaryl, SO$_2$NHCOaryl, CONHSO-$C_1$-$C_6$-alkyl, CONHSO$_2$aryl, aryl, or heteroaryl, where aryl is phenyl or naphthyl, optionally substituted by 1 or 2 groups selected independently from halogen, cyano, amino, nitro, $C_1$-$C_6$ alkyl, $C_1$-$C_6$ alkoxy, or hydroxy; and heteroaryl is a 5–10 membered mono or bicyclic heteroaryl group having 1 to 3 heteroatoms selected independently from O, S or N—$C_1$-$C_6$ alkyl;

alkyl of 1 to 18 carbon atoms, optionally substituted with one or two groups selected independently from $R^5$;

alkenyl of 3 to 18 carbon atoms having from 1 to 3 double bonds, optionally substituted with one or two groups selected independently from $R^5$;

alkynyl of 3 to 18 carbon atoms having from 1 to 3 triple bonds, optionally substituted with one or two groups selected independently from $R^5$;

arylalkyl of 7 to 16 carbon atoms, wherein aryl is optionally substituted with one or two groups selected independently from $R^5$;

heteroarylalkyl wherein alkyl is from 1 to 6 carbon atoms and heteroaryl contains 1 or 2 heteroatoms selected from O, S or N and is optionally substituted with one or two groups selected independently from $R^5$;

biphenylalkyl of 13 to 18 carbon atoms, wherein biphenyl is optionally substituted with one or two groups selected independently from $R^5$;

arylalkenyl of 8 to 16 carbon atoms, wherein aryl is optionally substituted with one or two groups selected independently from $R^5$;

cycloalkylalkyl or bicycloalkylalkyl of 4 to 12 carbon atoms, wherein the cycloalkyl or bicycloalkyl group is optionally substituted with one or two groups selected independently from $R^5$;

saturated or unsaturated mono or bicyclic heterocycle containing one heteroatom selected from O, S or N—$C_1$-$C_6$ alkyl, optionally substituted with one or two groups selected independently from $R^5$; or $R^8R^9N$—$C_1$-$C_6$-alkoxyaryl-$C_1$-$C^6$-alkyl where $R^8$ and $R^9$ are independently selected from $C_1$-$C_6$ alkyl or $R^8$ and $R^9$ together with the interposed nitrogen forms a 5–7 membered saturated heterocyclic ring optionally containing an oxygen atom, wherein the aryl group is phenyl or naphthyl;

or a pharmaceutically acceptable salt thereof.

5. A method according to claim 4 wherein the condition treated is atherosclerosis, atherosclerotic plaque formation, reduction of coronary thrombosis from atheroschlerotic plaque rupture, restenosis, MMP-mediated osteopenias, inflammatory diseases of the central nervous system, sking again, angiogenesis, tumor metastasis, tumor growth, osteoarthritis, rheumatoid arthritis, septic arthritis, corneal ulceration, abnormal wound healing, bone disease, ptoteinuria, aneurysmal aortic disease, degenerative cartilage loss following traumatic joint injury, demyelinating diseases of the nervous system, cirrhosis of the liver, glomerular disease of the kidney, premature rupture of fetal membranes, inflammatory bowel disease, or periodontal disease.

6. A method according to claim 4 wherein the condition treated is age related macular degeneration, diabetic retinopathy, proliferative vitreoretinopathy, retinopathy of prematurity, ocular inflammation, keratoconus, Sjogren's syndrome, myopia, ocular tumors, ocular angiogenesis/neovascularization and corneal graft rejection.

7. A method of treating a pathological condition or disorder mediated by TNF-α converting enzyme (TACE) in mammals which comprises administration to a mammal in need thereof a therapeutically effective amount of a TACE inhibiting compound of the formula

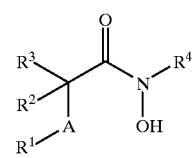

I wherein:
$R^1$ is alkyl of 1 to 18 carbon atoms, optionally substituted with one or two groups selected independently from $R^5$;

alkenyl of 3 to 18 carbon atoms having 1 to 3 double bonds, optionally substituted with one or two groups selected independently from $R^5$;

alkynyl of 3 to 18 carbon atoms having 1 to 3 triple bonds, optionally substituted with one or two groups selected independently from $R^5$;

aryl of 6 to 10 carbon atoms, optionally substituted with one or two groups selected independently from $R^5$;

cycloakyl of 3 to 8 carbon atoms, optionally substituted with one or two groups selected independently from $R^5$;

saturated or unsaturated 5 to 10 membered mono or bicyclic heterocycle containing one heteroatom selected from O, S or $NR^7$, optionally substituted with one or two groups selected independently from $R^5$;

or heteroaryl-$(CH_2)_{0-6}$- wherein the heteroaryl group is 5 to 6 membered with one or two heteroatoms selected independently from O, S, and N and may be optionally substituted with one or two groups selected independently from $R^5$;

A is —S—, —SO— or $SO_2$—;

$R^2$ and $R^3$, taken with the carbon atom to which they are attached, form a 5 to 7 membered heterocyclic ring containing O, S or N—$R^7$ optionally having one or two double bonds;

$R^4$ is hydrogen, alkyl of 1 to 6 carbon atoms, optionally substituted with one or two groups selected independently from $R^5$;

alkenyl of 3 to 18 carbon atoms having 1 to 3 double bonds, optionally substituted with one or two groups selected independently from $R^5$;

alkynyl of 3 to 18 carbon atoms having 1 to 3 triple bonds, optionally substituted with one or two groups selected independently from $R^5$;

phenyl or naphthyl optionally substituted with one or two soups selected independently from $R^5$;

$C_3$ to $C_8$ cycloalkyl or bicycloalkyl optionally substituted with one or two groups selected independently from $R^5$;

saturated or unsaturated 5 to 10 membered mono or bicyclic heterocycle containing one heteroatom selected from O, S or $NR^7$, optionally substituted with one or two groups selected independently from $R^5$;

$R^5$ is H, $C_7$-$C_{11}$ aroyl, $C_2$–$C_6$ alkanoyl, $C_1$ to $C_{12}$ alkyl, $C_2$ to $C_{12}$ alkenyl, $C_2$–$C_{12}$ alkynyl, F, Cl, Br, I, CN, CHO, $C_1$–$C_6$ alkoxy, aryloxy, heteroaryloxy, $C_3$–$C_6$ alkenyloxy, $C_3$–$C_6$ alkynyloxy, $C_1$–$C_6$ alkoxyaryl, $C_1$–$C_6$ alkoxyheteroaryl, $C_1$–$C_6$ alkylamino-$C_1$–$C_6$ alkoxy, $C_1$–$C_2$ alkylene dioxy, aryloxy-$C_1$–$C_6$ alkyl amine, $C_1$–$C_{12}$ perfluoro alkyl, $S(O)_n$-$C_1$–$C_6$ alkyl, $S(O)_n$-aryl where n is 0, 1 or 2; OCOO $C_1$–$C_6$ alkyl, OCOOaryl, $OCONR^6$, COOH, COO $C_1$–$C_6$ aLkyl, COOaryl, $CONR^6R^6$, CONHOH, $NR^6R^6$, $SO_2NR^6R^6$, $NR^6SO_2$aryl, —$NR^6CONR^6R^6$, $NHSO_2CF_3$, $SO_2$Nheteroaryl, $SO_2$NHCOaryl, $CONHSO_2$-$C_1$–$C_6$ alkyl, $CONHSO_2$aryl, $SO_2$NHCOaryl, $CONHSO_2$-$C_1$–$C_6$ alkyl, $CONHSO_2$aryl, $NH_2$, OH, aryl, heteroaryl, $C_3$ to $C_8$ cycloalkyl; or saturated or unsaturated 5 to 10 membered mono or bicyclic heterocycle containing one heteroatom selected from O, S or $NR^7$, wherein $C_1$–$C_6$ alkyl is straight or branched, heteroaryl is a 5–10 membered mono or bicyclic heteroaryl group having 1 to 3 heteroatoms selected independently from O, S or $NR^7$ and aryl is phenyl or naphthyl, optionally substituted by 1 or 2 groups selected from halogen, cyano, amino, nitro, $C_1$–$C_6$ alkyl, $C_1$–$C_6$ alkoxy, or hydroxy;

$R^6$ is H, $C_1$ to $C_{18}$ alkyl optionally substituted with OH; $C_3$ to $C_6$ alkenyl, $C_3$ to $C_6$ alkynyl, $C_1$ to $C_6$ perfluoro alkyl, $S(O)_n$-$C_1$–$C_6$ alkyl S(O)n aryl where n is 0, 1 or 2, or COheteroaryl, wherein heteroaryl is a 5–10 membered mono or bicyclic heteroaryl group having 1 to 3 heteroatoms selected independently from O, S or $NR^7$ and aryl is phenyl or naphthyl, optionally substituted by 1 or 2 groups selected from halogen, cyano, amino, nitro, $C_1$–$C_6$ alkyl, $C_1$–$C_6$ alkoxy, or hydroxy;

and $R^7$ is $C_7$-$C_{11}$ aroyl, $C_2$–$C_6$ alkanoyl, $C_1$–$C_{12}$ perfluoro alkyl, $S(O)_n$-$C_1$–$C_6$-alkyl, $S(O)_n$-aryl where n is 0, 1 or 2; COO-$C_1$–$C_6$-alkyl, COOaryl, $CONHR^6$, $CONR^6R^6$, CONHOH, $SO_2NR^6R^6$, $SO_2CF_3$, $SO_2$NHheteroaryl, $SO_2NHCOaryl$, $CONHSO$-$C_1$–$C_6$-alkyl, $CONHSO_2$aryl, aryl, or heteroaryl, where aryl is phenyl or naphthyl, optionally substituted by 1 or 2 groups selected independently from halogen, cyano, amino, nitro, $C_1$–$C_6$ alkyl, $C_1$–$C_6$ alkoxy, or hydroxy; and heteroaryl is a 5–10 membered mono or bicyclic heteroaryl group having 1 to 3 heteroatoms selected independently from O, S or N-$C_1$–$C_6$ alkyl;

alkyl of 1 to 18 carbon atoms, optionally substituted with one or two groups selected independently from $R^5$;

alkenyl of 3 to 18 carbon atoms having from 1 to 3 double bonds, optionally substituted with one or two groups selected independently from $R^5$;

alkynyl of 3 to 18 carbon atoms having from 1 to 3 triple bonds, optionally substituted with one or two groups selected independently from $R^5$;

arylalkyl of 7 to 16 carbon atoms, wherein aryl is optionally substituted with one or two groups selected independently from $R^5$;

heteroarylalkyl wherein alkyl is from 1 to 6 carbon atoms and heteroaryl contains 1 or 2 heteroatoms selected from O, S or N and is optionally substituted with one or two groups selected independently from $R^5$;

biphenylalkyl of 13 to 18 carbon atoms, wherein biphenyl is optionally substituted with one or two groups selected independently from $R^5$;

arylalkenyl of 8 to 16 carbon atoms, wherein aryl is optionally substituted with one or two groups selected independently from $R^5$;

cycloalkylalkyl or bicycloalkylalkyl of 4 to 12 carbon atoms, wherein the cycloalkyl or bicycloalkyl group is optionally substituted with one or two groups selected independently from $R^5$;

saturated or unsaturated mono or bicyclic heterocycle containing one heteroatom selected from O, S or N-$C_1$–$C_6$ alkyl, optionally substituted with one or two groups selected independently from $R^5$; or $R^8R^9$N-$C_1$–$C_6$-alkoxyaryl-$C_1$–$C_6$-alkyl where $R^8$ and $R^9$ are independently selected from $C_1$–$C_6$ alkyl or $R^8$ and $R^9$ together with the interposed nitrogen forms a 5–7 membered saturated heterocyclic ring optionally containing an oxygen atom, wherein the aryl group is phenyl or naphthyl;

or a pharmaceutically acceptable salt thereof.

8. The method according to claim 7 wherein the condition treated is rheumatoid arthritis, graft rejection, cachexia, anorexia, inflammation, fever, insulin resistance, septic shock, conjestive heard failure, inflammatory disease of the central nervous system, inflammatory bowel disease or HIV injection.

9. A pharmaceutical composition comprising a pharmaceutical carrier and a therapeutically effective amount of a matrix metalloproteinase or TACE inhibiting compound according to the formula

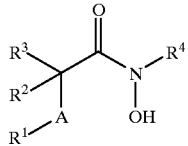

wherein:
$R^1$ is alkyl of 1 to 18 carbon atoms, optionally substituted with one or two groups selected independently from $R^5$;
alkenyl of 3 to 18 carbon atoms having 1 to 3 double bonds, optionally substituted with one or two groups selected independently from $R^5$;
alkynyl of 3 to 18 carbon atoms having 1 to 3 triple bonds, optionally substituted with one or two groups selected independently from $R^5$;
aryl of 6 to 10 carbon atoms, optionally substituted with one or two groups selected independently from $R^5$;
cycloalkyl of 3 to 8 carbon atoms, optionally substituted with one or two groups selected independently from $R^5$;
saturated or unsaturated 5 to 10 membered mono or bicyclic heterocycle containing one heteroatom selected from O, S or $NR^7$, optionally substituted with one or two groups selected independently from $R^5$;
or heteroaryl-$(CH_2)_{0-6}$- wherein the heteroaryl group is S to 6 membered with one or two heteroatoms selected independently from O, S, and N and may be optionally substituted with one or two groups selected independently from $R^5$;
A is —S—, —SO— or $SO_2$—;
$R^2$ and $R^3$, taken with the carbon atom to which they are attached, form a 5 to 7 membered heterocyclic ring containing O, S or N—$R^7$ optionally having one or two double bonds;
$R^4$ is hydrogen,
alkyl of 1 to 6 carbon atoms, optionally substituted with one or two groups selected independently from $R^5$;
alkenyl of 3 to 18 carbon atoms having 1 to 3 double bonds, optionally substituted with one or two groups selected independently from $R^5$;
alkynyl of 3 to 18 carbon atoms having 1 to 3 triple bonds, optionally substituted with one or two groups selected independently from $R^5$;
phenyl or naphthyl optionally substituted with one or two groups selected independently from $R^5$;
$C_3$ to $C_8$ cycloalkyl or bicycloalkyl optionally substituted with one or two groups selected independently from $R^5$;
saturated or unsaturated 5 to 10 membered mono or bicyclic heterocycle containing one heteroatom selected from O, S or $NR^7$, optionally substituted with one or two groups selected independently from $R^5$;
$R^5$ is H, $C_7$–$C_{11}$ aroyl, $C_2$–$C_6$ alkanoyl, $C_1$ to $C_{12}$ alkyl, $C_2$ to $C_{12}$ alkenyl, $C_2$–$C_{12}$ alkynyl, F, Cl, Br, I, CN, CHO, $C_1$–$C_6$ alkoxy, aryloxy, heteroaryloxy, $C_3$–$C_6$ alkenyloxy, $C_3$–$C_6$ alkynyloxy, $C_1$–$C_6$ alkoxyaryl, $C_1$–$C_6$ alkoxyheteroaryl, $C_1$–$C_6$ alkyamino-$C_1$–$C_6$ alkoxy, $C_1$–$C_2$ alkylene dioxy, aryloxy-$C_1$–$C_6$ alkyamine, $C_1$–$C_{12}$ perfluoro alkyl, $S(O)_n$-$C_1$–$C_6$ alkyl, $S(O)_n$-aryl where n is 0, 1 or 2; OCOO $C_1$–$C_6$ alkyl, OCOaryl, OCONR$^6$, COOH, COO $C_1$–$C_6$ alkyl, COOaryl, CONR$^6$R$^6$, CONHOH, NR$^6$R$^6$, $SO_2$NR$^6$R$^6$, NR$^6$SO$_2$aryl, -NR$^6$CONR$^6$R$^6$, NHSO$_2$CF$_3$, $SO_2$NHheteroaryl, $SO_2$NHCOaryl, CONHSO$_2$-$C_1$–$C_6$ alkyl, CONHSO$_2$aryl, SO$_2$NHCOaryl, CONHSO$_2$-$C_1$–$C_6$ alkyl, CONHSO$_2$aryl, NH2, OH, aryl, heteroaryl, $C_3$ to $C_8$ cycloalkyl; or saturated or unsaturated 5 to 10 membered mono or bicyclic heterocycle containing one heteroatom selected from O, S or $NR^7$, wherein $C_1$–$C_6$ alkyl is straight or branched, heteroaryl is a 5–10 membered mono or bicyclic heteroaryl group having 1 to 3 heteroatoms selected independently from O, S or $NR^7$ and aryl is phenyl or naphthyl, optionally substituted by 1 or 2 groups selected from halogen, cyano, amino, nitro, $C_1$–$C_6$ alkyl, $C_1$–$C_6$ alkoxy, or hydroxy;
$R^6$ is H, $C_1$ to $C_{18}$ alkyl optionally substituted with OH; CJ to $C_6$ alkenyl, $C_3$ to $C_6$ alkynyl, $C_1$ to $C_6$ perfluoro alkyl, $S(O)_n$-$C_1$–$C_6$ alkyl $S(O)$n aryl where n is 0, 1 or 2;, or COheteroaryl, wherein heteroaryl is a 5–10 membered mono or bicyclic heteroaryl group having 1 to 3 heteroatoms selected independently from O, S or $NR^7$ and aryl is phenyl or naphthyl, optionally substituted by 1 or 2 groups selected from halogen, cyano, amino, nitro, $C_1$–$C_6$ alkyl, $C_1$–$C_6$ alkoxy, or hydroxy;
and $R^7$ is $C_7$–$C_{11}$ aroyl, $C_2$–$C_6$ alkanoyl, $C_1$–$C_{12}$ perfluoro alkyl, $S(O)_n$-$C_1$–$C_6$-alkyl, $S(O)_n$-aryl where n is 0, 1 or 2; COO-$C_1$–$C_6$-alkyl, COOaryl, CONHR$^6$, CONR$^6$R$^6$, CONHOH, $SO_2$NR$^6$R$^6$, $SO_2$CF$_3$, $SO_2$Nheteroaryl, $SO_2$NHCOaryl, CONHSO-$C_1$–$C_6$-alkyl, CONHSO$_2$aryl, aryl, or heteroaryl, where aryl is phenyl or naphthyl, optionally substituted by 1 or 2 groups selected independently from halogen, cyano, amino, nitro, $C_1$–$C_6$ alkyl, $C_1$–$C_6$ alkoxy, or hydroxy; and heteroaryl is a 5–10 membered mono or bicyclic heteroaryl group having 1 to 3 heteroatoms selected independently from O, S or N—-$C_1$–$C_6$ alkyl;
alkyl of 1 to 18 carbon atoms, optionally substituted with one or two groups selected independently from $R^5$;
alkenyl of 3 to 18 carbon atoms having from 1 to 3 double bonds, optionally substituted with one or two groups selected independently from $R^5$;
alkynyl of 3 to 18 carbon atoms having from 1 to 3 triple bonds, optionally substituted with one or two groups selected independently from $R^5$;
arylalkyl of 7 to 16 carbon atoms, wherein aryl is optionally substituted with one or two groups selected independently from $R^5$;
heteroarylalkyl wherein alkyl is from 1 to 6 carbon atoms and heteroaryl contains 1 or 2 heteroatoms selected from O, S or N and is optionally substituted with one or two groups selected independently from $R^5$;
biphenylalkyl of 13 to 18 carbon atoms, wherein biphenyl is optionally substituted with one or two groups selected independently from $R^5$;
arylalkenyl of 8 to 16 carbon atoms, wherein aryl is optionally substituted with one or two groups selected independently from $R^5$;
cycloalkylalkyl or bicycloalkylalkyl of 4 to 12 carbon atoms, wherein the cycloalkyl or bicycloalkyl group is optionally substituted with one or two groups selected independently from $R^5$;

saturated or unsaturated mono or bicyclic heterocycle containing one heteroatom selected from O, S or N—$C_1$–$C_6$ alkyl, optionally substituted with one or two groups selected independently from $R^5$; or $R^8R^9N$—$C_1$–$C_6$-alkoxyaryl-$C_1$–$C_6$-alkyl where $R^8$ and $R^9$ are independently selected from $C_1$–$C_6$ alkyl or $R^8$ and $R^9$ together with the interposed nitrogen forms a 5–7 membered saturated heterocyclic ring optionally containing an oxygen atom, wherein the aryl group is phenyl or naphthyl;

or a pharmaceutically acceptable salt thereof.

* * * * *

UNITED STATES PATENT AND TRADEMARK OFFICE
CERTIFICATE OF CORRECTION

PATENT NO. : 6,441,023 B1
DATED : August 27, 2002
INVENTOR(S) : Aranapakam M. Venkatesan It is certified that error appears in the above-identified patent and that said Letters Patent is hereby corrected as shown below:

<u>Title page,</u>
Item [75], Inventors, amend the inventors to be -- Aranapakam Mudumbai Venkatesan -- instead of "Aranapakam Mudumbai Venkatesan; Jannie Lea Baker; Jeremy Ian Levin"

<u>Column 119,</u>
Line 30, insert -- alkynyl -- instead of "alknyl"
Line 40, insert -- COOaryl -- instead of "COaryl"
Line 41, insert -- $SO_2$Nheteroaryl -- instead of "$SO_2$iNheteroaryl"

<u>Column 120,</u>
Line 18, insert -- treating a -- instead of "inhibiting"

<u>Column 121,</u>
Line 14, insert -- $C_1$ -- instead of "CI"
Line 19, insert -- $C_1$-$C_6$ -- instead of "C-$C_6$"
Line 26, insert -- alkyl -- instead of "alyl"

<u>Column 122,</u>
Line 34, insert -- skin -- instead of "sking"
Line 35, insert -- aging -- instead of "again"

<u>Column 123,</u>
Line 8, insert -- cycloalkyl -- instead of "cycloakyl"
Line 52, insert -- alkyl -- instead of "aLkyl"

<u>Column 125,</u>
Line 35, insert -- 5 -- instead of "S"

UNITED STATES PATENT AND TRADEMARK OFFICE
CERTIFICATE OF CORRECTION

PATENT NO. : 6,441,023 B1
DATED : August 27, 2002
INVENTOR(S) : Aranapakam M. Venkatesan It is certified that error appears in the above-identified patent and that said Letters Patent is hereby corrected as shown below:

Column 126,
Line 1, insert -- alkylamino -- instead of "alkyamino"
Line 5, insert -- OCOOaryl -- instead of "OCOaryl"
Line 10, insert -- $NH_2$ -- instead of "NH2"
Line 21, insert -- $C_3$ -- instead of "CJ"

Signed and Sealed this

Nineteenth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,441,023 B1
DATED : August 27, 2002
INVENTOR(S) : Aranapakam Mudumbai Venkatesan It is certified that error appears in the above-identified patent and that said Letters Patent is hereby corrected as shown below:

<u>Title page,</u>
Item [73], Assignee, change "American Home Products Corporation" to
-- American Cyanamid Company --

Signed and Sealed this

Seventh Day of September, 2004

JON W. DUDAS
*Director of the United States Patent and Trademark Office*